US011826432B2

(12) United States Patent
Qin et al.

(10) Patent No.: US 11,826,432 B2
(45) Date of Patent: Nov. 28, 2023

(54) LINKERS, CONJUGATES AND APPLICATIONS THEREOF

(71) Applicant: GENEQUANTUM HEALTHCARE (SUZHOU) CO., LTD., Suzhou (CN)

(72) Inventors: Gang Qin, Suzhou (CN); Paul H. Song, Suzhou (CN); Mingyu Hu, Suzhou (CN)

(73) Assignee: GENEQUANTUM HEALTHCARE (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 17/720,523

(22) Filed: Apr. 14, 2022

(65) Prior Publication Data
US 2022/0395581 A1    Dec. 15, 2022

(30) Foreign Application Priority Data

Apr. 14, 2021  (WO) ................ PCT/CN2021/087323

(51) Int. Cl.
*A61K 47/68* (2017.01)
*A61K 47/65* (2017.01)
*A61P 35/00* (2006.01)

(52) U.S. Cl.
CPC .......... *A61K 47/6849* (2017.08); *A61K 47/65* (2017.08); *A61K 47/6803* (2017.08); *A61P 35/00* (2018.01)

(58) Field of Classification Search
None
See application file for complete search history.

(56) References Cited

U.S. PATENT DOCUMENTS

| 8,652,479 | B2 | 2/2014 | Ebens et al. |
| 8,703,714 | B2 | 4/2014 | Doronina et al. |
| 9,504,756 | B2 | 11/2016 | Lyon et al. |
| 9,872,923 | B2 | 1/2018 | Grawunder et al. |
| 10,035,817 | B2 | 7/2018 | Chen et al. |
| 11,040,084 | B2 * | 6/2021 | Qin .................... A61K 47/6851 |
| 2010/0129314 | A1 | 5/2010 | Singh et al. |
| 2017/0112944 | A1 * | 4/2017 | Qin ........................ A61P 35/00 |
| 2018/0104349 | A9 | 4/2018 | Qin et al. |
| 2020/0129639 | A1 | 4/2020 | Levengood |
| 2020/0276261 | A1 | 9/2020 | Zhao et al. |
| 2021/0187114 | A1 | 6/2021 | Qin et al. |
| 2021/0228728 | A1 | 7/2021 | Li et al. |

FOREIGN PATENT DOCUMENTS

| EP | 2907824 A1 * | 8/2015 | ......... A61K 31/4745 |
| WO | WO-2015165413 A1 * | 11/2015 | ........... A61K 31/337 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
Strop et al., Chemistry and Biology 20: 161-167 (Year: 2013).*
Alley et al., "Contribution of Linker Stability to the Activities of Anticancer Immunoconjugates," Bioconjug Chem., vol. 19, No. 3, pp. 759-765, (2008); DOI: 10.1021/bc7004329; Abstract Only—1 page.
Bauer, Dennis M. et al. "Clickable Tyrosine Binding Bifunctional Linkers for Preparation of DNA-Protein Conjugates" Bioconjugate Chemistry, vol. 24, No. 6, Jun. 9, 2013, pp. 1094-1101.
Chudasama et al., "Semi-Mechanistic Population Pharmacokinetic Model of Multivalent Trastuzumab Emtansine in Patients with Metastatic Breast Cancer," Clinical Pharmacology & Therapeutics, vol. 92, No. 4, pp. 520-527, (2012); DOI: 10.1038/clpt.2012.153; Abstract Only—2 pages.
Extended European Search Report, EP 15786402.6 dated Nov. 10, 2017.
International Search Report PCT/CN2015/077887 dated Aug. 28, 2015.
JP 2016-563404 Office Action dated Feb. 5, 2019.
Kornberger, et al. "Sortase-catalyzed in vitro functionalization of a HER2-specific recombinant Fab for tumor targeting of the plant cytotoxin gelonin", mAbs, 6(2), pp. 354-366, (2014).
Lyon et al., "Self-Hydrolyzing Maleimides Improve the Stability and Pharmacological Properties of Antibody-Drug Conjugates," Nat Biotechnol., vol. 32, No. 10, pp. 1059-1062, (2014); DOI: 10.1038/nbt.2968; Abstract Only—1 page.
Madej, Mariusz P. "Engineering of an anti-epidermal growth factor receptor antibody to single chain format and labeling by Sortase A-mediated protein ligation" Biotechnology and Bioengineering, vol. 109, No. 6, Jun. 1, 2012, pp. 1461-1470.
Ponte, Jose F. et al., "Understanding How the Stability of the Thiol-Maleimide Linkage Impacts the Pharmacokinetics of Lysine-Linked Antibody-Maytansinoid Conjugates", Bioconjugate Chemistry, vol. 27, No. 7, Jul. 20, 2016, pp. 588-1598.
Shen, Ben-Quan et al. "Conjugation site modulates the in vivo stability and therapeutic activity of antibody-drug conjugates" Nature Biotechnology, vol. 3, No. 2, Jan. 22, 2012, pp. 184-189.
Swee, Lee Kim et al. "Sortase-mediated modification of alpha DEC205 affords optimization of antigen presentation and immunization against a set of viral epitopes", Proceedings National Academy of Sciences PNAS, vol. 110, No. 4, Jan. 22, 2013, pp. 1428-1433.
Tsakiji, Shinya et al. "Sortase-Mediated Ligation: A Gift from Gram-Positive Bacteria to Protein Engineering" ChemBioChem—A European Journal of Chemical Biology, vol. 10, No. 5, Mar. 23, 2009. pp. 787-798.
Tumey, et al, "Mild Method for Succinimide Hydrolysis on ADCs: Impact on ADC Potency, Stability, Exposure, and Efficacy", Bioconjugate Chem., 25(10), pp. 1871-1880.

* cited by examiner

*Primary Examiner* — Phuong Huynh
(74) *Attorney, Agent, or Firm* — Hoxie & Associates LLC

(57) ABSTRACT

The present disclosure relates to a linker molecule for targeting molecule-drug conjugate, and the corresponding conjugate, the preparation and use thereof.

26 Claims, 4 Drawing Sheets

Specification includes a Sequence Listing.

SEQUENCE LISTING

<160> NUMBER OF SEQ ID NOS: 23

<210> SEQ ID NO 1
<211> LENGTH: 222
<212> TYPE: PRT
<213> ORGANISM: Artificial Sequence
<220> FEATURE:
<223> OTHER INFORMATION: Ab0001-LCCTL-HC Light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ala Leu Pro Glu Thr Gly Gly
    210                 215                 220

<210> SEQ ID NO 2
<211> LENGTH: 450
<212> TYPE: PRT
<213> ORGANISM: Artificial Sequence
<220> FEATURE:
<223> OTHER INFORMATION: Ab0001-LCCTL-HC Heavy chain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 222
<212> TYPE: PRT
<213> ORGANISM: Artificial Sequence
<220> FEATURE:
<223> OTHER INFORMATION: Ab0001-LCCTL-HCCTL Light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ala Leu Pro Glu Thr Gly Gly
    210                 215                 220

<210> SEQ ID NO 4
<211> LENGTH: 458
<212> TYPE: PRT
<213> ORGANISM: Artificial Sequence
<220> FEATURE:
<223> OTHER INFORMATION: Ab0001-LCCTL-HCCTL Heavy chain

<400> SEQUENCE: 4

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Asn Ile Lys Asp Thr
             20                  25                  30
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
            435                 440                 445

Gly Lys Gly Ala Leu Pro Glu Thr Gly Gly
        450                 455

<210> SEQ ID NO 5
<211> LENGTH: 5
<212> TYPE: PRT
<213> ORGANISM: Artificial Sequence
<220> FEATURE:
<223> OTHER INFORMATION: Spacer sequence

<400> SEQUENCE: 5

Gly Gly Gly Gly Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Spacer sequence

<400> SEQUENCE: 6

Gly Gly Gly Gly Ser Gly Gly Gly Gly Ser
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Spacer sequence

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 4
<212> TYPE: PRT
<213> ORGANISM: Artificial Sequence
<220> FEATURE:
<223> OTHER INFORMATION: Cleavable sequence

<400> SEQUENCE: 8

Gly Gly Phe Gly
1

<210> SEQ ID NO 9
<211> LENGTH: 4
<212> TYPE: PRT
<213> ORGANISM: Artificial Sequence
<220> FEATURE:
<223> OTHER INFORMATION: Cleavable sequence

<400> SEQUENCE: 9

Gly Phe Leu Gly
1

<210> SEQ ID NO 10
<211> LENGTH: 4
<212> TYPE: PRT
<213> ORGANISM: Artificial Sequence
<220> FEATURE:
<223> OTHER INFORMATION: Cleavable sequence

```
<400> SEQUENCE: 10

Ala Leu Ala Leu
1

<210> SEQ ID NO 11
<211> LENGTH: 5
<212> TYPE: PRT
<213> ORGANISM: Artificial Sequence
<220> FEATURE:
<223> OTHER INFORMATION: Recognition sequence of ligase donor substrate
<220> FEATURE:
<221> NAME/KEY: MISC_FEATURE
<222> LOCATION: (3)..(3)
<223> OTHER INFORMATION: X in 3 position: any amino acid that is natural
      or unnatural

<400> SEQUENCE: 11

Leu Pro Xaa Thr Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Recognition sequence of ligase donor substrate

<400> SEQUENCE: 12

Leu Pro Glu Thr Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Recognition sequence of ligase donor substrate

<400> SEQUENCE: 13

Leu Pro Glu Thr Gly Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Recognition sequence of ligase donor substrate

<400> SEQUENCE: 14

Asn Pro Gln Thr Asn
1               5

<210> SEQ ID NO 15
<211> LENGTH: 5
<212> TYPE: PRT
<213> ORGANISM: Artificial Sequence
<220> FEATURE:
<223> OTHER INFORMATION: Recognition sequence of ligase donor substrate

<400> SEQUENCE: 15

Asn Pro Lys Thr Gly
1               5

<210> SEQ ID NO 16
<211> LENGTH: 5
<212> TYPE: PRT
```

<213> ORGANISM: Artificial Sequence
<220> FEATURE:
<223> OTHER INFORMATION: Recognition sequence of ligase donor substrate
<220> FEATURE:
<221> NAME/KEY: MISC_FEATURE
<222> LOCATION: (3)..(3)
<223> OTHER INFORMATION: X in 3 position: any amino acid that is natural
      or unnatural

<400> SEQUENCE: 16

Leu Ala Xaa Thr Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Recognition sequence of ligase donor substrate

<400> SEQUENCE: 17

Leu Pro Gln Thr Ser Glu Gln
1               5

<210> SEQ ID NO 18
<211> LENGTH: 8
<212> TYPE: PRT
<213> ORGANISM: Artificial Sequence
<220> FEATURE:
<223> OTHER INFORMATION: spacer and recognition sequence of ligase donor
      substrate

<400> SEQUENCE: 18

Gly Ala Leu Pro Glu Thr Gly Gly
1               5

<210> SEQ ID NO 19
<211> LENGTH: 220
<212> TYPE: PRT
<213> ORGANISM: Artificial Sequence
<220> FEATURE:
<223> OTHER INFORMATION: Ab0001-LCCTL-HC Light chain

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ala Leu Pro Glu Thr
    210                 215                 220

<210> SEQ ID NO 20
<211> LENGTH: 220
<212> TYPE: PRT
<213> ORGANISM: Artificial Sequence
<220> FEATURE:
<223> OTHER INFORMATION: Ab0001-LCCTL-HCCTL Light chain

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ala Leu Pro Glu Thr
    210                 215                 220

<210> SEQ ID NO 21
<211> LENGTH: 456
<212> TYPE: PRT
<213> ORGANISM: Artificial Sequence
<220> FEATURE:
<223> OTHER INFORMATION: Ab0001-LCCTL-HCCTL Heavy chain
```

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

-continued

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys Gly Ala Leu Pro Glu Thr
    450                 455

<210> SEQ ID NO 22
<211> LENGTH: 4
<212> TYPE: PRT
<213> ORGANISM: Artificial Sequence
<220> FEATURE:
<223> OTHER INFORMATION: Recognition sequence of ligase donor substrate
<220> FEATURE:
<221> NAME/KEY: MISC_FEATURE
<222> LOCATION: (3)..(3)
<223> OTHER INFORMATION: X in 3 position: any amino acid that is natural
      or unnatural

<400> SEQUENCE: 22

Leu Pro Xaa Thr
1

<210> SEQ ID NO 23
<211> LENGTH: 6
<212> TYPE: PRT
<213> ORGANISM: Artificial Sequence
<220> FEATURE:
<223> OTHER INFORMATION: Spacer and recognition sequence of ligase donor
      substrate
<220> FEATURE:
<221> NAME/KEY: MISC_FEATURE
<222> LOCATION: (5)..(5)
<223> OTHER INFORMATION: X in 5 position: any amino acid that is natural
      or unnatural

<400> SEQUENCE: 23

Gly Ala Leu Pro Xaa Thr
1               5
```

LINKERS, CONJUGATES AND APPLICATIONS THEREOF

CROSS-REFERENCE TO RELATED APPLICATIONS

This application is a U.S. Non-Provisional application under 35 U.S.C. § 111(a), which claims priority to and the benefit of International Application No. PCT/CN2021/087323, filed on Apr. 14, 2021, the contents of which is hereby incorporated by reference in its entirety.

REFERENCE TO A SEQUENCE LISTING

This application contains a Sequence Listing as a separate part of the disclosure. The contents of the Sequence Listing 2023-05-08-GQH-10-US-SequenceListing.txt; Size: 23,761 bytes; and Date of Creation: May 8, 2023) is incorporated herein by reference.

TECHNICAL FIELD

The present disclosure relates to the biopharmaceutical field, in particular, to a linker for preparing targeting molecule-drug conjugates, and the corresponding conjugates, the preparing process and use thereof.

BACKGROUND

HER2 was found to be overexpressed in several cancer types, including breast cancer and gastric cancer, and proved to a promising target for cancer therapies. Multiple HER2 targeting therapeutic modalities has been approved, including HER2 tyrosine kinase inhibitors (Lapatinib, Tucatinib), therapeutic HER2 antibodies (Herceptin, Perjeta), and HER2 targeting ADC (Kadcyla, Enhertu). These therapeutic agents have significantly improved the survival of HER2 positive breast cancer and gastric cancer patients. Especially, Enhertu not only showed great efficacy in HER2 high patients, but also demonstrated sign of efficacy in HER2 medium/low patients, which may potentially benefit more HER2 expressing cancer patients. Albeit the great efficacy, Enhertu caused more than 10% of interstitial lung disease, which limited its usage in part of patients.

Enhertu, as well as the other commercially available ADCs and most of the ADCs in clinical trials, are prepared by chemical conjugation, using a thiosuccinimide structure (thiosuccinimide linkage) to conjugate the small molecule drug with the targeting antibody or protein. The thiosuccinimide structure is formed by the reaction of a thiol group and a maleimide. However, the thiosuccinimide linkage is not stable. In organisms, reverse Michael addition or exchange with other thiol groups leads to the fall-off of the cytotoxin from the ADC and off-target toxicity, which reduces the safety and limits the clinical application.

SUMMARY

In a first aspect, provided is a compound of formula (I):

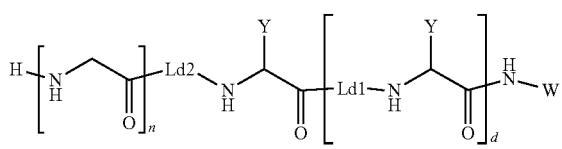

wherein,
W is hydrogen or is LKb;
Y is hydrogen or is LKa-LKb;
provided that W and Y are not simultaneously hydrogen;
each LKa is independently selected from

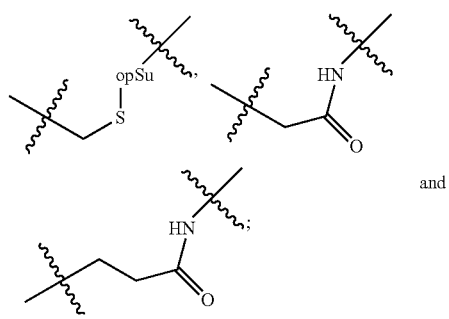

or a mixture thereof;

opSu is

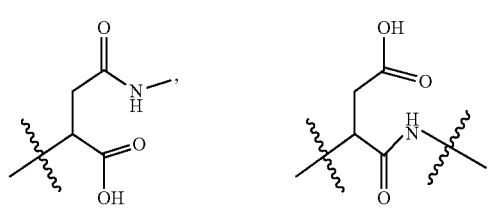

or a mixture thereof;

each LKb is independently $L^2$-$L^1$-B;
each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$;
$R^{10}$ is hydrogen, or a group which can leave when reacting with a group in the payload;
$L^1$ is Cleavable sequence 1 comprising an amino acid sequence which can be cleaved by enzyme, and Cleavable sequence 1 comprises 1-10 amino acids;
$L^2$ is a bond; or a $C_{2-20}$ alkylene wherein one or more —$CH_2$— structures in the alkylene is optionally replaced by —$CR^3R^4$—, —O—, —(CO)—, —S(=O)$_2$—, —$NR^5$—, —$N^{\oplus}R^6R^7$—, $C_{4-10}$ cycloalkylene, $C_{4-10}$ heterocyclylene, phenylene; wherein the cycloalkylene, heterocyclylene and phenylene are each independently unsubstituted or substituted with at least one substituent selected from halogen, —$C_{1-10}$ alkyl, —$C_{1-10}$ haloalkyl, —$C_{1-10}$ alkylene-NH—$R^8$ and —$C_{1-10}$ alkylene-O—$R^9$;
Ld2 and each Ld1 are independently a bond; or selected from —NH—$C_{1-20}$ alkylene-(CO)—, —NH-(PEG)$_i$-(CO)—, or is a natural amino acid or oligomeric natural amino acids having a degree of polymerization of 2-10 independently unsubstituted or substituted with -(PEG)$_j$-$R^{11}$ on the side chain;
-(PEG)$_i$- and -(PEG)$_j$- are each a PEG fragment, which comprises the denoted number of consecutive —(O—$C_2H_4$)— structure units or consecutive —($C_2H_4$—O)— structure units, with an optional additional $C_{1-10}$ alkylene at one terminal;

$R^1$, $R^2$, $R^3$, $R^4$, $R^5$, $R^6$, $R^7$, $R^8$, $R^9$ are each independently selected from hydrogen, halogen, —$C_{1-10}$ alkyl, —$C_{1-10}$ haloalkyl, $C_{4-10}$ cycloalkylene;

$R^{11}$ is $C_{1-10}$ alkyl;

n is any integer of 2 to 20;

d is 0, or is any integer of 1 to 6;

each i is independently an integer of 1-100, preferably 1 to 20; preferably each i is independently an integer of 1 to 12; more preferably 2 to 8; particularly 4;

each j is independently an integer of 1-100, preferably 1 to 20; preferably each j is independently an integer of 1 to 12; more preferably 8 to 12; particularly 8 or 12.

In a second aspect, provided is a compound having the structure of formula (II):

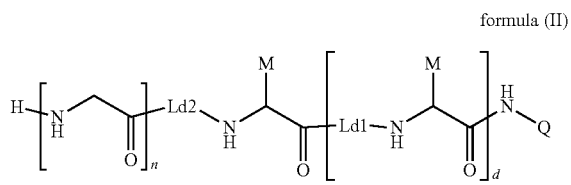

formula (II)

wherein

Q is hydrogen or LKb-P;

M is hydrogen or LKa-LKb-P;

provided that Q and M are not simultaneously hydrogen;

P is a payload which is linked to the B moiety or $L^1$ moiety of the compound of formula (I);

n, d, Ld1, Ld2, LKa and LKb are as defined in formula (I);

preferably, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—;

preferably, Sp1 is selected from PABC, acetal, heteroacetal and the combination thereof; more preferably, Sp1 is acetal, heteroacetal or PABC; further preferably, the heteroacetal is selected from N,O-heteroacetal; more preferably, Sp1 is —O—CH$_2$—U— or —NH—CH$_2$—U—; wherein the —O— or the —NH— is connected to Cleavable sequence 1, and U is O, S or NH, preferably O or S.

In a third aspect, provided is a conjugate having the structure of formula III:

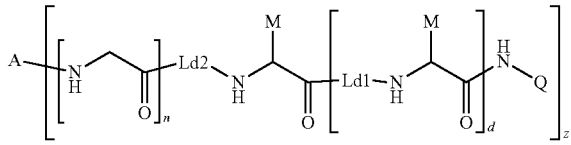

formula (III)

wherein, n, d, Ld1, Ld2, LKa and LKb are as defined in formula (I);

Q is hydrogen or LKb-P;

M is hydrogen or LKa-LKb-P;

preferably, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; preferably, B is —NH—CH$_2$—U— or absent or —NH—CH$_2$—U—(CH$_2$)$_g$—(CO)—;

provided that Q and M are not simultaneously hydrogen;

P is a payload which is linked to the B moiety or $L^1$ moiety of the compound of formula (I);

A is a targeting molecule which is linked to the $G_n$ moiety of the compound of formula (I); G is glycine;

z is an integer of 1 to 20.

In a fourth aspect, provided is use of the conjugate of the present invention or the pharmaceutical composition thereof in the manufacture of a medicament for treating a disease; wherein the disease is a tumor or an autoimmune disease.

DETAILED DESCRIPTION

Figure 1:
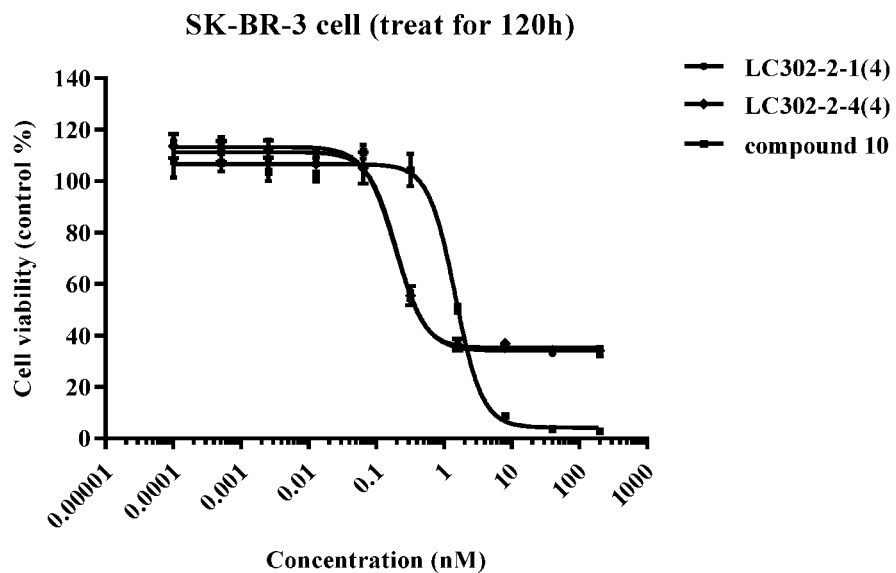
FIG. 1 shows the efficacy of conjugates and the corresponding payload in the SK-BR-3 HER2-high cell line.

The specific embodiments are provided below to illustrate technical contents of the present disclosure. Those skilled in the art can easily understand other advantages and effects of the present disclosure through the contents disclosed in the specification. The present disclosure can also be implemented or applied through other different specific embodiments. Various modifications and variations can be made by those skilled in the art without departing from the spirit of the present disclosure.

Definitions

Unless otherwise defined hereinafter, all technical and scientific terms used herein have the same meaning as commonly understood by those skilled in the art. The techniques used herein refer to those that are generally understood in the art, including the variants and equivalent substitutions that are obvious to those skilled in the art. While the following terms are believed to be readily comprehensible by those skilled in the art, the following definitions are set forth to better illustrate the present disclosure. When a trade name is present herein, it refers to the corresponding commodity or the active ingredient thereof. All patents, published patent applications and publications cited herein are hereby incorporated by reference.

When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the said range is explicitly recited. Unless otherwise stated, the numerical ranges listed herein are intended to include the endpoints of the range and all integers and fractions (decimals) within the range. For example, the expression "i is an integer of 1 to 20" means that i is any integer of 1 to 20, for example, i can be 1, 2, 3, 4, 5, 6, 7, 8, 9, 10, 11, 12, 13, 14, 15, 16, 17, 18, 19 or 20. Other similar expressions such as j, k and g should also be understood in a similar manner.

Unless the context clearly dictates otherwise, singular forms like "a" and "the" include the plural forms. The expression "one or more" or "at least one" may mean 1, 2, 3, 4, 5, 6, 7, 8, 9 or more.

The terms "about" and "approximately", when used in connection with a numerical variable, generally mean that the value of the variable and all values of the variable are within experimental error (for example, within a 95% confidence interval for the mean) or within ±10% of a specified value, or a wider range.

The term "stoichiometric ratio" means matching various substances according to a certain amount by weight. For example, in the present disclosure, the active ingredient is mixed with a filler, a binder, and a lubricant in a designated weight ratio.

The term "optional" or "optionally" means the event described subsequent thereto may, but not necessarily happen, and the description includes the cases wherein said event or circumstance happens or does not happen.

The expressions "comprising", "including", "containing" and "having" are open-ended, and do not exclude additional unrecited elements, steps, or ingredients. The expression "consisting of" excludes any element, step, or ingredient not designated. The expression "consisting essentially of" means that the scope is limited to the designated elements, steps or ingredients, plus elements, steps or ingredients that are optionally present that do not substantially affect the essential and novel characteristics of the claimed subject matter. It should be understood that the expression "comprising" encompasses the expressions "consisting essentially of" and "consisting of".

The term "targeting molecule" refers to a molecule that has an affinity for a particular target (e.g., a receptor, a cell surface protein, a cytokine, a tumor specific antigen, etc.). A targeting molecule can deliver the payload to a specific site in vivo through targeted delivery. A targeting molecule can recognize one or more targets. The specific target sites are defined by the targets it recognizes. For example, a targeting molecule that targets a receptor can deliver a cytotoxin to a site containing a large number of the receptor. Examples of targeting molecules include, but are not limited to antibodies, antibody fragments, binding proteins for a given antigen, antibody mimics, scaffold proteins having affinity for a given target, ligands, and the like.

As used herein, the term "antibody" is used in a broad way and particularly includes intact monoclonal antibodies, polyclonal antibodies, monospecific antibodies, multispecific antibodies (e.g., bispecific antibodies), and antibody fragments, as long as they have the desired biological activity. The antibody may be of any subtype (such as IgG, IgE, IgM, IgD, and IgA) or subclass, and may be derived from any suitable species. In some embodiments, the antibody is of human or murine origin. The antibody may also be a fully human antibody, humanized antibody or chimeric antibody prepared by recombinant methods.

Monoclonal antibodies are used herein to refer to antibodies obtained from a substantially homogeneous population of antibodies, i.e., the individual antibodies constituting the population are identical except for a small number of possible natural mutations. Monoclonal antibodies are highly specific for a single antigenic site. The word "monoclonal" refers to that the characteristics of the antibody are derived from a substantially homogeneous population of antibodies and are not to be construed as requiring some particular methods to produce the antibody.

An intact antibody or full-length antibody essentially comprises the antigen-binding variable region(s) as well as the light chain constant region(s) (CL) and heavy chain constant region(s) (CH), which could include CH1, CH2, CH3 and CH4, depending on the subtype of the antibody. An antigen-biding variable region (also known as a fragment variable region, Fv fragment) typically comprises a light chain variable region (VL) and a heavy chain variable region (VH). A constant region can be a constant region with a native sequence (such as a constant region with a human native sequence) or an amino acid sequence variant thereof. The variable region recognizes and interacts with the target antigen. The constant region can be recognized by and interacts with the immune system.

An antibody fragment may comprise a portion of an intact antibody, preferably its antigen binding region or variable region. Examples of antibody fragments include Fab, Fab', F(ab')2, Fd fragment consisting of VH and CH1 domains, Fv fragment, single-domain antibody (dAb) fragment, and isolated complementarity determining region (CDR). The Fab fragment is an antibody fragment obtained by papain digestion of a full-length immunoglobulin, or a fragment having the same structure produced by, for example, recombinant expression. A Fab fragment comprises a light chain (comprising a VL and a CL) and another chain, wherein the said other chain comprises a variable domain of the heavy chain (VH) and a constant region domain of the heavy chain (CH1). The F(ab')2 fragment is an antibody fragment obtained by pepsin digestion of an immunoglobulin at pH 4.0-4.5, or a fragment having the same structure produced by, for example, recombinant expression. The F(ab')2 fragment essentially comprises two Fab fragments, wherein each heavy chain portion comprises a few additional amino acids, including the cysteines that form disulfide bonds connecting the two fragments. A Fab' fragment is a fragment comprising one half of a F(ab')2 fragment (one heavy chain and one light chain). The antibody fragment may comprise a plurality of chains joined together, for example, via a disulfide bond and/or via a peptide linker. Examples of antibody fragments also include single-chain Fv (scFv), Fv, dsFv, diabody, Fd and Fd' fragments, and other fragments, including modified fragments. An antibody fragment typically comprises at least or about 50 amino acids, and typically at least or about 200 amino acids. An antigen-binding fragment can include any antibody fragment that, when inserted into an antibody framework (e.g., by substitution of the corresponding region), can result in an antibody that immunospecifically binds to the antigen.

Antibodies according to the present disclosure can be prepared using techniques well known in the art, such as the following techniques or a combination thereof: recombinant techniques, phage display techniques, synthetic techniques, or other techniques known in the art. For example, a genetically engineered recombinant antibody (or antibody mimic) can be expressed by a suitable culture system (e.g., E. coli or mammalian cells). The engineering can refer to, for example, the introduction of a ligase-specific recognition sequence at its terminals.

HER2 refers to human epidermal growth factor receptor-2, which belongs to the epidermal growth factor (EGFR) receptor tyrosine kinase family. In the present application, the terms ErbB2 and HER2 have the same meaning and can be used interchangeably.

As used herein, the term "targeting molecule-drug conjugate" is referred to as "conjugate". Examples of conjugates include, but are not limited to, antibody-drug conjugates.

A small molecule compound refers to a molecule with a size comparable to that of an organic molecule commonly used in medicine. The term does not encompass biological macromolecules (e.g., proteins, nucleic acids, etc.), but encompasses low molecular weight peptides or derivatives thereof, such as dipeptides, tripeptides, tetrapeptides, pentapeptides, and the like. Typically, the molecular weight of the small molecule compound can be, for example, about 100 to about 2000 Da, about 200 to about 1000 Da, about 200 to about 900 Da, about 200 to about 800 Da, about 200 to about 700 Da, about 200 to about 600 Da, about 200 to about 500 Da.

Cytotoxin refers to a substance that inhibits or prevents the expression activity of a cell, cellular function, and/or causes destruction of cells. The cytotoxins currently used in ADCs are more toxic than chemotherapeutic drugs. Examples of cytotoxins include, but are not limited to, drugs that target the following targets: microtubule cytoskeleton, DNA, RNA, kinesin-mediated protein transport, regulation of apoptosis. The drug that targets microtubule cytoskeleton may be, for example, a microtubule-stabilizing agent or a tubulin polymerization inhibitor. Examples of microtubule-stabilizing agents include but are not limited to taxanes. Examples of tubulin polymerization inhibitors include but are not limited to maytansinoids, auristatins, vinblastines, colchicines, and dolastatins. The DNA-targeting drug can be, for example, a drug that directly disrupts the DNA structure or a topoisomerase inhibitor. Examples of drugs that directly disrupt DNA structure include but are not limited to DNA double strand breakers, DNA alkylating agents, DNA intercalators. The DNA double strand breakers can be, for example, an enediyne antibiotic, including but not limited to dynemicin, esperamicin, neocarzinostatin, uncialamycin, and the like. The DNA alkylating agent may be, for example, a DNA bis-alkylator (i.e. DNA-cross linker) or a DNA mono-alkylator. Examples of DNA alkylating agents include but are not limited to pyrrolo[2,1-c][1,4]benzodiazepine (PBD) dimer, 1-(chloromethyl)-2,3-dihydrogen-1H-benzo[e]indole (CBI) dimer, CBI-PBD heterodimer, dihydroindolobenzodiazepine (IGN) dimer, duocarmycin-like compound, and the like. Examples of topoisomerase inhibitors include but are not limited to exatecan and derivatives thereof (such as DX8951f, DXd-(1) and DXd-(2), the structures of which are depicted below), camptothecins and anthracyclines. The RNA-targeting drug may be, for example, a drug that inhibits splicing, and examples thereof include but are not limited to pladienolide. Drugs that target kinesin-mediated protein transport can be, for example, mitotic kinesin inhibitors including, but not limited to, kinesin spindle protein (KSP) inhibitors.

A spacer is a structure that is located between different structural modules and can spatially separate the structural modules. The definition of spacer is not limited by whether it has a certain function or whether it can be cleaved or degraded in vivo. Examples of spacers include but are not limited to amino acids and non-amino acid structures, wherein non-amino acid structures can be, but are not limited to, amino acid derivatives or analogues. "Spacer sequence" refers to an amino acid sequence serving as a spacer, and examples thereof include but are not limited to a single amino acid, a sequence containing a plurality of amino acids, for example, a sequence containing two amino acids such as GA, etc., or, for example, GGGGS (SEQ ID NO: 5), GGGGSGGGGS (SEQ ID NO: 6), GGGGGGGGSGGGGS (SEQ ID NO: 7), etc. Self-immolative spacers are covalent assemblies tailored to correlate the cleavage of two chemical bonds after activation of a protective part in a precursor: Upon stimulation, the protective moiety (such as a cleavable sequence) is removed, which generates a cascade of disassembling reactions leading to the temporally sequential release of smaller molecules. Examples of self-immolative spacers include but not limited to PABC (p-aminobenzyloxycarbonyl), acetal, heteroacetal and the combination thereof.

The term "alkyl" refers to a straight or branched saturated aliphatic hydrocarbon group consisting of carbon atoms and hydrogen atoms, which is connected to the rest of the molecule through a single bond. The alkyl group may contain 1 to 20 carbon atoms, referring to $C_1$-$C_{20}$ alkyl group, for example, $C_1$-$C_4$ alkyl group, $C_1$-$C_3$ alkyl group, $C_1$-$C_2$ alkyl, $C_3$ alkyl, $C_4$ alkyl, $C_3$-$C_6$ alkyl. Non-limiting examples of alkyl groups include but are not limited to methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethyl butyl, 1,1-dimethylbutyl, 2,3-dimethylbutyl, 1,3-dimethylbutyl or 1,2-dimethylbutyl, or their isomers. A bivalent radical refers to a group obtained from the corresponding monovalent radical by removing one hydrogen atom from a carbon atom with free valence electron(s). A bivalent radical have two connecting sites which are connected to the rest of the molecule. For example, an "alkylene" or an "alkylidene" refers to a saturated divalent hydrocarbon group, either straight or branched. Examples of alkylene groups include but are not limited to methylene (—$CH_2$—), ethylene (—$C_2H_4$—), propylene (—$C_3H_6$—), butylene (—$C_4H_8$—), pentylene (—$C_5H_{10}$—), hexylene (—$C_6H_{12}$—), 1-methylethylene (—CH($CH_3$)$CH_2$—), 2-methylethylene (—$CH_2$CH($CH_3$)—), methylpropylene, ethylpropylene, and the like.

As used herein, when a group is combined with another group, the connection of the groups may be linear or branched, provided that a chemically stable structure is formed. The structure formed by such a combination can be connected to other moieties of the molecule via any suitable atom in the structure, preferably via a designated chemical bond. For example, when two or more of the bivalent groups selected from: —$CR^1R^2$—, $C_{1-10}$ alkylene, $C_{4-10}$ cycloalkylene, $C_{4-10}$ heterocyclylene and —(CO)— are combined together to form a combination, the two or more of the bivalent groups may form a linear connection with each other, such as —$CR^1R^2$—$C_{1-10}$ alkylene-(CO)—, —$CR^1R^2$—$C_{4-10}$ cycloalkylene-(CO)—, —$CR^1R^2$—$C_{4-10}$ cycloalkylene-$C_{1-10}$ alkylene-(CO)—, —$CR^1R^2$—$CR^{1'}R^{2'}$—(CO)—, —$CR^1R^2$—$CR^{1'}R^{2'}$—$CR^{1''}R^{2''}$—(CO)—, etc. The resulting bivalent structure can be further connected to other moieties of the molecule.

As used herein, the expressions "antibody-conjugated drug" and "antibody-drug conjugate" has the same meaning. Compound of Formula (I)

In one aspect, provide is a compound of formula (I):

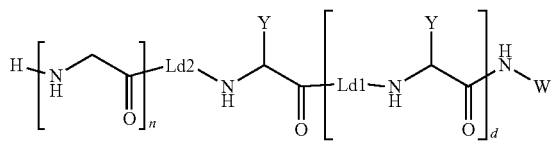

wherein,
W is hydrogen or is LKb;
Y is hydrogen or is LKa-LKb;
provided that W and Y are not simultaneously hydrogen;
each LKa is independently selected from

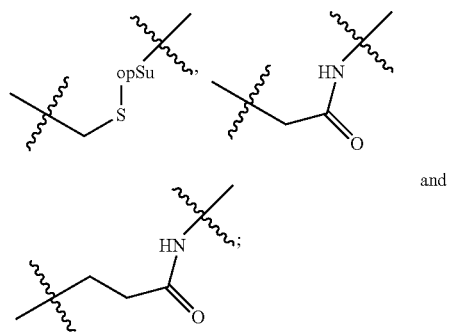

or a mixture thereof;
each LKb is independently L²-L¹-B;
each B is independently a terminal group $R^{10}$, or a combination of the following 1), 2) and 3): 1) a self-immolative spacer Sp1; 2) a bond, or one of or a combination of two or more of the bivalent groups selected from: —CR¹R²—, $C_{1-10}$ alkylene, $C_{4-10}$ cycloalkylene, $C_{4-10}$ heterocyclylene and —(CO)—; and 3) a terminal group $R^{10}$;
$R^{10}$ is hydrogen, or a group which can leave when reacting with a group in the payload;
L¹ is Cleavable sequence 1 comprising an amino acid sequence which can be cleaved by enzyme, and Cleavable sequence 1 comprises 1-10 amino acids;
L² is a bond; or a $C_{2-20}$ alkylene wherein one or more —CH₂— structures in the alkylene is optionally replaced by —CR³R⁴—, —O—, —(CO)—, —S(=O)₂—, —NR⁵—, —N⁺R⁶R⁷—, $C_{4-10}$ cycloalkylene, $C_{4-10}$ heterocyclylene, phenylene; wherein the cycloalkylene, heterocyclylene and phenylene are each independently unsubstituted or substituted with at least one substituent selected from halogen, —$C_{1-10}$ alkyl, —$C_{1-10}$ haloalkyl, —$C_{1-10}$ alkylene-NH—R⁸ and —$C_{1-10}$ alkylene-O—R⁹;

Ld2 and each Ld1 are independently a bond; or selected from —NH—$C_{1-20}$ alkylene-(CO)—, —NH-(PEG)$_i$-(CO)—, or is a natural amino acid or oligomeric natural amino acids having a degree of polymerization of 2-10 independently unsubstituted or substituted with -(PEG)$_j$-$R^{11}$ on the side chain;
-(PEG)$_i$- and -(PEG)$_j$- are each a PEG fragment, which comprises the denoted number of consecutive —(O—C₂H₄)— structure units or consecutive —(C₂H₄—O)— structure units, with an optional additional $C_{1-10}$ alkylene at one terminal;
$R^1$, $R^2$, $R^3$, $R^4$, $R^5$, $R^6$, $R^7$, $R^8$, $R^9$ are each independently selected from hydrogen, halogen, —$C_{1-10}$ alkyl, —$C_{1-10}$ haloalkyl, $C_{4-10}$ cycloalkylene;
$R^{11}$ is $C_{1-10}$ alkyl;
n is any integer of 2 to 20;
d is 0, or is any integer of 1 to 6;
each i is independently an integer of 1-100, preferably 1 to 20; preferably each i is independently an integer of 1 to 12; more preferably 2 to 8; particularly 4;
each j is independently an integer of 1-100, preferably 1 to 20; preferably each j is independently an integer of 1 to 12; more preferably 8 to 12; particularly 8 or 12.

In one embodiment, L² is selected from: —(CH₂)$_p$—(CH₂)₂(CO)—, p is 0, or an integer of 1 to 5;

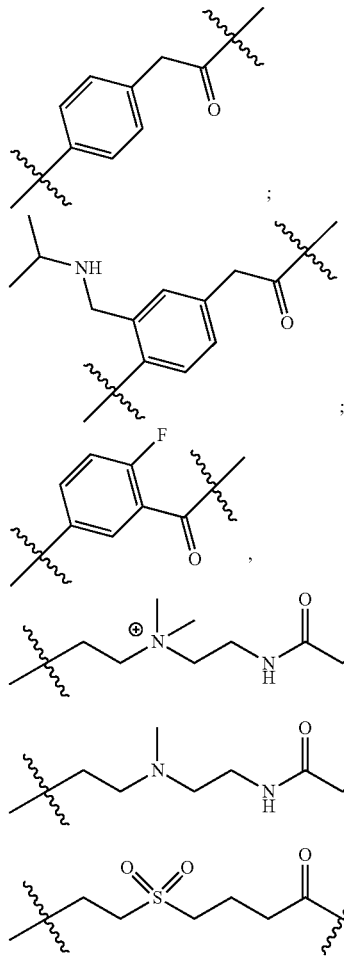

-continued

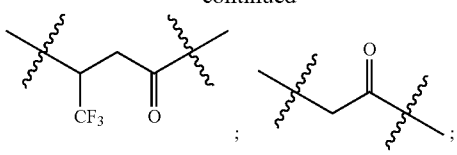

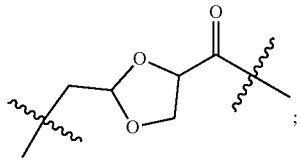

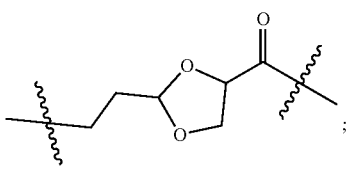

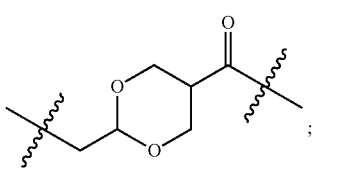

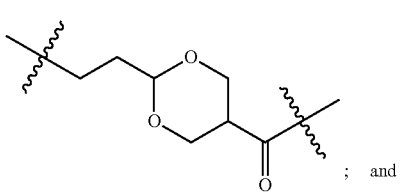

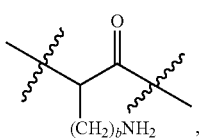

b is an integer of 1 to 10.

In one embodiment, the carbonyl group in each of the above structure of $L^2$ is connected to $L^1$, and the other linking site is connected to opSu.

In one embodiment, p is 0 to 3; preferably 3.

Ld2 and each Ld1 are independently a bond or

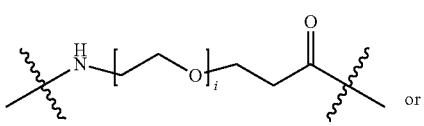

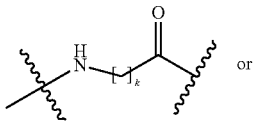

-continued

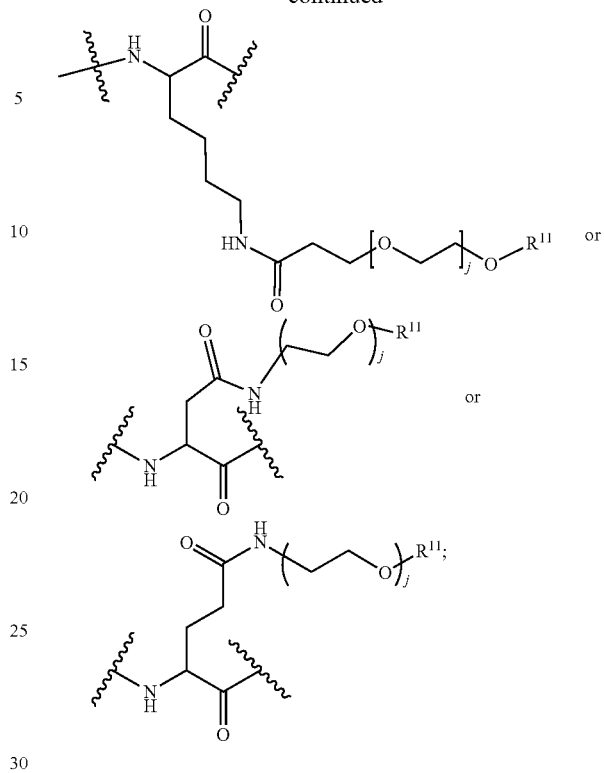

each i, j and k are independently an integer of 1-100.

In one embodiment, each i, j and k are independently an integer of 1 to 20. In one embodiment, each i, j and k are independently an integer of 1 to 12.

In one embodiment, each i is independently an integer of 2 to 8; particularly 4.

In one embodiment, each j is independently an integer of 8 to 12; particularly 8 or 12.

In one embodiment, each k is independently an integer of 1 to 7; particularly 1, or 3 or 5.

In one embodiment, Ld2 and each Ld1 are independently a bond; or a $C_{1-20}$ alkylene with an amino and a carbonyl at the two terminals respectively, or a PEG fragment of a certain length (denoted as -(PEG)$_i$-) with an amino and a carbonyl at the two terminals respectively, or one or more natural amino acids independently unsubstituted or substituted with a PEG fragment of a certain length (denoted as -(PEG)$_j$-) on the side chain.

In one embodiment, -(PEG)$_i$- comprises —(O—C$_2$H$_4$)$_i$— or —(C$_2$H$_4$—O)$_i$—, and an optional additional $C_{1-10}$ alkylene at one terminal; -(PEG)$_j$-, comprises —(O—C$_2$H$_4$)$_j$— or —(C$_2$H$_4$—O)$_j$—, and an optional additional $C_{1-10}$ alkylene at one terminal. In a very specific -(PEG)$_i$- comprises —C$_2$H$_4$—(O—C$_2$H$_4$)$_i$— or —(C$_2$H$_4$—O)$_i$—C$_2$H$_4$—, It is to be understood that when there are two or more Ld1, B, $L^2$ or $L^1$ structures in the molecule, the structure of each Ld1, B, $L^2$ or $L^1$ is selected independently. When there are two or more $R^x$ (x being 1, 2, 3, 4, 5, 6, 7, 8, 9, etc.) in the molecule, each $R^x$ is selected independently. In some embodiments, the "x"s in the molecule are denoted with or without additional apostrophe (') or apostrophes (such as '', ''', '''', etc.), for example R, $R^{1'}$, $R^{1''}$, $R^{1'''}$, $R^{2'}$, $R^{2''}$, $R^{2'''}$, etc, wherein each $R^x$, with or without additional apostrophe or apostrophes, are selected independently. The other $R^x$s such as $R^3$, $R^4$, $R^5$, $R^6$, $R^7$, $R^8$, $R^9$, and "Ld1"s, "B"s, "$L^2$"s and "$L^1$"s should be understood in a similar way. In some embodiments, the "i"s in the molecule are denoted with or without additional numbers, for example i1, i2, i3, i4, etc., wherein the numbers do not indicate any sequence, but are used merely to differentiate the "i"s. And each "i"s, with or without additional numbers, are selected independently.

In one embodiment, Cleavable sequence 1 is selected from GLy-GLy-Phe-GLy (SEQ ID NO: 8), Phe-Lys, Val-Cit, Val-Lys, GLy-Phe-Leu-Gly (SEQ ID NO: 9), Ala-Leu-Ala-Leu (SEQ ID NO: 10), Ala-Ala-Ala and the combination thereof; preferably, Cleavable sequence 1 is GLy-GLy-Phe-Gly (SEQ ID NO: 8).

In one embodiment, W is hydrogen.

In one embodiment, $R^{11}$ is $C_{1-6}$ alkyl, preferably methyl.

In one embodiment, n is an integer of 2 to 5, especially 3.

In one embodiment, d is 0, or is any integer of 1 to 4; preferably 0, 1, 2 or 3.

Thiosuccinimide is unstable under physiological conditions and is liable to reverse Michael addition which leads to cleavage at the conjugation site. Moreover, when another thiol compound is present in the system, thiosuccinimide may also undergo thiol exchange with the other thiol compound. Both of these reactions cause the fall-off of the payload and result in toxic side effects. In the present disclosure, when applied in the linker, the ring-opened succinimide structure no longer undergoes reverse Michael addition or thiol exchange, and thus the product is more stable. Method of ring opening reaction can be found in WO2015165413A1.

The compound comprising ring-opened succinimide moiety can be purified by semi-preparative/preparative HPLC or other suitable separation means to obtain with high purity and defined composition, regardless of the efficiency of the succinimide ring opening reaction.

Moiety Comprising Recognition Sequence of the Ligase Acceptor or Donor Substrate In one embodiment, the $G_n$ moiety of the compound of formula (I) is a recognition sequence of a ligase acceptor or donor substrate, which facilitates enzyme-catalyzed coupling of compound of formula (I) with the targeting molecule under the catalysis of the ligase. The targeting molecule optionally modified and comprises the corresponding recognition sequence of a ligase acceptor or donor substrate.

In one embodiment, the ligase is a transpeptidase. In one embodiment, the ligase is selected from the group consisting of a natural transpeptidase, an unnatural transpeptidase, variants thereof, and the combination thereof. Unnatural transpeptidase enzymes can be, but are not limited to, those obtained by engineering of natural transpeptidase. In a preferred embodiment, the ligase is selected from the group consisting of a natural Sortase, an unnatural Sortase, and the combination thereof. The species of natural Sortase include Sortase A, Sortase B, Sortase C, Sortase D, Sortase L. plantarum, etc. (US20110321183A1). The type of ligase corresponds to the ligase recognition sequence and is thereby used to achieve specific conjugation between different molecules or structural fragments.

In some embodiments, the ligase is a Sortase selected from Sortase A, Sortase B, Sortase C, Sortase D and Sortase L. plantarum. In these embodiments, the recognition sequence of the ligase acceptor substrate is selected from the group consisting of oligomeric glycine, oligomeric alanine, and a mixture of oligomeric glycine/alanine having a degree of polymerization of 3-10. In a particular embodiment, the recognition sequence of the ligase acceptor substrate is $G_n$, wherein G is glycine (Gly), and n is an integer of 2 to 10.

In another particular embodiment, the ligase is Sortase A from Staphylococcus aureus. Accordingly, the ligase recognition sequence may be the typical recognition sequence LPXTG (SEQ ID NO: 11) of the enzyme. In yet another particular embodiment, the recognition sequence of the ligase donor substrate is LPXTGJ, and the recognition sequence of the ligase acceptor substrate is $G_n$, wherein X can be any single amino acid that is natural or unnatural; J is absent, or is an amino acid fragment comprising 1-10 amino acids, optionally labeled. In one embodiment, J is absent. In yet another embodiment, J is an amino acid fragment comprising 1-10 amino acids, wherein each amino acid is independently any natural or unnatural amino acid. In another embodiment, J is $G_m$, wherein m is an integer of 1 to 10. In yet another particular embodiment, the recognition sequence of the ligase donor substrate is LPETG (SEQ ID NO: 12). In another particular embodiment, the recognition sequence of the ligase donor substrate is LPETGG (SEQ ID NO: 13).

In one embodiment, the ligase is Sortase B from Staphylococcus aureus and the corresponding donor substrate recognition sequence can be NPQTN (SEQ ID NO: 14). In another embodiment, the ligase is Sortase B from Bacillus anthracis and the corresponding donor substrate recognition sequence can be NPKTG (SEQ ID NO: 15).

In yet another embodiment, the ligase is Sortase A from Streptococcus pyogenes and the corresponding donor substrate recognition sequence can be LPXTGJ, wherein J is as defined above. In another embodiment, the ligase is Sortase subfamily 5 from Streptomyces coelicolor, and the corresponding donor substrate recognition sequence can be LAXTG (SEQ ID NO: 16).

In yet another embodiment, the ligase is Sortase A from Lactobacillus plantarum and the corresponding donor substrate recognition sequence can be LPQTSEQ (SEQ ID NO: 17).

The ligase recognition sequence can also be other totally new recognition sequence for transpeptidase optimized by manual screening.

Moiety Comprising Reactive Group

Reactive Group for Connection with Payload

In one embodiment, B is a terminal group $R^{10}$, and the Cleavable sequence 1 in $L^1$ is connected to the payload. In such case, B is absent in the resulting molecule of the connection of Cleavable sequence 1 with the payload. In one embodiment, B is used for connection to the payload. For connection with the payload, the compound of formula (I) comprises a reactive group. In one embodiment, B in the compound of formula (I) is connected to the payload through an amide bond or an ester bond or an ether bond. In one embodiment, the reactive group in B in formula (I) is independently a reactive group for condensation reaction, nucleophilic addition or electrophilic addition (such as reactive C=O moiety, reactive C=C—C=O moiety, amino group, amine group, hydroxy group or thiol group), or a reactive group for substitution reaction (such as a leaving group attached to an O, C, N or S atom). In one embodiment, the reactive group in B is independently selected from carboxyl group, active ester, aldehyde group, amino group, amine group, hydroxy group and thiol group. In a specific embodiment, the reactive group in B which is used to connect to the payload is independently selected from amino group, amine group, hydroxy group, thiol group, carboxyl group and active ester.

In one embodiment, the reactive group in B is independently amino group, amine group or hydroxy group, which reacts with corresponding groups (such as carboxyl group, sulfonic acid group, phosphoryl group with free —OH end, active ester, acid chloride or isocyanate group) in the payload. In another embodiment, the reactive group in B is independently carboxyl group or active ester, which reacts with corresponding groups (such as amino group, amine group or hydroxy group) in the payload.

In one embodiment, the reactive group in B is independently amino group, hydroxy group or thiol group, which reacts with corresponding groups (such as halogen, hydroxy group, aldehyde group) in the payload. In another embodiment, the reactive group in B is independently hydroxy group, which reacts with corresponding groups (such as halogen or hydroxy group) in the payload.

In one embodiment, each B is independently $R^{10}$, or a combination of the following 1), 2) and 3): 1) a self-immolative spacer Sp1; 2) a bond, or one of or a combination of two or more of the bivalent groups selected from: $-CR^1R^2-$, $C_{1-10}$ alkylene and $-(CO)-$; and 3) a terminal group $R^{10}$.

In one embodiment, Sp1 is selected from PABC, acetal, heteroacetal and the combination thereof. In one embodiment, Sp1 is acetal, heteroacetal or PABC. In one embodiment, the heteroacetal is selected from N,O-heteroacetal. In one embodiment, Sp1 is $-O-CH_2-U-$, or $-NH-CH_2-U-$ wherein the $-O-$ or the $-NH-$ is connected to Cleavable sequence 1. U is O, S or NH, preferably O or S. In one embodiment, U is O, S or N, preferably O or S.

In one embodiment, B is $^{10}$ or is $-NH-CH_2-U-R^{10}$ or is $-NH-CH_2-U-(CH_2)_g-(CO)-R^{10}$.

In one embodiment, $R^{10}$ is hydrogen, hydroxy or

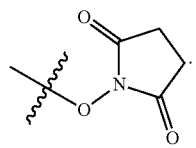

In one embodiment, $R^{10}$ is hydrogen. In one embodiment, $R^{10}$ is hydroxy or

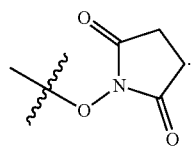 [SMILES: *ON1C(=O)CCC1=O]

In one embodiment, $R^{10}$ represents the part of structure which would not appear in the product molecule resulting from the reaction of B with the payload.

Specific Embodiment of the Formula (I) Compound

In one embodiment, W is hydrogen, each LKa is

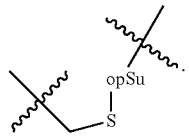

In one embodiment, formula (I) has the structure of formula (I-1)

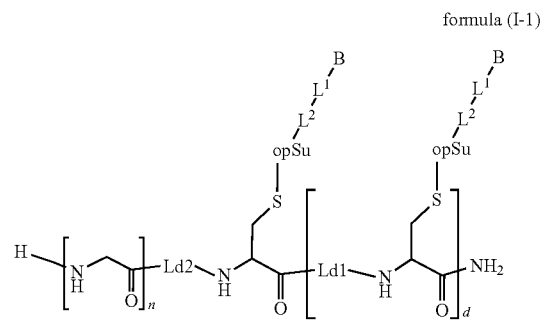

formula (I-1)

In one embodiment, Ld2 is a bond, d is 0. In one embodiment, the compound of formula (I-1) is as follows:

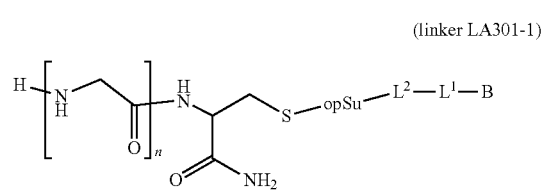

(linker LA301-1)

In one embodiment, d is 0, Ld2 is

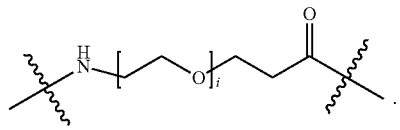

In one embodiment, the compound of formula (I-1) is as follows:

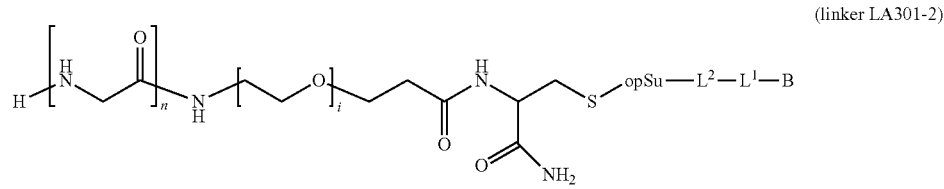

(linker LA301-2)

In one embodiment, d is 1, 2 or 3, Ld2 and each Ld1 are independently selected from
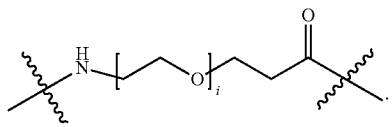
In one embodiment, the compound of formula (I-1) is as follows:
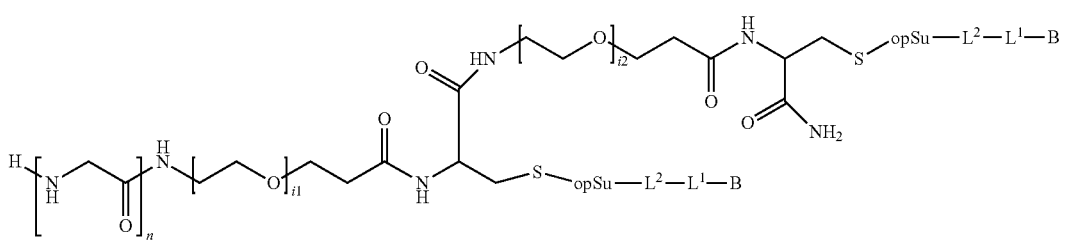
(linker LA301-3)
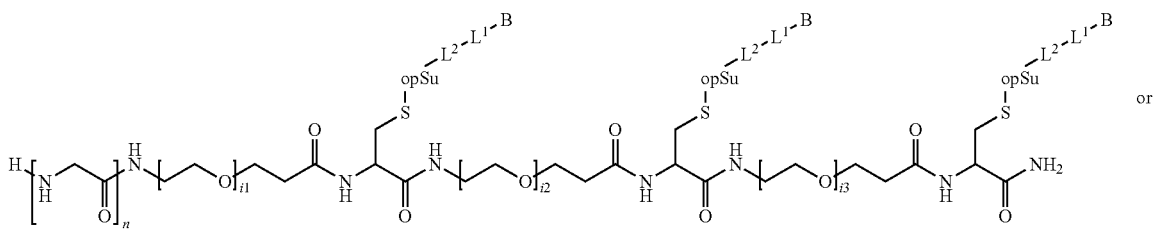
(linker LA301-4)
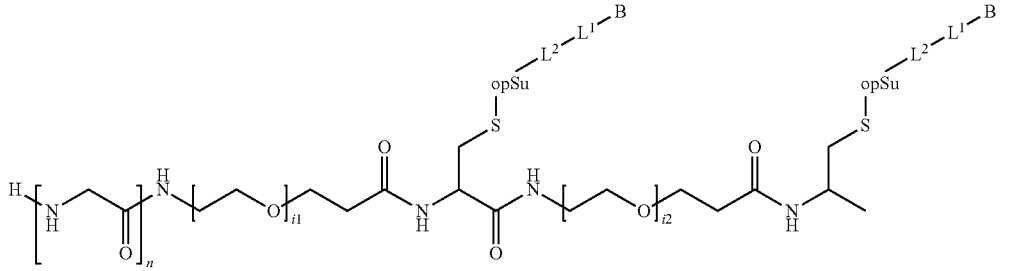
(linker LA301-5)
or
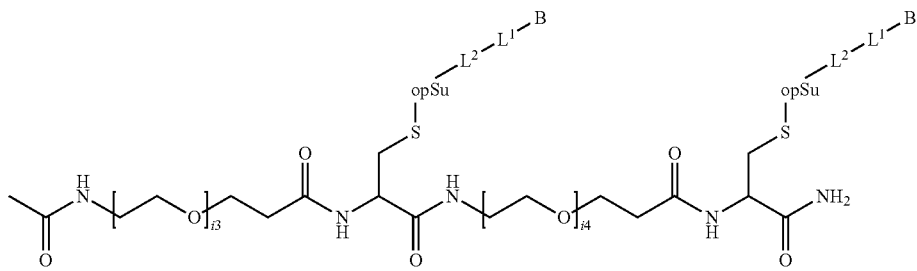

In one embodiment, Ld2 is
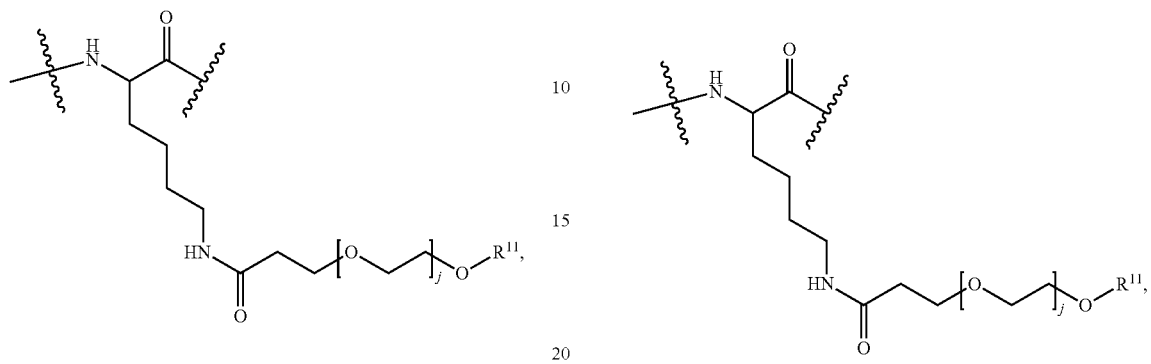
d is 0. In one embodiment, the compound of formula (I-1) is as follows:
(linker LA302-1)
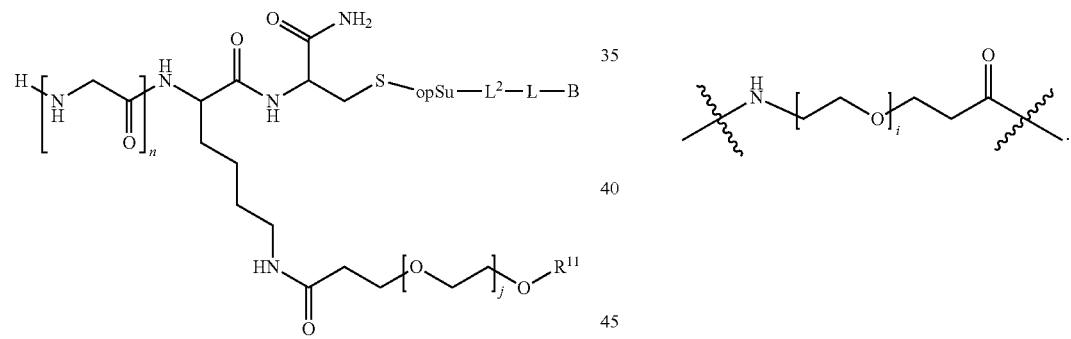
In one embodiment, d is 1, 2 or 3, Ld2 is
and each Ld1 is independently selected from
In one embodiment, the compound of formula (I-1) is as follows:
(linker LA302-2)
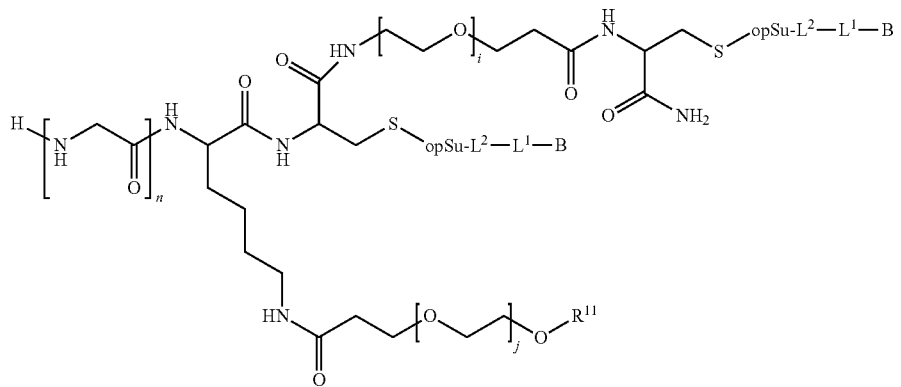

(linker LA302-3)
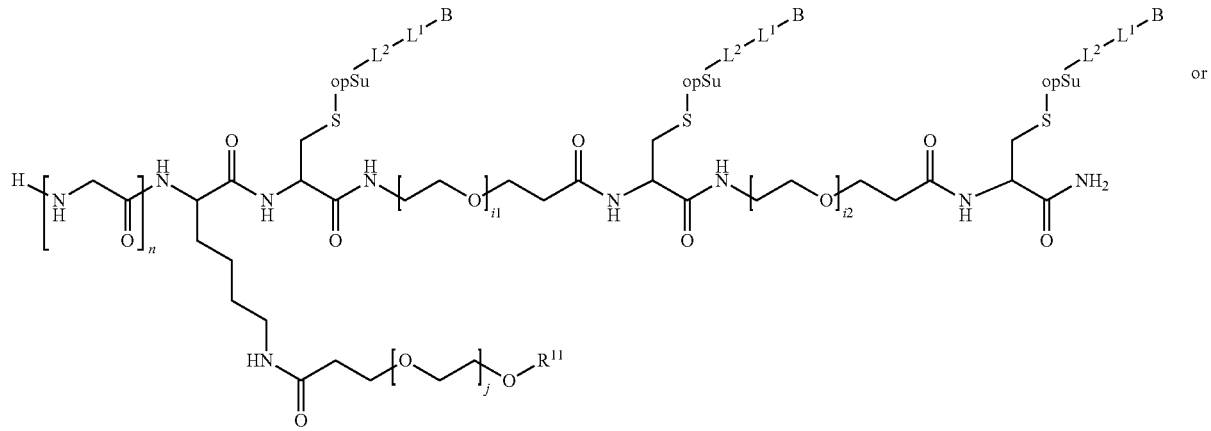
or
(linker LA302-4)
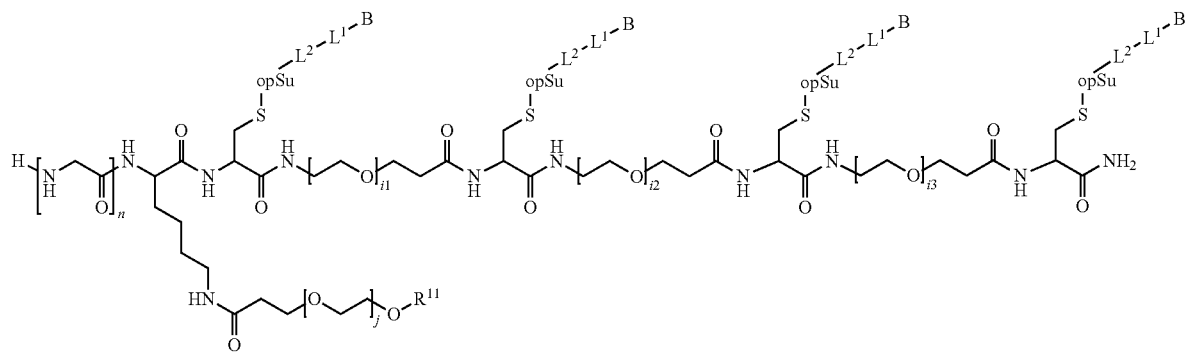
In one embodiment, n is 3, $L^2$ is —$(CH_2)_p$—$(CH_2)_2$(CO)—, p is 3, $L^1$ is GGFG, B is —NH—$CH_2$—U—$R^{10}$ or —$R^{10}$ or —NH—$CH_2$—U—$(CH_2)_g$—(CO)—$R^{10}$, U is O, g is 1. In one embodiment, linker LA301-1 has the structure of:
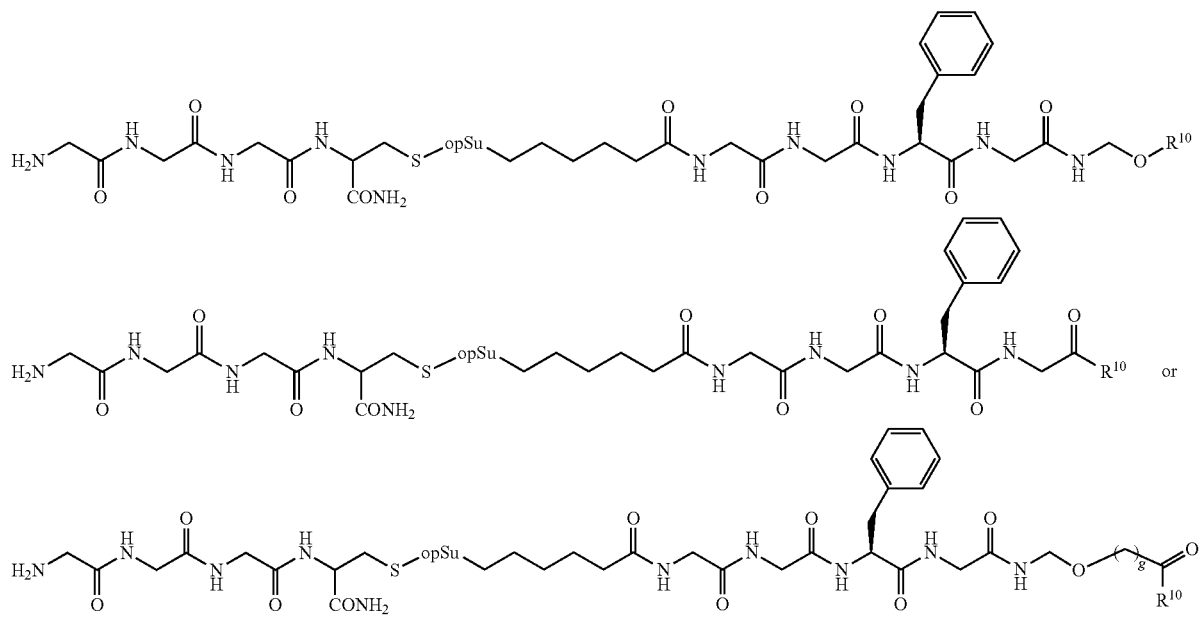

In one embodiment, linker LA301-2 has the structure of:
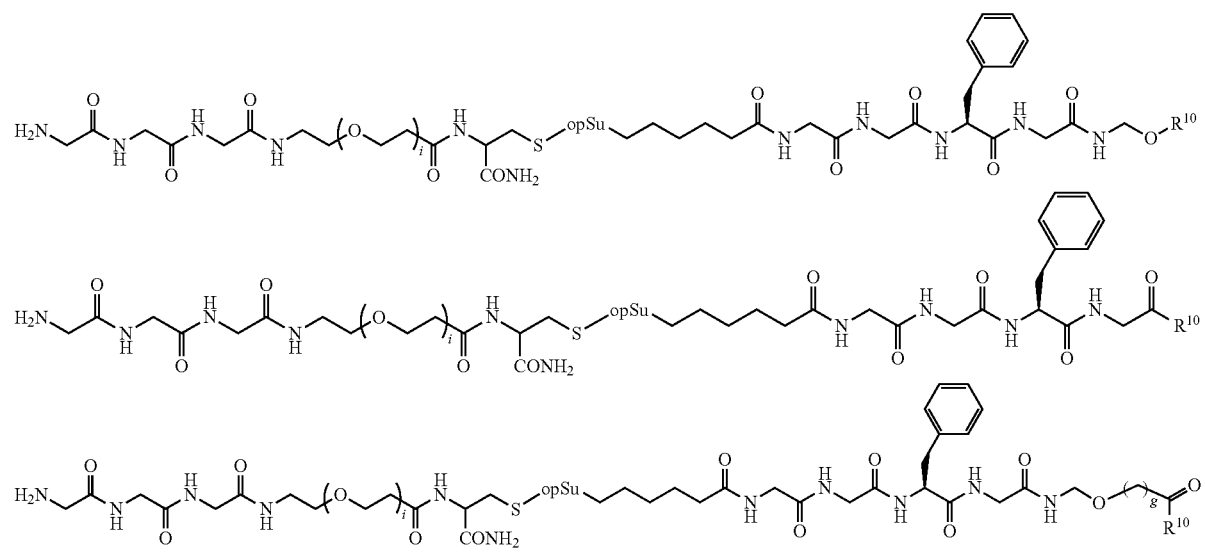
In one embodiment, linker LA301-3 has the structure of:
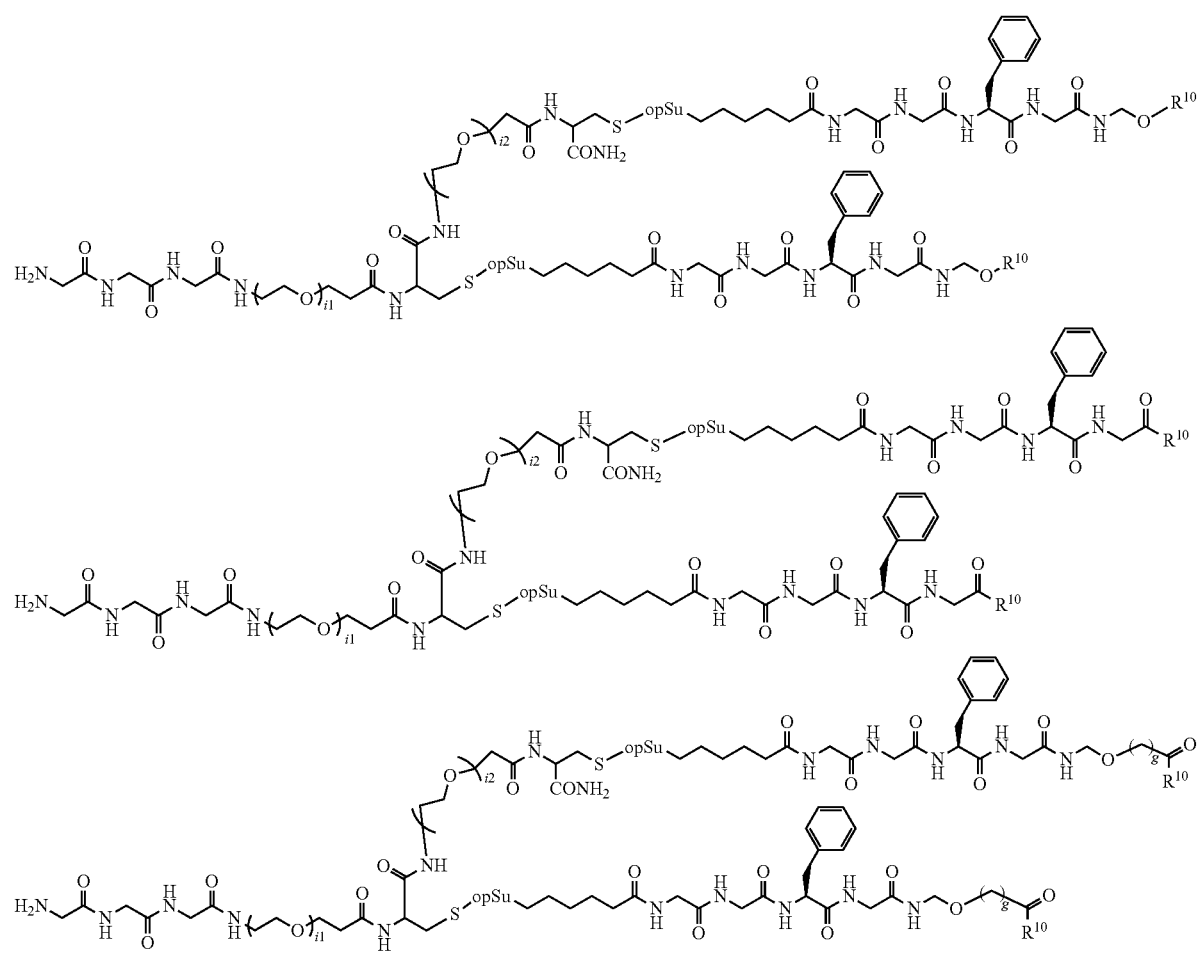
In one embodiment, linker LA301-4 has the structure of:

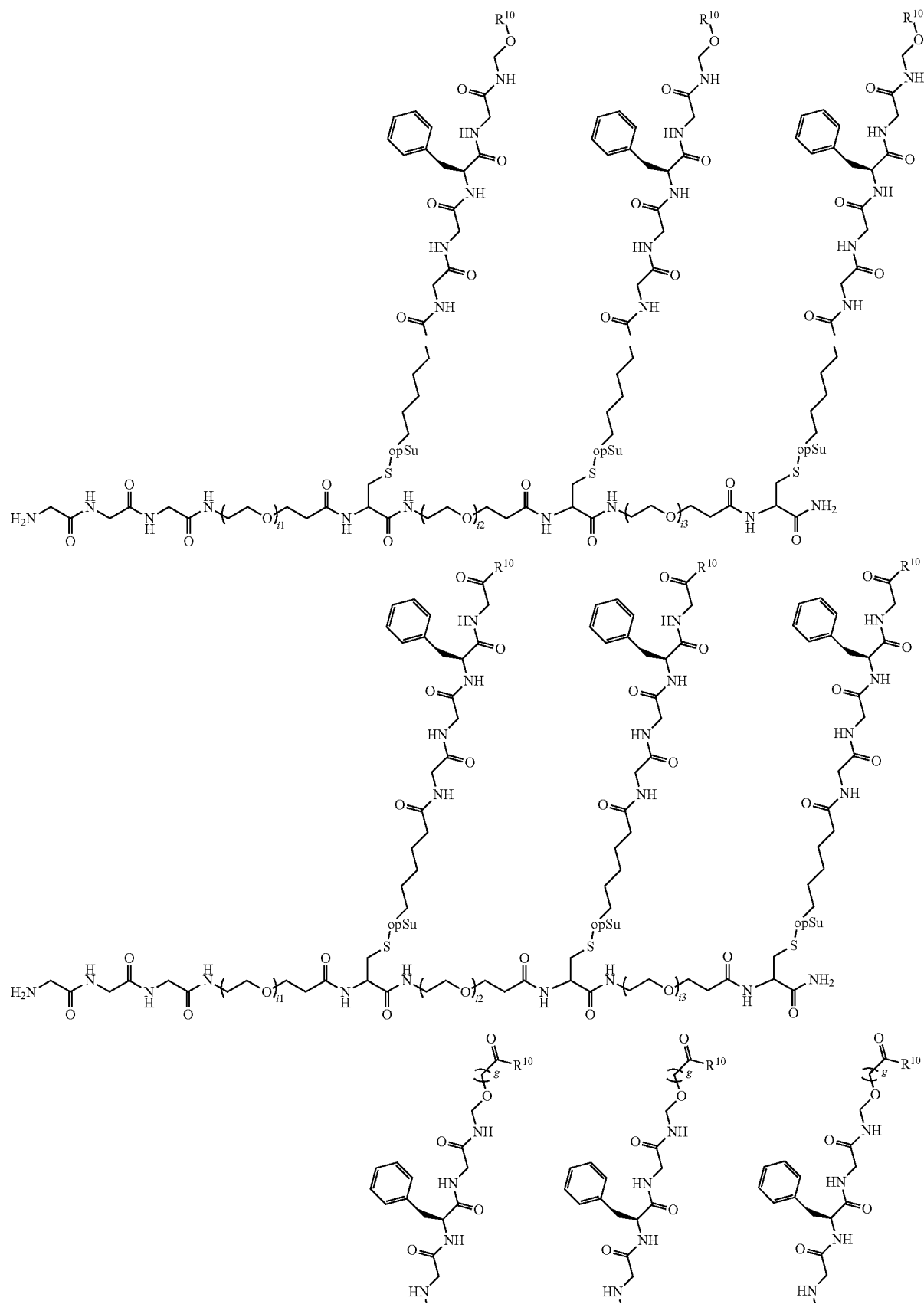

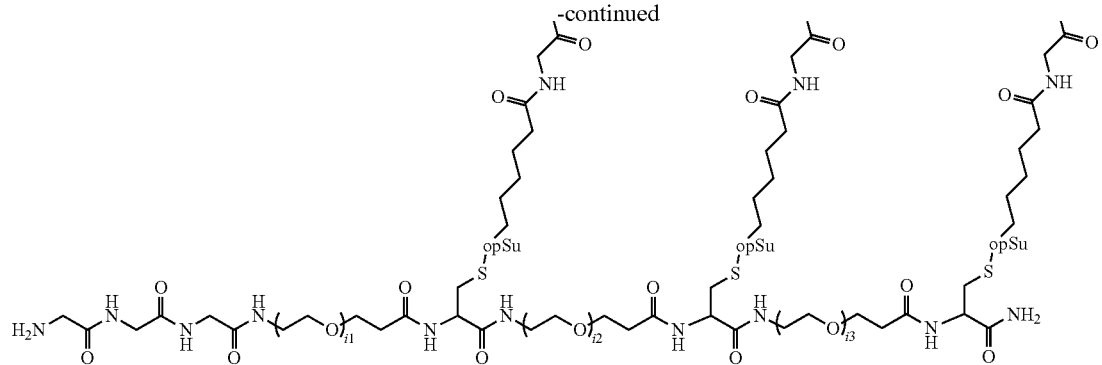
In one embodiment, linker LA301-5 has the structure of:
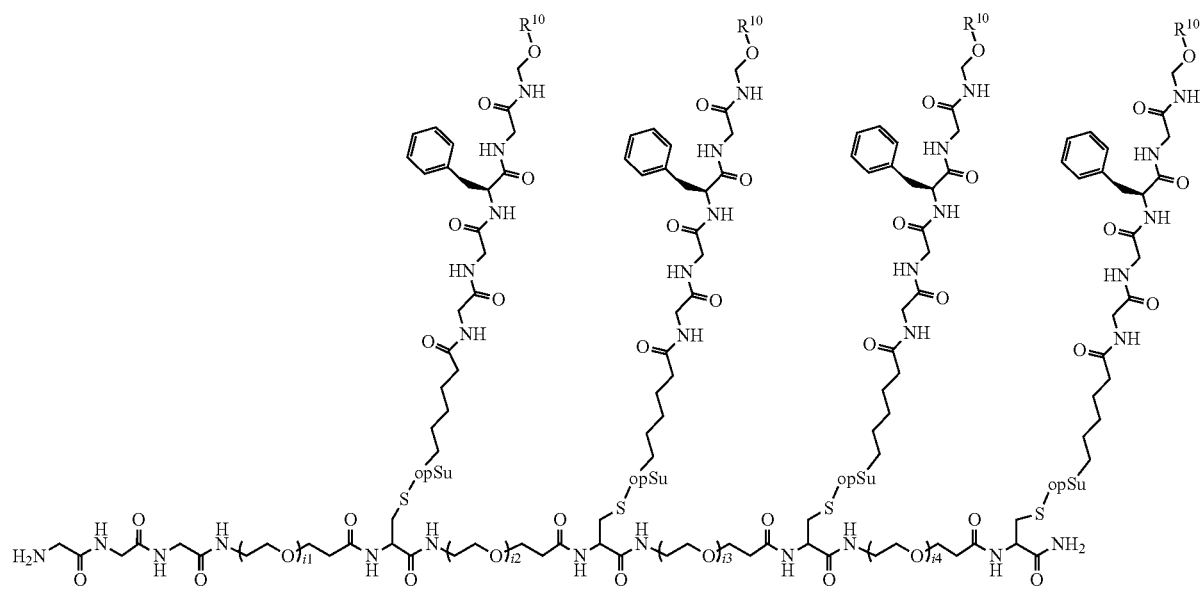
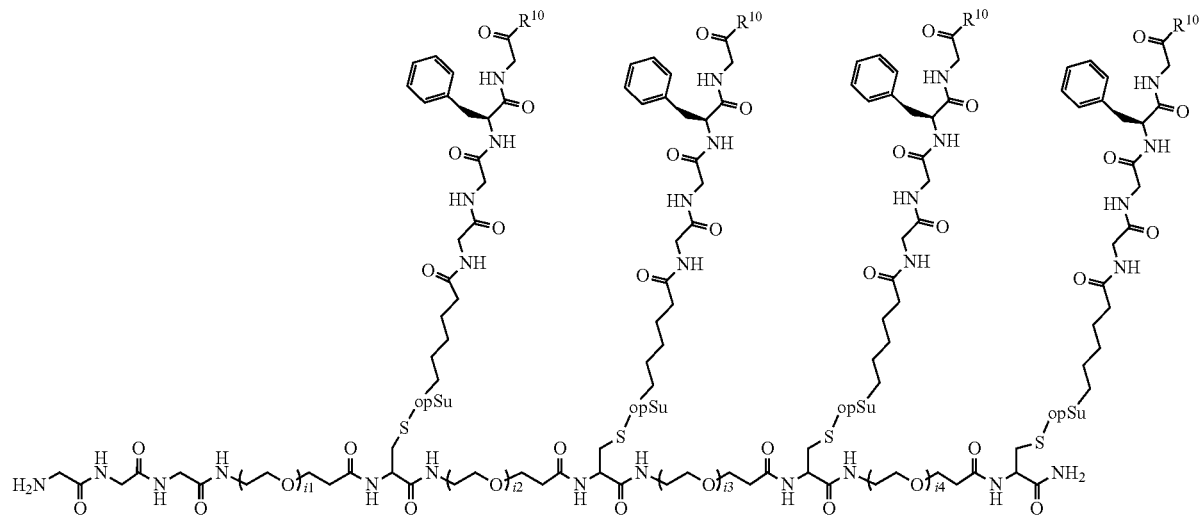

-continued
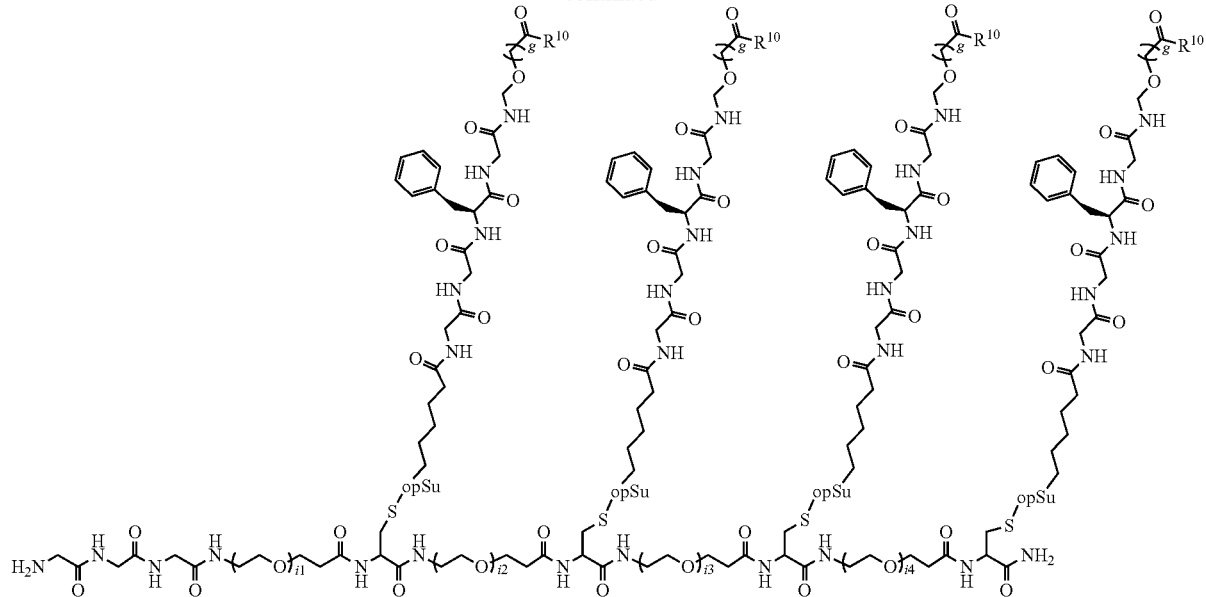
In one embodiment, linker LA302-1 has the structure of:
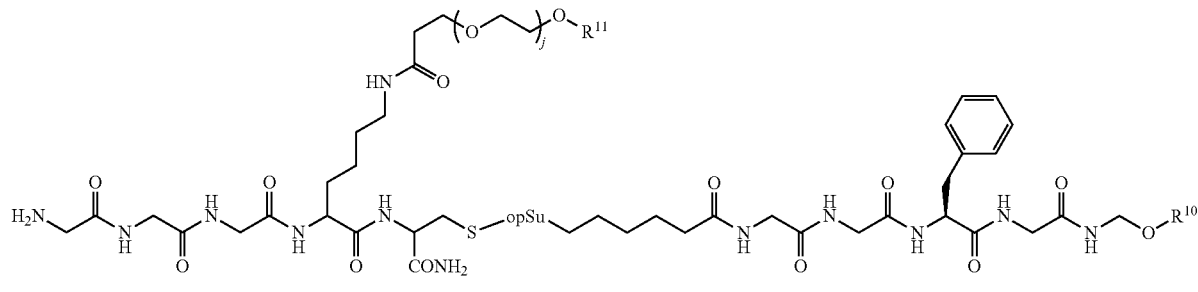
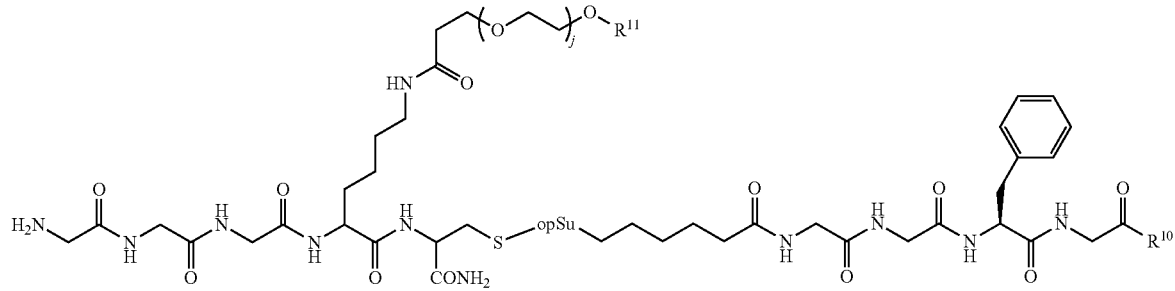
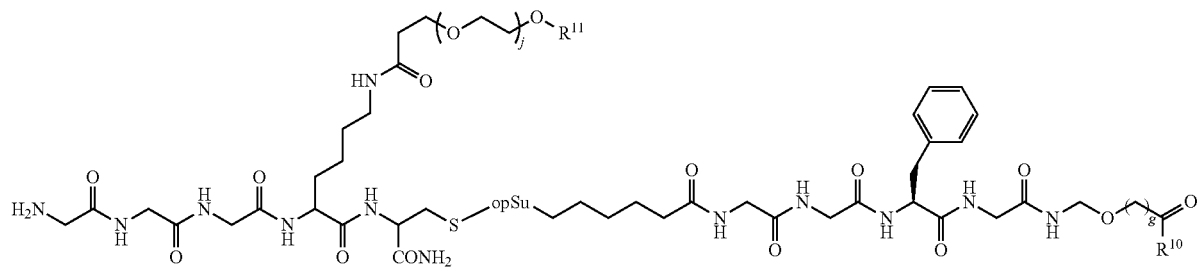

In one embodiment linker LA302-2 has the structure of:
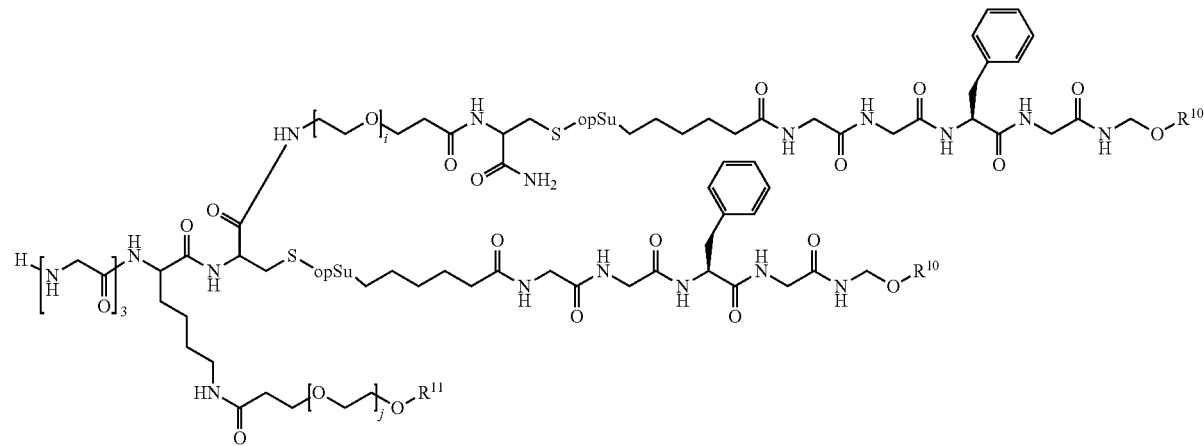
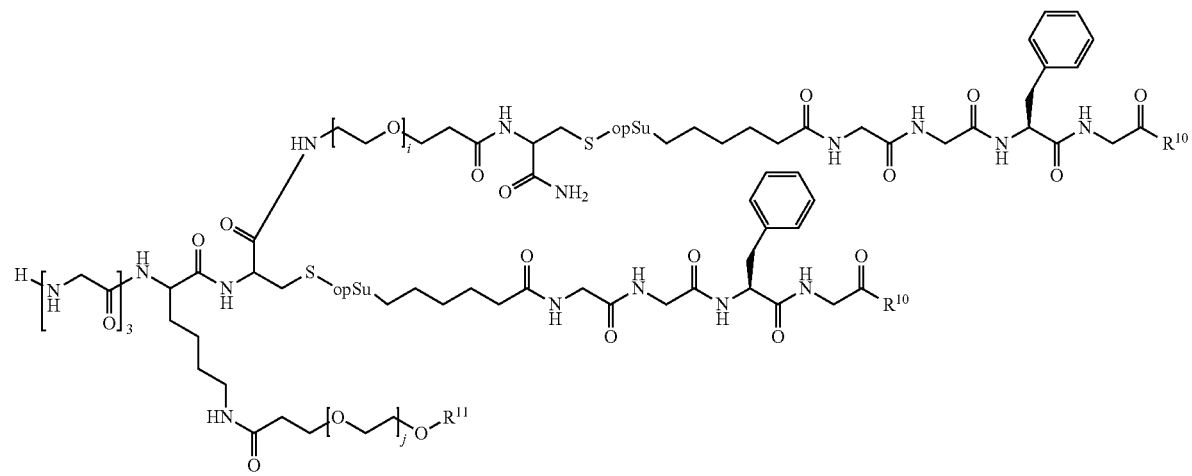
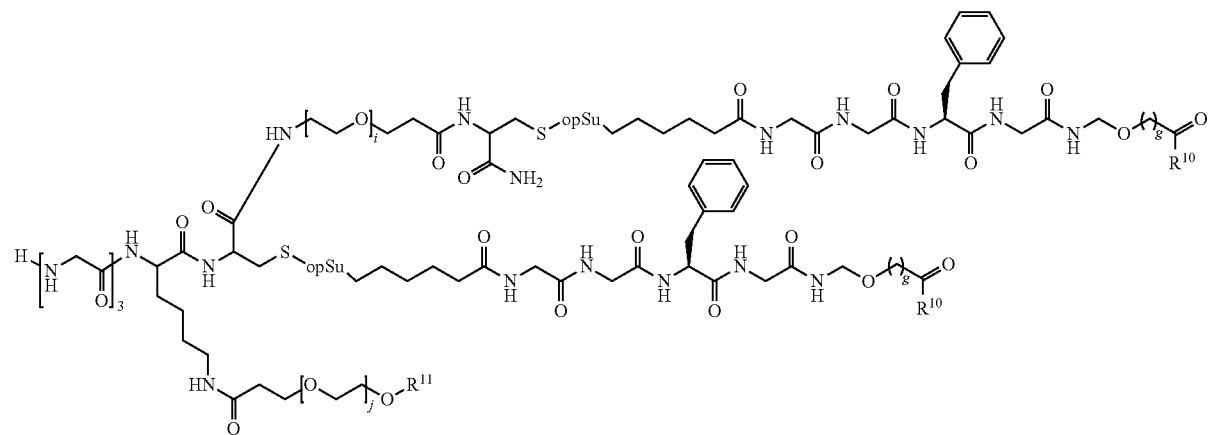

In one embodiment, linker LA302-3 has the structure of:
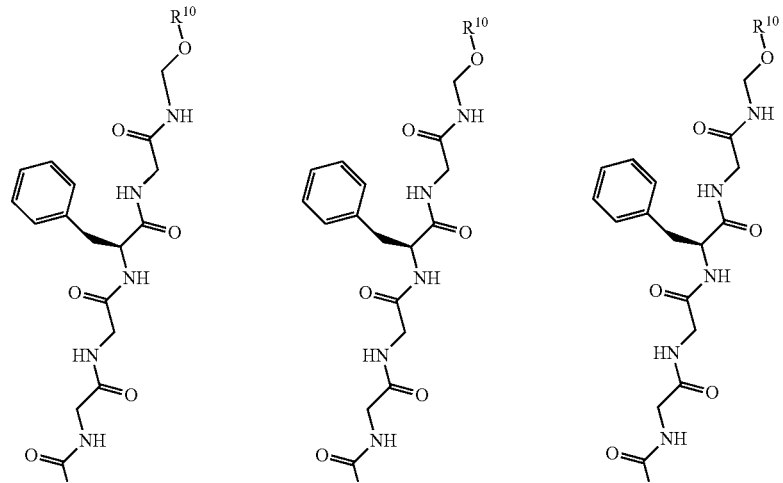
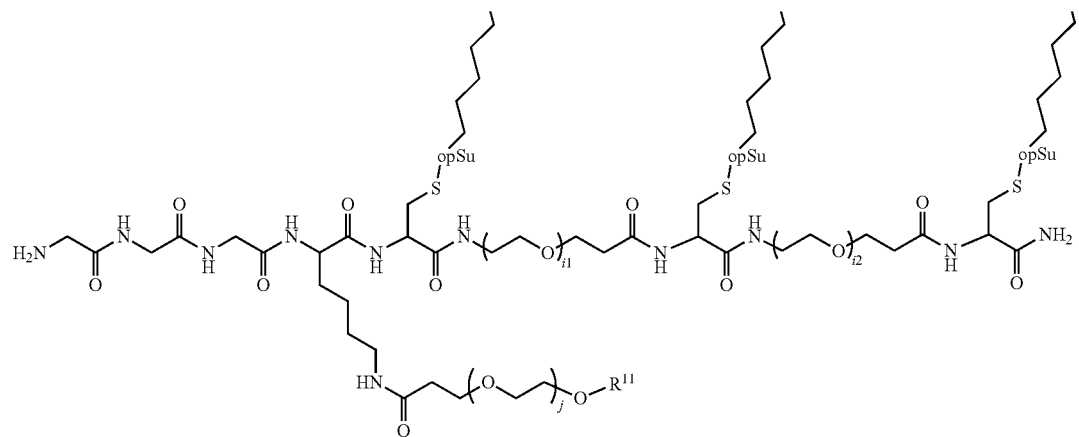
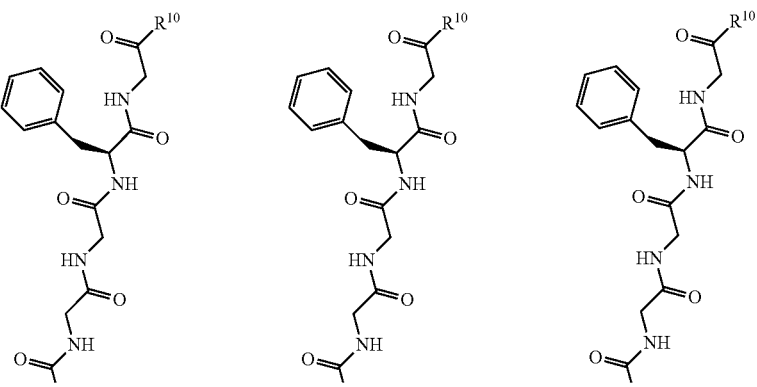

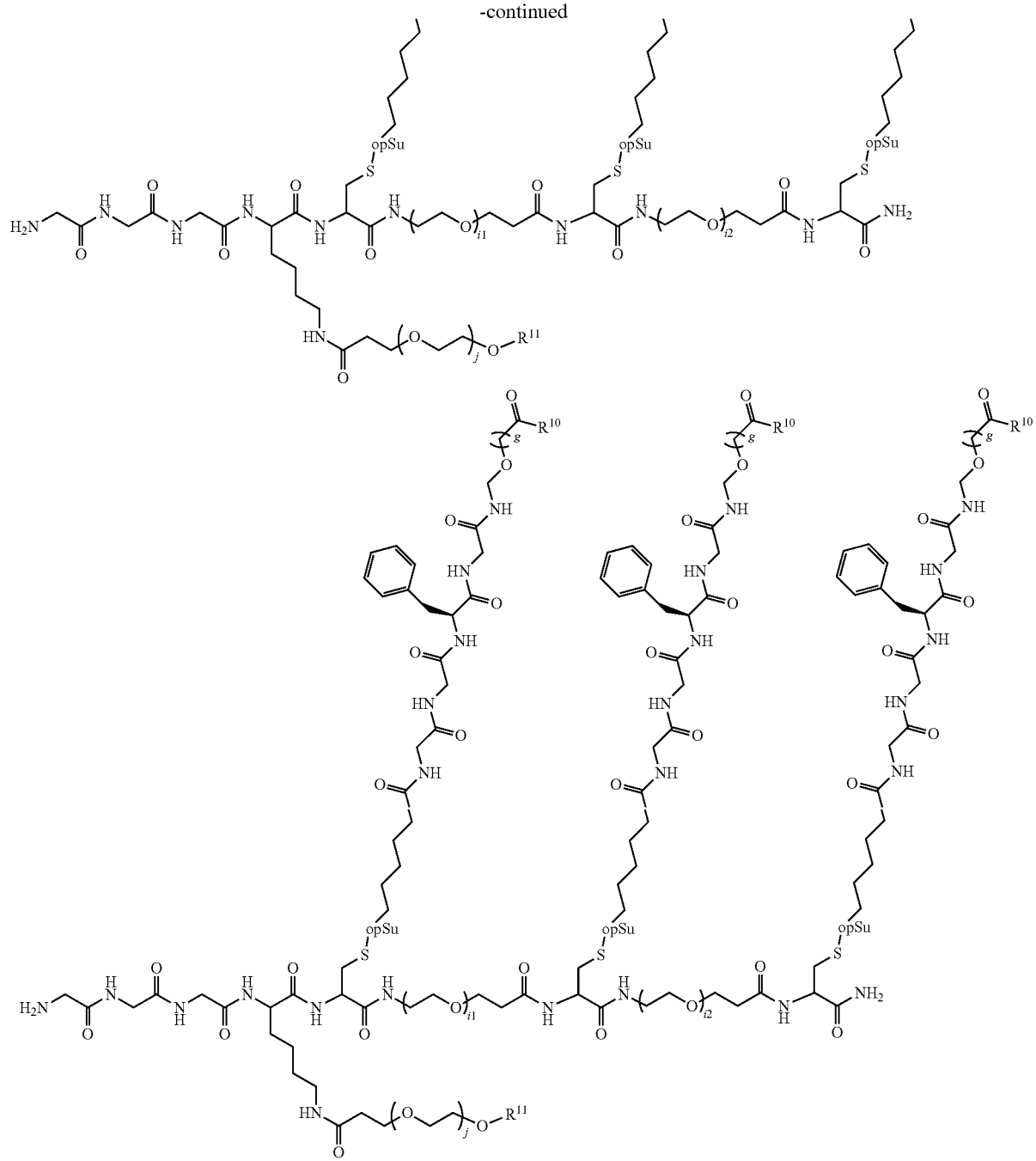
In one embodiment, linker LA302-4 has the structure of:

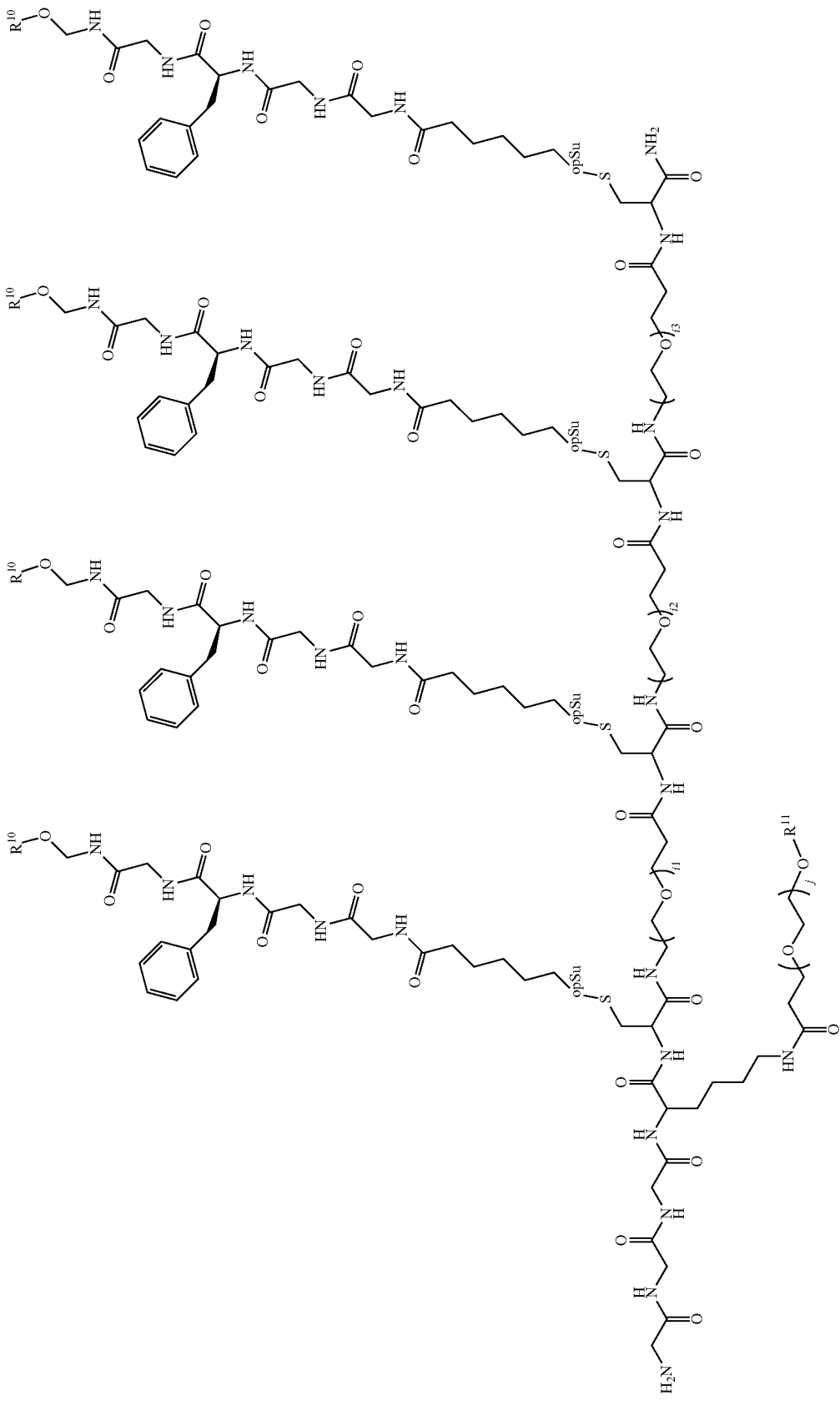

-continued
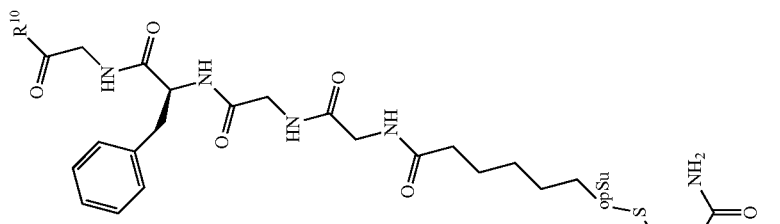
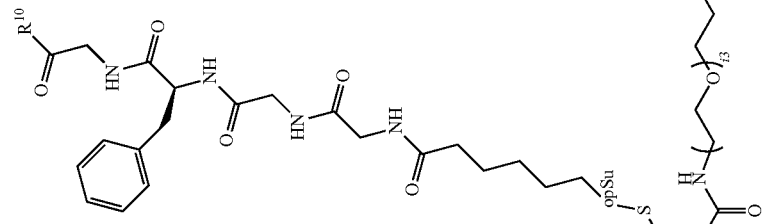
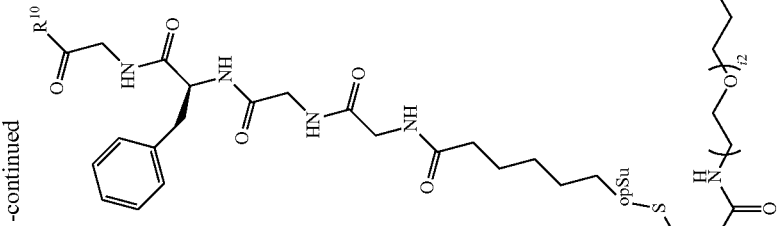
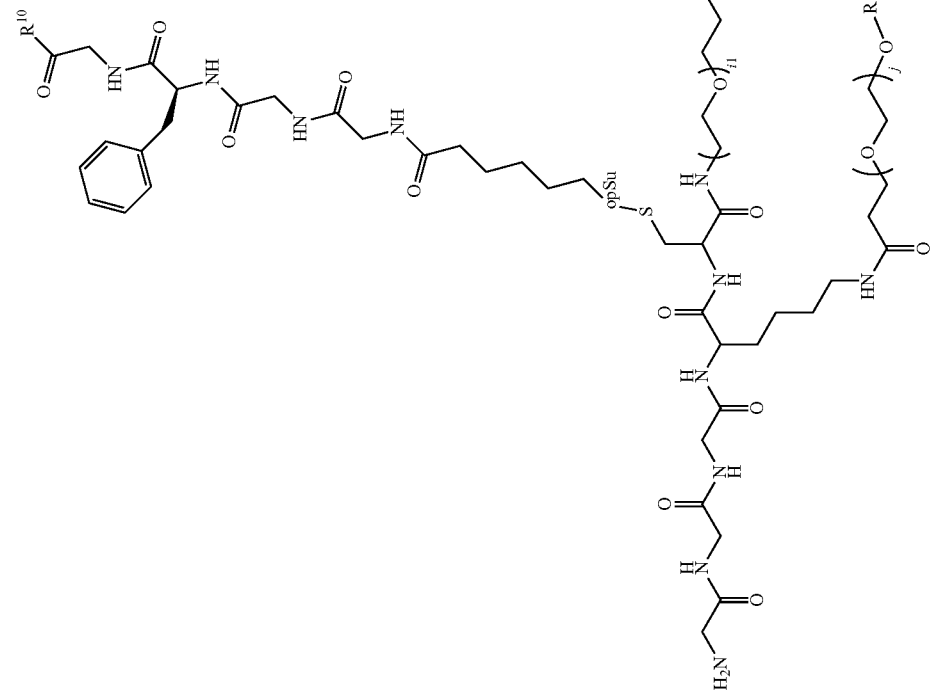

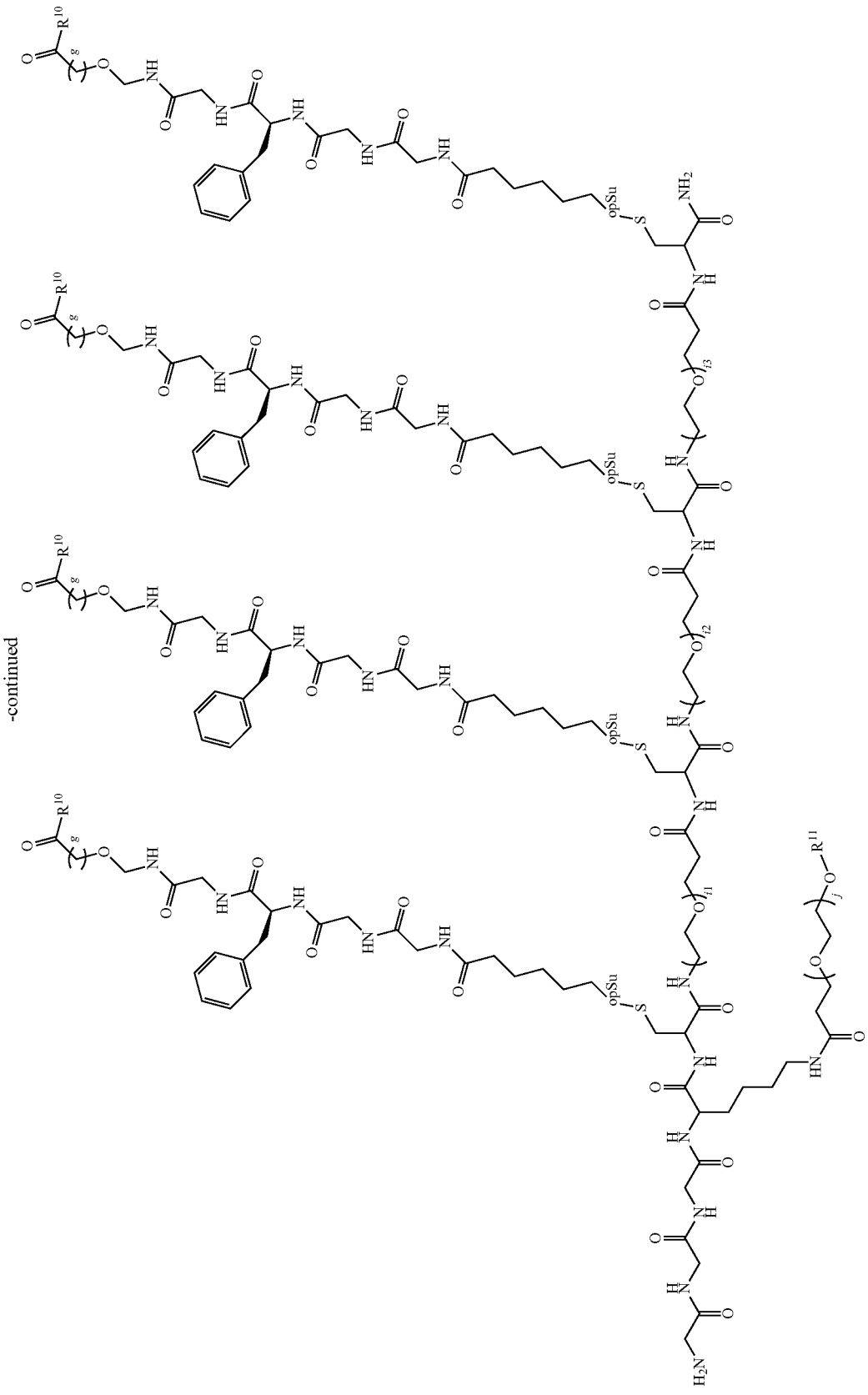

In an embodiment, i is 4, g is 1, $R^{11}$ is methyl.
In one embodiment, linker LA301-2 is as follows (linker LA301-2-1 to LA301-2-3):
(linker LA301-2-1)
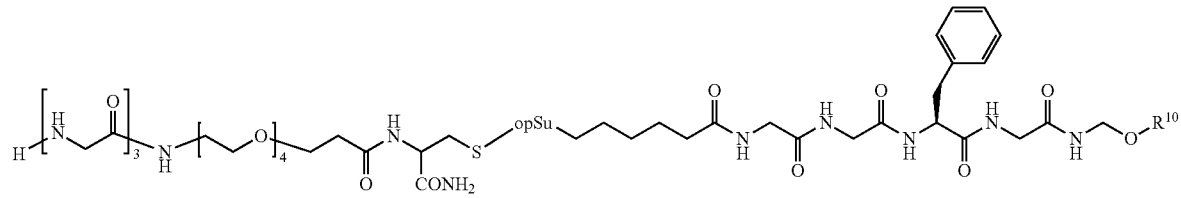
(linker LA301-2-2)
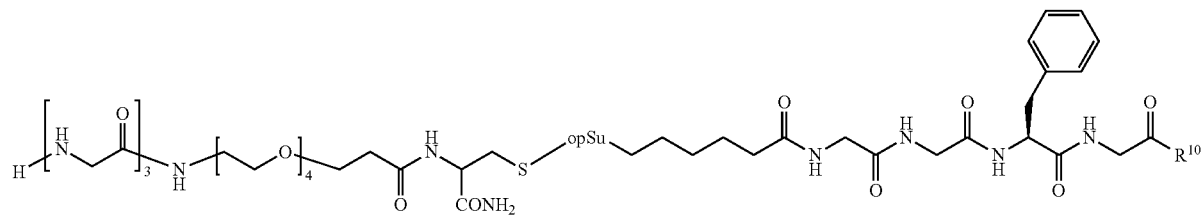
(linker LA301-2-3)
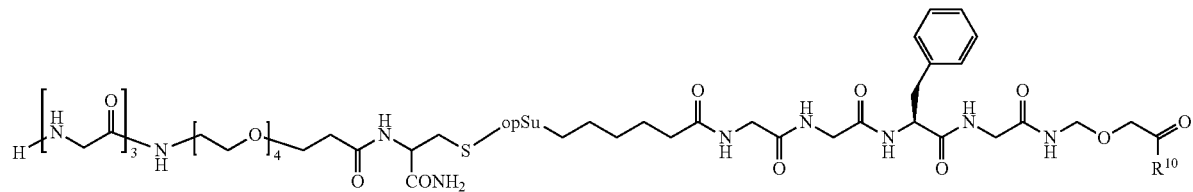
In an embodiment, i is 4, j is 8, g is 1, $R^{11}$ is methyl. In an embodiment, linker LA302-2 is as follows (linker LA302-2-1 to LA302-2-3):
(linker LA302-2-1)
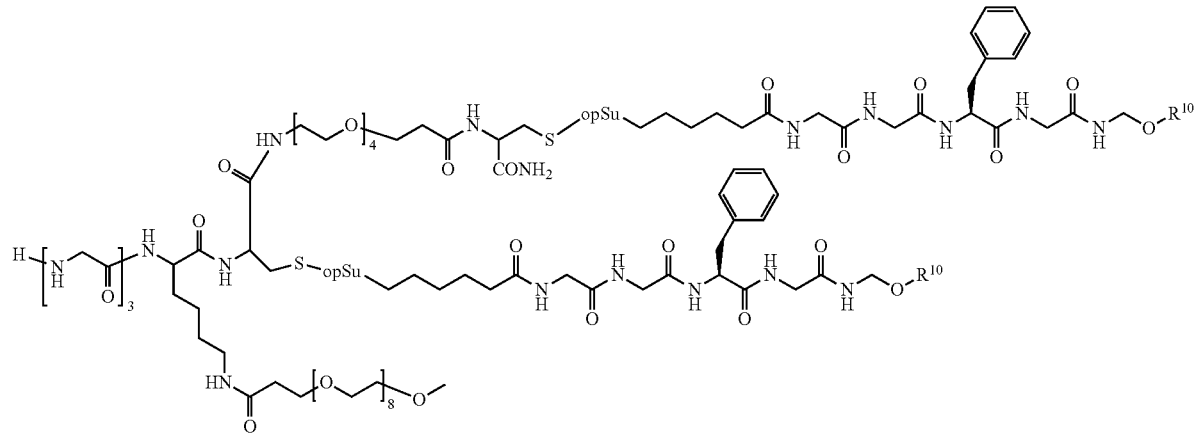

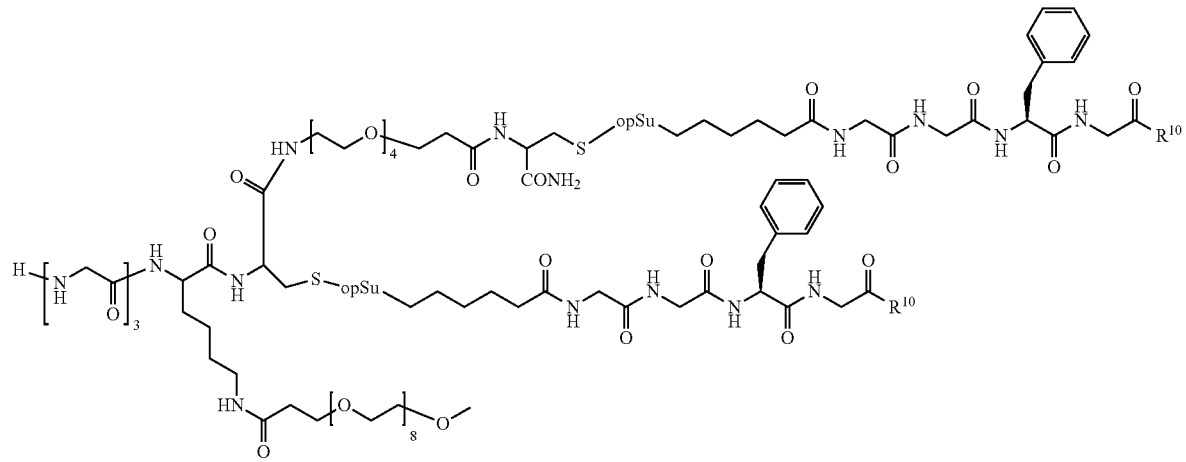
(linker LA302-2-2)
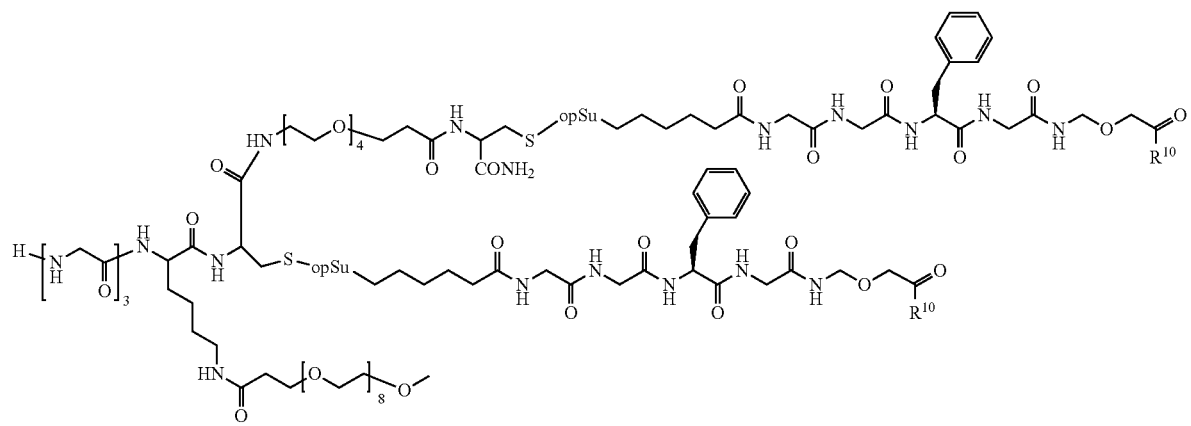
(linker LA302-2-3)
In an embodiment, i is 4, j is 12, g is 1, R is methyl. In an embodiment, linker LA302-2 is as follows (linker LA302-2-4 to LA302-2-6):
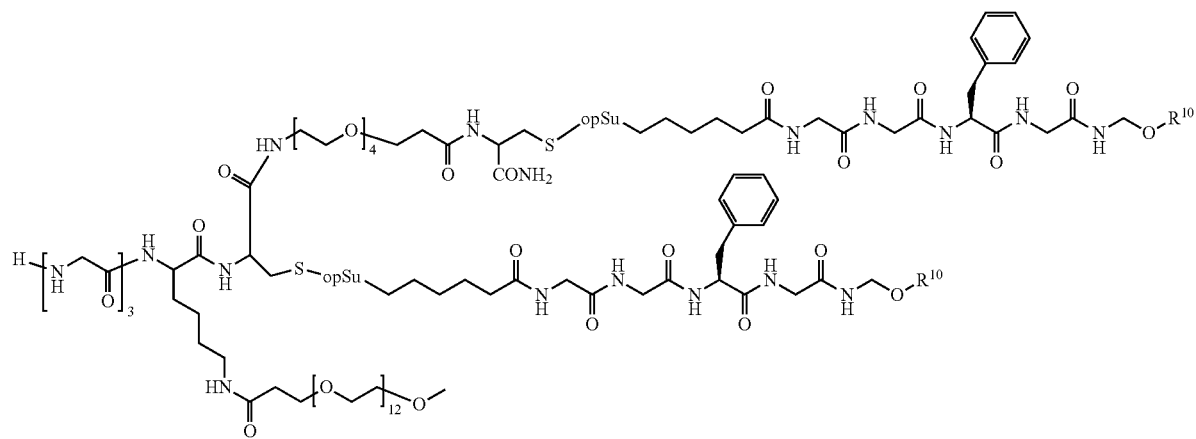
(linker LA302-2-4)

(linker LA302-2-5)

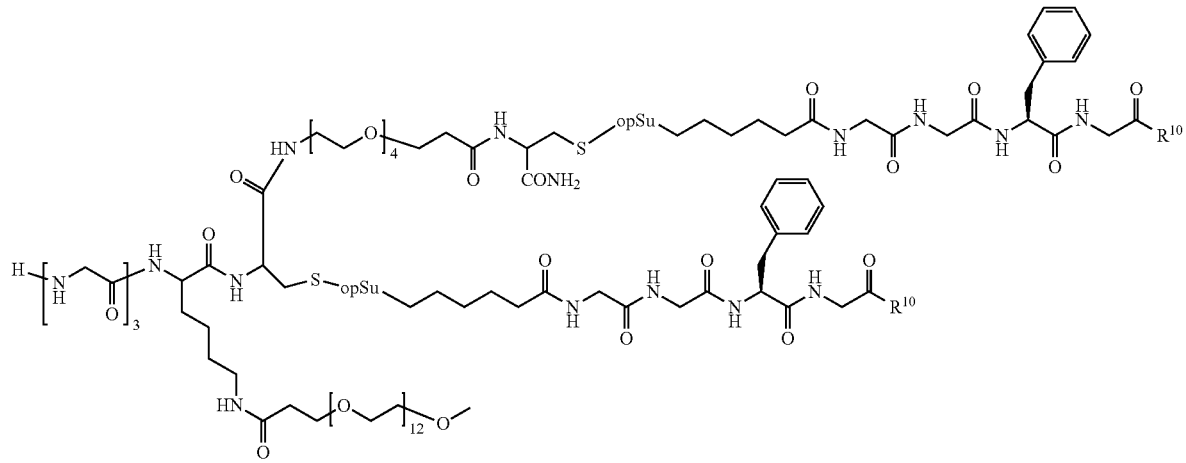

(linker LA302-2-6)

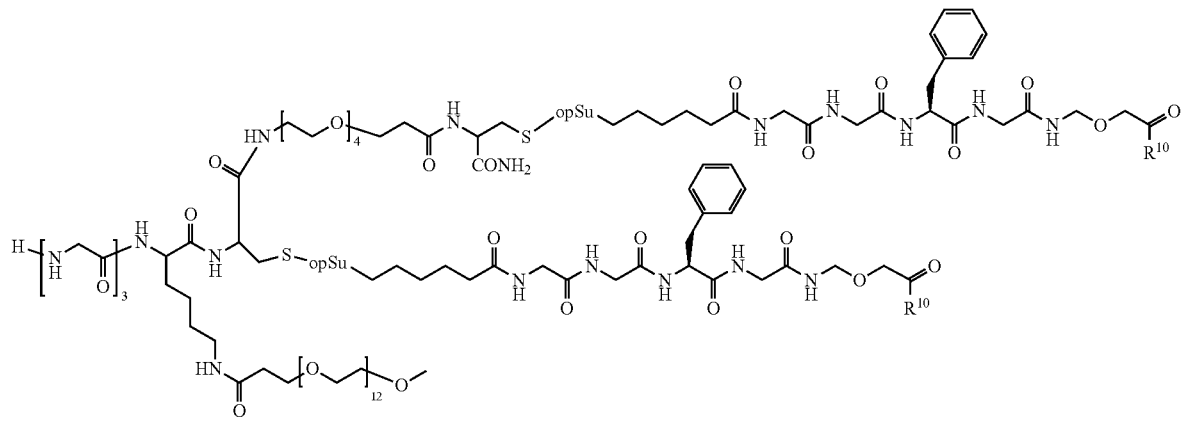

Payload-Bearing Formula (I) Compound

The reactive group comprised by B is covalently conjugated with a payload containing another reactive group to give a payload-bearing formula (I) compound.

In yet another aspect, provided is a compound having the structure of formula (II)

formula (II)

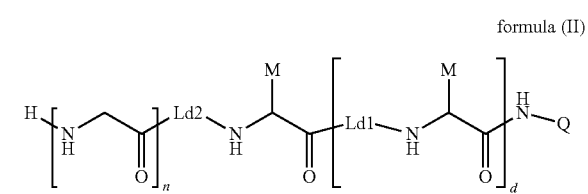

wherein
Q is hydrogen or LKb-P;
M is hydrogen or LKa-LKb-P;
provided that Q and M are not simultaneously hydrogen;
P is a payload which is linked to the B moiety or $L^1$ moiety of the compound of formula (I);
n, d, Ld1, Ld2, LKa and LKb are as defined in formula (I).

As defined herein above, in the compound of formula (I), each LKb is independently $L^2$-$L^1$-B; each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$; $R^{10}$ is hydrogen, or a group which can leave when reacting with a group in the payload. In one embodiment, $R^{10}$ represents the part of structure which would not appear in the product molecule resulting from the reaction of B with the payload.

In one embodiment, P is linked to the B moiety of the compound of formula (I) to form the compound of formula (II). As defined above, $R^{10}$ would not appear in the B—P structure of the compound of formula (II).

It should be understood that, when B in the compound of formula (I) is a terminal group $R^{10}$, $R^{10}$ would not appear in the compound of formula (II). Therefore, as a result, B is absent in the B—P structure of the compound of formula (II).

In one embodiment, M is hydrogen or LKa-$L^2$-$L^1$-B—P; wherein P is a payload which is linked to the B moiety or $L^1$ moiety of the compound of formula (I); each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$; $R^{10}$ is hydrogen, or a group which can leave when reacting with a group in the payload;

$R^{10}$ represents the part of structure which would not appear in the product molecule resulting from the reaction of B with the payload.

In one embodiment, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In a preferred embodiment, M is hydrogen or LKa-$L^2$-$L^1$-B—P; wherein each B is independently absent, or is —NH—$CH_2$—U— or is —NH—$CH_2$—U—$(CH_2)_g$—(CO)—. In another embodiment, M is hydrogen or LKa-$L^2$-$L^1$-B—P. In one embodiment, in LKa-$L^2$-$L^1$-B—P, B is absent. In one embodiment, in LKa-$L^2$-$L^1$-B—P, B is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In one embodiment, in LKa-$L^2$-$L^1$-B—P, B is —NH—$CH_2$—U— or is —NH—$CH_2$—U—$(CH_2)_g$—(CO)—. U is O, S or NH, preferably O or S. In one embodiment, B in the compound of formula (I) is connected to the payload through an amide bond or an ester bond or an ether bond.

As defined herein above, when B in the compound of formula (I) is a terminal group $R^{10}$, B is absent in the B—P structure of the compound of formula (II). In such case, it can also be understood to be that the Cleavable sequence 1 in $L^1$ is connected to the payload to form the compound of formula (II), wherein B is absent in the resulting molecule of the connection of Cleavable sequence 1 with the payload. Accordingly, in one embodiment, P is linked to the $L^1$ moiety of the compound of formula (I) to form the compound of formula (II). Accordingly, in one embodiment, M is LKa-$L^2$-$L^1$-B—P, and B is absent; and M can also be denoted as LKa-$L^2$-$L^1$-P.

4. Payload

In the present disclosure, the payload may be selected from the group consisting of small molecule compounds, nucleic acids and analogues, tracer molecules (including fluorescent molecules, etc.), short peptides, polypeptides, peptidomimetics, and proteins. In one embodiment, the payload is selected from the group consisting of small molecule compounds, nucleic acid molecules, and tracer molecules. In a preferred embodiment, the payload is selected from small molecule compounds. In a more preferred embodiment, the payload is selected from the group consisting of cytotoxin and fragments thereof.

In one embodiment, the cytotoxin is selected from the group consisting of drugs that target microtubule cytoskeleton. In a preferred embodiment, the cytotoxin is selected from the group consisting of taxanes, maytansinoids, auristatins, epothilones, combretastatin A-4 phosphate, combretastatin A-4 and derivatives thereof, indol-sulfonamides, vinblastines such as vinblastine, vincristine, vindesine, vinorelbine, vinflunine, vinglycinate, anhy-drovinblastine, dolastatin 10 and analogues, halichondrin B and eribulin, indole-3-oxoacetamide, podophyllotoxins, 7-diethylamino-3-(2'-benzoxazolyl)-coumarin (DBC), discodermolide, laulimalide. In another embodiment, the cytotoxin is selected from the group consisting of DNA topoisomerase inhibitors such as camptothecins and derivatives thereof, mitoxantrone, mitoguazone. In a preferred embodiment, the cytotoxin is selected from the group consisting of nitrogen mustards such as chlorambucil, chlornaphazine, cholophosphamide, estramustine, ifosfamide, mechlorethamine, mechlorethamine oxide hydrochloride, melphalan, novembichin, phenamet, phenesterine, prednimustine, trofosfamide, uracil mustard. In yet another preferred embodiment, the cytotoxin is selected from the group consisting of nitrosoureas such as carmustine, flubenzuron, formoterol, lomustine, nimustine, ramustine. In one embodiment, the cytotoxin is selected from the group consisting of aziridines. In a preferred embodiment, the cytotoxin is selected from the group consisting of benzodopa, carboquone, meturedepa, and uredepa. In one embodiment, the cytotoxin is selected from the group consisting of an anti-tumor antibiotic. In a preferred embodiment, the cytotoxin is selected from the group consisting of enediyne antibiotics. In a more preferred embodiment, the cytotoxin is selected from the group consisting of dynemicin, esperamicin, neocarzinostatin, and aclacinomycin. In another preferred embodiment, the cytotoxin is selected from the group consisting of actinomycin, antramycin, bleomycins, actinomycin C, carabicin, carminomycin, and cardinophyllin, carminomycin, actinomycin D, daunorubicin, detorubicin, adriamycin, epirubicin, esorubicin, idarubicin, marcellomycin, mitomycins, nogalamycin, olivomycin, peplomycin, porfiromycin, puromycin, ferric adriamycin, rodorubicin, rufocromomycin, streptozocin, zinostatin, zorubicin. In yet another preferred embodiment, the cytotoxin is selected from the group consisting of trichothecene. In a more preferred embodiment, the cytotoxin is selected from the group consisting of T-2 toxin, verracurin A, bacillocporin A, and anguidine. In one embodiment, the cytotoxin is selected from the group consisting of an anti-tumor amino acid derivatives. In a preferred embodiment, the cytotoxin is selected from the group consisting of ubenimex, azaserine, 6-diazo-5-oxo-L-norleucine. In another embodiment, the cytotoxin is selected from the group consisting of folic acid analogues. In a preferred embodiment, the cytotoxin is selected from the group consisting of dimethyl folic acid, methotrexate, pteropterin, trimetrexate, and edatrexate. In one embodiment, the cytotoxin is selected from the group consisting of purine analogues. In a preferred embodiment, the cytotoxin is selected from the group consisting of fludarabine, 6-mercaptopurine, tiamiprine, thioguanine. In yet another embodiment, the cytotoxin is selected from pyrimidine analogues. In a preferred embodiment, the cytotoxin is selected from the group consisting of ancitabine, gemcitabine, enocitabine, azacitidine, 6-azauridine, carmofur, cytarabine, dideoxyuridine, doxifluridine, floxuridine. In one embodiment, the cytotoxin is selected from the group consisting of androgens. In a preferred embodiment, the cytotoxin is selected from the group consisting of calusterone, dromostanolone propionate, epitiostanol, mepitiostane, testolactone. In another embodiment, the cytotoxin is selected from the group consisting of anti-adrenals. In a preferred embodiment, the cytotoxin is selected from the group consisting of aminoglutethimide, mitotane, and trilostane. In one embodiment, the cytotoxin is selected from the group consisting of anti-androgens. In a preferred embodiment, the cytotoxin is selected from the group consisting of flutamide, nilutamide, bicalutamide, leuprorelin acetate, and goserelin. In yet another embodiment, the cytotoxin is selected from the group consisting of a protein kinase inhibitor and a proteasome inhibitor. In another embodiment, the cytotoxin is selected from the group consisting of vinblastines, colchicines, taxanes, auristatins, maytansinoids, calicheamicin, doxonubicin, duocarmucin, SN-38, cryptophycin analogue, deruxtecan, duocarmazine, calicheamicin, centanamycin, dolastansine, and pyrrolobenzodiazepine (PBD). In a particular embodiment, the cytotoxin is selected from the group consisting of vinblastines, colchicines, taxanes, auristatins, and maytansinoids.

In a particular embodiment, the cytotoxin is exatecan or a derivative thereof, such as DX8951f and the like.

In another particular embodiment, the cytotoxin is an maytansinoid, such as DM1 and the like. Note that where a cytotoxin comprising a thiol moiety is used, the thiol moiety being capable of reaction with a maleimide moiety to form a thiosuccinimide, for example a maytansinoid, e.g., DM1, the cytotoxin can link directly via the thiosuccinimide. In such case, it could be understood that in some embodiments Payload and the thiol moiety together constitutes a cytotoxin, and therefore in such case Payload represents the rest moiety of the cytotoxin molecule except for the thiol moiety.

In a particular embodiment, the cytotoxin is an auristatin, such as MMAE (monomethyl auristatin E), MMAF (monomethyl auristatin F), MMAD (monomethyl auristatin D) and the like. The synthesis and structure of auristatin compounds are described in US20060229253, the entire disclosure of which is incorporated herein by reference.

The payload contains a reactive group which can react with the reactive group in the compound of formula (I) and thus covalently conjugate the payload with the compound of formula (I). Compounds that do not contain reactive groups require appropriate derivatization to give the payload.

In a particular embodiment, the cytotoxin is a compound of the following formula (i)

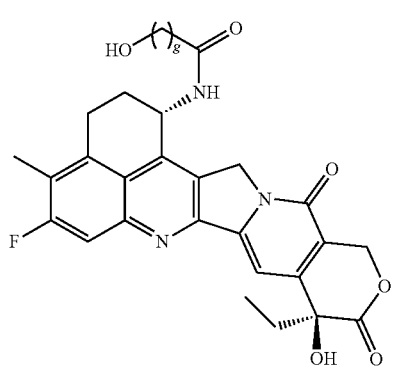

(i)

wherein, g is any integer of 1 to 6.

In an embodiment, g is any integer of 1 to 3, preferably 1.

In an embodiment, the cytotoxin is selected from the following compounds 1 to 14; wherein the wavy bond shows the connection site for connection with the compound of formula (I).

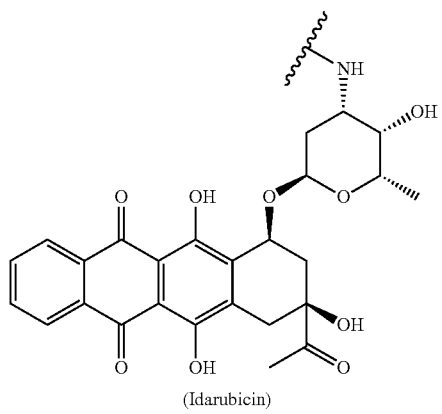

1

(Idarubicin)

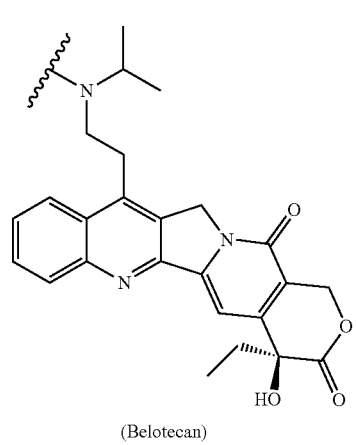

2

(Belotecan)

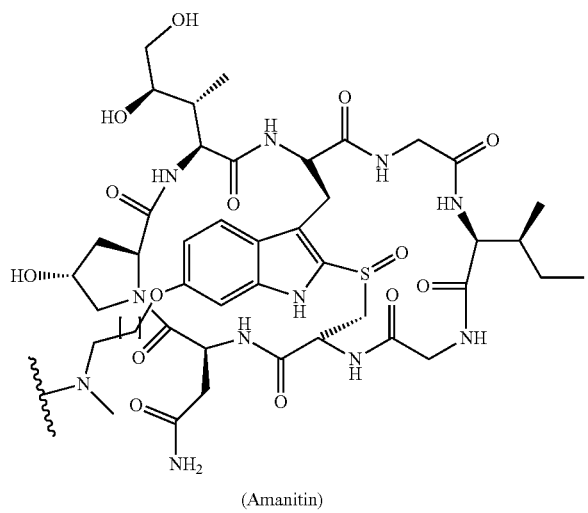

3

(Amanitin)

-continued
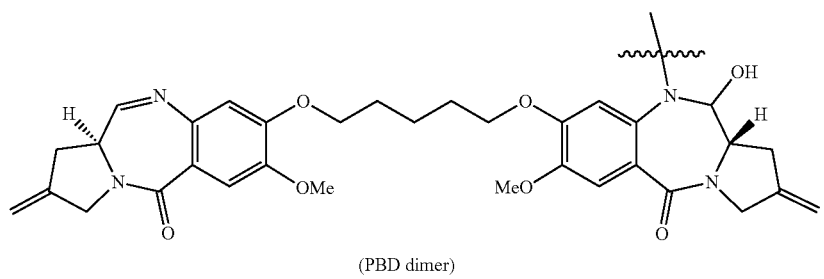
(PBD dimer) 4
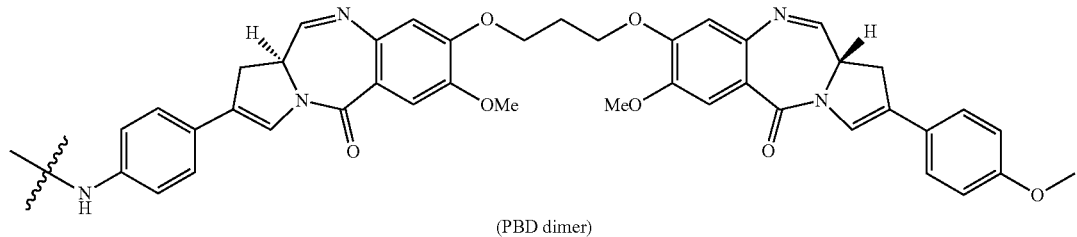
(PBD dimer) 5
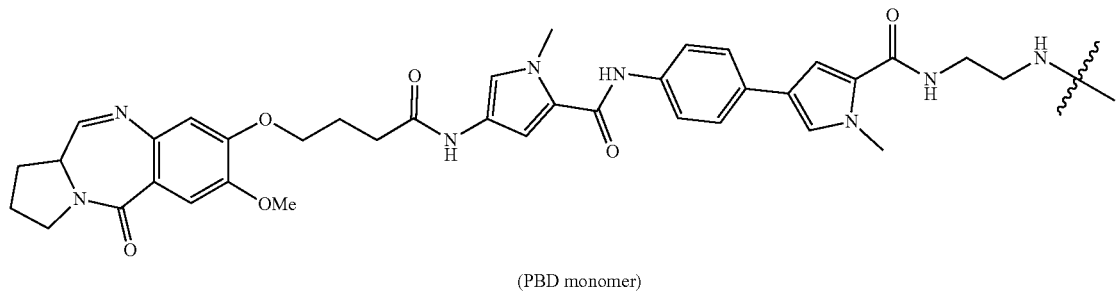
(PBD monomer) 6
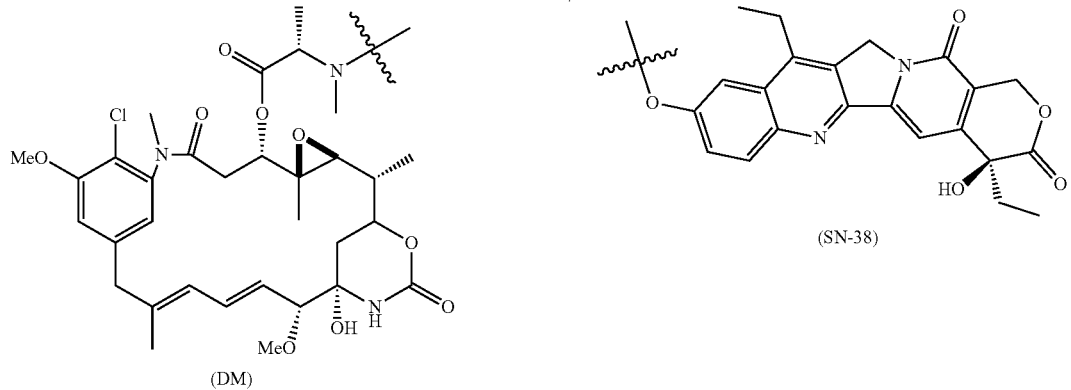
(DM) 7  (SN-38) 8
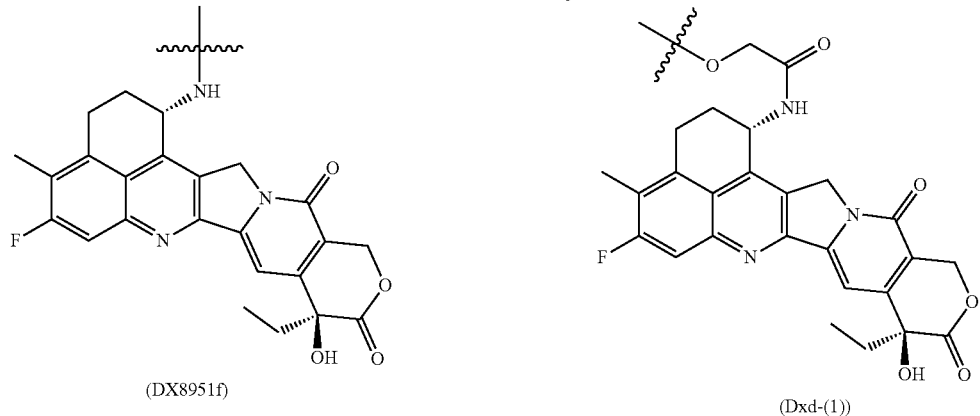
(DX8951f) 9  (Dxd-(1)) 10

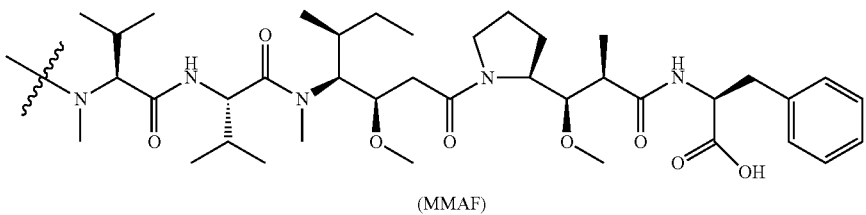

(MMAF)

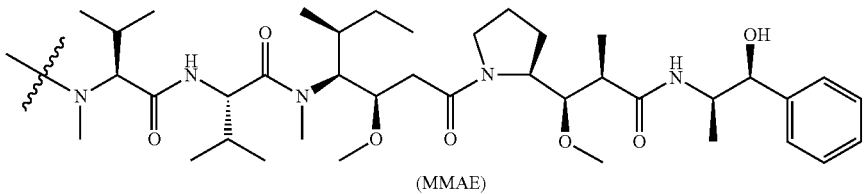

(MMAE)

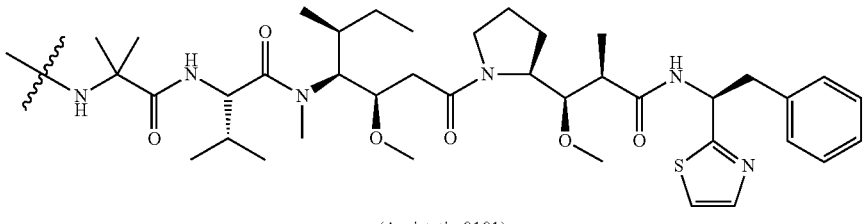

(Auristatin 0101)

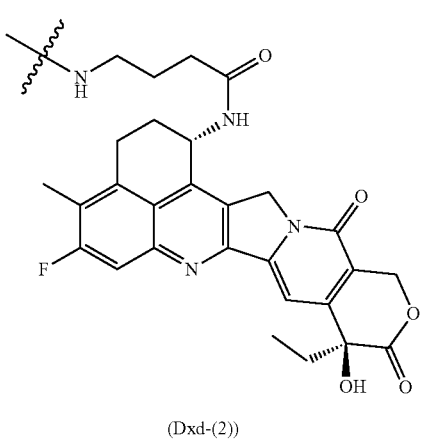

(Dxd-(2))

In some embodiments, the payload is selected from DX8951f (compound 9), DXd-(1) (compound 10) and DXd-(2) (compound 14), preferably DX8951f or DXd-(1), more preferably DXd-(1).

Preparation of the Payload-Bearing Formula (I) Compound

In one embodiment, the linking unit and the Payload are connected via reactive groups as defined above, using any reaction known in the art, including but not limit to condensation reaction, nucleophilic addition, electrophilic addition, etc.

In one embodiment, the payload is a cytotoxin. In one embodiment, the linking unit-payload intermediate (numbered as LBx) is as shown in the following table.

| Compound of formula (II) | Linker | Formula of Linker | Values of i and j (when applicable)* | Payload |
|---|---|---|---|---|
| LB301-1-1 | LA301-1-1 | LA301-1 | — | compound 10 |
| LB301-2-1 | LA301-2-1 | LA301-2 | i is 4 | compound 10 |
| LB301-3-1 | LA301-3-1 | LA301-3 | i1 is 4, i2 is 4 | compound 10 |
| LB301-4-1 | LA301-4-1 | LA301-4 | i1, i2, i3 are 4, respectively | compound 10 |
| LB301-5-1 | LA301-5-1 | LA301-5 | i1, i2, i3 and i4 are 4, respectively | compound 10 |
| LB302-1-1 | LA302-1-1 | LA302-1 | j is 8 | compound 10 |
| LB302-1-4 | LA302-1-4 | LA302-1 | j is 12 | compound 10 |
| LB302-2-1 | LA302-2-1 | LA302-2 | i is 4, j is 8 | compound 10 |

-continued

| Compound of formula (II) | Linker | Formula of Linker | Values of i and j (when applicable)* | Payload |
|---|---|---|---|---|
| LB302-2-4 | LA302-2-4 | LA302-2 | i is 4, j is 12 | compound 10 |
| LB302-3-1 | LA302-3-1 | LA302-3 | i1 is 4, i2 is 4, j is 8 | compound 10 |
| LB302-3-4 | LA302-3-4 | LA302-3 | i1 is 4, i2 is 4, j is 12 | compound 10 |
| LB302-4-1 | LA302-4-1 | LA302-4 | i1, i2, i3 are 4, respectively, j is 8 | compound 10 |
| LB302-4-4 | LA302-4-4 | LA302-4 | i1, i2, i3 are 4, respectively, j is 12 | compound 10 |

*For all the linkers listed, n is 3.

Conjugates and Preparation Thereof

Furthermore, the payload-bearing formula (I) compound which has the moiety comprising ligase recognition sequence can be conjugated with other molecules comprising a ligase recognition sequence, and can be thereby used in for example, the preparation of a targeting molecule-drug conjugate, such as an antibody-drug conjugate. Accordingly, in yet another aspect, provided is a conjugate which comprises a compound of formula (I), a targeting molecule, and a payload.

In yet another aspect, provided is a conjugate having the structure of formula (III):

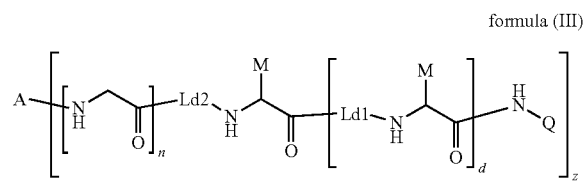

formula (III)

wherein, n, d, Ld1 and Ld2 are as defined in formula (I);

Q is hydrogen or LKb-P;

M is hydrogen or LKa-LKb-P;

provided that Q and M are not simultaneously hydrogen;

P is a payload which is linked to the B moiety or $L^1$ moiety of the compound of formula (I);

A is a targeting molecule which is linked to the $G_n$ moiety of the compound of formula (I); G is glycine;

z is an integer of 1 to 20.

In one embodiment, LKa and LKb are as defined in formula (I).

As defined herein above, in one embodiment, the $G_n$ moiety of the compound of formula (I) is a recognition sequence of a ligase acceptor or donor substrate, which facilitates enzyme-catalyzed coupling of compound of formula (I) with the targeting molecule under the catalysis of the ligase. The targeting molecule optionally modified and comprises the corresponding recognition sequence of a ligase acceptor or donor substrate.

It should be understood that, when the targeting molecule A conjugates with the $G_n$ moiety of the compound of formula (I) under the catalysis of the ligase, the recognition sequence of the ligase acceptor substrate and the recognition sequence of the ligase donor substrate react with each other and form a resulting sequence.

In one embodiment, the targeting molecule A comprises LPXTGJ as the recognition sequence of the ligase donor substrate, wherein J is as defined above (LPXTG: SEQ ID NO: 11). When conjugates with $G_n$, which is the corresponding recognition sequence of the ligase acceptor substrate, the upstream peptide bond of the glycine in the LPXTGJ sequence is cleaved by Sortase A, and the resulting intermediate is linked to the free N-terminal of $G_n$ to generate a new peptide bond. The resulting sequence is LPXTG$_n$. The sequences $G_n$ and LPXTGJ are as defined above.

In one embodiment, P is linked to the B moiety or $L^1$ moiety of the compound of formula (I) and A is linked to the $G_n$ moiety of the compound of formula (I) to form the compound of formula (III).

As defined above, $R^{10}$ would not appear in the B—P structure of the compound of formula (III). As defined above, when B in the compound of formula (I) is a terminal group $R^{10}$, B is absent in the B—P structure of the compound of formula (III).

As defined above, in the A-$G_n$ structure of the compound of formula (III), A optionally comprises the corresponding sequence resulting from the reaction of the recognition sequence of the ligase acceptor substrate with the recognition sequence of the ligase donor substrate.

In one embodiment, M is hydrogen or LKa-$L^2$-$L^1$-B—P; wherein P is a payload which is linked to the B moiety or $L^1$ moiety of the compound of formula (I); each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$; $R^{10}$ is hydrogen, or a group which can leave when reacting with a group in the payload; $R^{10}$ represents the part of structure which would not appear in the product molecule resulting from the reaction of B with the payload.

In one embodiment, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In a preferred embodiment, M is hydrogen or LKa-$L^2$-$L^1$-B—P; wherein each B is independently absent, or is —NH—$CH_2$—U— or is —NH—$CH_2$—U—$(CH_2)_g$—(CO)—. In another embodiment, M is hydrogen or LKa-$L^2$-$L^1$-B—P. In one embodiment, in LKa-$L^2$-$L^1$-B—P, B is absent. In one embodiment, in LKa-$L^2$-$L^1$-B—P, B is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In one embodiment, in LKa-$L^2$-$L^1$-B—P, B is —NH—$CH_2$—U— or is —NH—$CH_2$—U—$(CH_2)_g$—(CO)—. U is O, S or NH, preferably O or S. In one embodiment, B in the compound of formula (I) is connected to the payload through an amide bond or an ester bond or an ether bond. In one embodiment, M is LKa-$L^2$-$L^1$-B—P, and B is absent; and M can also be denoted as LKa-$L^2$-$L^1$-P.

Targeting Molecule

In one embodiment, the targeting molecule is an antibody or an antigen binding fragment thereof.

In one embodiment, the targeting molecule is an anti-human HER2 antibody or antigen binding fragment thereof. Examples of anti-human HER2 antibodies include but are not limited to Pertuzumab and Trastuzumab. Pertuzumab binds to the second extracellular domain (ECD2) of HER2 and is approved for the treatment of HER2-positive breast cancer. Trastuzumab binds to the fourth extracellular domain (ECD4) of HER2 and is approved for the treatment of Her2-positive breast cancer and gastric cancer.

In a preferred embodiment, the anti-human HER2 antibody is one or more selected from engineered anti-HER2 antibodies based on Trastuzumab.

In a preferred embodiment, the anti-human HER2 antibody is a recombinant antibody selected from monoclonal antibody, chimeric antibody, humanized antibody, antibody fragment, and antibody mimic. In one embodiment, the antibody mimic is selected from scFv, minibody, diabody, nanobody. For the conjugation with the compound of formula (I), the targeting molecule of the present disclosure may comprise a modified moiety to connect with D1 or D2 in the compound of formula (I). The introduction position of such modified moiety is not limited, for example, when the targeting molecule is an antibody, its introduction position can be, but not limited to, located at the C-terminal or the N-terminal of the heavy chain or light chain of the antibody.

In an alternative embodiment, a modified moiety for the conjugation with D1 or D2 in the compound of formula (I) can be introduced at a non-terminal position of the heavy chain or light chain of the antibody using, for example, chemical modification methods.

In one embodiment, the targeting molecule of the present disclosure is an antibody or antigen-binding fragment thereof, which may comprise terminal modification. A terminal modification refers to a modification at the C-terminal or N-terminal of the heavy chain or light chain of the antibody, which for example comprises a ligase recognition sequence. In another embodiment, the terminal modification may further comprise spacer Sp2 comprising 2-100 amino acids, wherein the antibody, Sp2 and the ligase recognition sequence are sequentially linked. In a preferred embodiment, Sp2 is a spacer sequence containing 2-20 amino acids. In a particular embodiment, Sp2 is a spacer sequence selected from GA, GGGGS (SEQ ID NO: 5), GGGGSGGGGS (SEQ ID NO: 6) and GGGGSGGGGSGGGGS (SEQ ID NO: 7), especially GA.

In a preferred embodiment, the light chain of the antibody or antigen-binding fragment thereof includes 3 types: wild-type (LC); the C-terminus modified light chain (LCCT), which is modified by direct introduction of a ligase recognition sequence LPXTG (SEQ ID NO: 11) and C-terminus modified light chain (LCCT$_L$), which is modified by introduction of short peptide spacers plus the ligase donor substrate recognition sequence LPXTG (SEQ ID NO: 11). The heavy chain of the antibody or antigen-binding fragment thereof includes 3 types: wild-type (HC); the C-terminus modified heavy chain (HCCT), which is modified by direct introduction of a ligase recognition sequence LPXTG (SEQ ID NO: 11); and C-terminus modified heavy chain (HCCT$_L$), which is modified by introduction of short peptide spacers plus the ligase donor substrate recognition sequence LPXTG (SEQ ID NO: 11). X can be any natural or non-natural single amino acid. When z in the compound of formula (VII) is 1 or 2, the combination of the above heavy and light chains can form 8 preferred antibody molecules, see the amino acid sequence table.

The conjugates of the present disclosure can further comprise a payload. The payload is as described above.

Specific Embodiments for the Conjugate

In one embodiment, Q is hydrogen, each LKa is

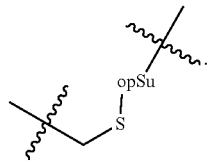

In one embodiment, formula (III) has the structure of formula (III-1):

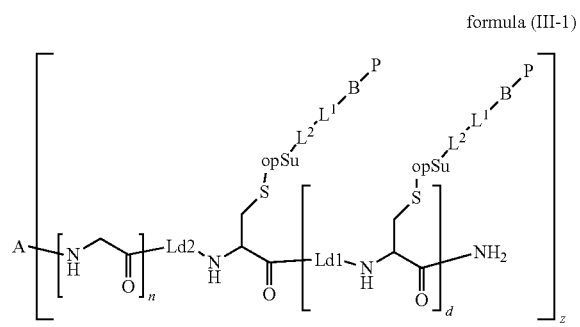

formula (III-1)

In one embodiment, Ld2 is a bond, d is 0. In one embodiment, the compound of formula (III-1) is as follows:

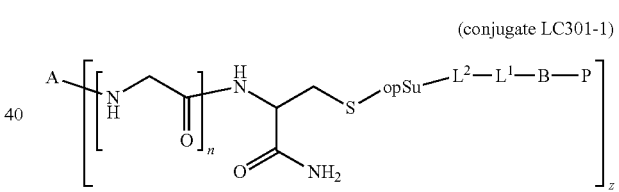

(conjugate LC301-1)

In one embodiment, d is 0, Ld2 is

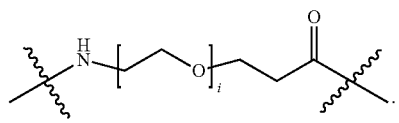

In one embodiment, the compound of formula (III-1) is as follows:

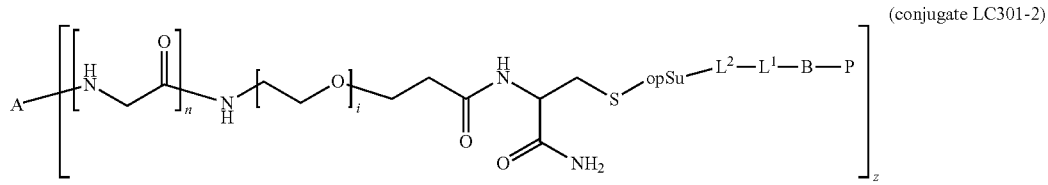

(conjugate LC301-2)

In one embodiment, d is 1, 2 or 3, Ld2 and each Ld1 are independently selected from
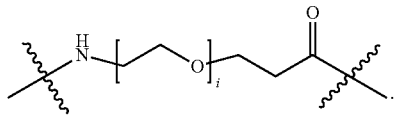
In one embodiment, the compound of formula (III-1) is as follows:
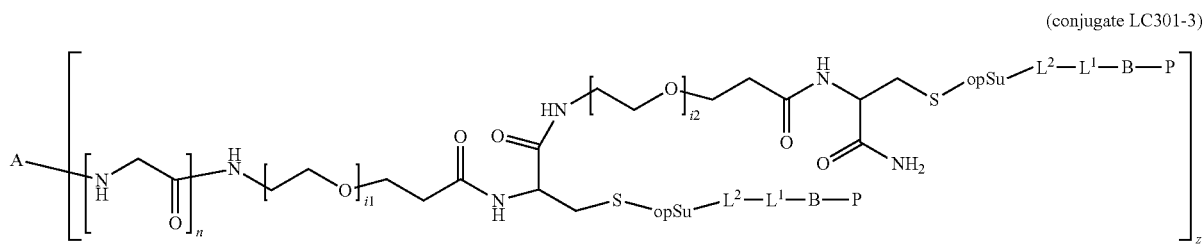
(conjugate LC301-3)
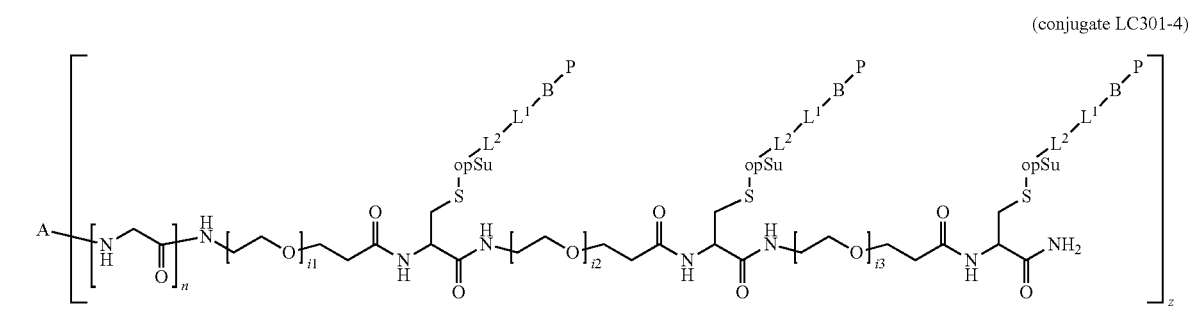
(conjugate LC301-4)
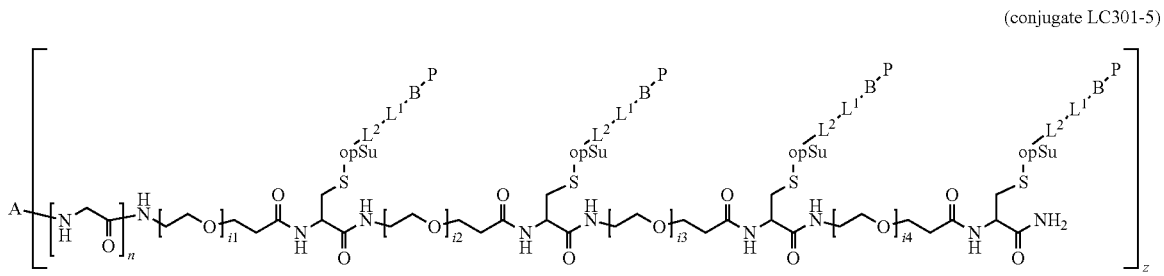
(conjugate LC301-5)
In one embodiment, Ld2 is
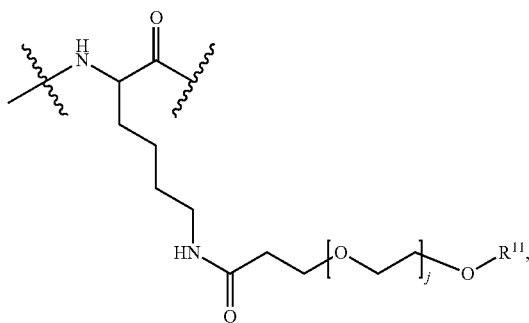
d is 0. In one embodiment, the compound of formula (III-1) is as follows:
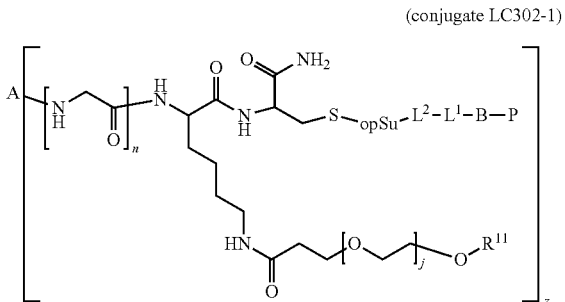
(conjugate LC302-1)

In one embodiment, d is 1, 2 or 3, Ld2 is
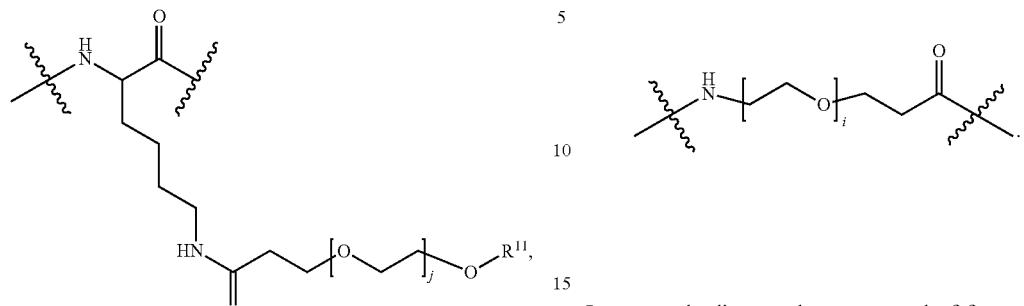
and each Ld1 is independently selected from
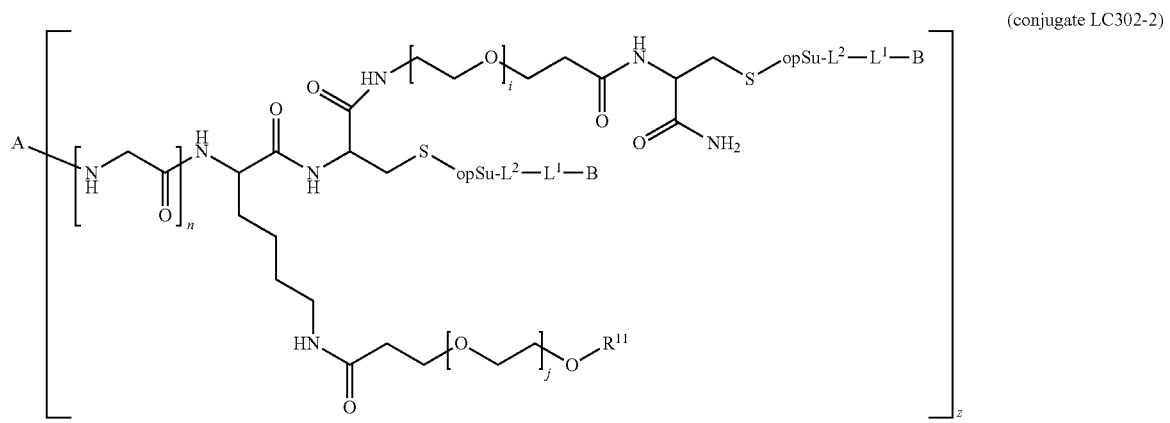
In one embodiment, the compound of formula (III-1) is as follows:
(conjugate LC302-2)
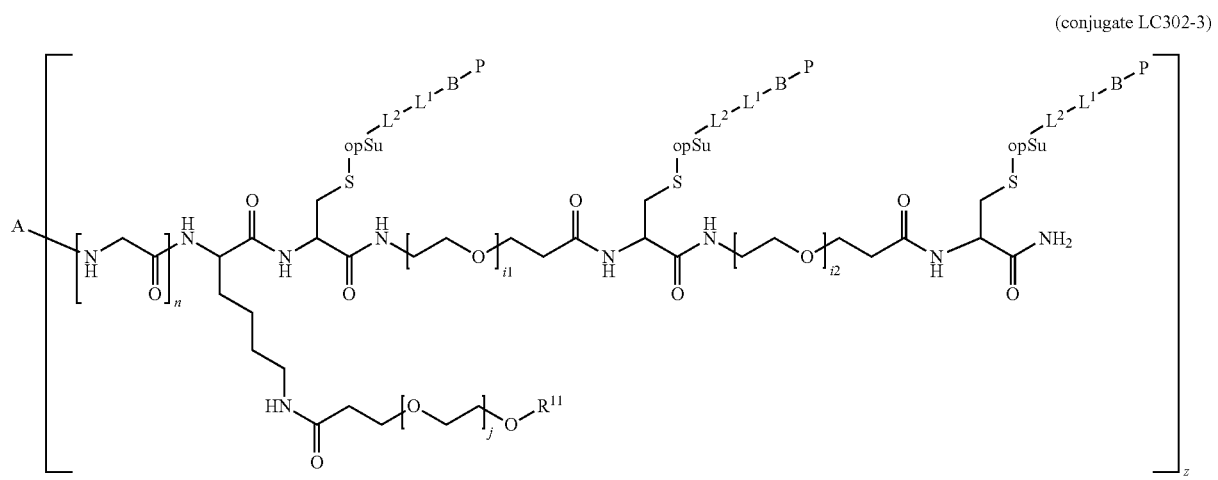
(conjugate LC302-3)

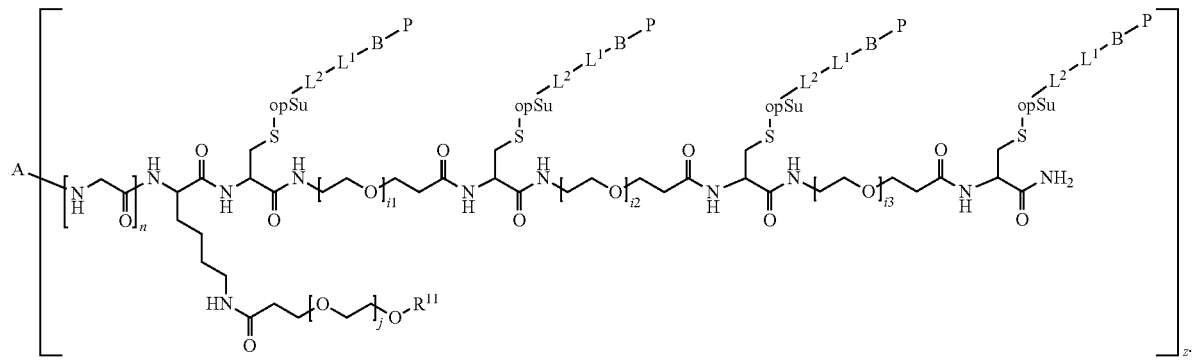
(conjugate LC302-4)

In an embodiment, z is 1 to 4. In an embodiment, z is 2 or 4. In an embodiment, z is 2. In an embodiment, in conjugate LC301-1, LC301-2, LC302-1, z is 2 or 4. In an embodiment, in conjugate LC301-3, LC301-4, LC301-5, LC302-2, LC302-3 and LC302-4, z is 2.

In one embodiment, B in compound of formula (I) is a terminal group $R^{10}$, and the Cleavable sequence 1 in $L^1$ is connected to the payload to form a compound of formula (II) wherein B is absent in the resulting molecule of the connection of Cleavable sequence 1 with the payload. In such case, M can be understood to be LKa-L2-L1-B—P, wherein B does not present. In such case, M can also be denoted as LKa-$L^2$-$L^1$-P. In one embodiment, n is 3, $L^2$ is —(CH$_2$)$_p$—(CH$_2$)$_2$(CO)—, p is 3, $L^1$ is GGFG, B is —NH—CH$_2$—U— or absent or —NH—CH$_2$—U—(CH$_2$)$_g$—(CO)—, U is O, g is 1. In one embodiment, conjugate LC301-1 has the structure of:

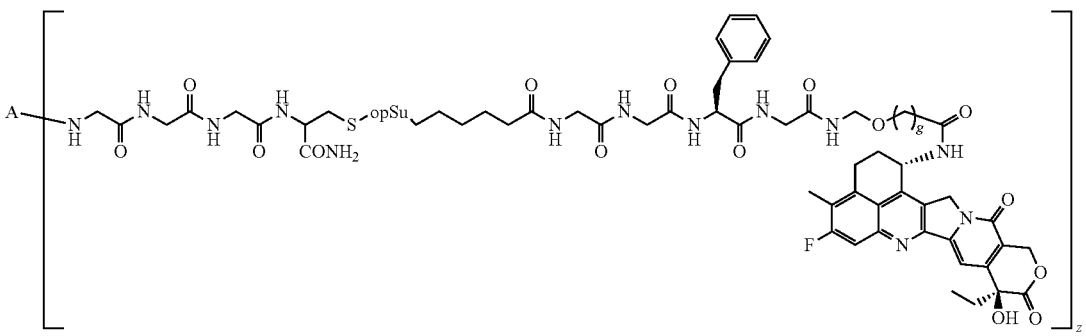

In one embodiment, conjugate LC301-2 has the structure of:

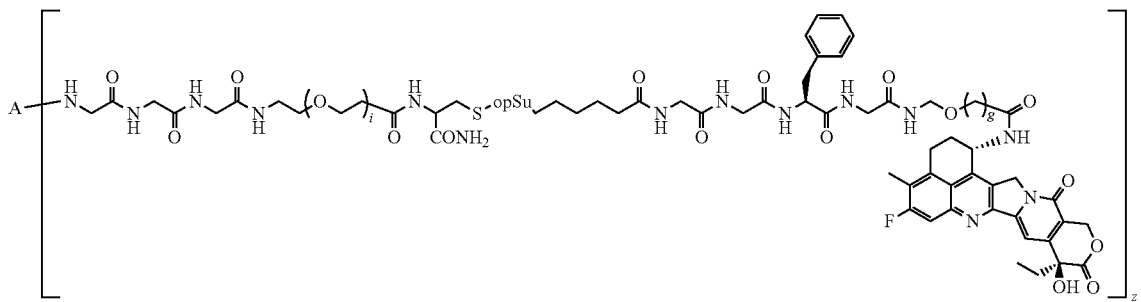

In one embodiment, conjugate LC301-3 has the structure of:

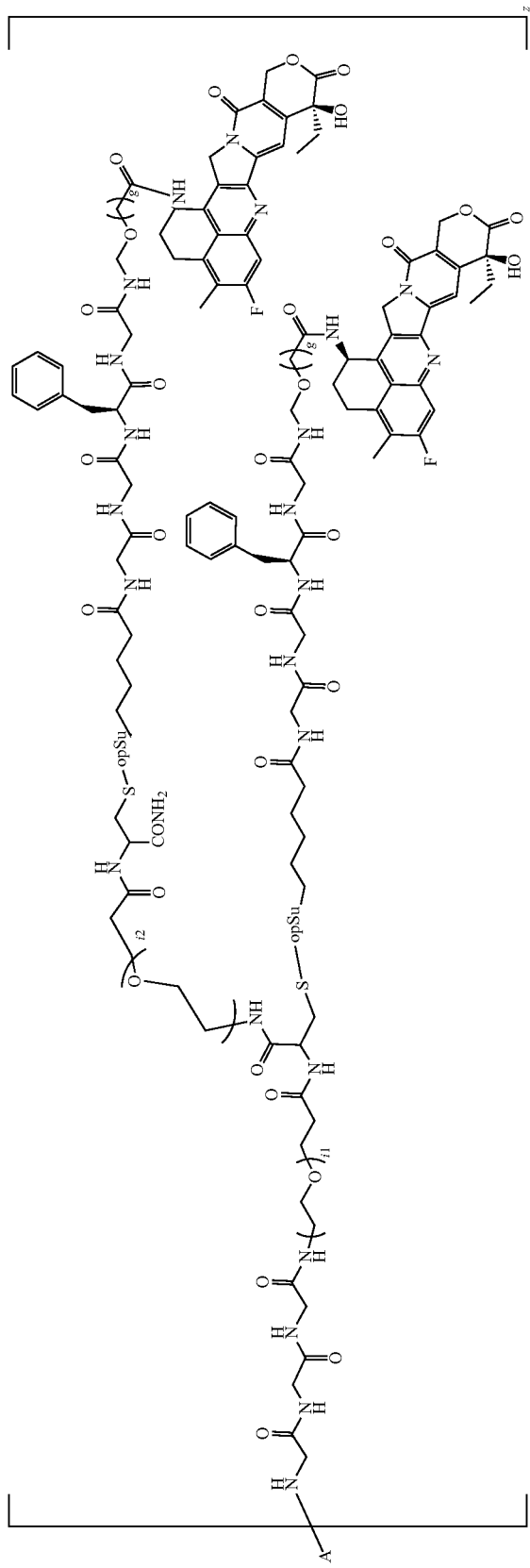

In one embodiment, conjugate LC301-4 has the structure of:

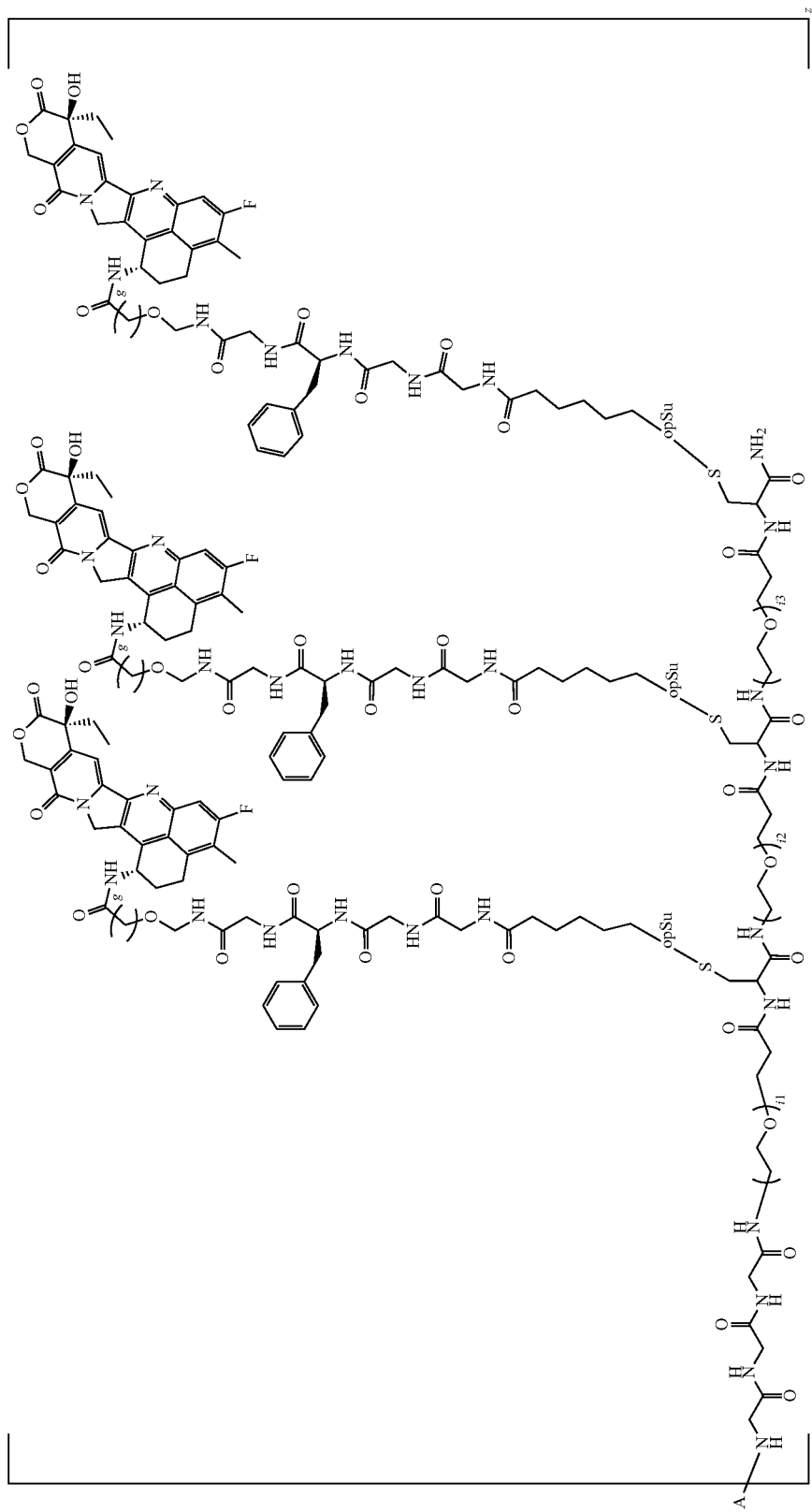

In one embodiment, conjugate LC301-5 has the structure of:

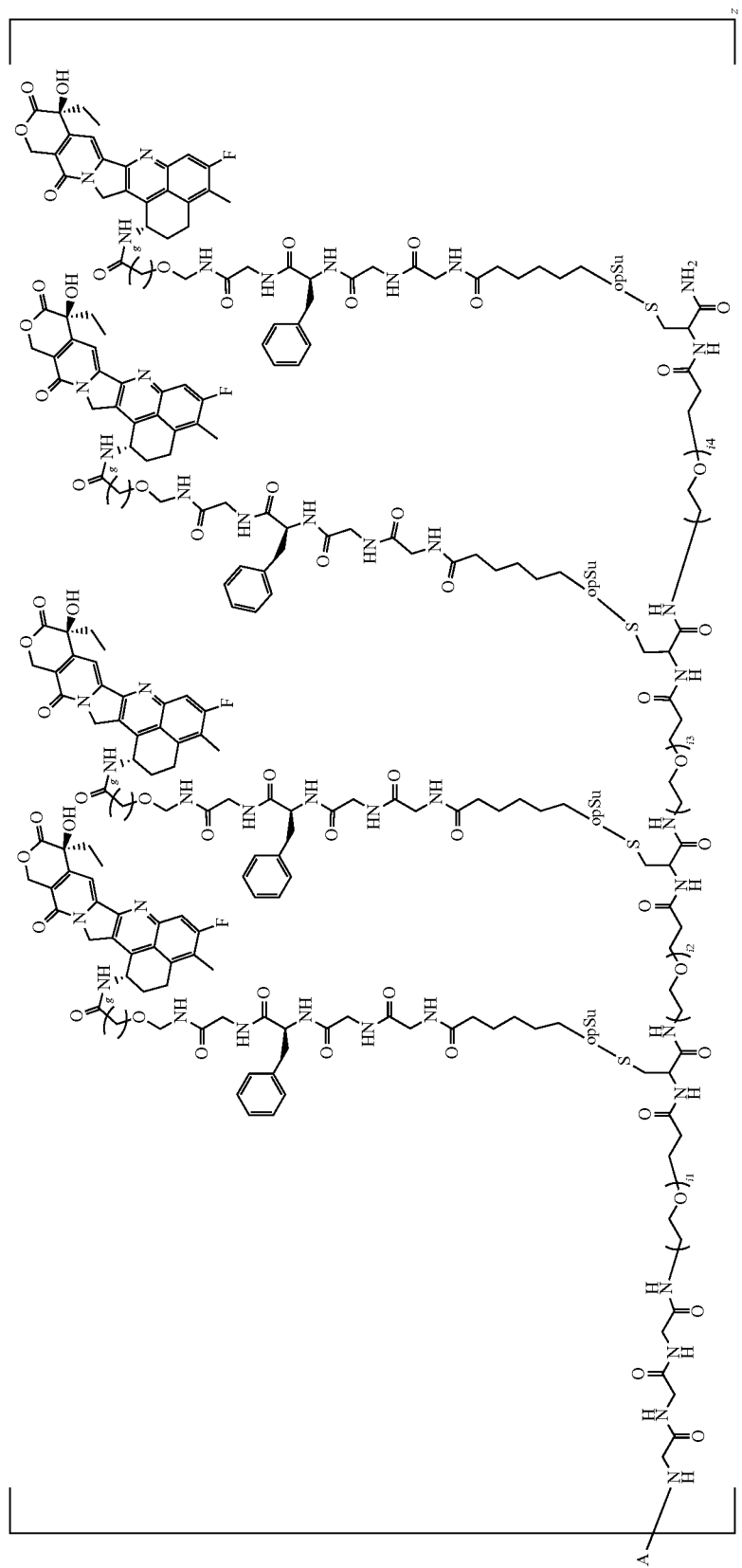

In one embodiment, conjugate LC302-1 has the structure of:

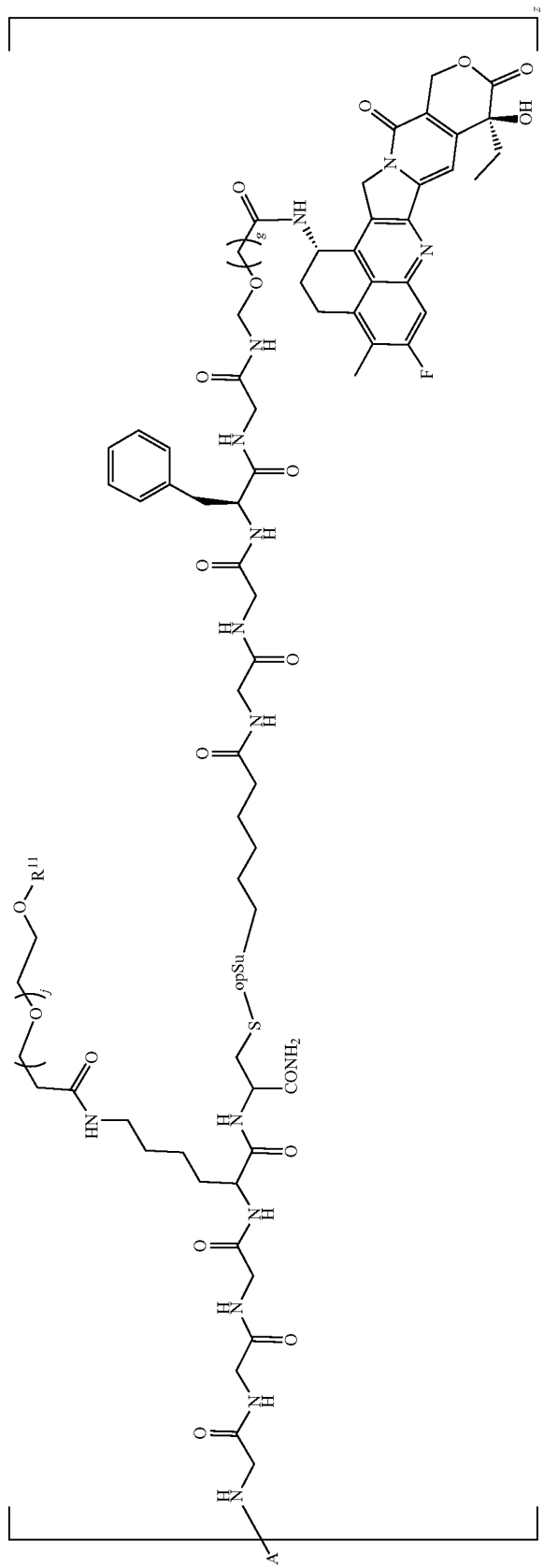

In one embodiment, conjugate LC302-2 has the structure of:

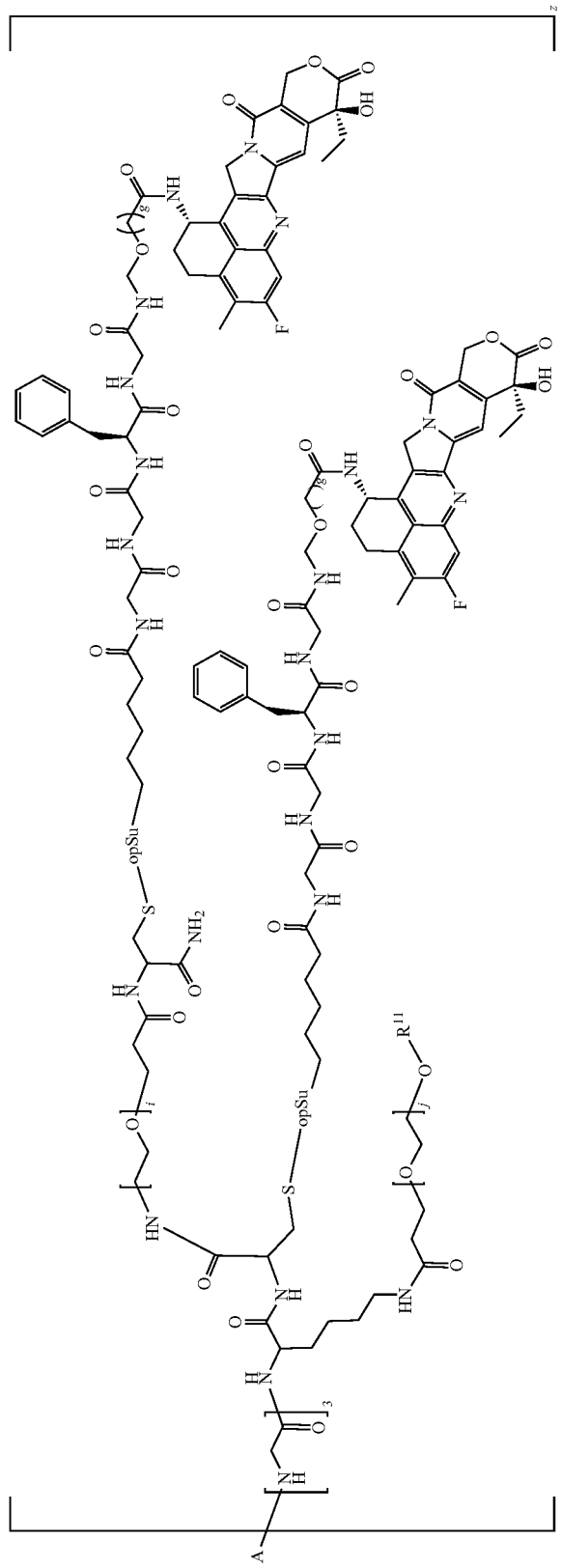

In one embodiment, conjugate LC302-3 has the structure of:

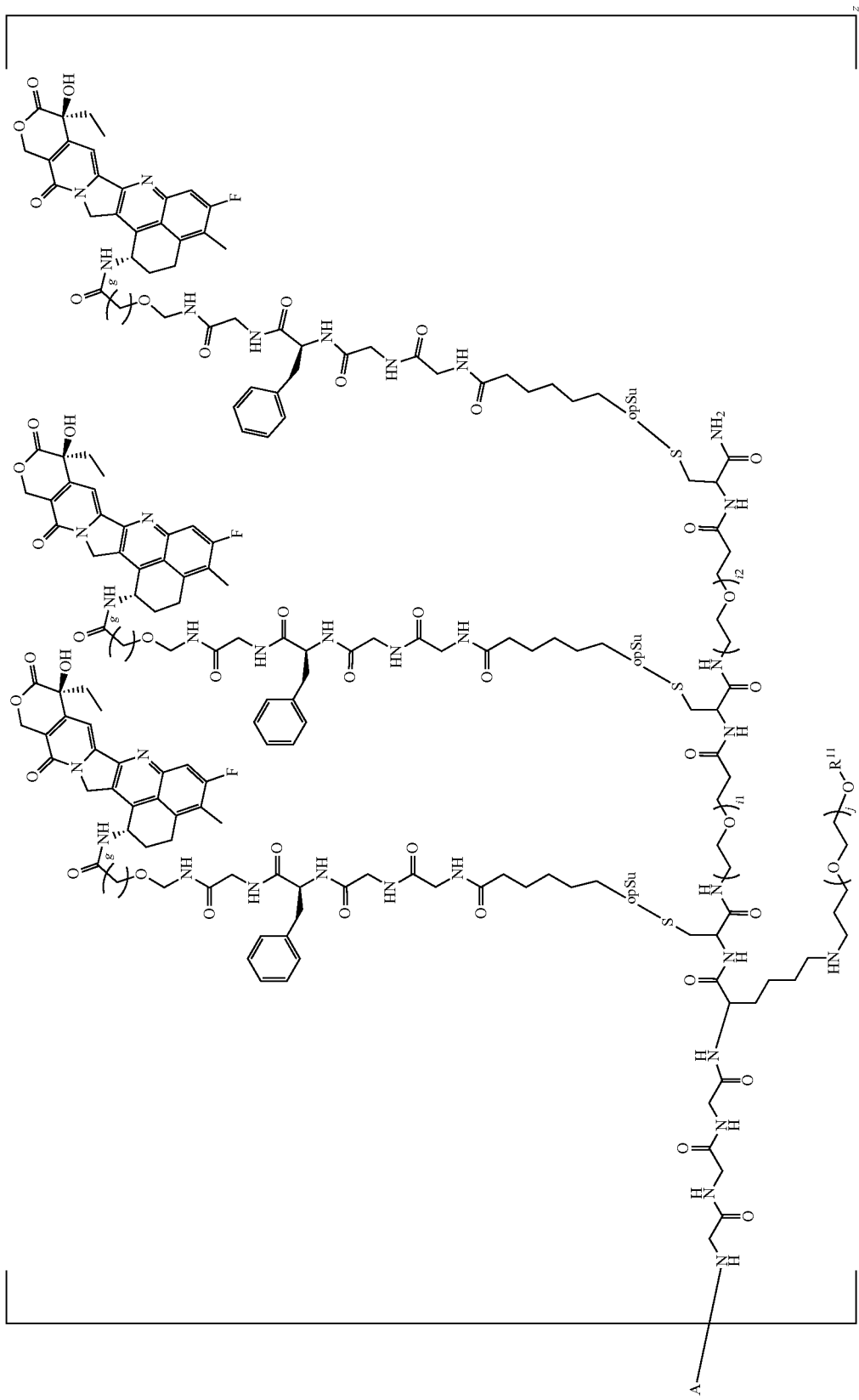

In one embodiment, conjugate LC302-4 has the structure of:

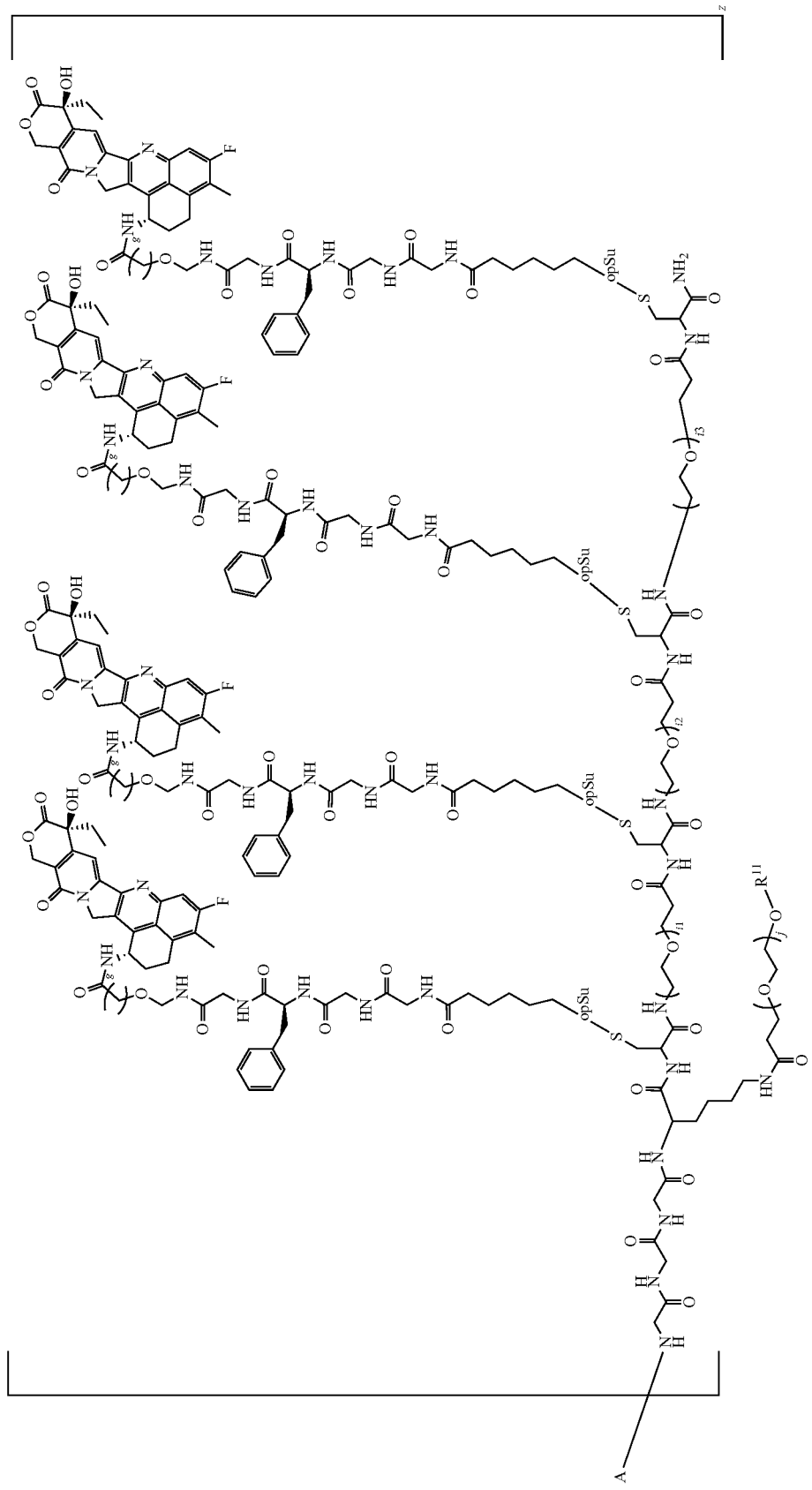

In an embodiment, i is 4, g is 1, $R^{11}$ is methyl.

In an embodiment, conjugate LC301-2 is as follows (conjugate LC301-2-1):

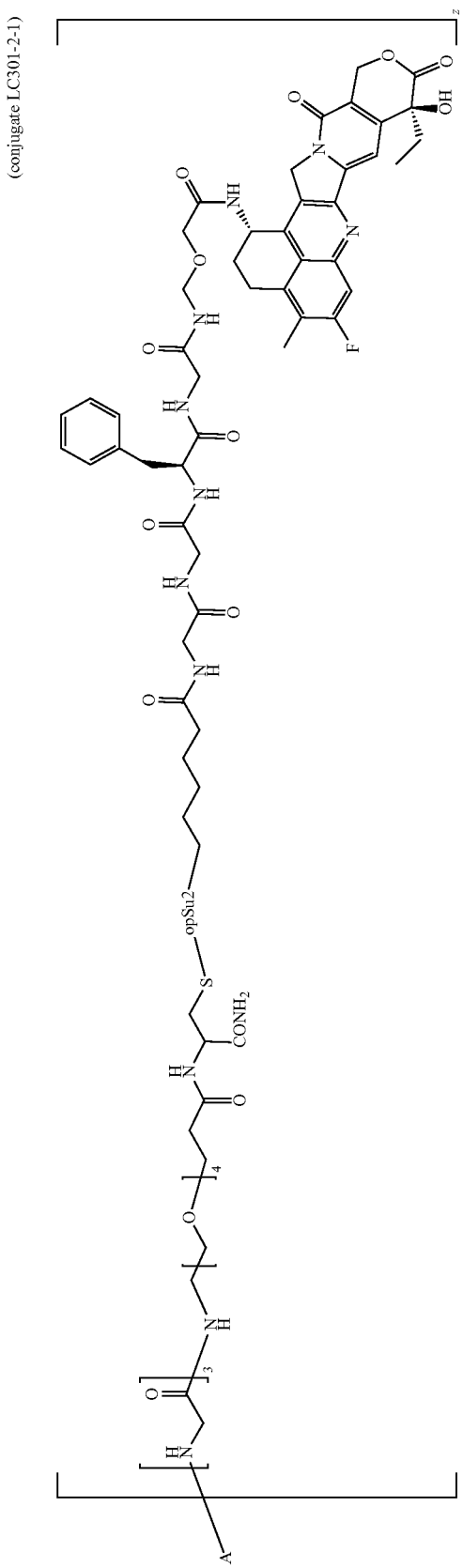

In an embodiment, i is 4, j is 8, g is 1, $R^{11}$ is methyl. In an embodiment, conjugate LC302-2 is as follows (conjugate LC302-2-1):

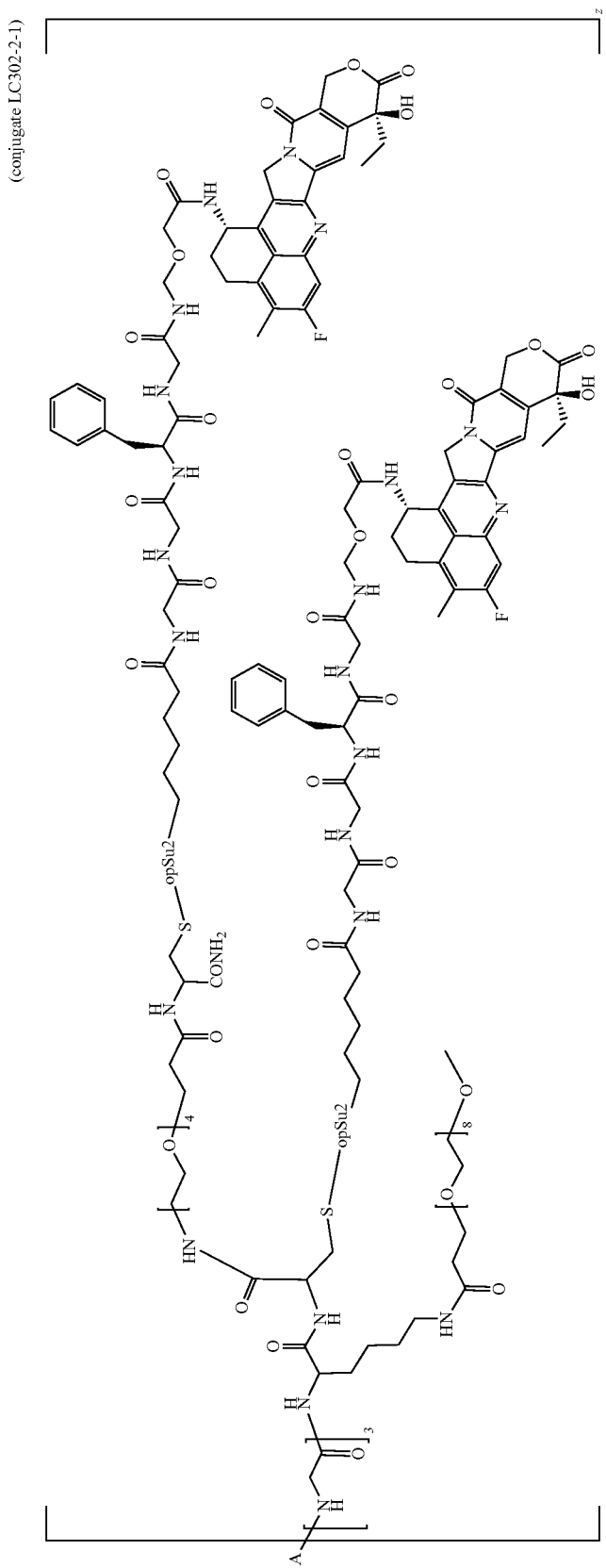

In an embodiment, i is 4, j is 12, g is 1, $R^{11}$ is methyl. In an embodiment, conjugate LC302-2 is as follows (conjugate LC302-2-4):

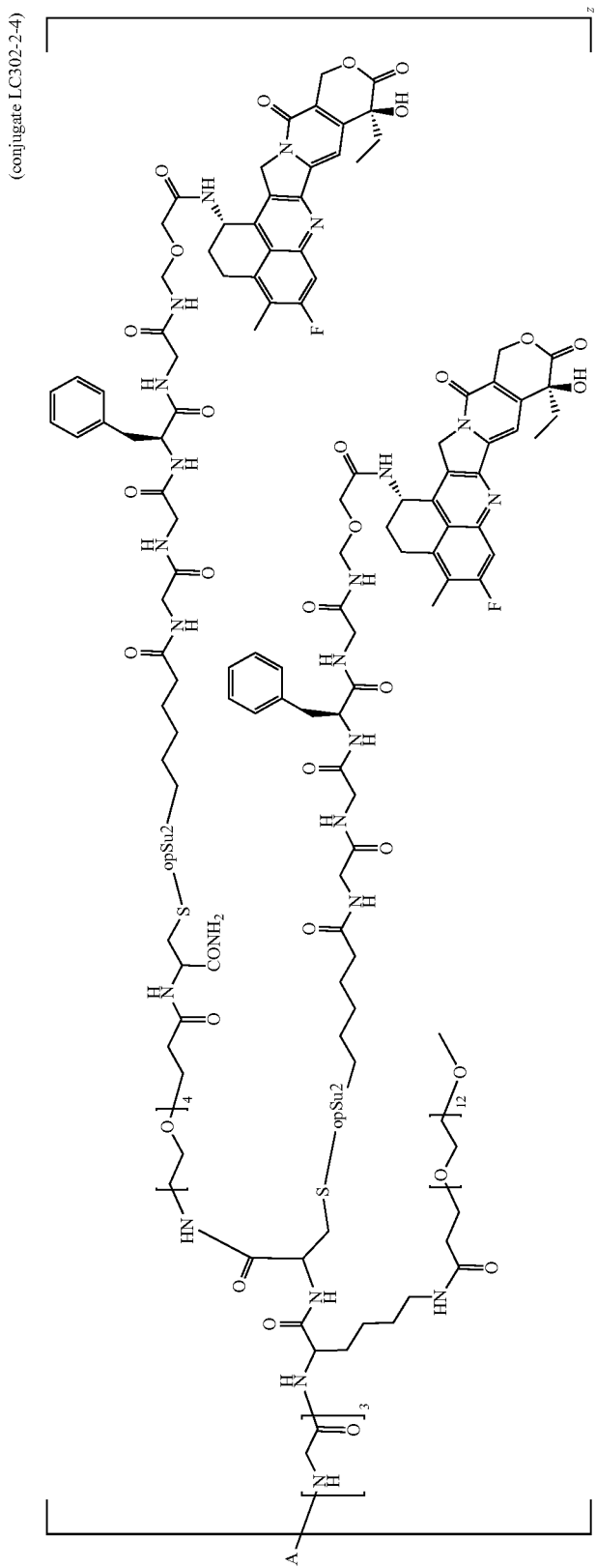

Preparation of the Conjugate

The conjugates of the present disclosure can be prepared by any method known in the art. In some embodiments, the conjugate is prepared by the ligase-catalyzed site-specific conjugation of a targeting molecule and a payload-bearing formula (I) compound, wherein the targeting molecule is modified by a ligase recognition sequence. The method comprises step A and step B.

Step A. Preparation of the Linking Unit-Payload Intermediate

In a preferred embodiment, B in the compound of formula (I) is covalently linked via a reactive group to a payload containing another reactive group.

The linking unit-payload intermediate prepared using the compound of formula (I) of the present disclosure has defined structure, defined composition and high purity, so that when the conjugation reaction with an antibody is conducted, fewer impurities are introduced or no other impurities are introduced. When such an intermediate is used for the ligase-catalyzed site-specific conjugation with a modified antibody containing a ligase recognition sequence, a homogeneous ADC with highly controllable quality is obtained.

Step B. Linking the Targeting Molecule to the Payload-Bearing Formula (I) Compound The targeting molecule of the present disclosure can be conjugated with the payload-bearing formula (I) compound (i.e., the compound of formula (II)) by any method known in the art.

The targeting molecule and the payload-bearing formula (I) compound are linked to each other via the ligase-specific recognition sequences of the substrates. The recognition sequence depends on the particular ligase employed. In one embodiment, the targeting molecule is an antibody with recognition sequence-based terminal modifications introduced at the C-terminal of the light chain and/or the heavy chain, and the targeting molecule is conjugated with the compound of formula (II), under the catalysis of the wild type or optimized engineered ligase or any combination thereof, and under suitable catalytic reaction conditions.

In a specific embodiment, the ligase is Sortase A and the conjugation reaction can be represented by the following scheme:

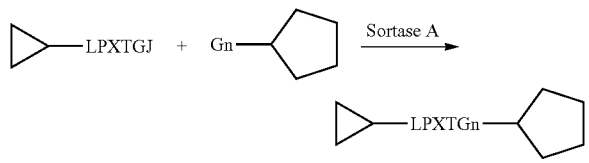

The triangle represents a portion of an antibody; and the pentagon represents a portion of a compound of formula (II). n, X and J are respectively as defined above. When conjugated with $G_n$, which is the corresponding recognition sequence of the acceptor substrate, the upstream peptide bond of the glycine in the LPXTGJ sequence is cleaved by Sortase A, and the resulting intermediate is linked to the free N-terminal of $G_n$ to generate a new peptide bond. The resulting amino acid sequence is $LPXTG_n$. The sequences $G_n$ and LPXTGJ are as defined above.

Metabolism of the Conjugate in a Physiological Environment

When a part or whole linker is cleaved in tumor cells, the antitumor compound moiety is released to exhibit the antitumor effect of the antitumor compound. As the linker is cleaved at a connecting position to drug, the antitumor compound is released in its intrinsic structure to exhibit its intrinsic antitumor effect.

In an embodiment, Cleavable sequence 1 (such as GGFG (SEQ ID NO: 8)) can be cleaved by lysosomal enzymes (such as cathepsin B and/or cathepsin L).

In an embodiment, Sp1 comprises a self-immolative spacer. In an embodiment, Sp1 comprises PABC, an acetal or a heteroacetal. In an embodiment, $L^1$ is GGFG (SEQ ID NO: 8). In an embodiment, the linker comprises -GGFG-NH—CH$_2$—O—. In an embodiment, -GGFG-NH—CH$_2$—O— represents a combination of a restriction enzyme site and a self-immolative spacer, which would cleave in the cell and release the aimed molecule (such as the drug).

Table of Specific Conjugates

In one embodiment, the payload is a cytotoxin or a fragment thereof. In one embodiment, the antibody is a modified Trastuzumab, preferably Ab0001-LCCT$_L$-HC (light chain SEQ ID NO: 1, heavy chain: SEQ ID NO: 2) or Ab0001-LCCT$_L$-HCCT$_L$ (light chain SEQ ID NO: 3, heavy chain: SEQ ID NO: 4). The sequence of each of Ab0001-LCCT$_L$-HC and Ab0001-LCCT$_L$-HCCT$_L$ is based on the amino acid sequence of Ab0001 (Trastuzumab), and GAL-PETGG (SEQ ID NO: 18) was introduced at the C-terminal of the light chain (Ab0001-LCCT$_L$-HC) or at the C-terminal of the light chain and the heavy chain (Ab0001-LCCT$_L$-HCCT$_L$), wherein LPETGG (SEQ ID NO: 13) is the recognition sequence of the ligase donor substrate, and GA is a spacer sequence. In Ab0001-LCCT$_L$-HCCT$_L$, the lysine at the C-terminal of the heavy chain of Ab0001 can be maintained as in SEQ ID NO: 4 or removed (resulting sequence not shown in the sequence list) before the GALPETGG (SEQ ID NO: 18) is introduced. In one embodiment, the antibody-drug conjugate is as shown in the following table.

Nomenclature of the ADCs: the number in the parenthesis indicates the number of payload (drug) molecules that is intended to be connected to the antibody.

| ADC | Linker-Payload formula | Palyload | A (targeting molecule) |
|---|---|---|---|
| LC301-1-1(2) | LB301-1-1 | compound 10 | Ab0001-LCCT$_L$-HC |
| LC301-1-1(4) | LB301-1-1 | compound 10 | Ab0001-LCCT$_L$-HCCT$_L$ |
| LC301-2-1(2) | LB301-2-1 | compound 10 | Ab0001-LCCT$_L$-HC |
| LC301-2-1(4) | LB301-2-1 | compound 10 | Ab0001-LCCT$_L$-HCCT$_L$ |
| LC301-3-1(4) | LB301-3-1 | compound 10 | Ab0001-LCCT$_L$-HC |
| LC301-4-1(6) | LB301-4-1 | compound 10 | Ab0001-LCCT$_L$-HC |
| LC301-5-1(8) | LB301-5-1 | compound 10 | Ab0001-LCCT$_L$-HC |
| LC302-1-1(2) | LB302-1-1 | compound 10 | Ab0001-LCCT$_L$-HC |
| LC302-1-1(4) | LB302-1-1 | compound 10 | Ab0001-LCCT$_L$-HCCT$_L$ |
| LC302-1-4(2) | LB302-1-4 | compound 10 | Ab0001-LCCT$_L$-HC |
| LC302-1-4(4) | LB302-1-4 | compound 10 | Ab0001-LCCT$_L$-HCCT$_L$ |
| LC302-2-1(4) | LB302-2-1 | compound 10 | Ab0001-LCCT$_L$-HC |
| LC302-2-4(4) | LB302-2-4 | compound 10 | Ab0001-LCCT$_L$-HC |
| LC302-3-1(6) | LB302-3-1 | compound 10 | Ab0001-LCCT$_L$-HC |
| LC302-3-4(6) | LB302-3-4 | compound 10 | Ab0001-LCCT$_L$-HC |
| LC302-4-1(8) | LB302-4-1 | compound 10 | Ab0001-LCCT$_L$-HC |
| LC302-4-4(8) | LB302-4-4 | compound 10 | Ab0001-LCCT$_L$-HC |

Pharmaceutical Composition and Pharmaceutical Preparation

Another object of the disclosure is to provide a pharmaceutical composition comprising a prophylactically or therapeutically effective amount of a conjugate of the present disclosure, and at least one pharmaceutically acceptable carrier.

The pharmaceutical composition of the present disclosure may be administered in any manner as long as it achieves the effect of preventing, alleviating, preventing or curing the symptoms of a human or animal. For example, various suitable dosage forms can be prepared according to the administration route, especially injections such as lyophilized powder for injection, injection, or sterile powder for injection.

The term "pharmaceutically acceptable" means that when contacted with tissues of the patient within the scope of normal medical judgment, no undue toxicity, irritation or allergic reaction, etc. shall arise, having reasonable advantage-disadvantage ratios and effective for the intended use.

The term pharmaceutically acceptable carrier refers to those carrier materials which are pharmaceutically acceptable and which do not interfere with the bioactivities and properties of the conjugate. Examples of aqueous carriers include but are not limited to buffered saline, and the like. The pharmaceutically acceptable carrier also includes carrier materials which brings the composition close to physiological conditions, such as pH adjusting agents, buffering agents, toxicity adjusting agents and the like, and sodium acetate, sodium chloride, potassium chloride, calcium chloride, sodium lactate, and the like.

In one embodiment, the pharmaceutical composition of the present disclosure has a drug to antibody ratio (DAR) of an integer or non-integer of about 1 to about 20, such as about 1 to about 10, about 1 to about 8, about 1 to about 6, about 1 to about 4, about 1 to about 3, about 1 to about 2.5, about 1 to about 2. In a particular embodiment, the conjugate of the present disclosure has a DAR of about 2, about 4, about 6 or about 8.

Treatment Method and Use

The conjugates of the present disclosure are useful for the treatment of tumors and/or autoimmune diseases. Tumors susceptible to conjugate treatment include those characterized by specific tumor-associated antigens or cell surface receptors, and those will be recognized by the targeting molecule in the conjugate and can be killed by the payload/cytotoxin in the conjugate.

Accordingly, in yet another aspect, also provided is use of a conjugate of the present disclosure or a pharmaceutical composition of the present disclosure in the manufacture of a medicament for treating a disease, disorder or condition selected from a tumor or an autoimmune disease.

In another aspect, provided is a conjugate of the present disclosure or a pharmaceutical composition of the present disclosure for use in the treatment of a tumor or an autoimmune disease.

In a further aspect, provided is a method of treating a tumor or an autoimmune disease, the method comprising administering to an individual in need thereof an effective amount of a conjugate of the present disclosure or a pharmaceutical composition of the present disclosure In a preferred embodiment, the conjugate of the present disclosure formed by conjugation of the anti-human HER2 antibody and the small molecule cytotoxin can specifically bind to HER2 on the surface of the tumor cell and selectively kill the HER2-expressing tumor cells. In another preferred embodiment, provided is use of a conjugate of the present disclosure or a pharmaceutical composition of the present disclosure in the manufacture of a medicament for treating a disease, disorder or condition selected from HER2-positive tumors. In a more preferred embodiment, the disease, disorder or condition is selected from the group consisting of breast cancer, gastric cancer, lung cancer, ovarian cancer, urothelial cancer, and the like.

The dosage of the conjugate administered to the subject can be adjusted to a considerable extent. The dosage can vary according to the particular route of administration and the needs of the subject, and can be subjected to the judgment of the health care professional.

As defined above, the embodiments of the present disclosure can also be described as follows:

[1] A compound of formula (I'):

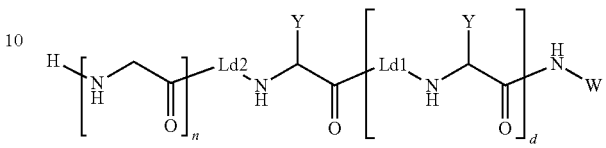

wherein,
W is hydrogen or is LKb;
Y is hydrogen or is LKa-LKb;
provided that W and Y are not simultaneously hydrogen;
each LKa is independently selected from

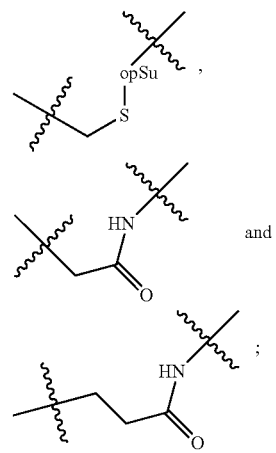

opSu is

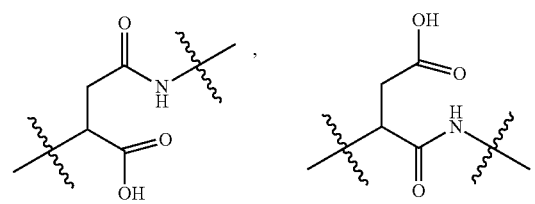 [SMILES: *NC(=O)CC(*)C(=O)O ; *NC(=O)C(*)CC(=O)O]

or a mixture thereof;
each LKb is independently $L^2$-$L^1$-B;
each B is independently a terminal group $R^{10}$, or a combination of 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$;
$R^{10}$ is hydrogen, or a group which can leave when reacting with a group in the payload;
$L^1$ is Cleavable sequence 1 comprising an amino acid sequence which can be cleaved by enzyme, and Cleavable sequence 1 comprises 1-10 amino acids;
$L^2$ is a bond; or a $C_{2-20}$ alkylene wherein one or more —$CH_2$— structures in the alkylene is optionally replaced by —CR³R⁴—, —O—, —(CO)—, —S(=O)₂—, —NR⁵—, —N⊕R⁶R⁷—, $C_{4-10}$ cycloalkylene, $C_{4-10}$ heterocyclylene, phenylene; wherein the cycloalkylene, heterocyclylene and phenylene are each independently unsubstituted or substituted with at least one substituent selected from halogen, —$C_{1-10}$ alkyl, —$C_{1-10}$ haloalkyl, —$C_{1-10}$ alkylene-NH—R⁸ and —$C_{1-10}$ alkylene-O—R⁹;

Ld2 and each Ld1 are independently a bond; or selected from —NH—$C_{1-20}$ alkylene-(CO)—, —NH-(PEG)$_i$-(CO)—, or is a natural amino acid or oligomeric natural amino acids having a degree of polymerization of 2-10 independently unsubstituted or substituted with -(PEG)$_j$-R¹¹ on the side chain;

-(PEG)$_i$- and -(PEG)$_j$- are each a PEG fragment, which comprises the denoted number of consecutive —(O—C₂H₄)— structure units or consecutive —(C₂H₄—O)— structure units, with an optional additional $C_{1-10}$ alkylene at one terminal;

R¹, R², R³, R⁴, R⁵, R⁶, R⁷, R⁸, R⁹ are each independently selected from hydrogen, halogen, —$C_{1-10}$ alkyl, —$C_{1-10}$ haloalkyl, $C_{4-10}$ cycloalkylene;

R¹¹ is $C_{1-10}$ alkyl;

n is any integer of 2 to 20;

d is 0, or is any integer of 1 to 6;

each i is independently an integer of 1-100, preferably 1 to 20; preferably each i is independently an integer of 1 to 12; more preferably 2 to 8; particularly 4;

each j is independently an integer of 1-100, preferably 1 to 20; preferably each j is independently an integer of 1 to 12; more preferably 8 to 12; particularly 8 or 12.

[2] The compound of the above [1], selected from

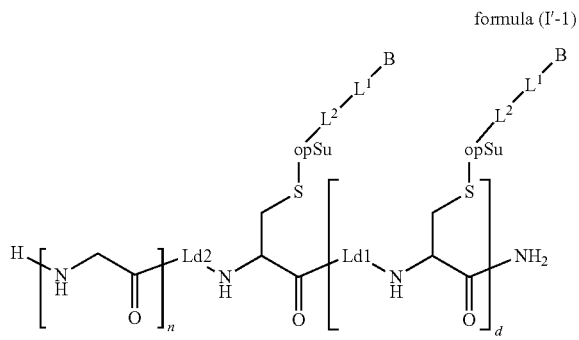

formula (I'-1)

[3] The compound of any one of the above [1]-[2], selected from

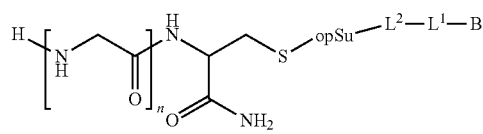

(linker LA'301-1)

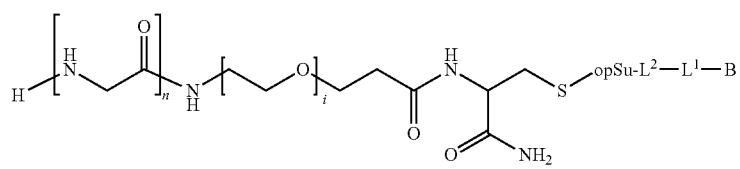

(linker LA'301-2)

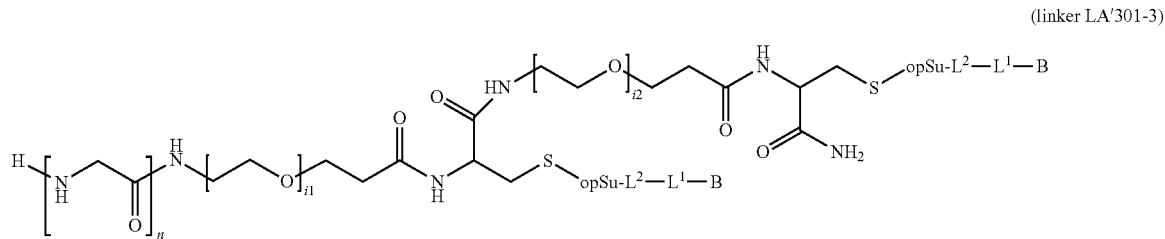

(linker LA'301-3)

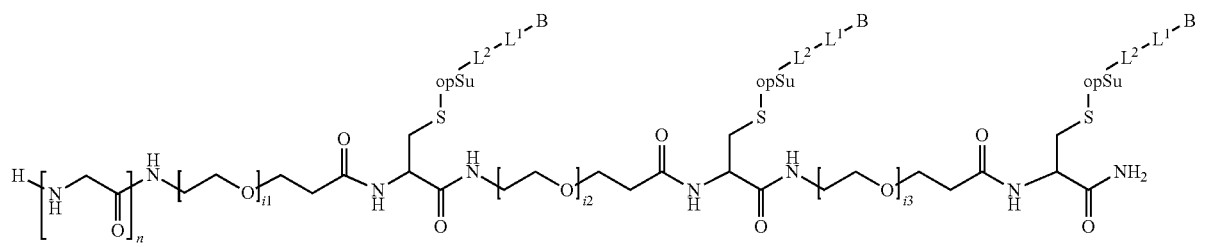

(linker LA'301-4)

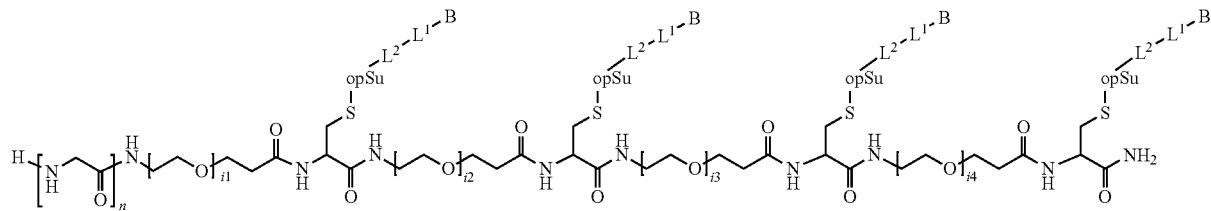
(linker LA'301-5)
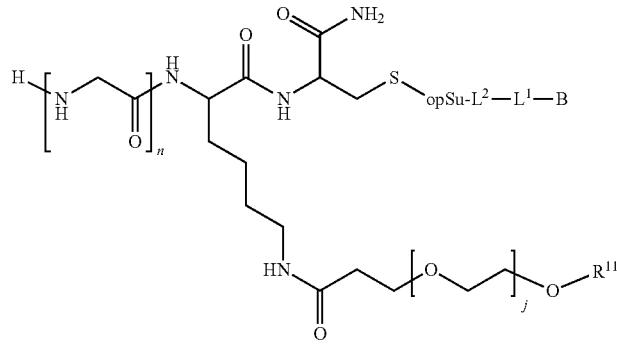
(linker LA'302-1)
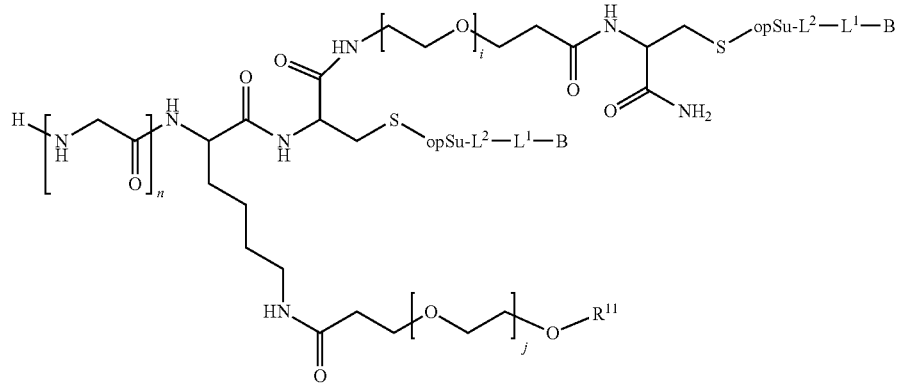
(linker LA'302-2)
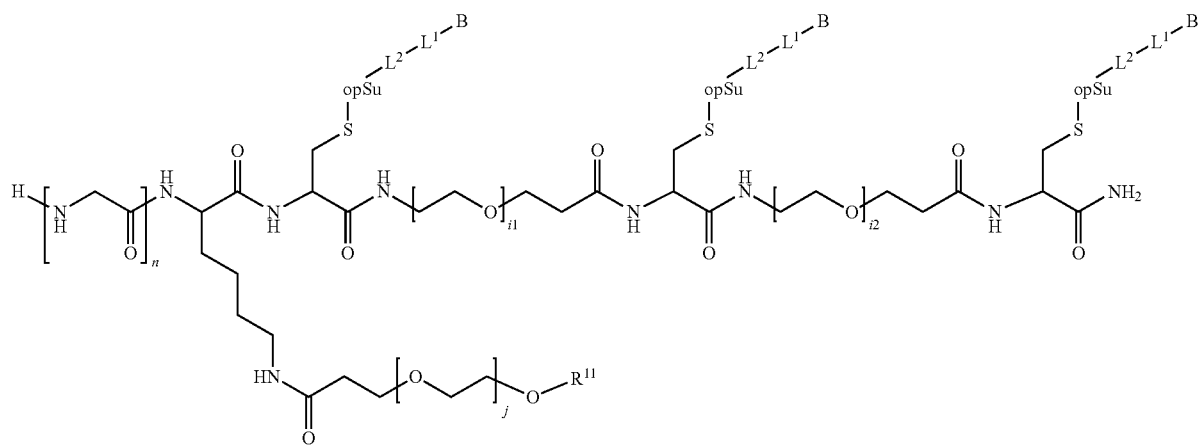
(linker LA'302-3)

(linker LA'302-4)

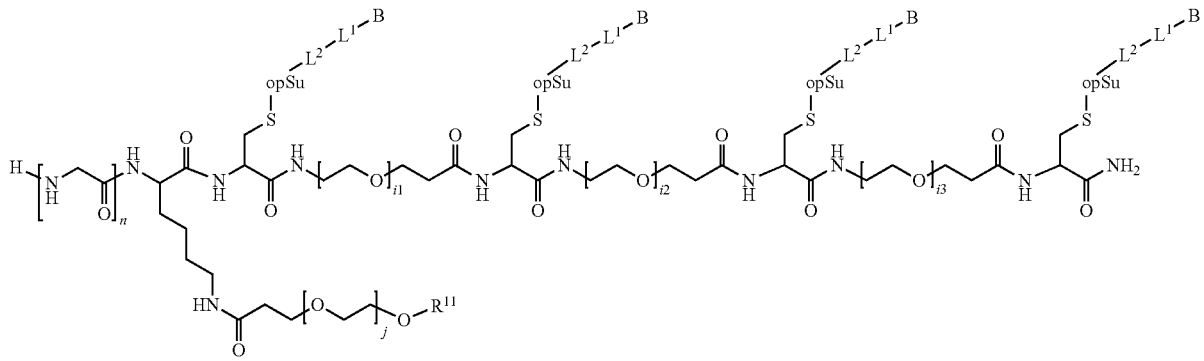

wherein, each i, i1, i2, i3, i4 is independently an integer of 1-100, preferably 1 to 20; preferably each i, i1, i2, i3, i4 is independently an integer of 1 to 12; more preferably 2 to 8; particularly 4.

[4] The compound of any one of the above [1]-[2], wherein

Ld2 and each Ld1 are independently a bond or

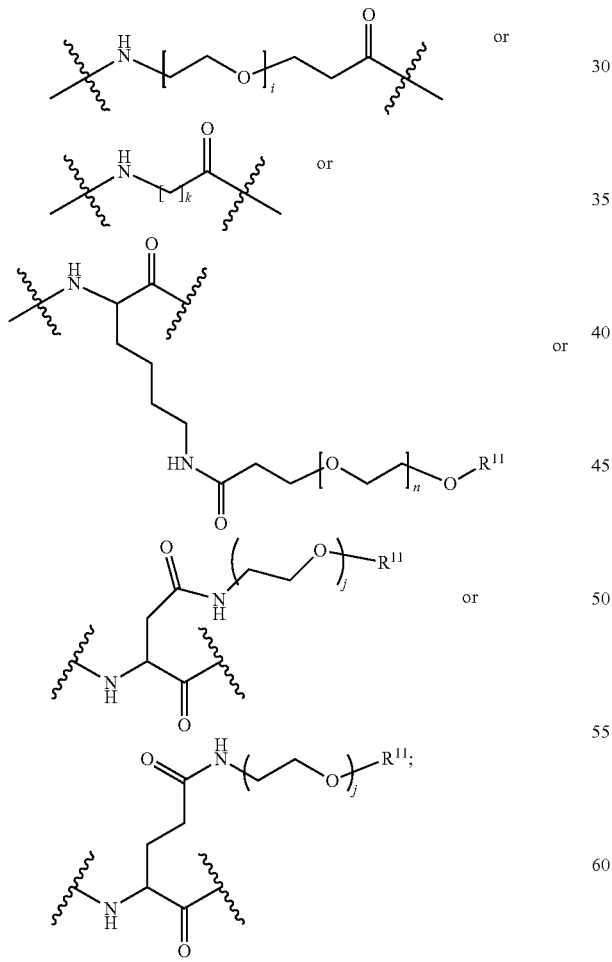

each k is independently an integer of 1-100, preferably 1 to 20; preferably each k is independently an integer of 1 to 12; more preferably 1 to 7; particularly 1, or 3 or 5.

[5] The compound of any one of the above [1]-[4], wherein

Cleavable sequence 1 is selected from GLy-GLy-Phe-GLy (SEQ ID NO: 8), Phe-Lys, Val-Cit, Val-Lys, GLy-Phe-Leu-Gly (SEQ ID NO: 9), Ala-Leu-Ala-Leu (SEQ ID NO: 10), Ala-Ala-Ala and the combination thereof, preferably, Cleavable sequence 1 is GLy-GLy-Phe-Gly (SEQ ID NO: 8);

and/or

Sp1 is selected from PABC, acetal, heteroacetal and the combination thereof, preferably, Sp1 is acetal, heteroacetal or PABC; preferably, the heteroacetal is selected from N,O-heteroacetal; preferably, Sp1 is —O—CH$_2$—U— or —NH—CH$_2$—U—; wherein the —O— or the —NH— is connected to Cleavable sequence 1, and U is O, S or N, preferably O or S.

[6] The compound of any one of the above [1]-[5], wherein

W is hydrogen; and/or

R$^{10}$ is hydrogen, hydroxy, or

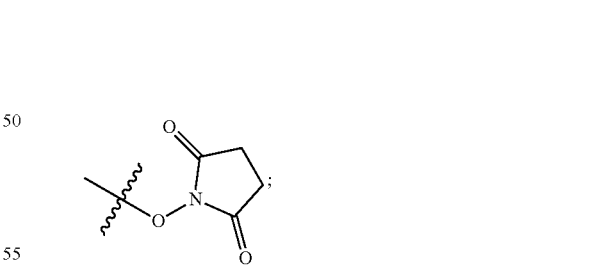

R$^{11}$ is C$_{1-6}$ alkyl, preferably methyl; and/or n is an integer of 2 to 5, especially 3; and/or d is 0, or is any integer of 1 to 4; preferably 0, 1, 2 or 3.

[7] The compound of any one of the above [1]-[6], selected from

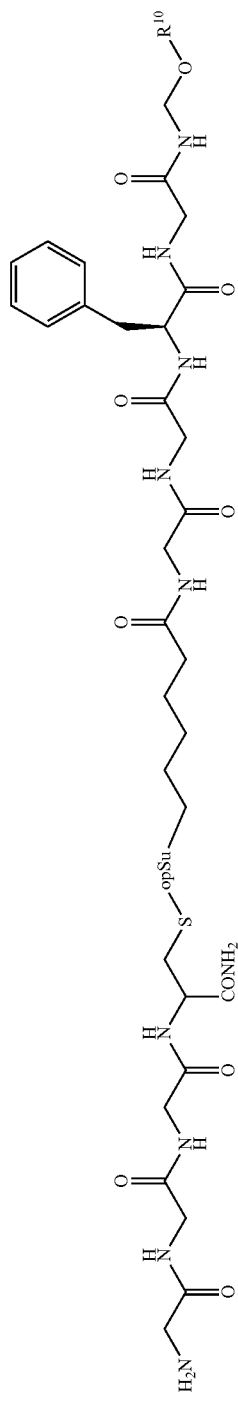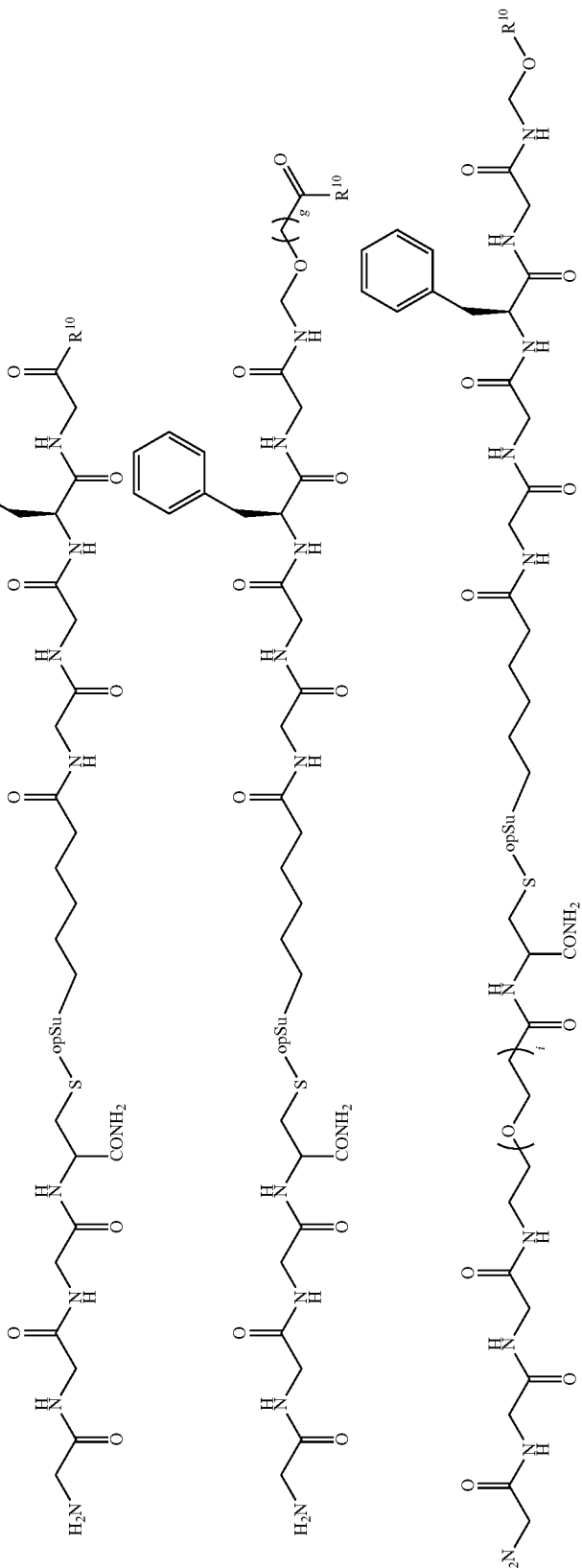

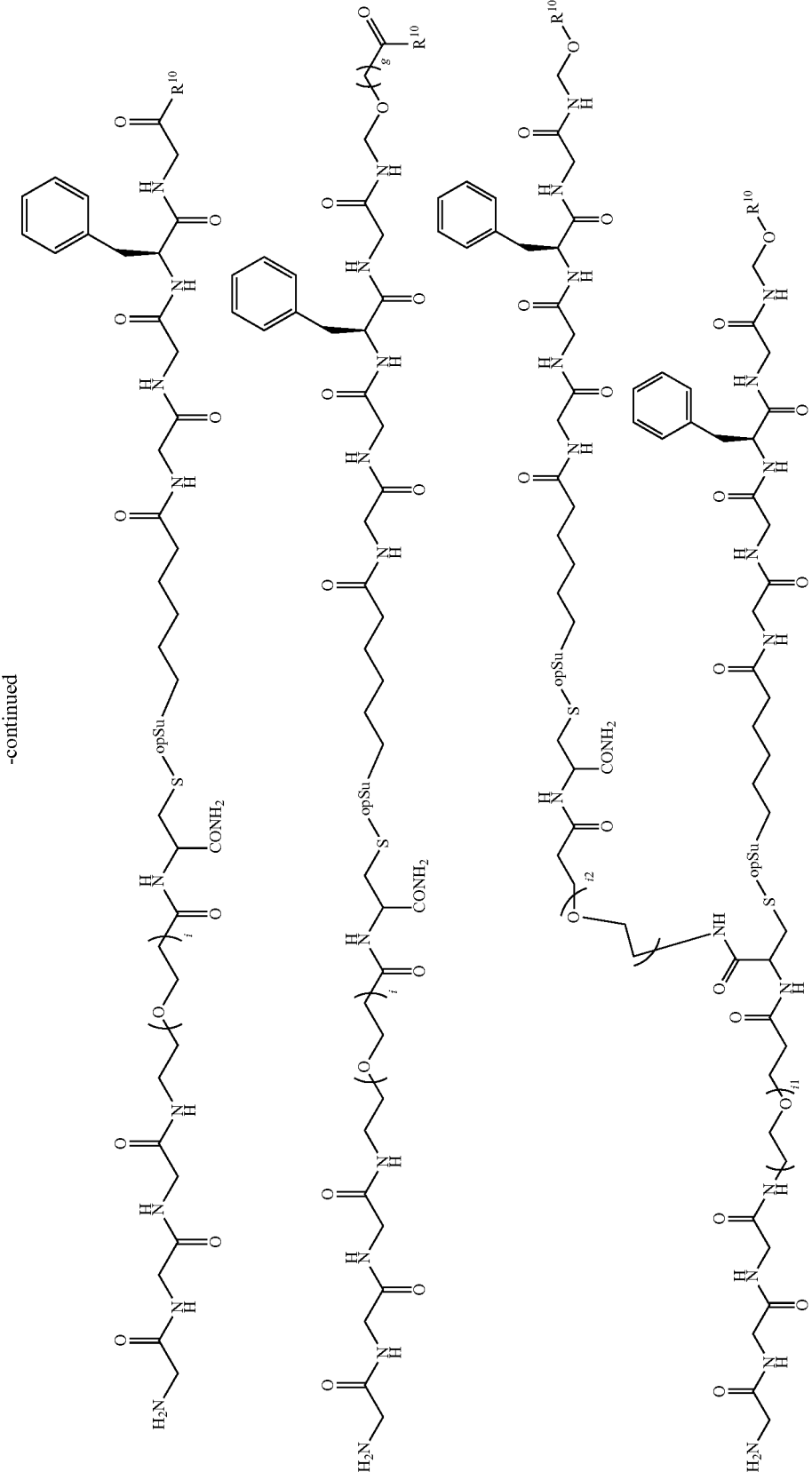

-continued
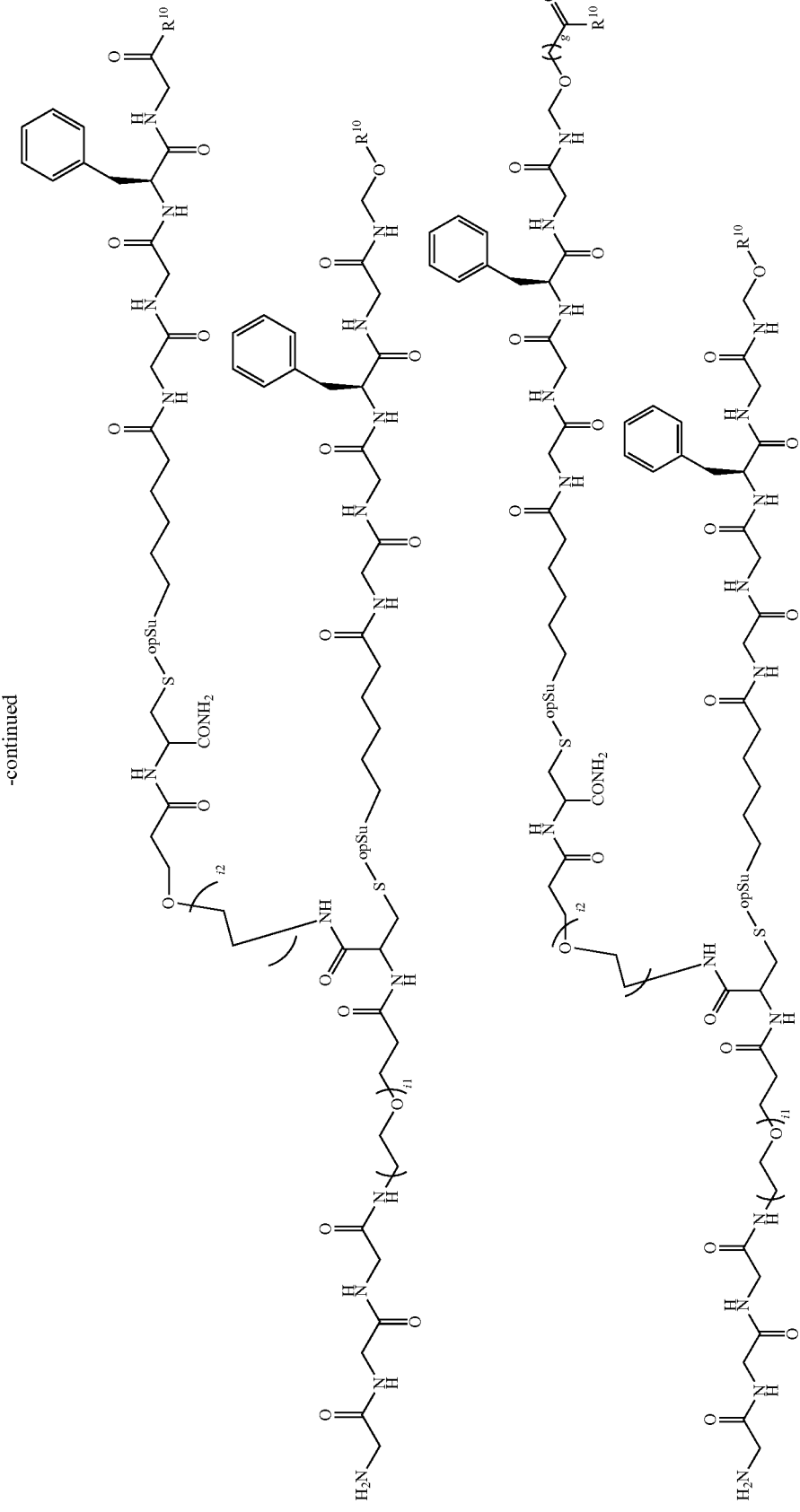

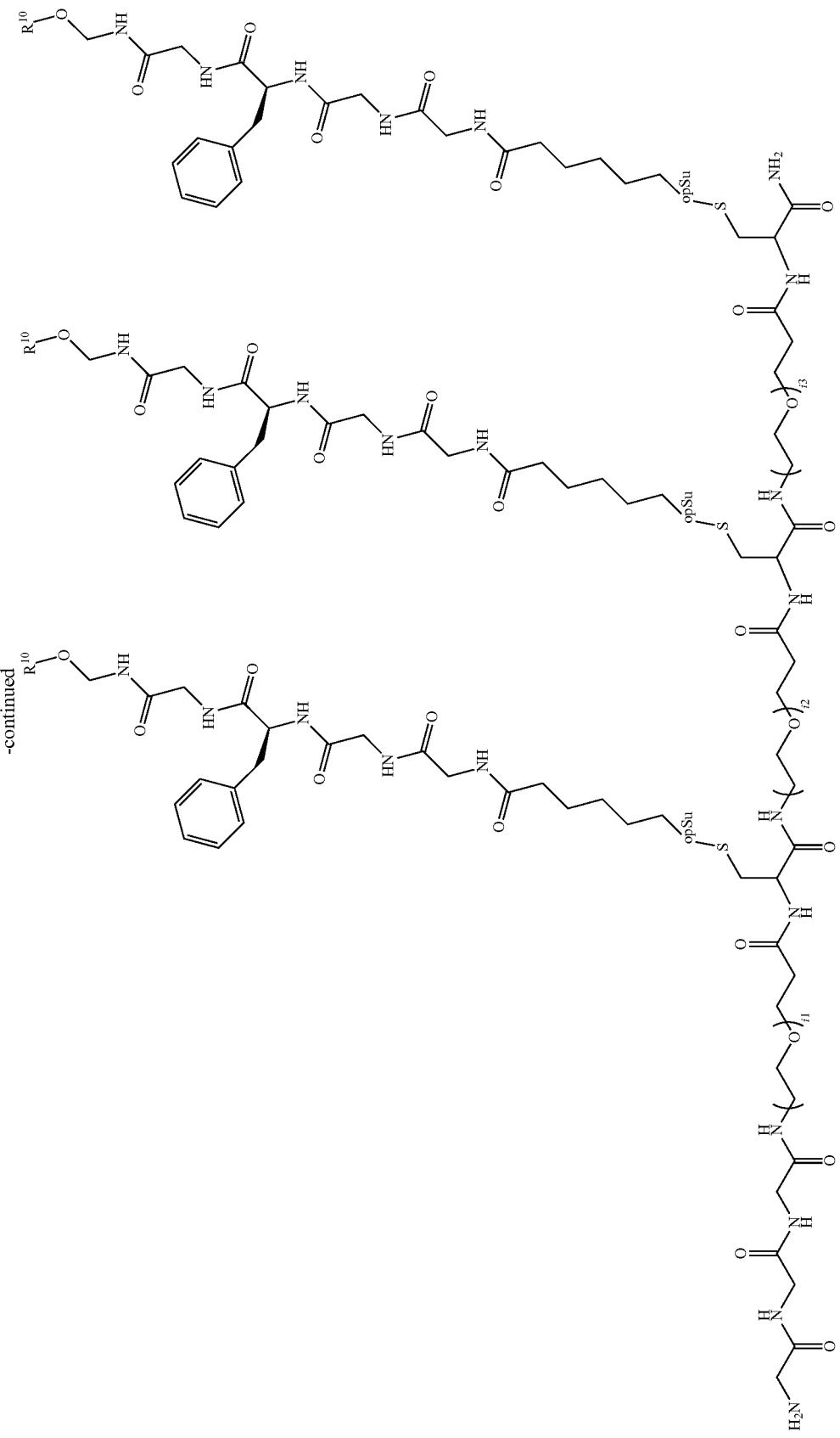

-continued
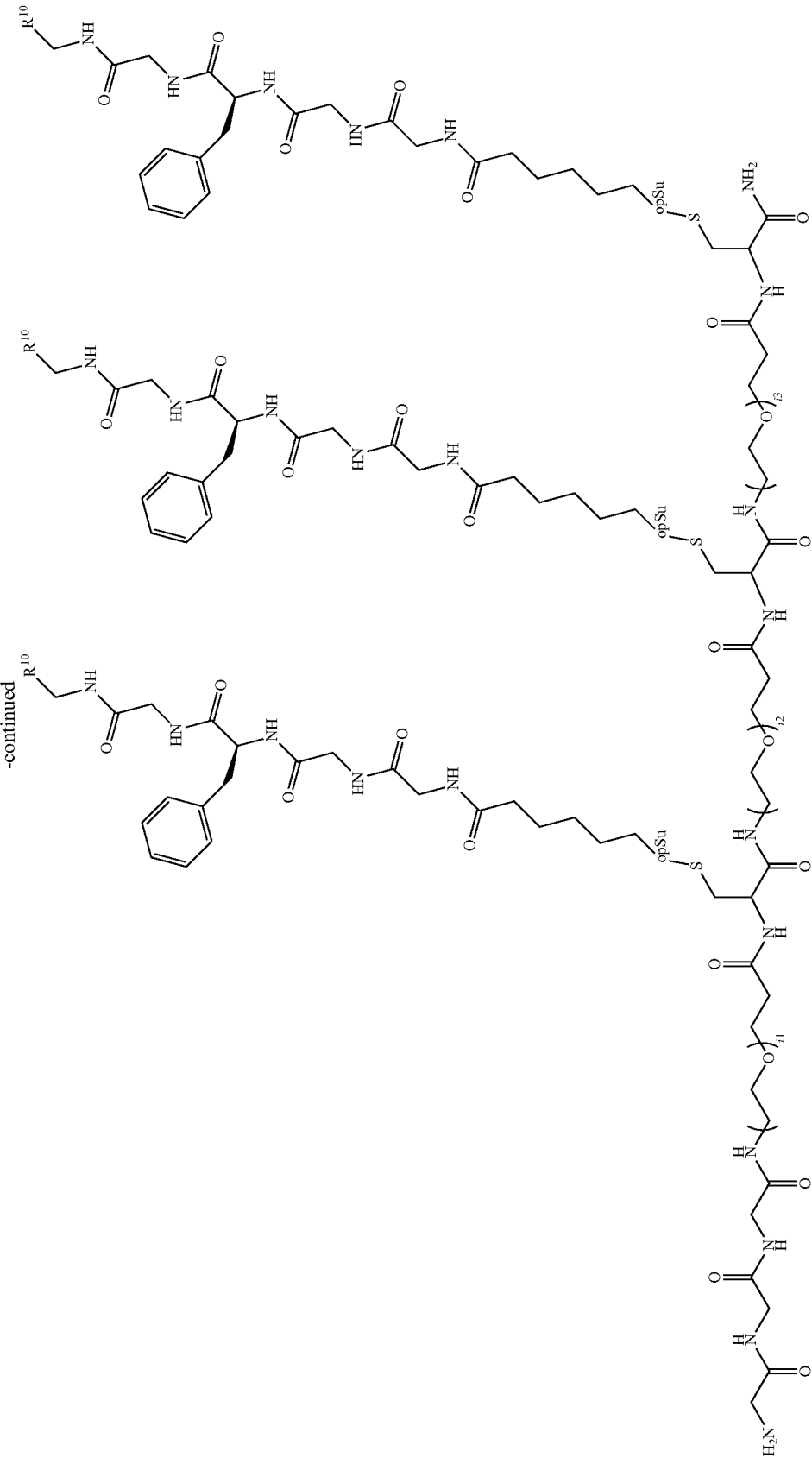

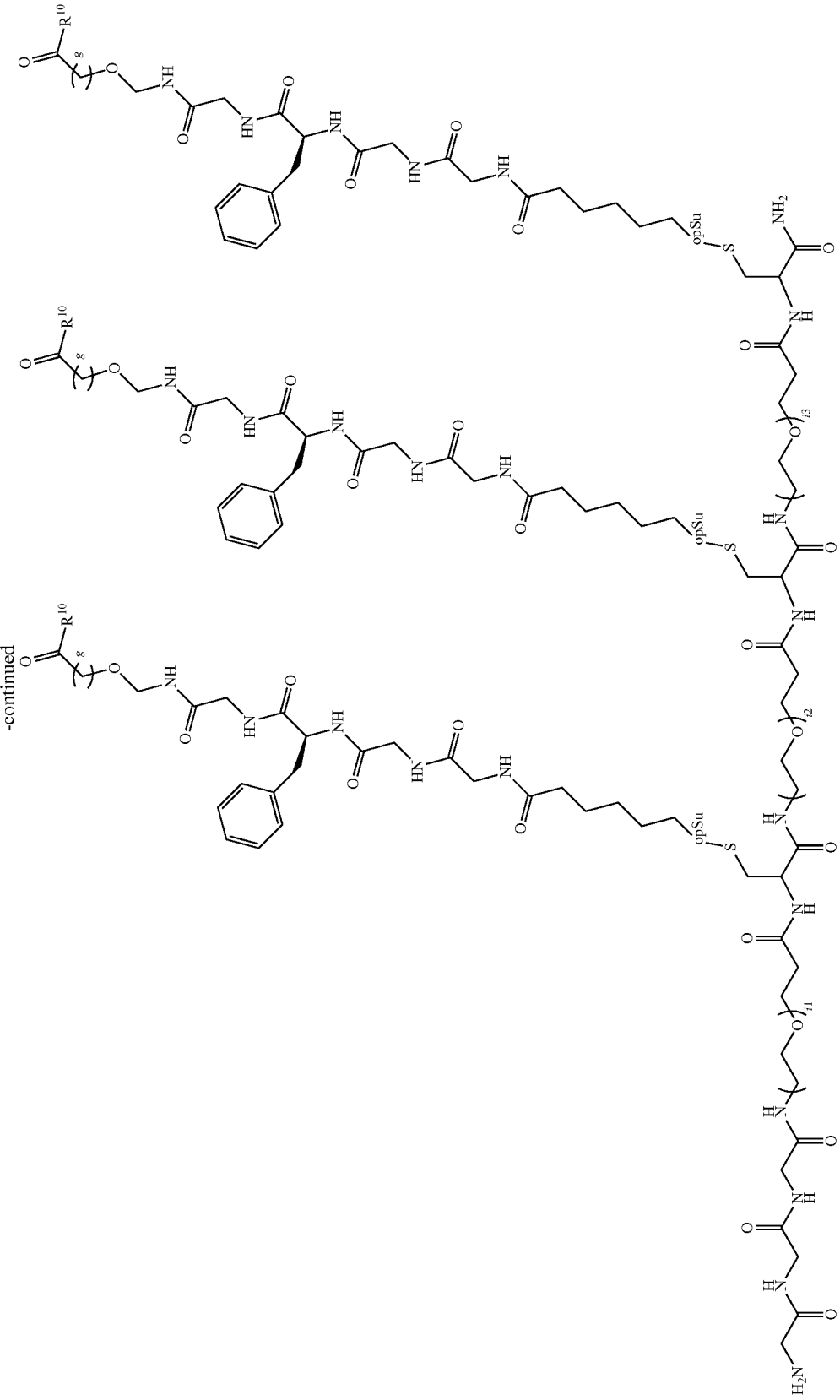

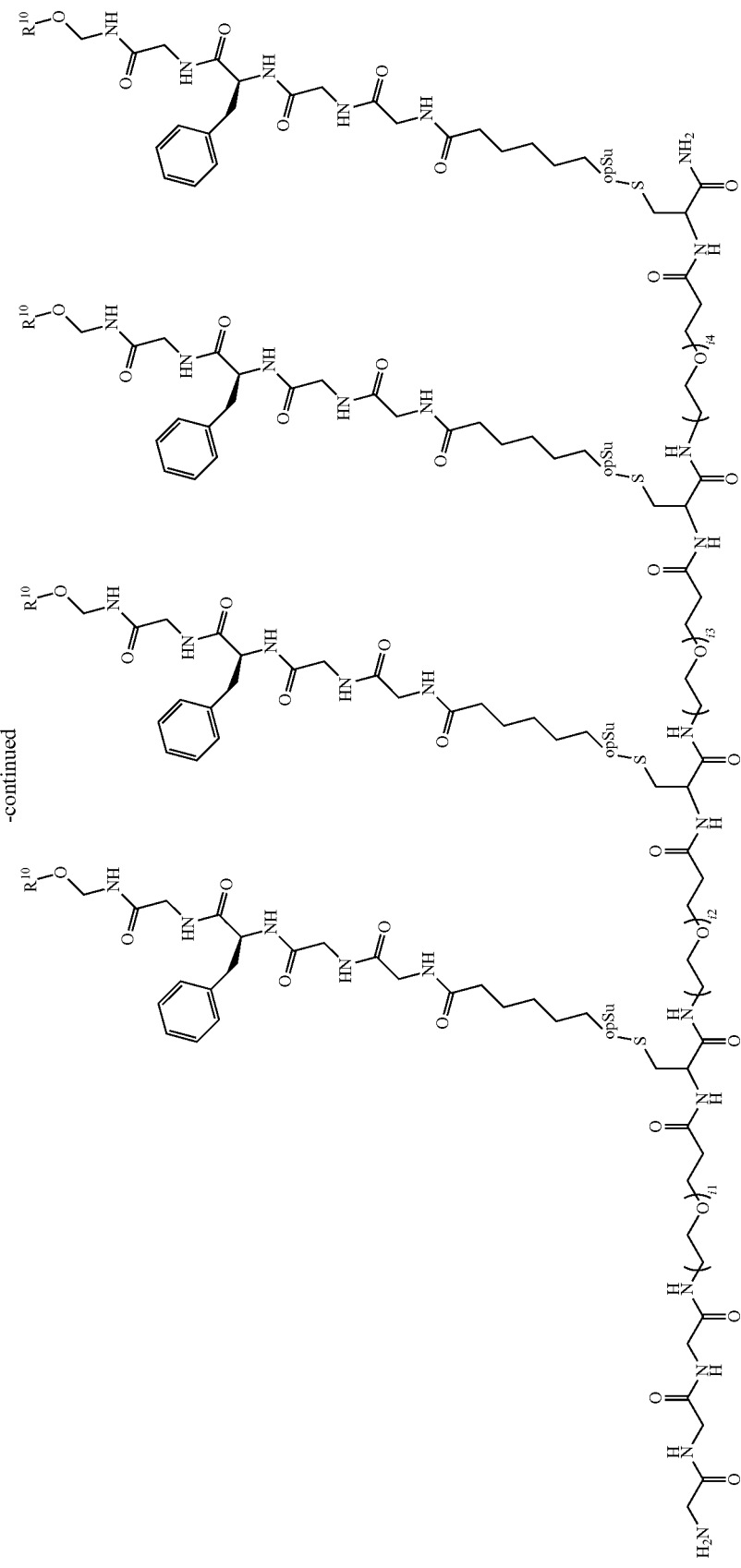

-continued
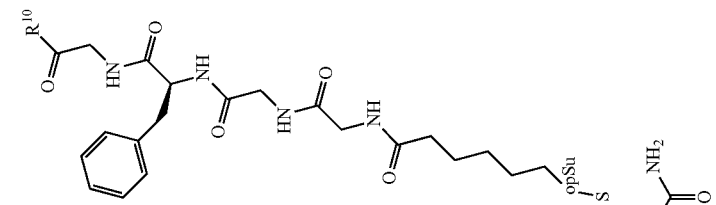
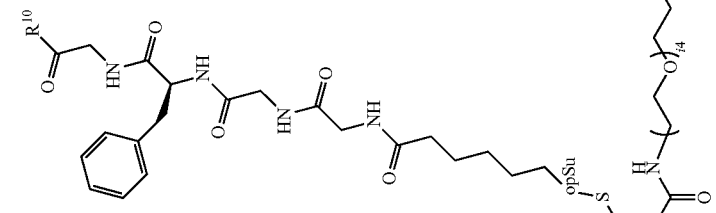
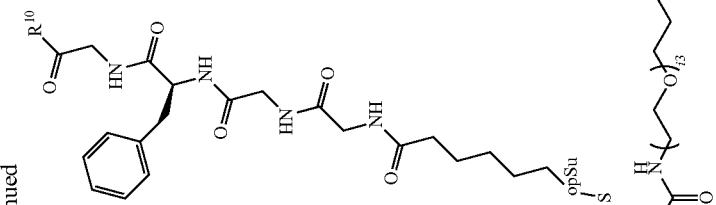
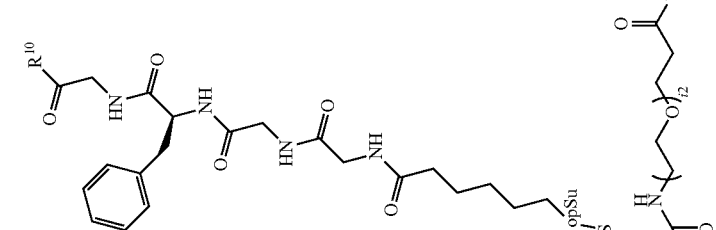

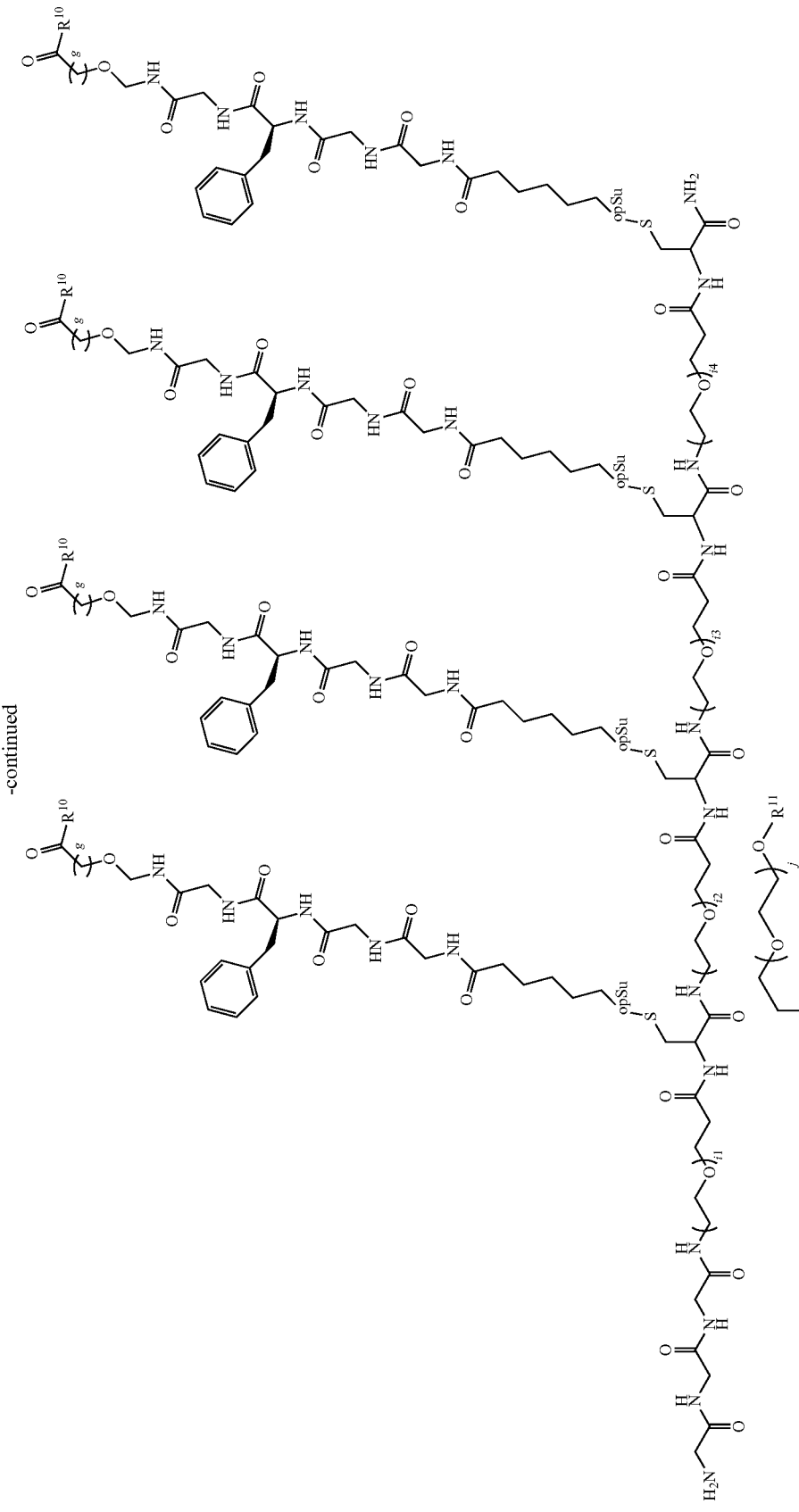
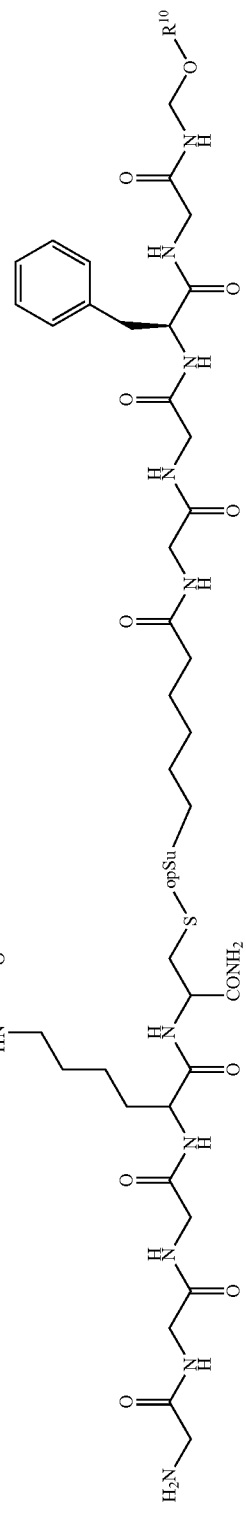

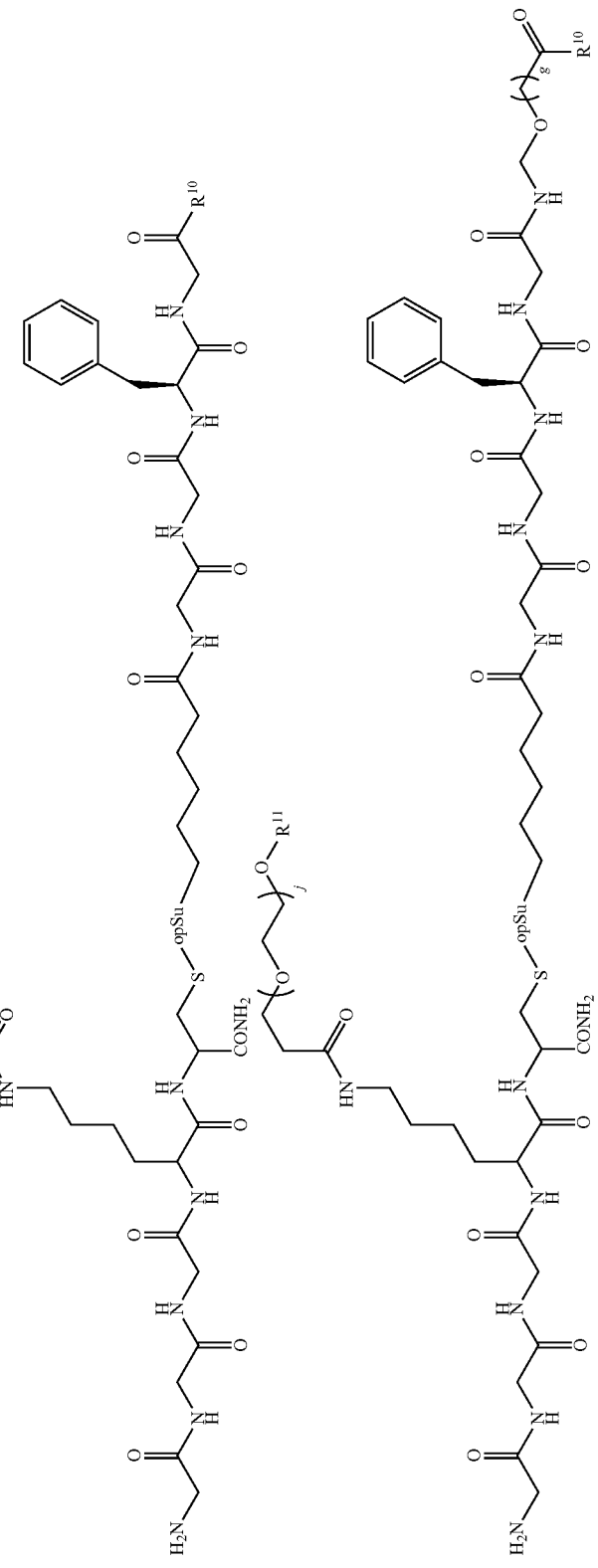

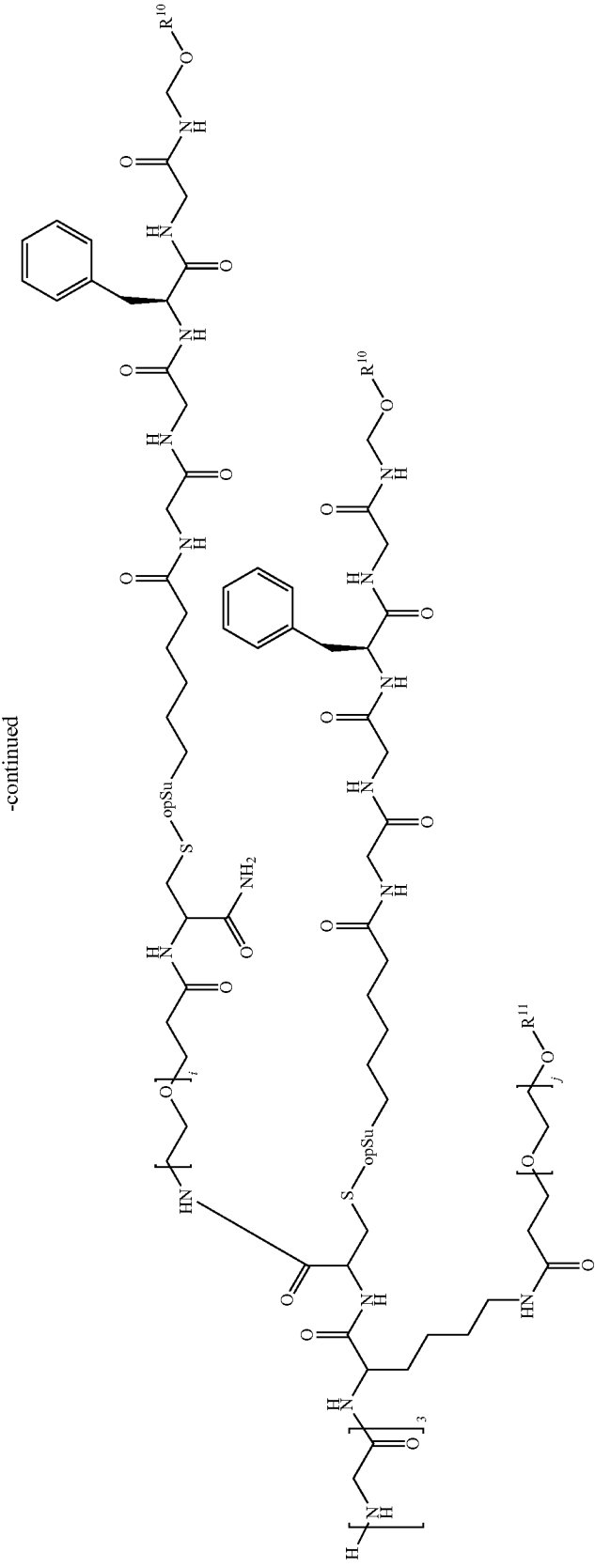

-continued
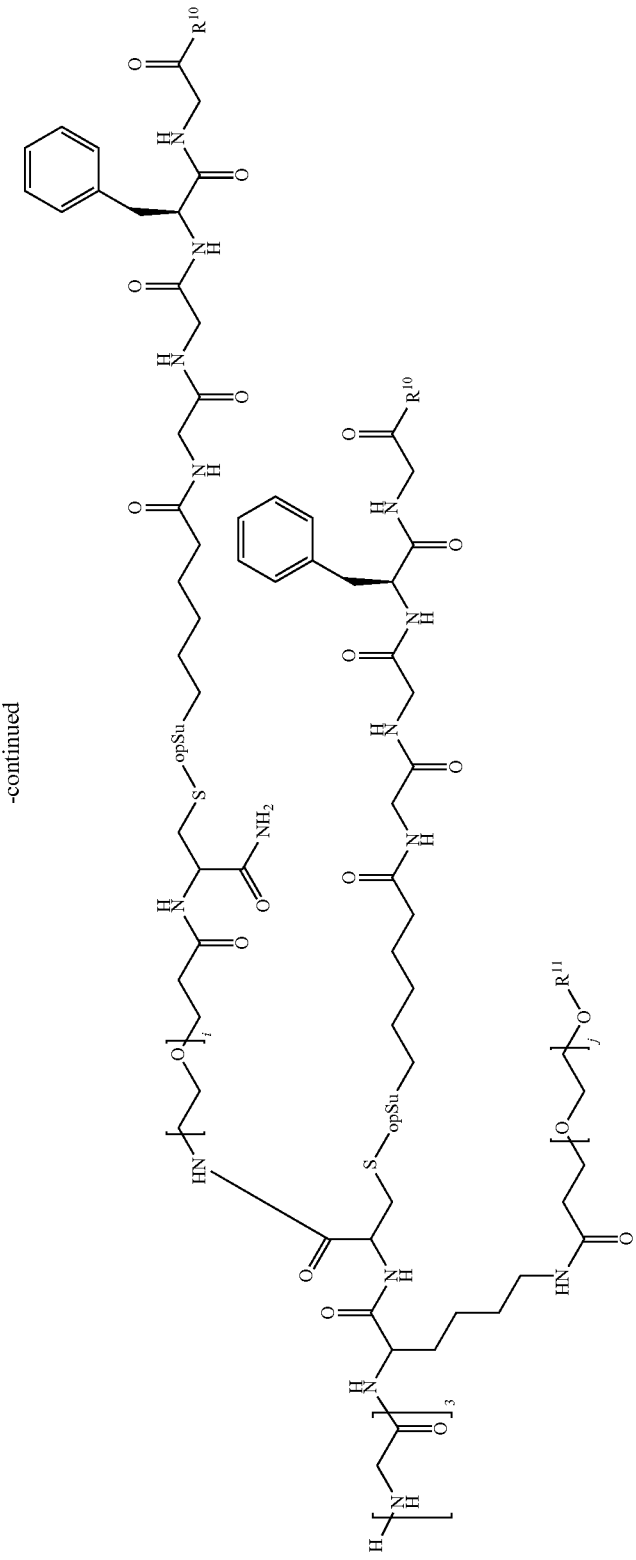

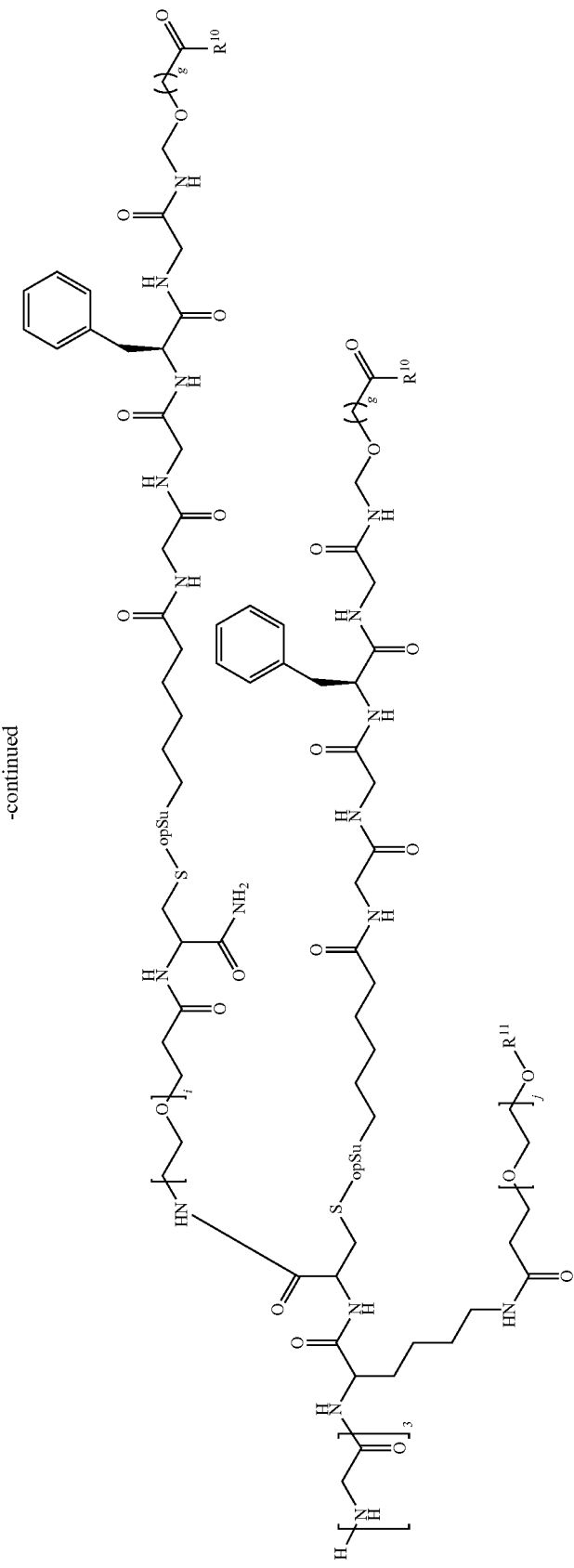

-continued
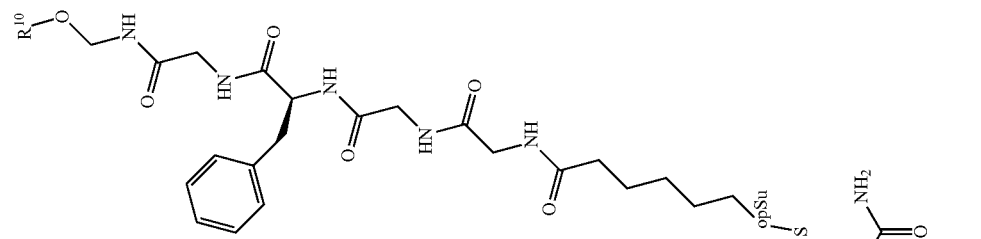
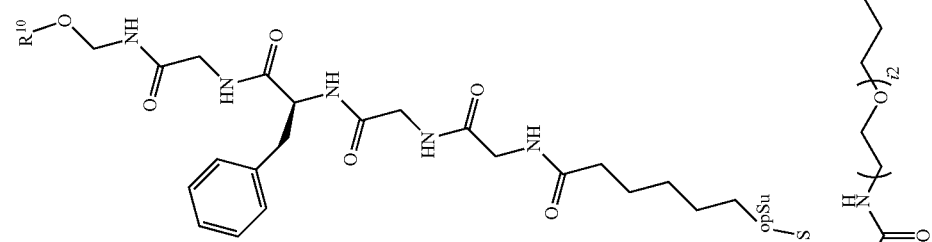
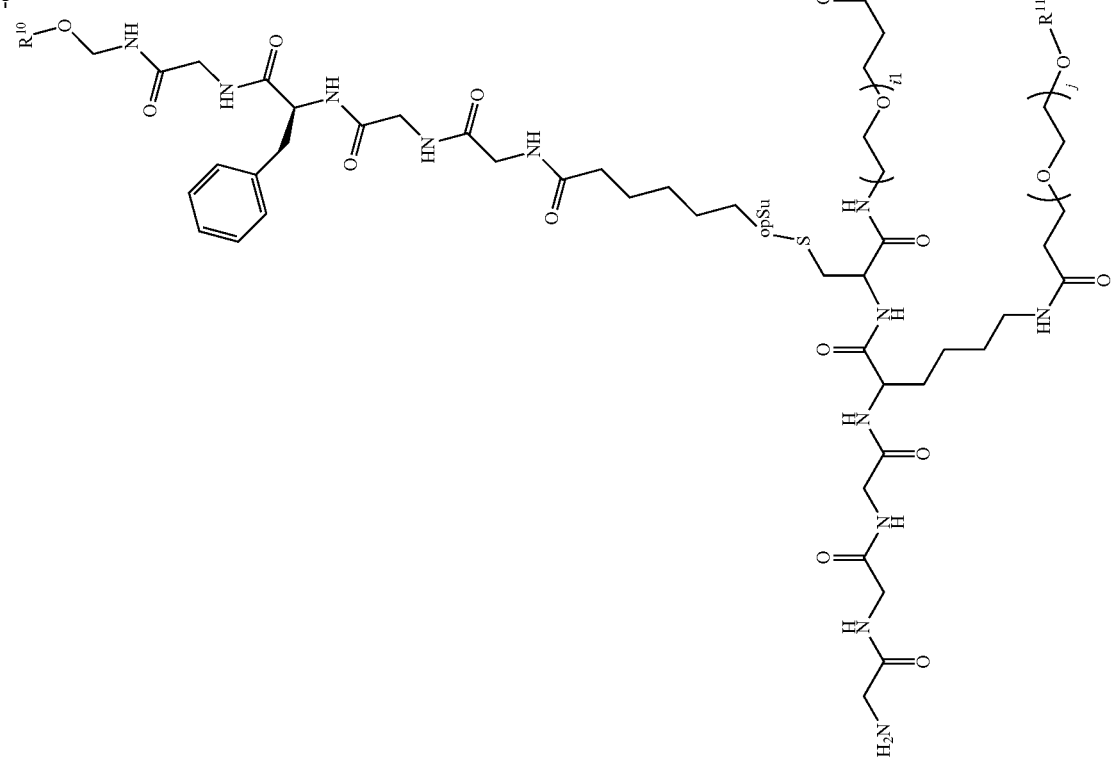

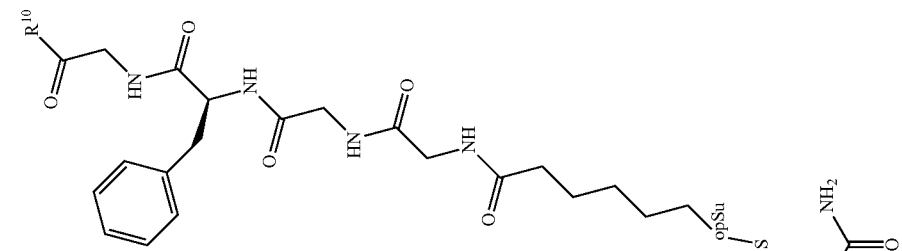
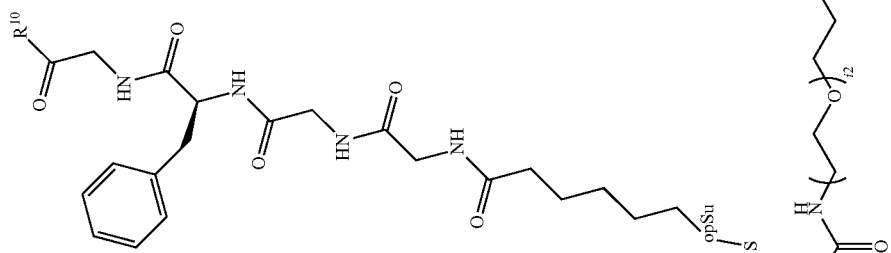
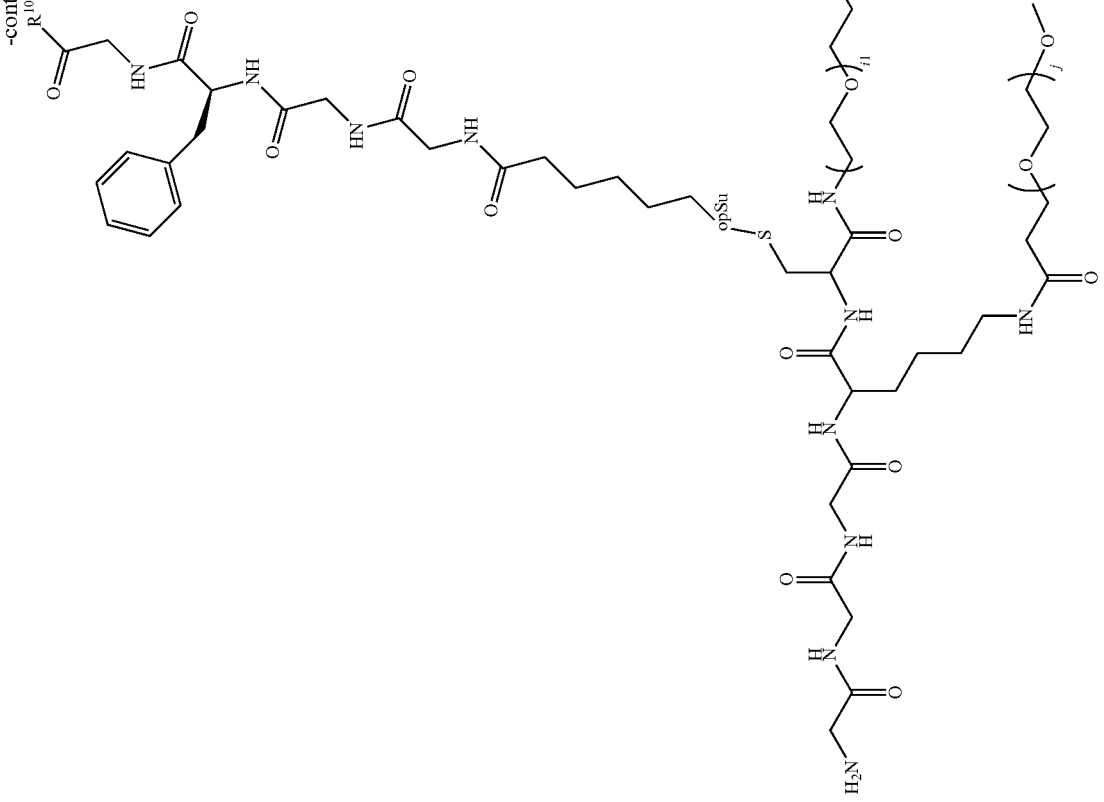

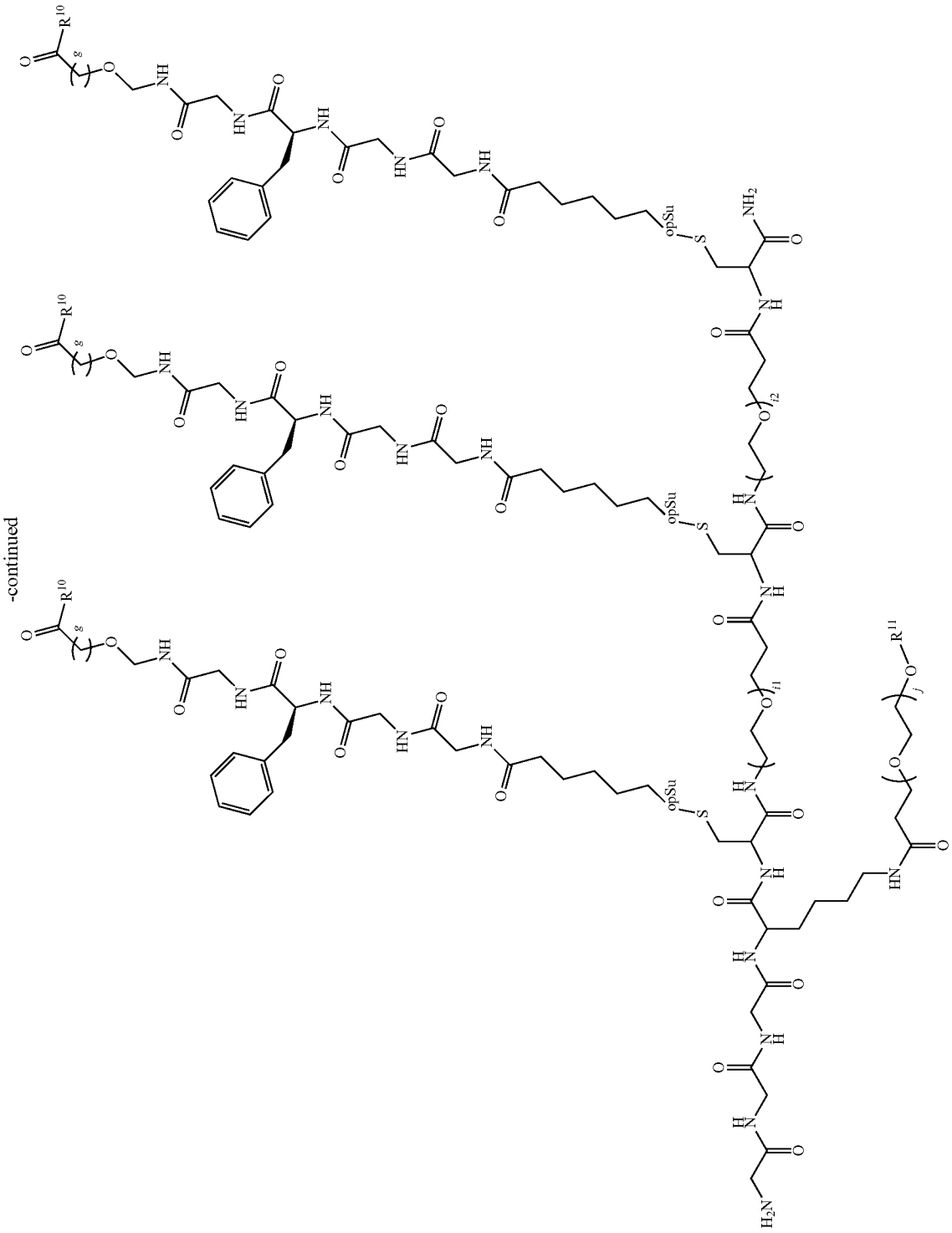

-continued
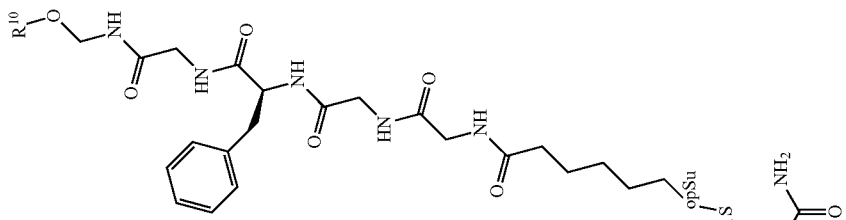
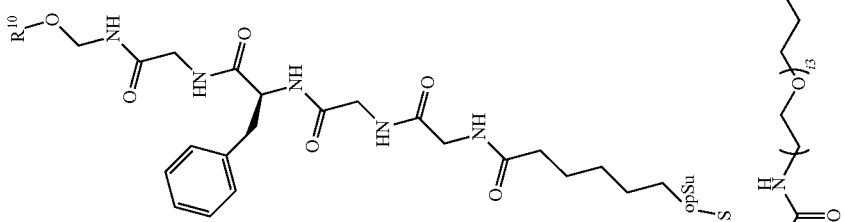
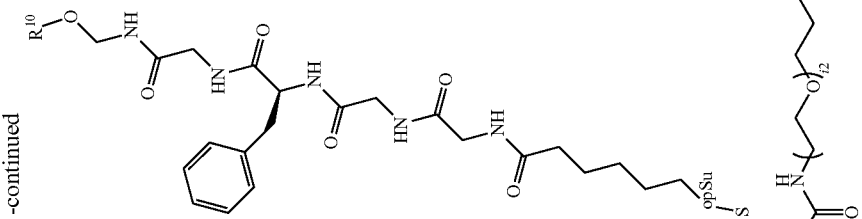
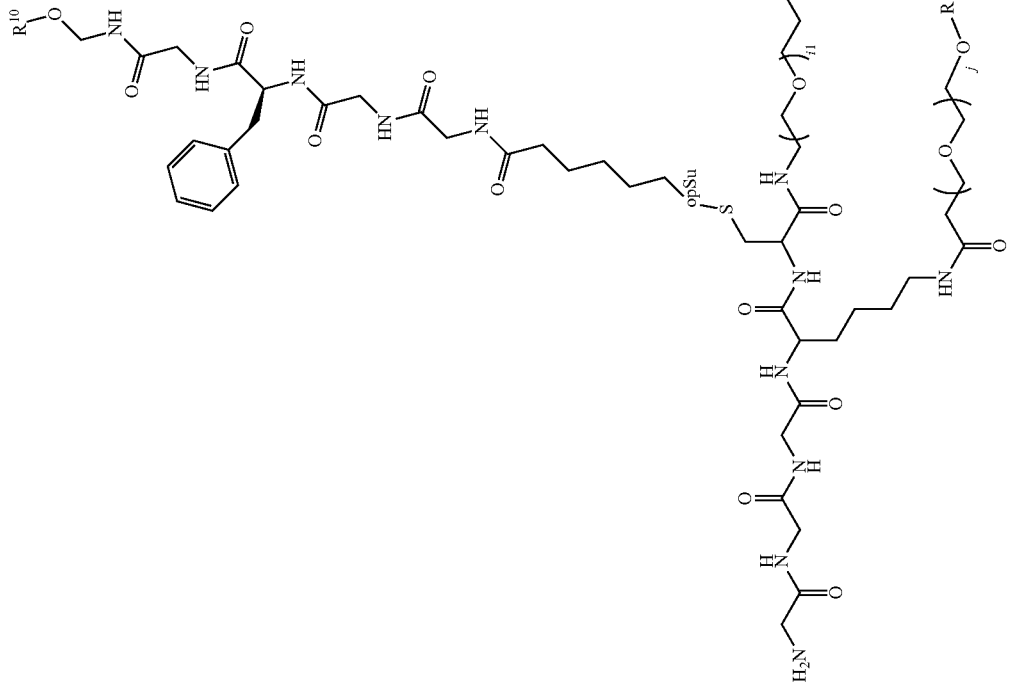

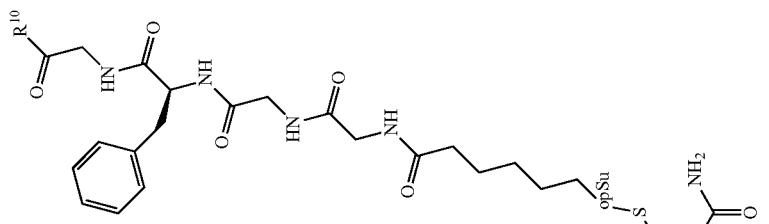
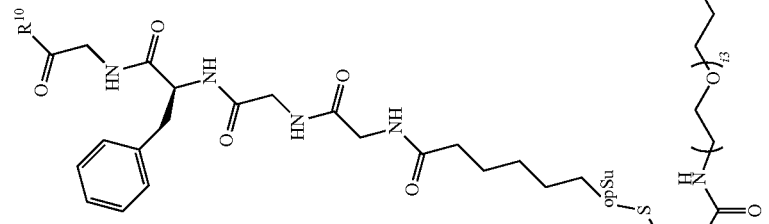
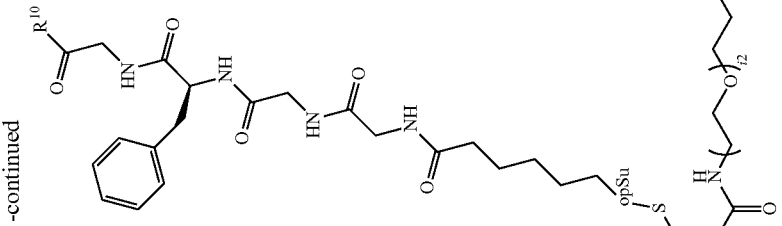
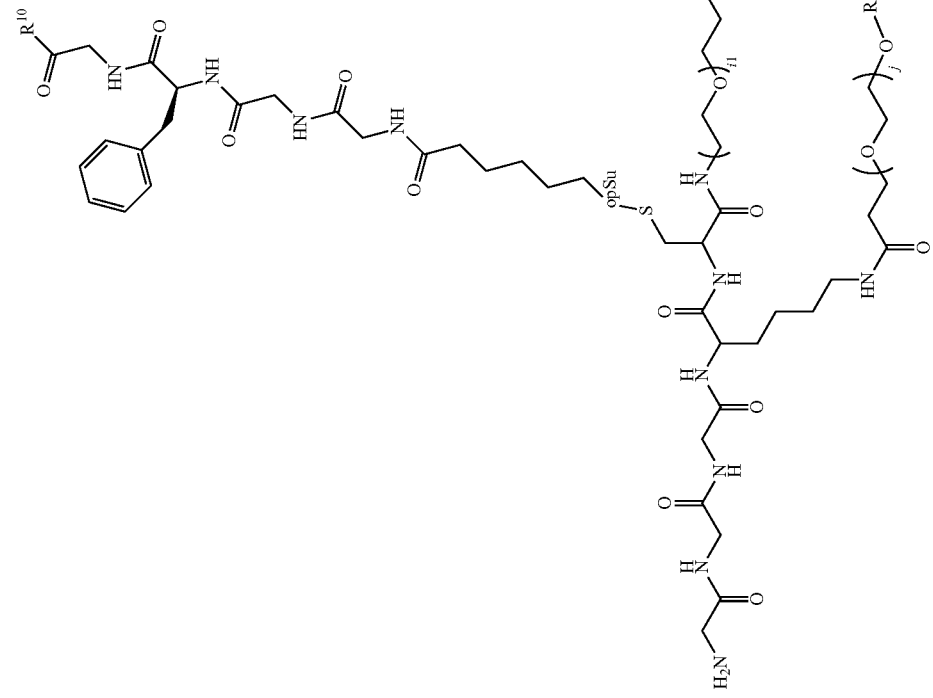

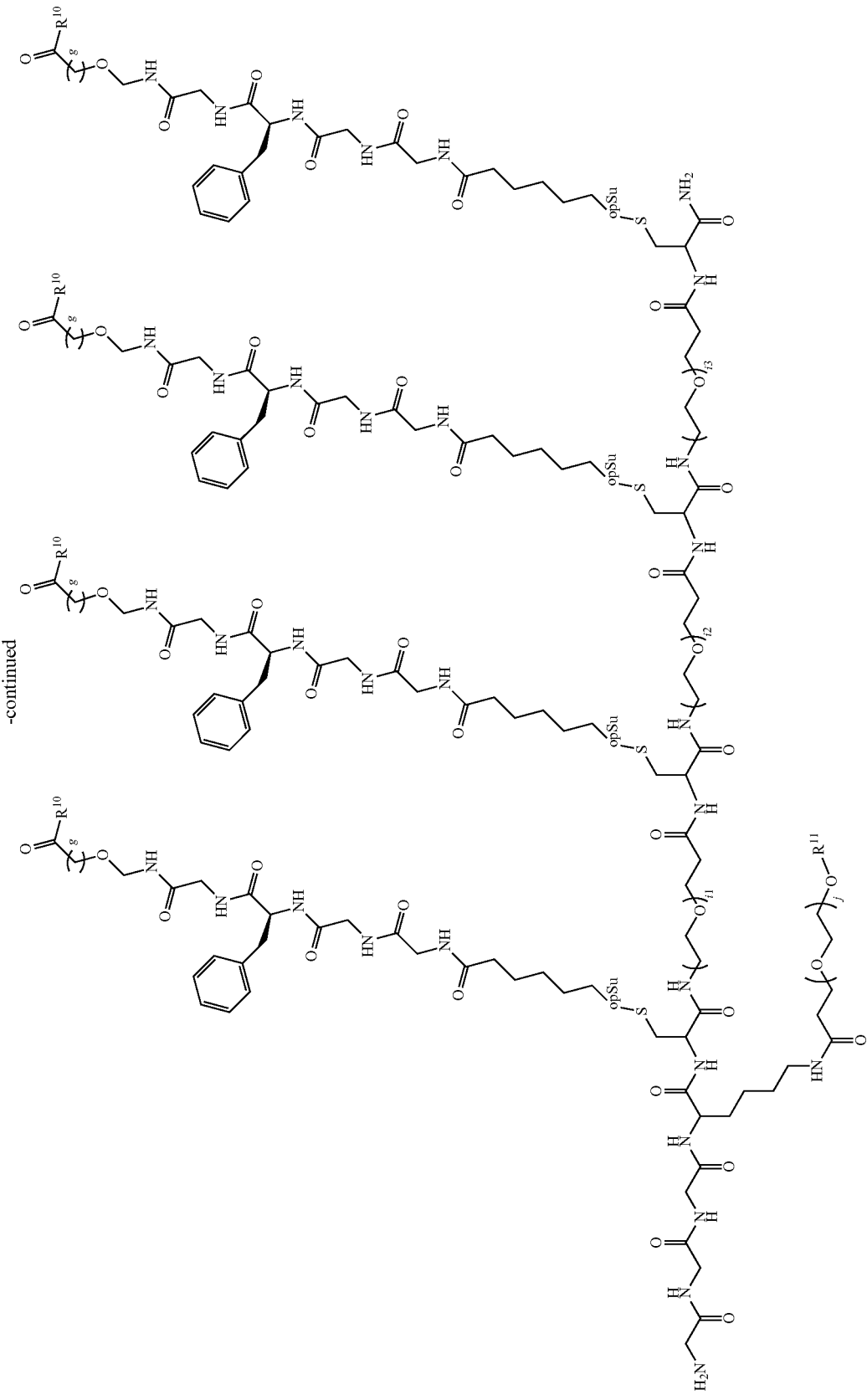

each i, i1, i2, i3, i4 is independently an integer of 1-100, preferably 1 to 20; preferably each i, i1, i2, i3, i4 is independently an integer of 1 to 12; more preferably 2 to 8; particularly 4; each g is independently an integer of 1 to 6, preferably 1 to 3; more preferably 1.

[8] A compound having the structure of formula (II')

formula (II')

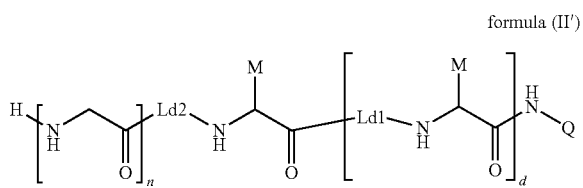

wherein
Q is hydrogen or LKb-P;
M is hydrogen or LKa-LKb-P;
provided that Q and M are not simultaneously hydrogen;
P is a payload which is linked to the B moiety or $L^1$ moiety of the compound of formula (I');
n, d, Ld1, Ld2, LKa and LKb are as defined in the above [1].

[9] A conjugate having the structure of formula (III'):

formula (III')

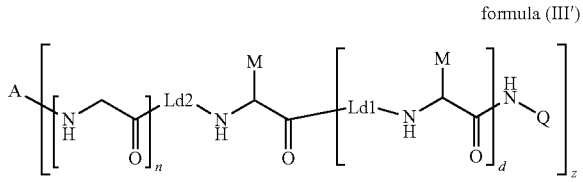

wherein,
n, d, Ld1 and Ld2 are as defined in the above [1];
Q is hydrogen or LKb-P;
M is hydrogen or LKa-LKb-P;
provided that Q and M are not simultaneously hydrogen;
P is a payload which is linked to the B moiety or $L^1$ moiety of the compound of formula (I');
A is a targeting molecule which is linked to the $G_n$ moiety of the compound of formula (I'); G is glycine;
z is an integer of 1 to 20.

[10] The conjugate of the above [9], wherein the conjugate has the structure of the following formula (III'-1):

formula (III'-1)

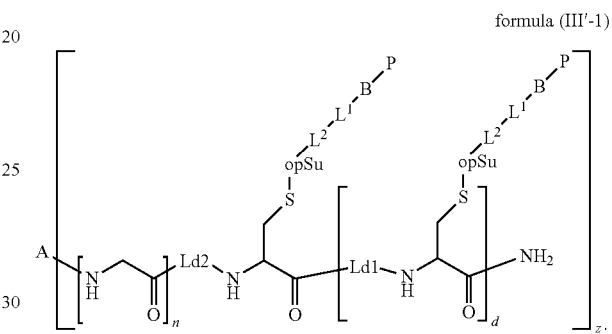

[11] The conjugate of the above [9] or [10], wherein the conjugate has the structure of the following:

(conjugate LC'301-1)

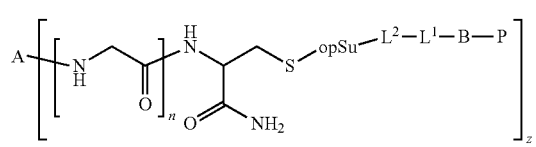

(conjugate LC'301-2)

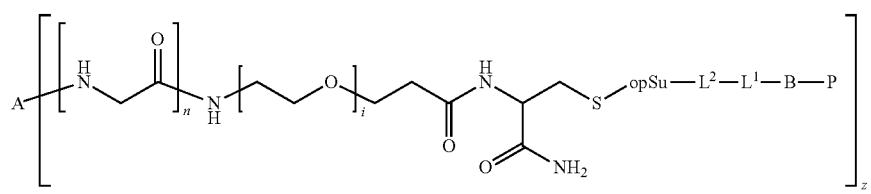

(conjugate LC'301-3)

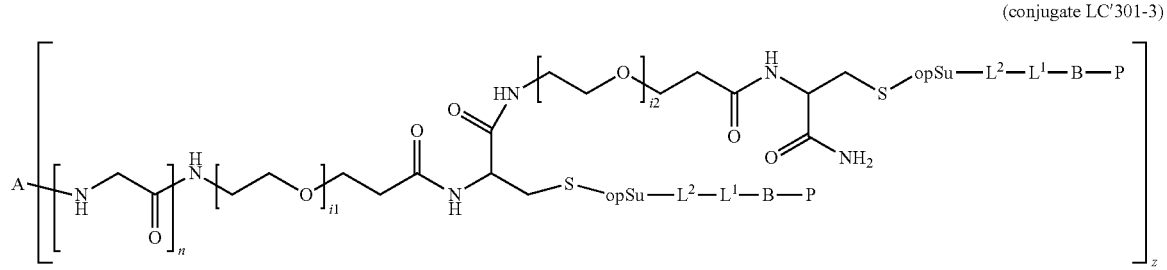

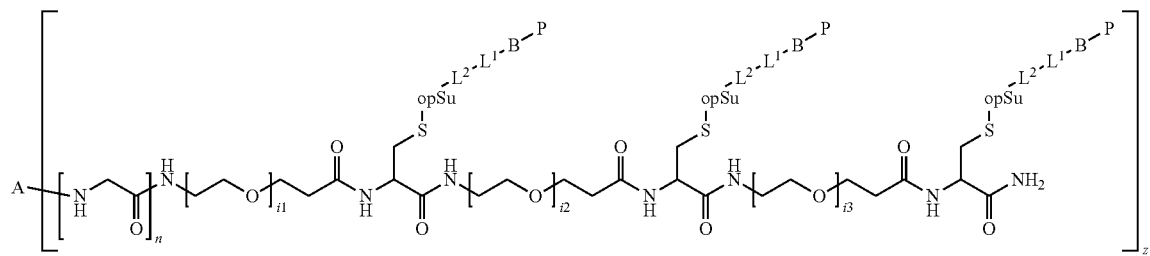
(conjugate LC'301-4)
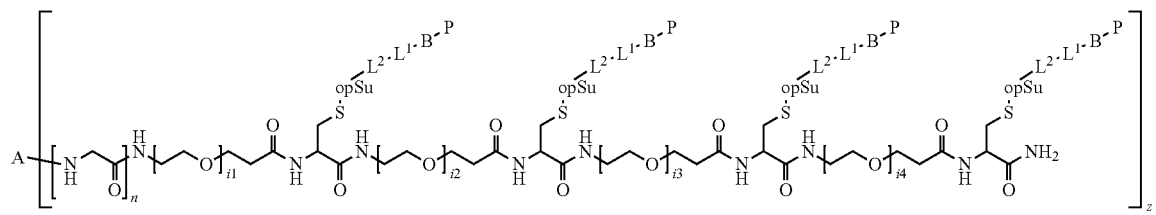
(conjugate LC'301-5)
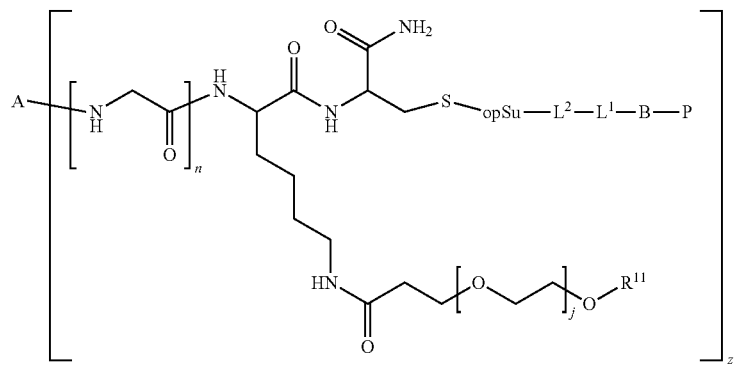
(conjugate LC'302-1)
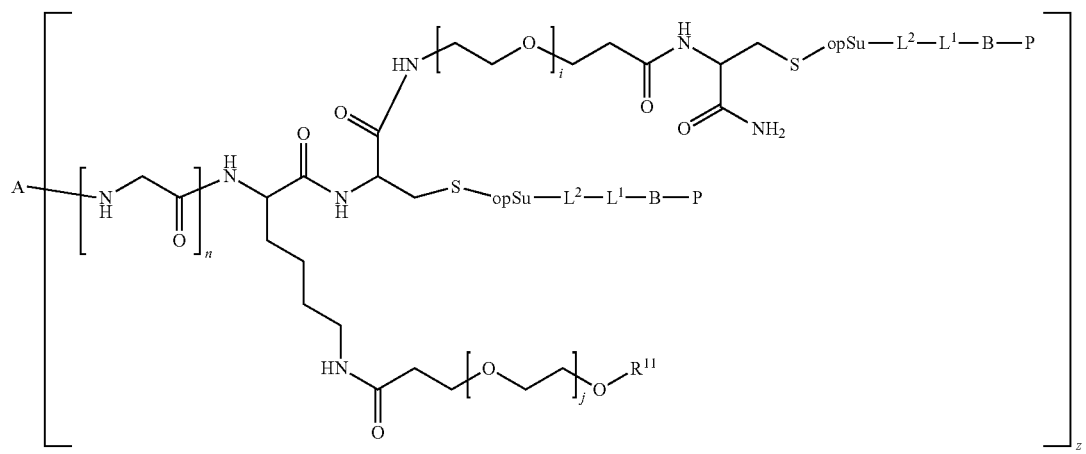
(conjugate LC'302-2)

-continued (conjugate LC'302-3)

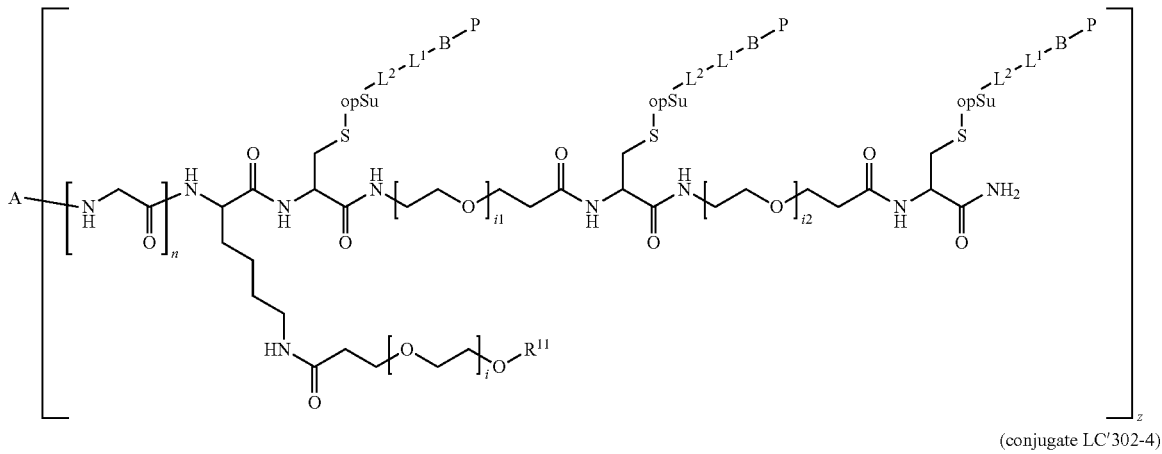

(conjugate LC'302-4)

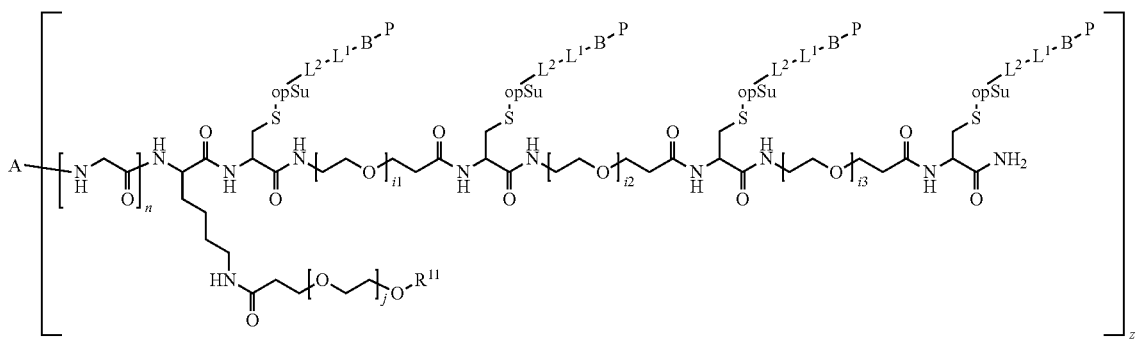

preferably, z is 1 to 4; preferably 2;

each i, i1, i2, i3, i4 is independently an integer of 1-100, preferably 1 to 20; preferably each i, i1, i2, i3, i4 is independently an integer of 1 to 12; more preferably 2 to 8; particularly 4;

each j is independently an integer of 1-100, preferably 1 to 20; preferably each j is independently an integer of 1 to 12; more preferably 8 to 12; particularly 8 or 12.

[12] The conjugate of any one of the above [9]-[11], wherein the targeting molecule is an antibody or an antigen binding fragment thereof, the antibody or antigen binding fragment is preferably modified to connect with the $G_n$ moiety in the compound of formula (I');

preferably, the antibody is an anti-human HER2 antibody.

[13] The conjugate of any one of the above [9]-[12], wherein the payload is a cytotoxin or a fragment thereof, with an optional derivatization in order to connect to the B moiety or $L^1$ moiety in the compound of formula (I');

preferably, the cytotoxin is selected from the group consisting of taxanes, maytansinoids, auristatins, epothilones, combretastatin A-4 phosphate, combretastatin A-4 and derivatives thereof, indol-sulfonamides, vinblastines such as vinblastine, vincristine, vindesine, vinorelbine, vinflunine, vinglycinate, anhy-drovinblastine, dolastatin 10 and analogues, halichondrin B, eribulin, indole-3-oxoacetamide, podophyllotoxins, 7-diethylamino-3-(2'-benzoxazolyl)-coumarin (DBC), discodermolide, laulimalide, camptothecins and derivatives thereof, mitoxantrone, mitoguazone, nitrogen mustards, nitrosoureasm, aziridines, benzodopa, carboquone, meturedepa, uredepa, dynemicin, esperamicin, neocarzinostatin, aclacinomycin, actinomycin, antramycin, bleomycins, actinomycin C, carabicin, carminomycin, cardinophyllin, carminomycin, actinomycin D, daunorubicin, detorubicin, adriamycin, epirubicin, esorubicin, idarubicin, marcellomycin, mitomycins, nogalamycin, olivomycin, peplomycin, porfiromycin, puromycin, ferric adriamycin, rodorubicin, rufocromomycin, streptozocin, zinostatin, zorubicin, trichothecene, T-2 toxin, verracurin A, bacillocporin A, anguidine, ubenimex, azaserine, 6-diazo-5-oxo-L-norleucine, dimethyl folic acid, methotrexate, pteropterin, trimetrexate, edatrexate, fludarabine, 6-mercaptopurine, tiamiprine, thioguanine, ancitabine, gemcitabine, enocitabine, azacitidine, 6-azauridine, carmofur, cytarabine, dideoxyuridine, doxifluridine, floxuridine, calusterone, dromostanolone propionate, epitiostanol, mepitiostane, testolactone, aminoglutethimide, mitotane, trilostane, flutamide, nilutamide, bicalutamide, leuprorelin acetate, protein kinase inhibitors and a proteasome inhibitors; and/or selected from vinblastines, colchicines, taxanes, auristatins, maytansinoids, calicheamicin, doxonubicin, duocarmucin, SN-38, cryptophycin analogue, deruxtecan, duocarmazine, calicheamicin, centanamycin, dolastansine, pyrrolobenzodiazepine, exatecan and derivatives thereof; and/or selected from auristatins, especially MMAE, MMAF or MMAD; and/or selected from exatecan and derivatives thereof, such as DX8951f; and/or selected from DXd-(1) and DXd-(2); preferably DXd-(1).

[14] The conjugate of any one of the above [9]-[13], wherein the payload is selected from
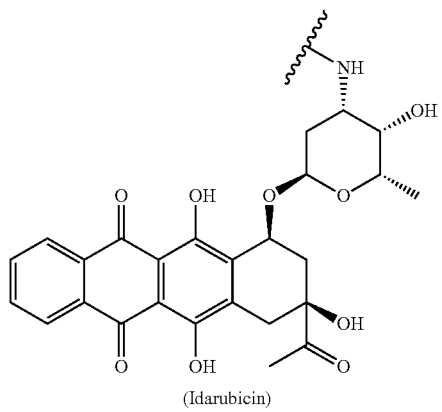
(Idarubicin)
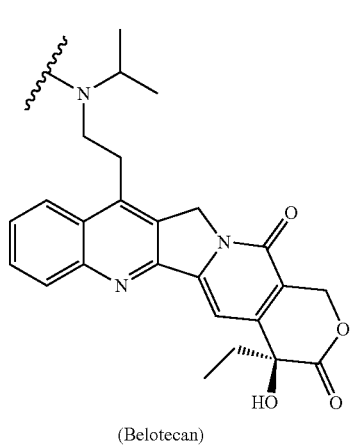
(Belotecan)
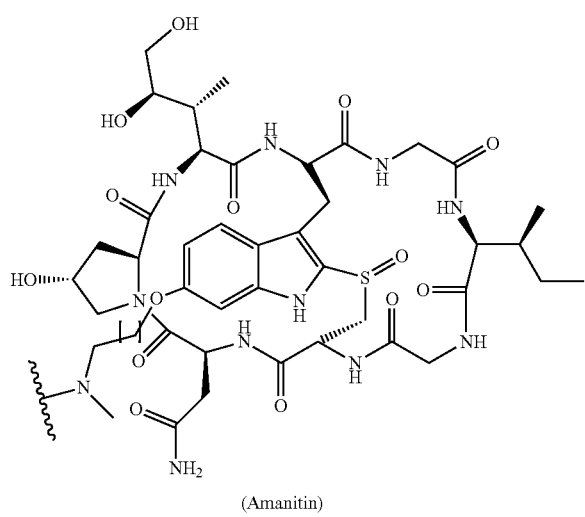
(Amanitin)
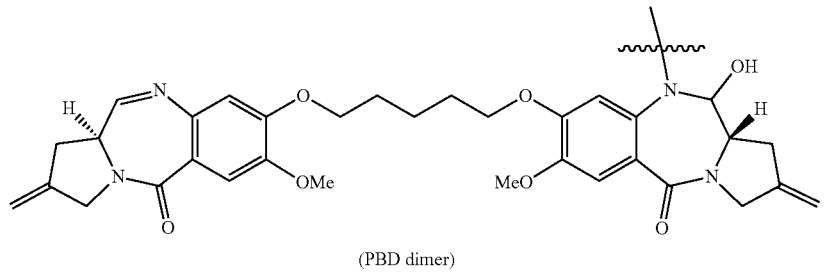
(PBD dimer)
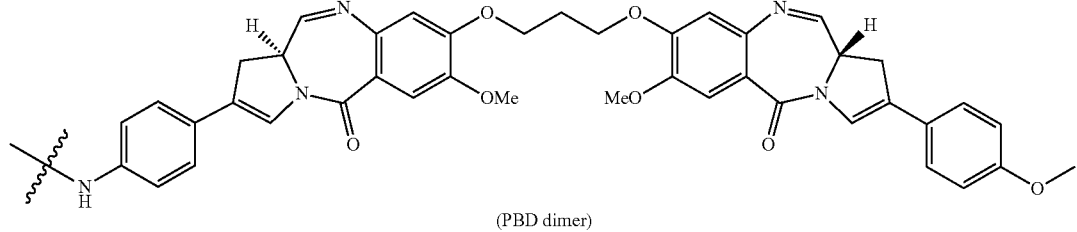
(PBD dimer)

-continued
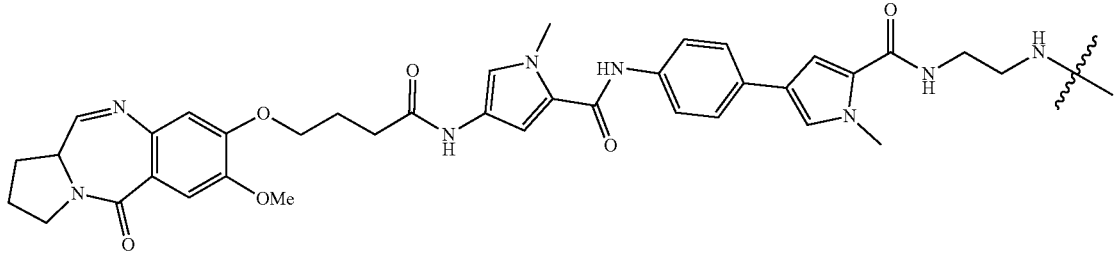
(PBD monomer)
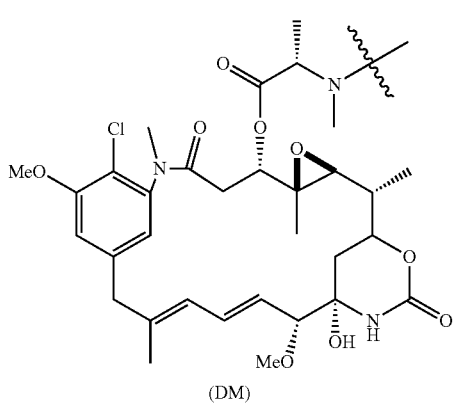
(DM)
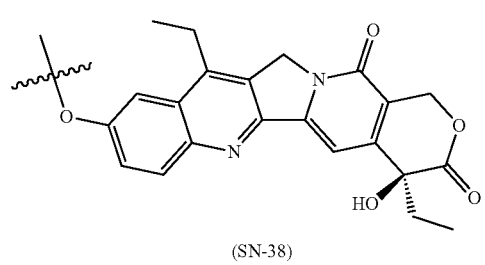
(SN-38)
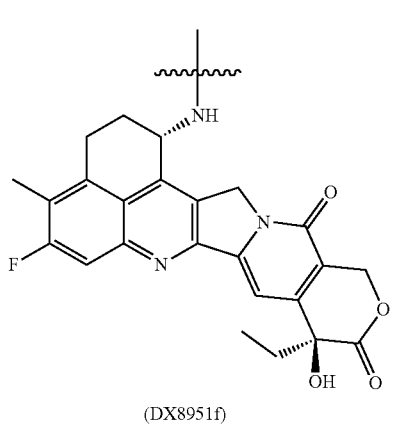
(DX8951f)
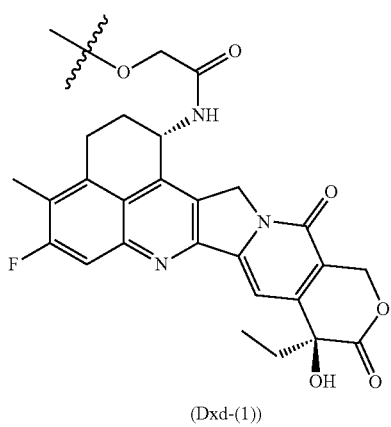
(Dxd-(1))
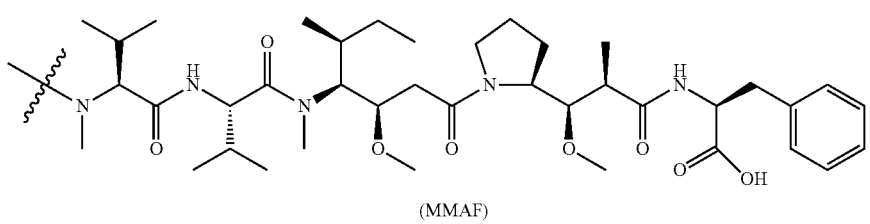
(MMAF)
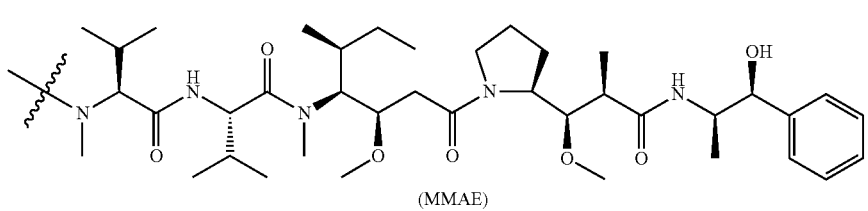
(MMAE)

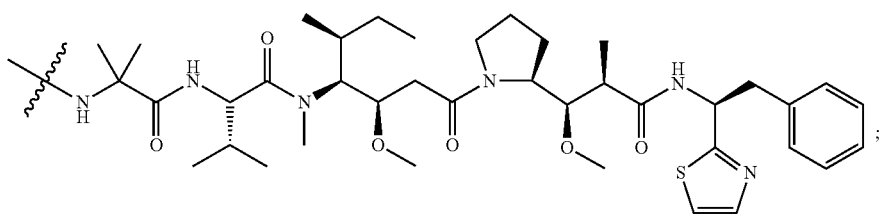
(Auristatin 0101)
especially selected from
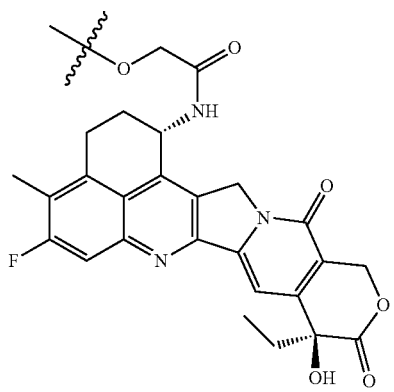
(Dxd-(1))
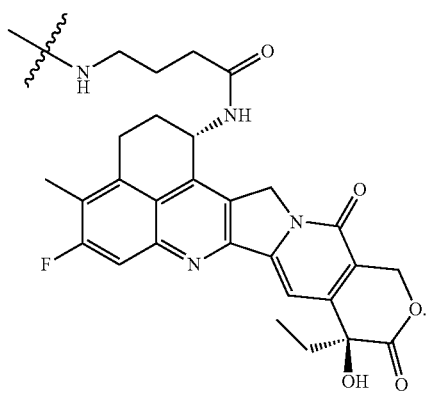
(Dxd-(2)).
[15] The conjugate of any one of the above [9]-[14], wherein

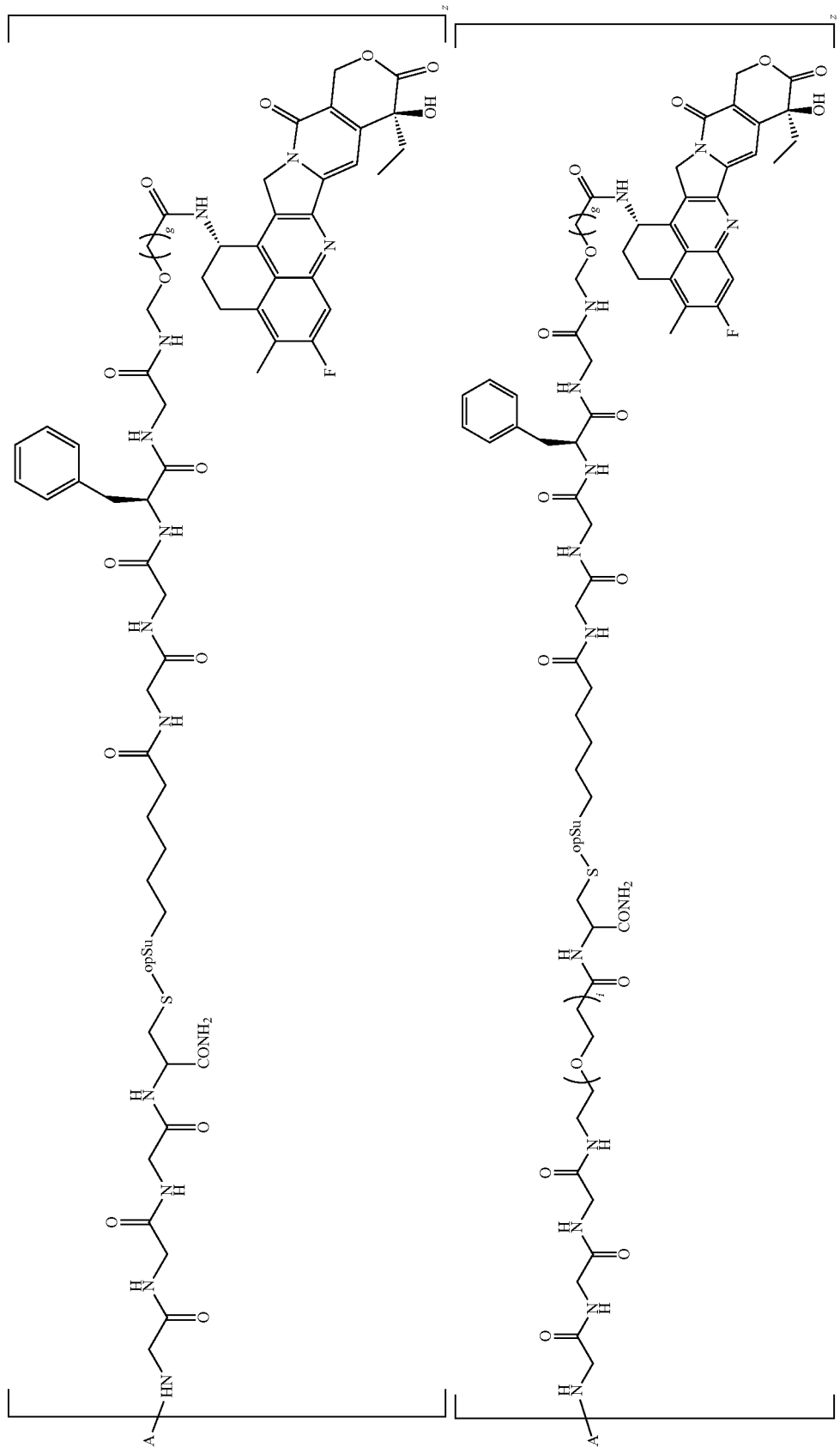

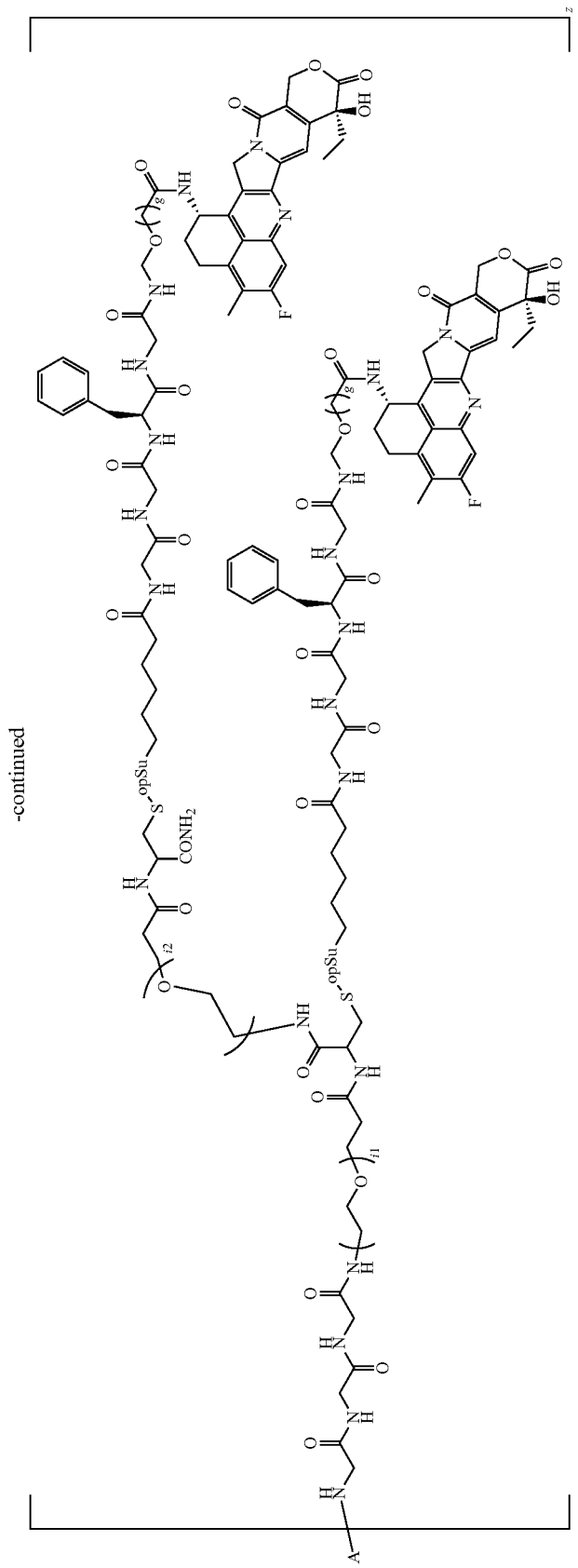

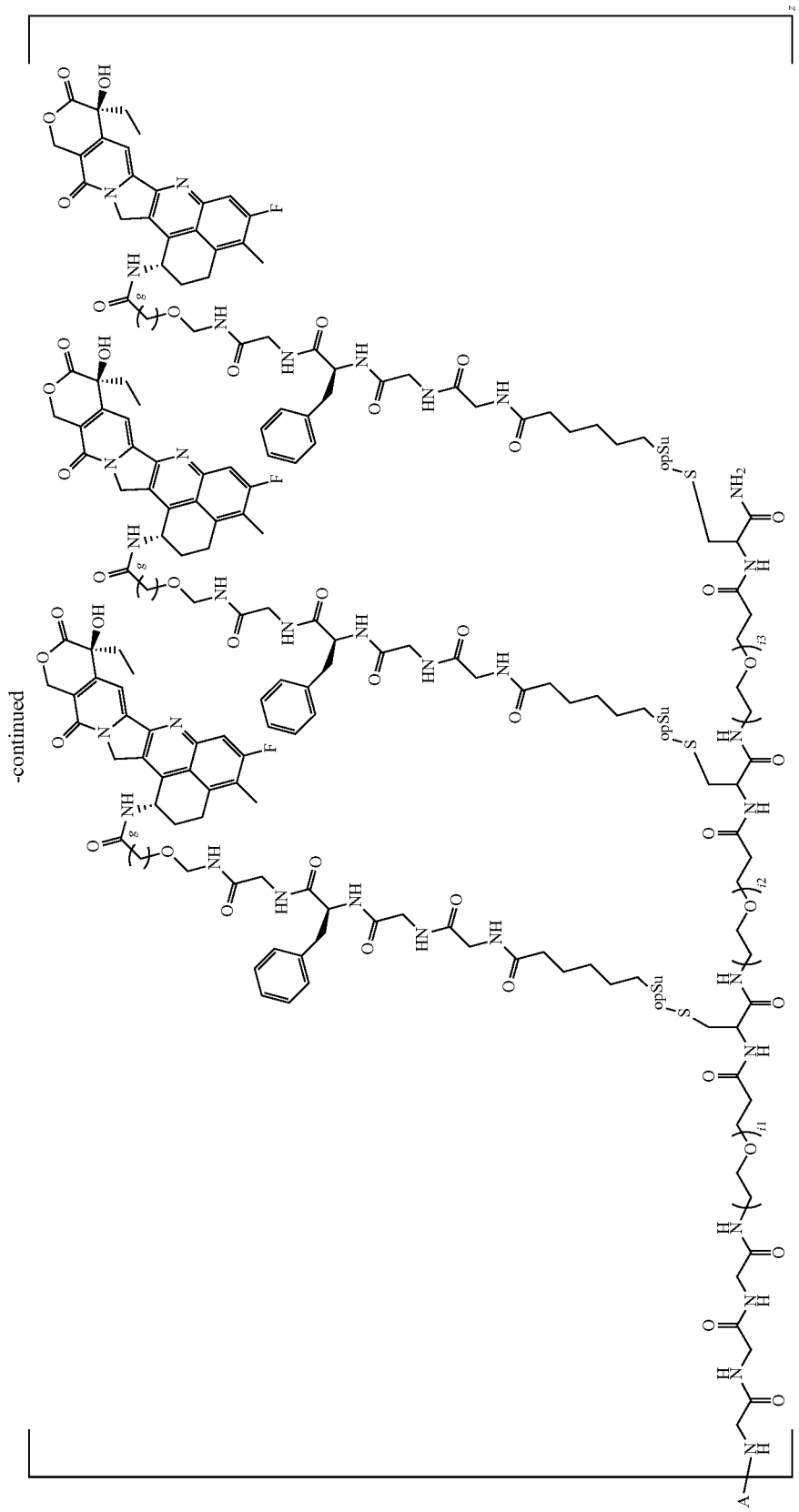

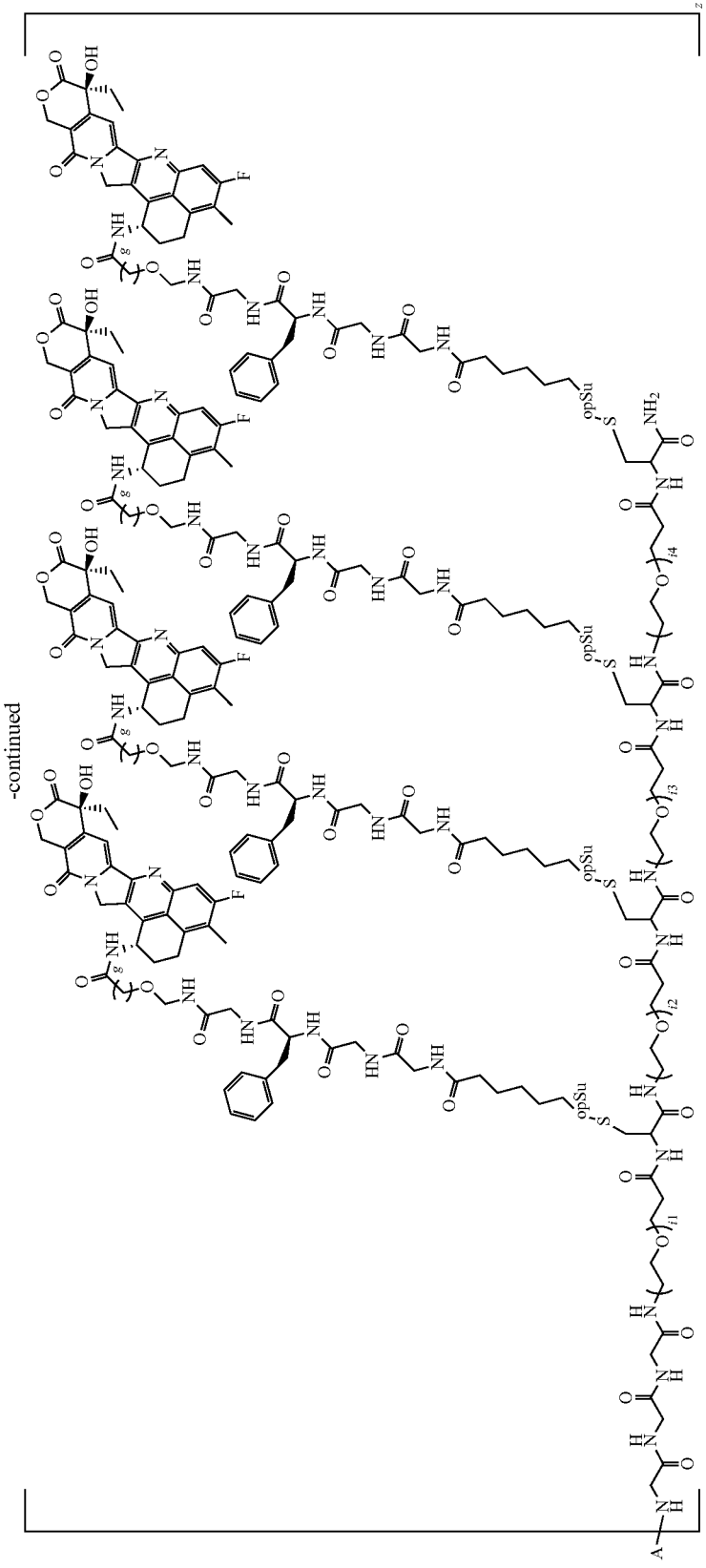

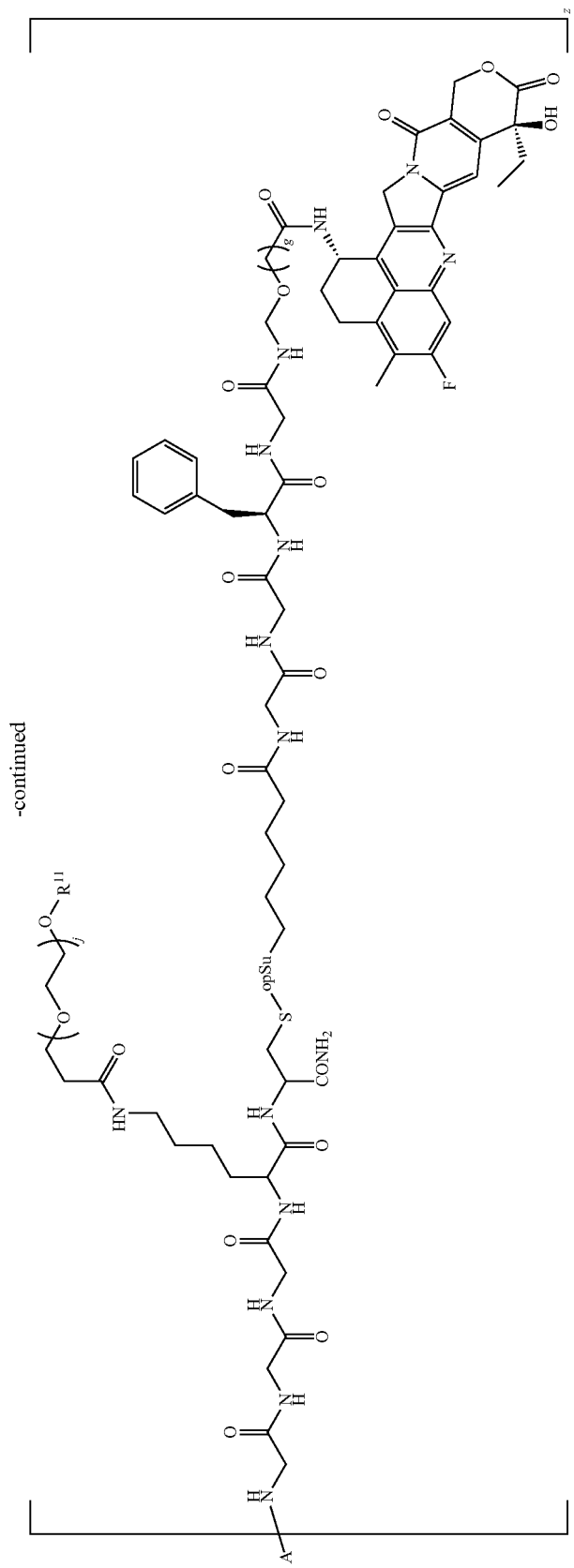

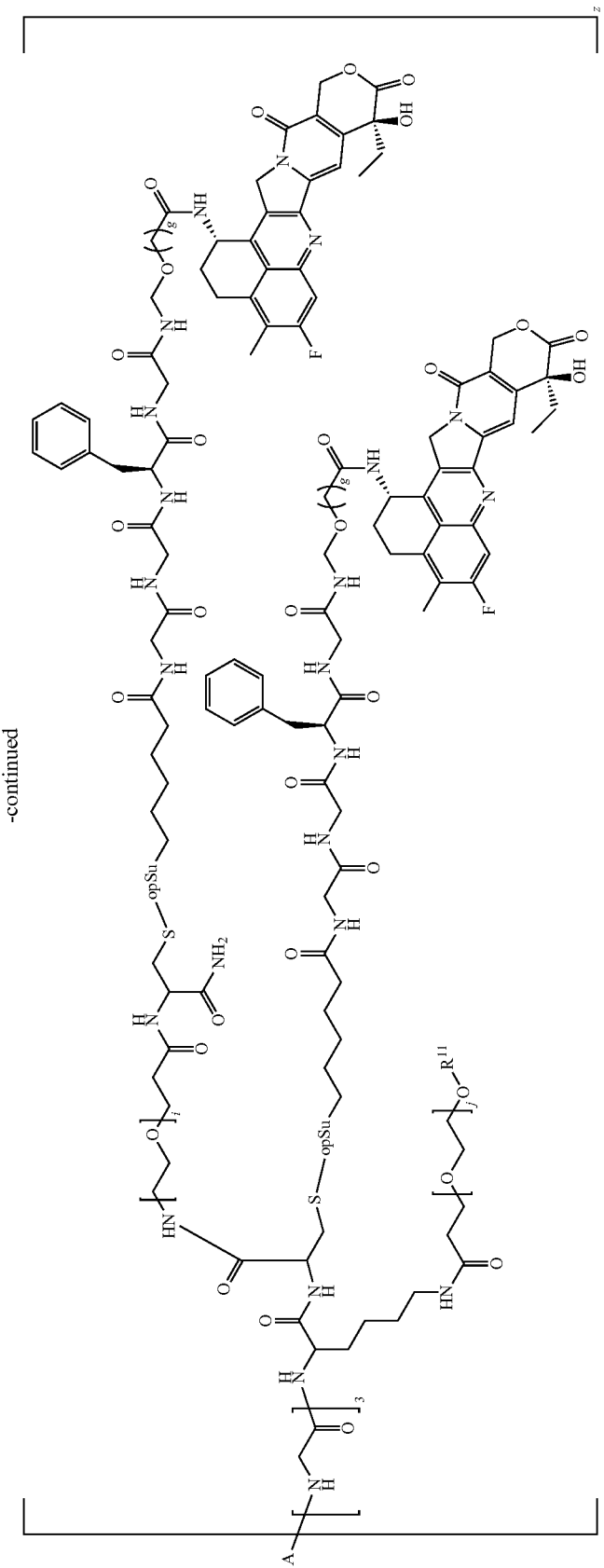

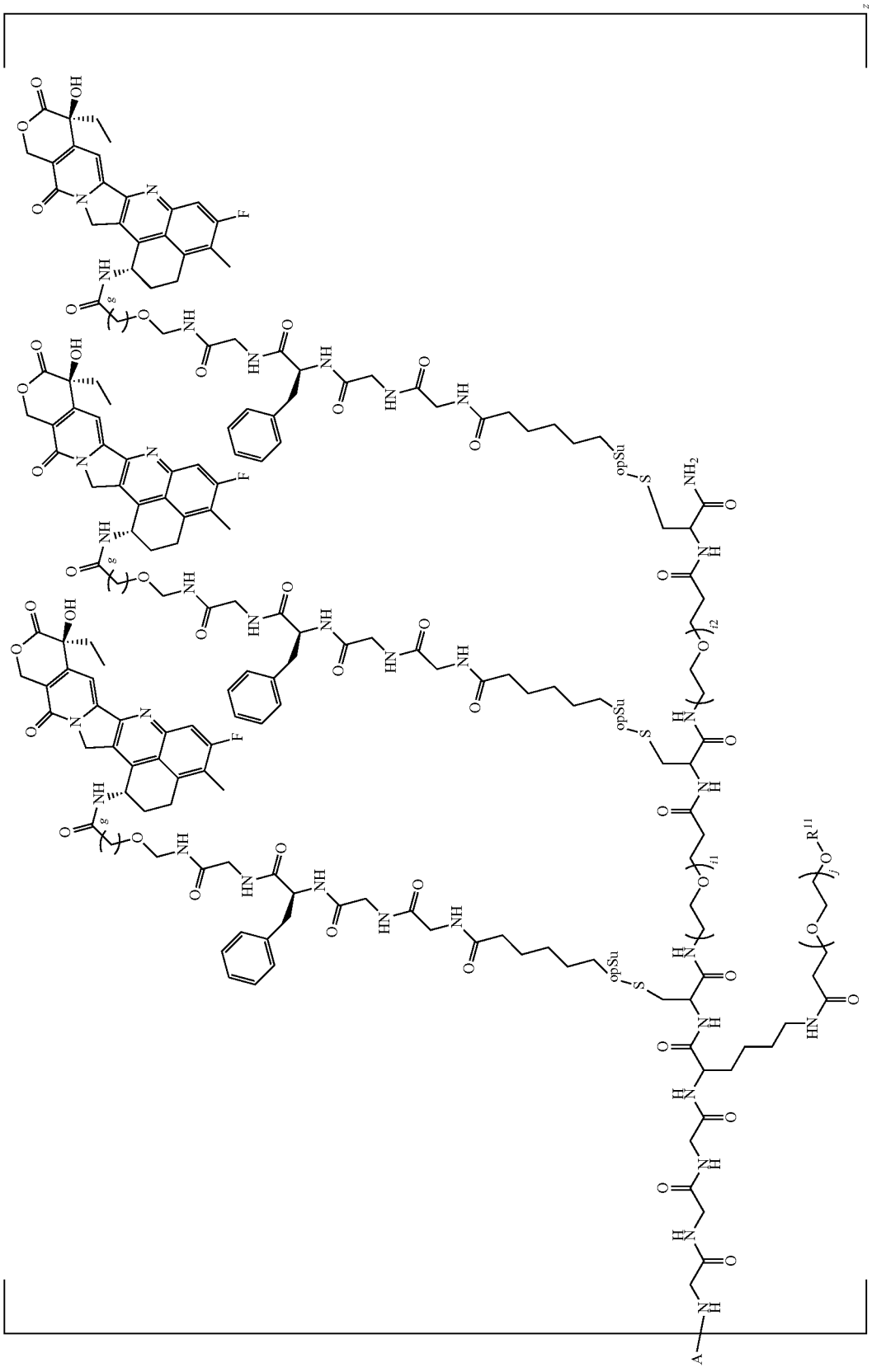

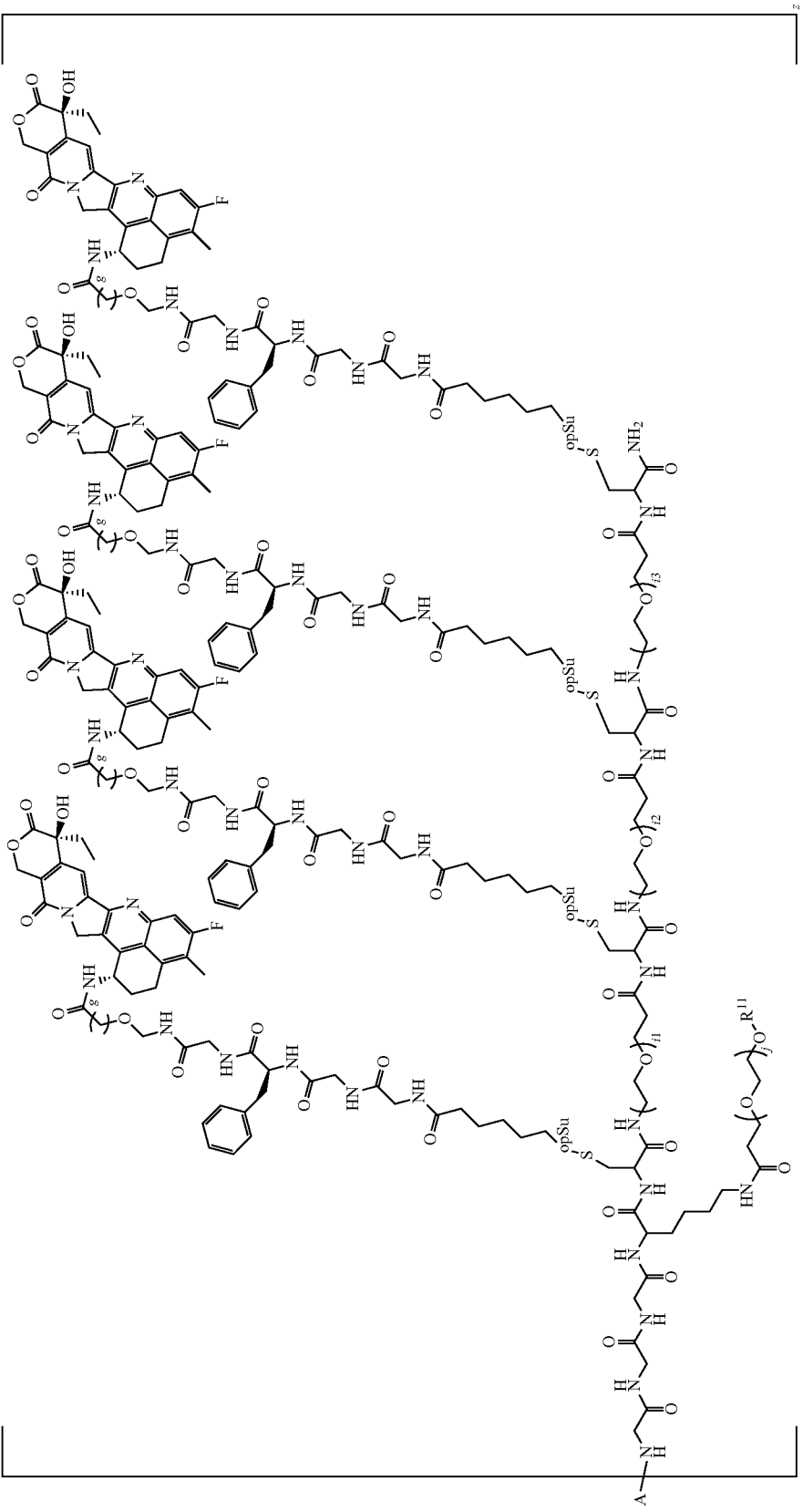

each g is independently an integer of 1 to 6, preferably 1 to 3; more preferably 1.

[16] A pharmaceutical composition comprising a prophylactically or therapeutically effective amount of a conjugate of any one of the above [9]-[15], and at least one pharmaceutically acceptable carrier.

[17] Use of the conjugate of any one of the above [9]-[15] or the pharmaceutical composition of the above [16] in the manufacture of a medicament for treating a disease; wherein the disease is a tumor or an autoimmune disease; preferably a HER2-positive tumor;

preferably, the HER2-positive tumor is selected from breast cancer, gastric cancer, lung cancer, ovarian cancer, and urothelial cancer.

Beneficial Effects

The antibody-drug conjugate of the present invention uses specially designed linker-payload, and is more stable and can achieve great efficacy in lower DAR, and therefore can reduce side effects and increase the therapeutic index.

The present disclosure utilizes a linking unit with unique structure and uses a ligase to catalyze the conjugation of the targeting molecule and the payload. The conjugate of the present disclosure has good homogeneity, high activity and high selectivity. Furthermore, the toxicity of the linking unit-payload intermediate is much lower than that of the free payload, and thus the manufacture process of the drug is less detrimental, which is advantageous for industrial production.

The conjugate of the present disclosure achieves at least one of the following technical effects:

(1) High inhibitory activity against target cells, or strong killing effect on target cells.
(2) Good physicochemical properties (e.g., solubility, physical and/or chemical stability).
(3) Good pharmacokinetic properties (e.g., good stability in plasma, appropriate half-life and duration of action).
(4) Good safety (low toxicity on non-target normal cells or tissues, and/or fewer side effects, wider treatment window), etc.
(5) Highly modular design, simple assembly of multiple drugs.

EXAMPLES

Preparation Example

In order to more clearly illustrate the objects and technical solutions, the present disclosure is further described below with reference to specific examples. It is to be understood that the examples are not intended to limit the scope of the disclosure. The specific experimental methods which were not mentioned in the following examples were carried out according to conventional experimental method.

Instruments, Materials and Reagents

Unless otherwise stated, the instruments and reagents used in the examples are commercially available. The reagents can be used directly without further purification.

MS: Thermo Fisher Q Exactive Plus, Water2795-Quattro micro triple quadrupole mass spectrometer
HPLC: Waters 2695, Agilent 1100, Agilent 1200
Semi-preparative HPLC: Lisure HP plus 50D
Flow Cytometry: CytoFLEX S
HIC-HPLC: Butyl-HIC; mobile phase A: 25 mM PB, 2M $(NH_4)_2SO_4$, pH 7.0; mobile phase B: 25 mM PB, pH 7.0; flow rate: 0.8 ml/min; acquisition time: 25 min; injection amount: 20 µg; column temperature: 25° C.; detection wavelength: 280 nm; sample chamber temperature: 8° C.

SEC-HPLC: column: TSK-gel G3000 SWXL, TOSOH 7.8 mm ID×300 mm, 5 µm; mobile phase: 0.2 M $KH_2PO_4$, 0.25 M KCl, pH 6.2; flow rate: 0.5 ml/min; acquisition time: 30 min; injection volume: 50 µl; column temperature: 25° C.; detection wavelength; 280 nm; sample tray temperature: 8° C.

CHO was obtained from Thermo Fisher Scientific; pcDNA 3.3 was obtained from Life Technology; HEK293F was obtained from Prejin; PEIMAX transfection reagent was obtained from Polyscience; MabSelect Sure ProA was obtained from GE; Capto S ImpAct was obtained from GE; Rink-amide-MBHA-resin and dichloro resin were obtained from Nankai synthesis; HCC1954 was obtained from ATCC CAT #CRL-2338; SK-BR-3 was obtained from ATCC CAT #HTB-30; BT-474 was obtained from ATCC CAT #HTB-20; NCI-N87 cells was obtained from ATCC CAT #CRL-5822; MCF7 was obtained from ATCC CAT #HTB-22; MDA-MB-231 was obtained from ATCC CAT #HTB-26; MDA-MB-468 was obtained from ATCC CAT #HTB-132; CFPAC-1 was obtained from ATCC CAT #CRL-1918; NCI-H2110 was obtained from ATCC CAT #CRL-5924; JIMT-1 was obtained from Wuxi Apptech; Capan-1 was obtained from ATCC CAT #CRL-1573; antibody Trastuzumab is prepared according to the known sequence; optimized recombinant enzyme Sortase A derived from *Staphylococcus aureus* is prepared in *E. coli*.

Example 1 Construction of Antibody Expression Vector, Antibody Expression, Purification and Identification 1.1 Production of the Modified Anti-Human HER2 Antibody Ab0001-$LCCT_L$-HC The expression plasmids for antibody Ab0001-$LCCT_L$-HC (light chain SEQ ID NO: 1, heavy chain: SEQ ID NO: 2) were constructed as follows. The sequence of the antibody Ab0001-$LCCT_L$-HC: based on the amino acid sequence of Trastuzumab, and GALPETGG was introduced at the C-terminal of the light chain, wherein LPETGG is the recognition sequence of the ligase donor substrate, and GA is a spacer sequence. The plasmids were transfected into CHO cells and the cell population was established and screened for a highly expressed cell population, which was cultured with reference to the culture process of Trastuzumab in a 5-10 L reactor, and supernatant was collected.

1.2 The Purification of Antibody Ab0001-$LCCT_L$-HC

The purification of Ab0001-$LCCT_L$-HC was carried out in a standard process using the combination of MabSelect affinity chromatography and Sepharose S cation exchange chromatography, the purified products were dissolved in the original Trastuzumab drug buffer (5 mM histidine-HCl, 2% Trehalose, 0.009% Polysorbate 20, PH 6.0), and frozen in small aliquots.

1.3 The Quality Control of Antibody Ab0001-$LCCT_L$-HC

The purity of the above purified antibody Ab0001-$LCCT_L$-HC is 98.5% by SDS-PAGE; the content of high molecular weight polymer of the sample is less than 0.4% by SEC-HPLC; endotoxin content is less than 0.098 EU/mg.

1.4 Preparation of Other Modified Anti-Human Antibodies

According to a similar method, a terminal modification based on the ligase recognition sequence was introduced at the C-terminal of the light and/or heavy chain of the Trastuzumab, respectively, giving a modified antibody.

The modified anti-human HER2 antibodies based on Ab0001 (Trastuzumab) are listed in Table 1. LPETGG in the terminal modification sequence is a recognition sequence of the ligase donor substrate, and GA is a spacer sequence.

TABLE 1

| Modified anti-human HER2 antibodies | | |
|---|---|---|
| | Sequence | Sequence introduced at the terminal |
| Ab0001-LCCT$_L$-HC light chain | SEQ ID NO: 1 | GALPETGG |
| Ab0001-LCCT$_L$-HC heavy chain | SEQ ID NO: 2 | —* |

TABLE 1-continued

| Modified anti-human HER2 antibodies | | |
|---|---|---|
| | Sequence | Sequence introduced at the terminal |
| Ab0001-LCCT$_L$-HCCT$_L$ light chain | SEQ ID NO: 3 | GALPETGG |
| Ab0001-LCCT$_L$-HCCT$_L$ heavy chain | SEQ ID NO: 4 | GALPETGG |

* "—" indicates no terminal modification

Example 2 Preparation of Intermediates 2.1 Preparation of Intermediate Mc-GGFG-Dxd (RF1184)

The intermediate Mc-GGFG-Dxd (RF1184) is commercial available or prepared following the procedures as described in EP2907824. This compound is used to prepare the Linker-Payload intermediate (formula (IV) compound), and is also used to directly connect to the (optionally modified) antibody to prepare reference ADCs.

2.2 Preparation of Linker-Payload Intermediate LB301-2-1

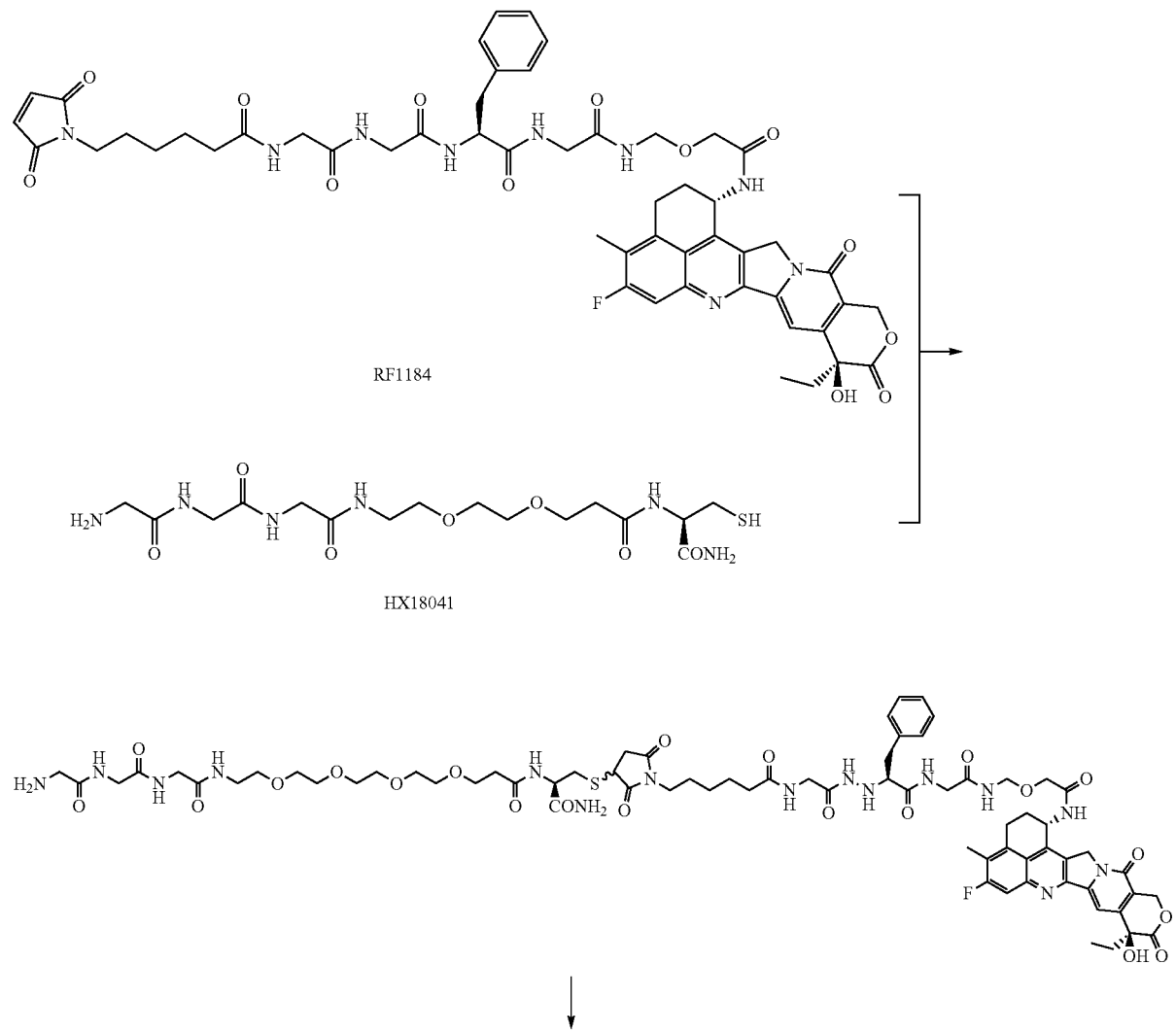

-continued

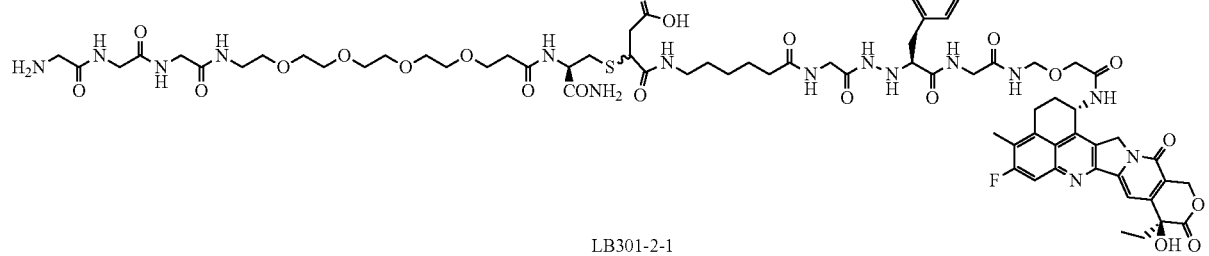

LB301-2-1

Step 1: Preparation of Linker HX18041

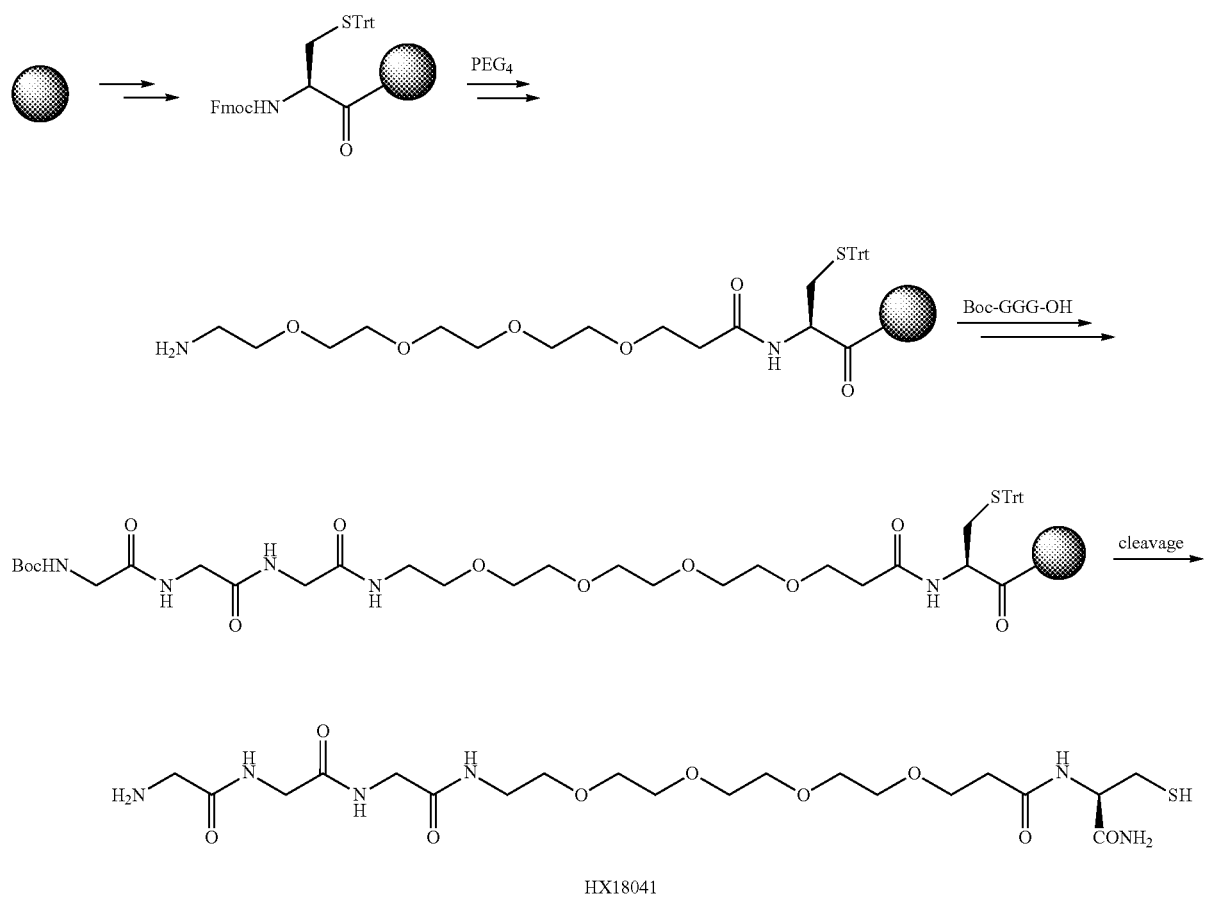

HX18041

HX18041 was synthesized by a conventional solid phase polypeptide synthesis using Rink-amide-MBHA-resin. Fmoc was used to protect the amino acid in the linking unit. The conjugation reagent was selected from HOBT, HOAt/DIC, DCC, EDCI or HATU. After synthesis, the resin was cleaved using trifluoroacetic acid. The product was purified by HPLC, lyophilized and stored for use. Theoretical molecular weight: 538.24, measured: [M+H]$^+$=539.2.

Step 2: Preparation of Linker-Payload Intermediate LB301-2-1

HX18041 and intermediate MC-GGFG-Dxd (molar ratio ~1.2:1) were weighed and dissolved in water and DMF, respectively, and then thoroughly mixed to give a mixture, which was reacted at 0-40° ° C. for 0.5-20 h. Once the reaction was completed, the reaction mixture was directly added with an appropriate amount of Tris Base solution or other solution that promotes the ring-opening reaction, and the reaction was performed at 0-40° C. for another 0.2-20 h. After the reaction was completed, the product was purified by semi-preparative/preparative HPLC and lyophilized to obtain linker-payload LB301-2-1. Theoretical Mass: 1589.65, measured: [(M+2H)/2]$^+$=796.6.

2.3 Preparation of Linker-Payload Intermediate LB302-2-1
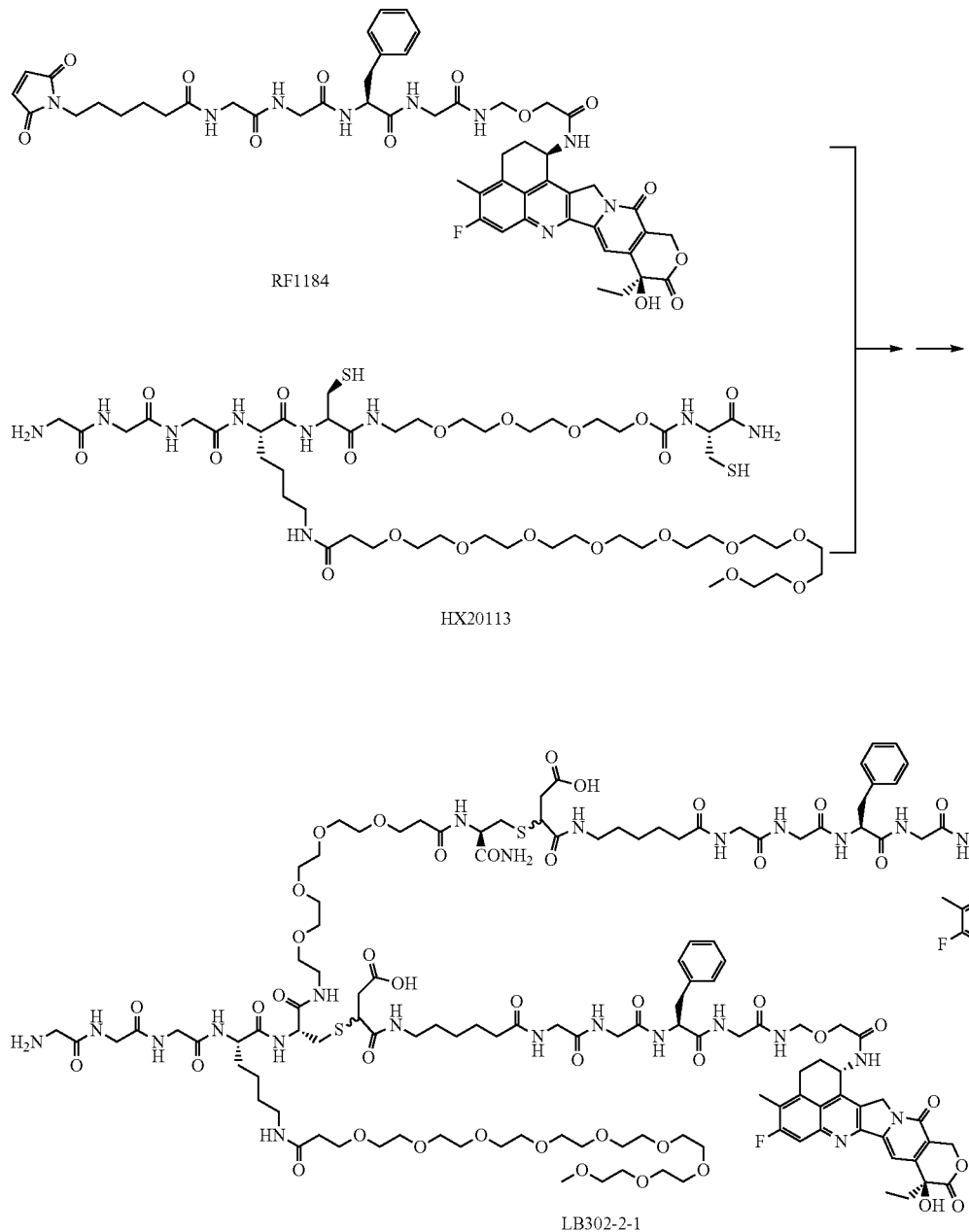
Step 1: Preparation of Linker HX20113
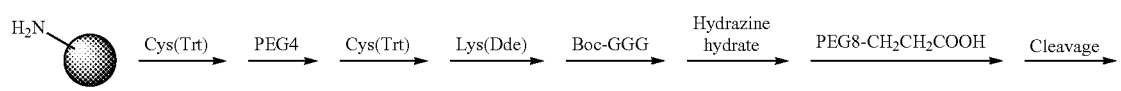

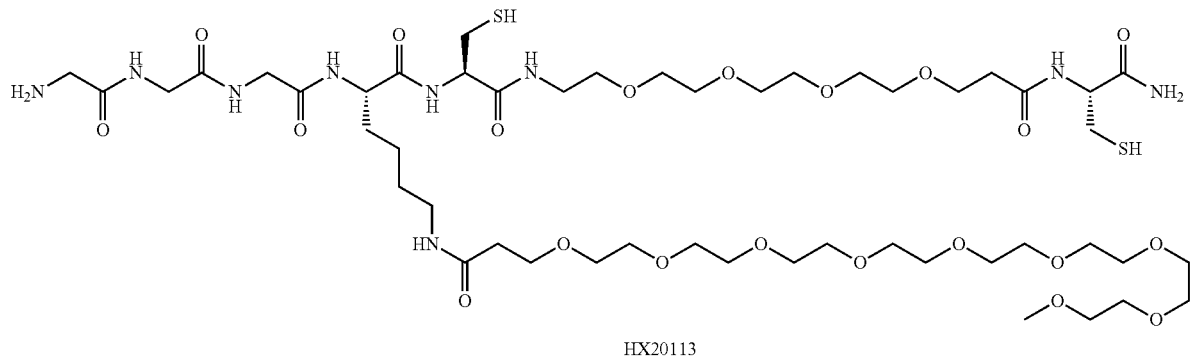

HX20113

HX20113 synthesized by a conventional solid phase polypeptide synthesis using Rink-amide-MBHA-resin. Fmoc was used to protect the amino acid in the linking unit. The conjugation reagent was selected from HOBT, HOAt/DIC, DCC, EDCI or HATU. After synthesis, the resin was cleaved using trifluoroacetic acid. The product was purified by HPLC, lyophilized and stored for use. Theoretical Mass: 1207.59, measured: [M−H]⁻=1206.7.

Step 2: Preparation of Linker-Payload Intermediate LB302-2-1

HX20113 and intermediate MC-GGFG-Dxd (molar ratio ~1:2) were weighed and dissolved in water and DMF, respectively, and then thoroughly mixed to give a mixture, which was reacted at 0-40° ° C. for 0.5-30 h. Once the reaction was completed, the reaction mixture was directly added with an appropriate amount of Tris Base solution or other solution that promotes the ring-opening reaction, and the reaction was performed at 0-40° C. for another 0.2-20 h. After the reaction was completed, the product was purified by semi-preparative/preparative HPLC and lyophilized to obtain linker-payload intermediate LB302-2-1. Theoretical Mass: 3310.41, measured: $[(M+3H)/3]^+$=1104.5.

2.4 Preparation of Linker-Payload Intermediate LB302-2-4

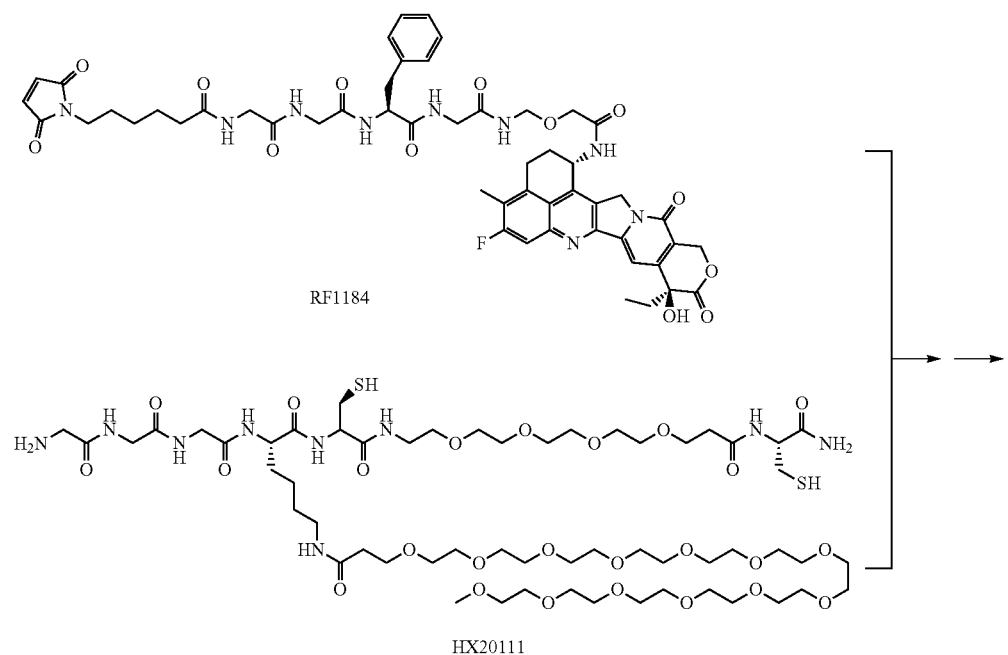

RF1184

HX20111

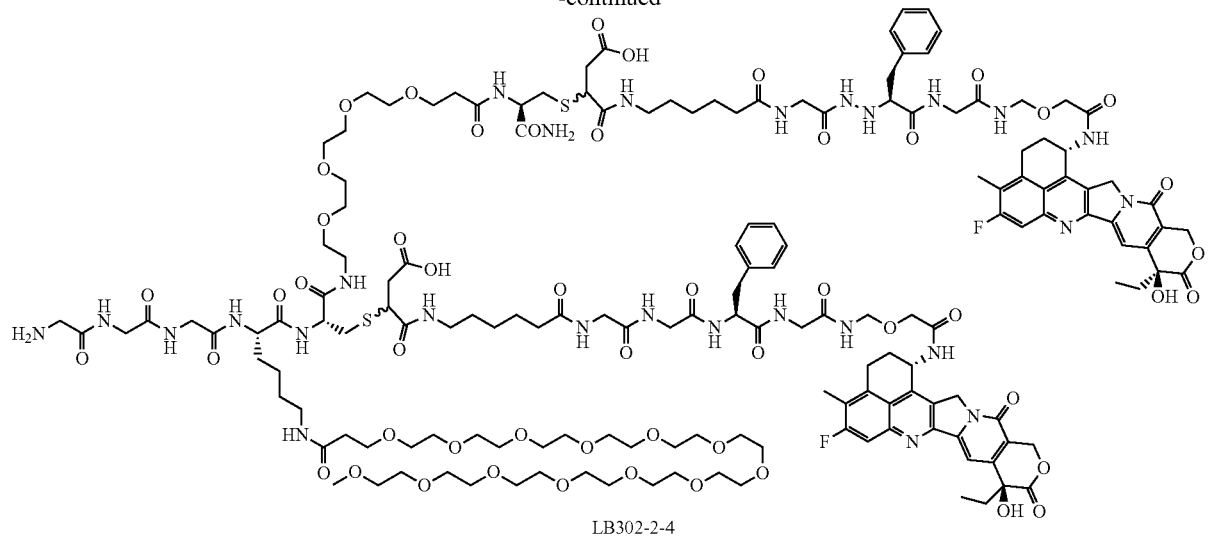

LB302-2-4

Step 1: Preparation of Linker HX20111

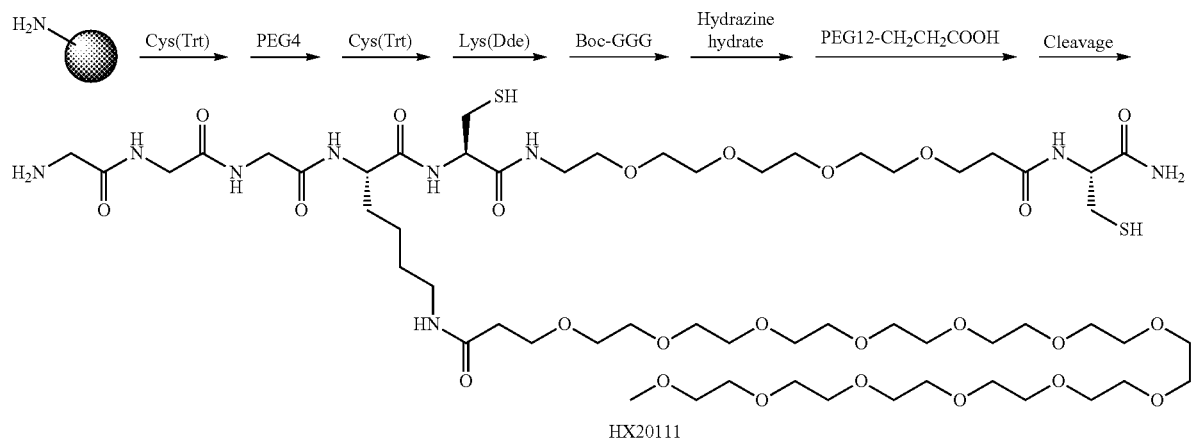

HX20111

HX20111 synthesized by a conventional solid phase polypeptide synthesis using Rink-amide-MBHA-resin. Fmoc was used to protect the amino acid in the linking unit. The conjugation reagent was selected from HOBT, HOAt/DIC, DCC, EDCI or HATU. After synthesis, the resin was cleaved using trifluoroacetic acid. The product was purified by HPLC, lyophilized and stored for use. Theoretical Mass: 1383.70, measured: $[M-H]^-=1382.6$.

Step 2: Preparation of Linker-Payload Intermediate LB302-2-4

HX20111 and intermediate MC-GGFG-Dxd (molar ratio ~1:2) were weighed and dissolved in water and DMF, respectively, and then thoroughly mixed to give a mixture, which was reacted at 0-40° ° C. for 0.5-30 h. Once the reaction was completed, the reaction mixture was directly added with an appropriate amount of Tris Base solution or other solution that promotes the ring-opening reaction, and the reaction was performed at 0-40° ° C. for another 0.2-20 h. After the reaction was completed, the product was purified by semi-preparative/preparative HPLC and lyophilized to obtain linker-payload intermediate LB302-2-4. Theoretical Mass: 3486.52, measured: $[(M+3H)/3]^+=1163.3$.

Example 3 Preparation of Targeting Molecule-Pharmaceutical Conjugates 3.1 The Linker-payload intermediates were respectively conjugated to an antibody in a site-specific manner by a ligase to form an ADC. The method for conjugation reaction can be found in WO2015165413A1. The resulting ADCs are as listed in the following table:

| Name of ADC | Linker-Payload | Antibody |
|---|---|---|
| LC301-2-1(2) | LB301-2-1 | Ab0001-LCCT$_L$-HC |
| LC302-2-1(4) | LB302-2-1 | Ab0001-LCCT$_L$-HC |
| LC302-2-4(4) | LB302-2-4 | Ab0001-LCCT$_L$-HC |
| LC301-2-1(4) | LB301-2-1 | Ab0001-LCCT$_L$-HCCT$_L$ |

3.2 The reference ADCs LC1184(8) and LC1184(4) are prepared by directly connecting the intermediate RF1184 to the (optionally modified) antibody (Cys conjugation, i.e. conjugation through connections formed by maleimide structure(s) with thiol group(s) of Cys). The method for conjugation reaction is known in the art. LC1184(8) has eight RF1184 introduced to the reduced inter-chain cysteines. LC1184(4) has four RF1184 introduced to the reduced inter-chain cysteines.

Effect Example 1 Effect of Conjugates Targeting HER2 on Cell Proliferation

Figure 2:
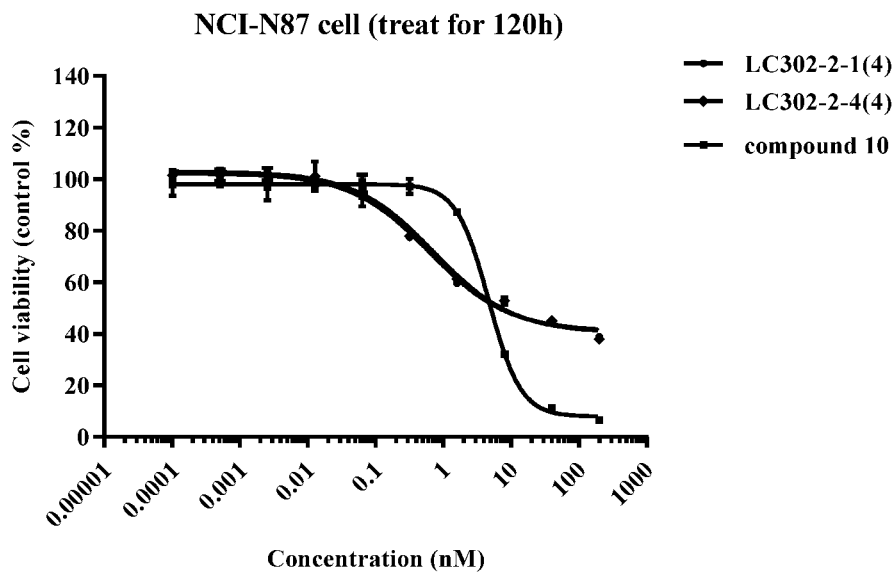
FIG. 2 shows the efficacy of conjugates and the corresponding payload in the NCI-N87 HER2-high cell line.
Figure 3:
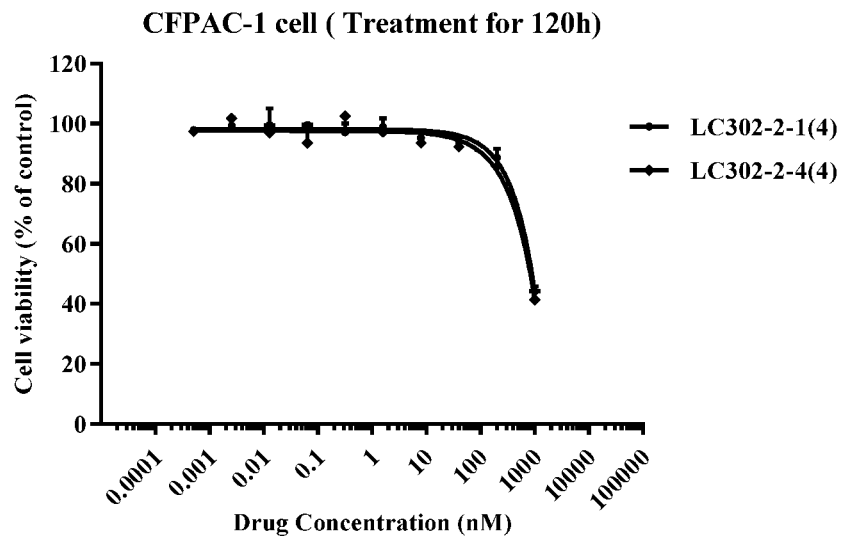
FIG. 3 shows the efficacy of conjugates in the CFPAC-1 HER2-low cell line.
Figure 4:
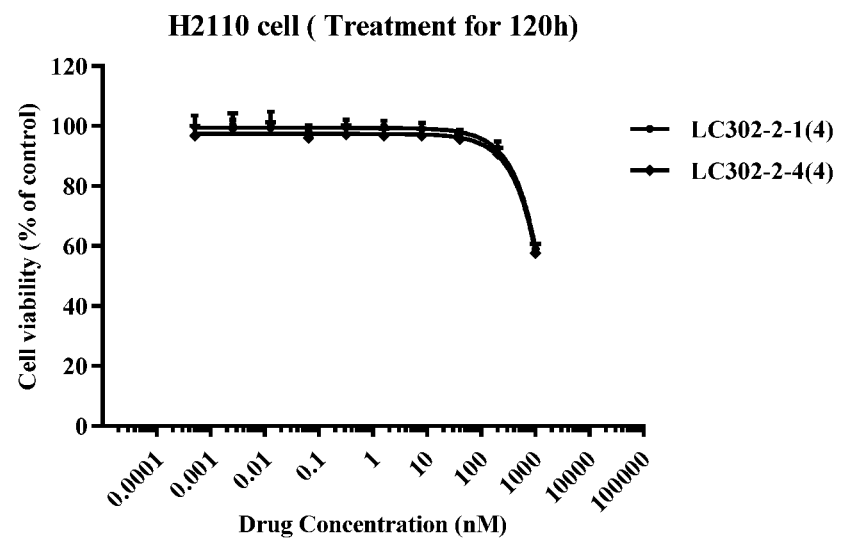
FIG. 4 shows the efficacy of conjugates in the NCI-H2110 HER2-low cell line.
Figure 5:
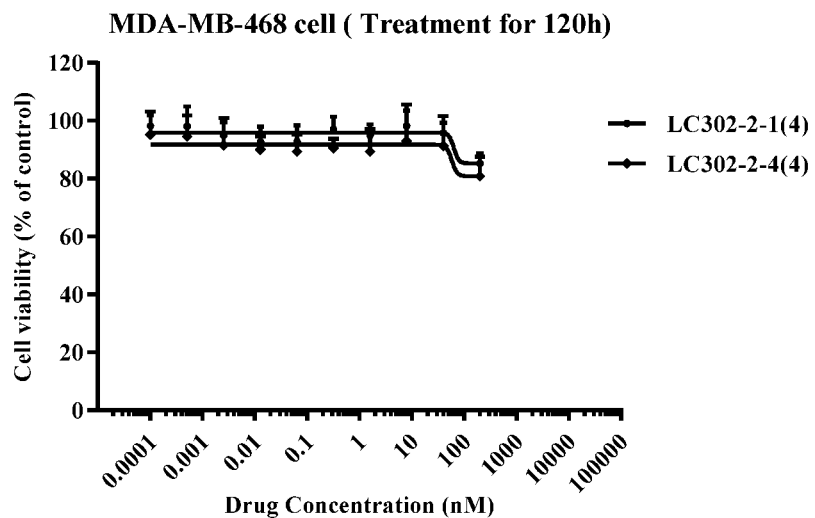
FIG. 5 shows the efficacy of conjugates in the MDA-MB-468 HER2-negative cell line.

Cytotoxicity assays were performed using HER2 high-expressing cancer cells SK-BR-3 (FIG. 1) and NCI-N87 (FIG. 2), HER2 low-expressing cancer cells CFPAC-1 (FIG. 3) and NCI-H2110 (FIG. 4), as well as a HER2 negative cell line MDA-MB-468 (FIG. 5) to analyze the effect of conjugates on tumor cell proliferation. The tested articles included conjugates LC302-2-1(4), LC302-2-4(4), and a small molecule compound 10 (structure is depicted above). In brief, 3000 to 5000 cells were plated in 96-well plates, and cells were able to attach overnight. Cells were treated with indicated drugs with various concentrations for 120 h. Cell viabilities were examined by CellTiter-Glo® Luminescent Cell Viability Assay, and percentage of cell viability was calculated.

In HER2 high-expressing SK-BR-3 and NCI-N87, the conjugates LC302-2-1(4), LC302-2-4(4) exhibited similar efficacy. The $IC_{50}$ values of LC302-2-1(4) and LC302-2-4(4) are lower than the small molecule payload Dxd. In HER2 low-expressing and negative cells, the conjugates LC302-2-1(4) and LC302-2-4(4) exhibited minimal efficacy.

| | $IC_{50}$ (nM) | | | | |
|---|---|---|---|---|---|
| Samples | SK-BR-3 | N87 | CFPAC-1 | H2110 | MDA-MB-468 |
| LC302-2-1(4) | 0.1926 | 0.6353 | N/A | N/A | N/A |
| LC302-2-4(4) | 0.1985 | 0.6353 | N/A | N/A | N/A |
| compound 10 | 1.472 | 4.682 | — | — | — |

Effect Example 2: Assessment of Conjugates In Vivo

Figure 6:
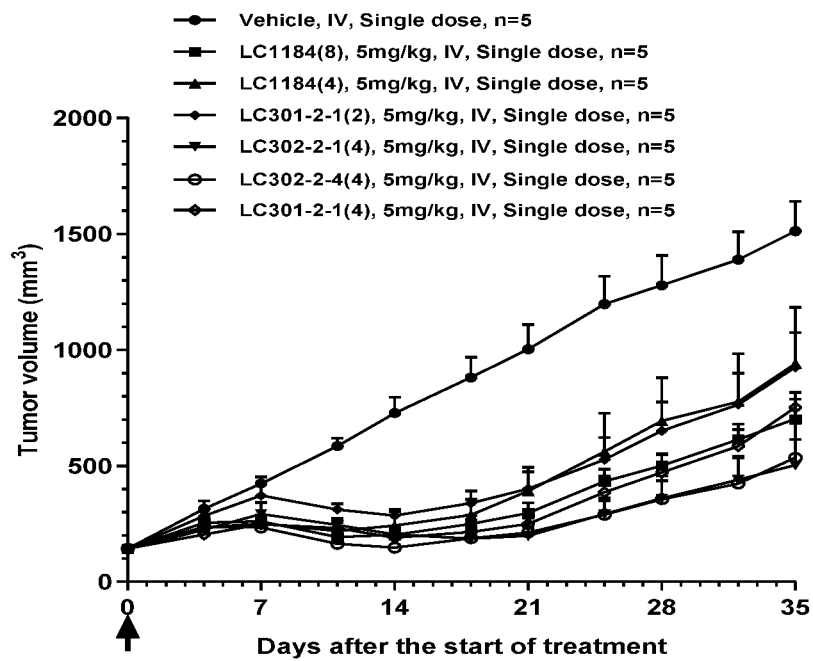
FIG. 6 shows the mean tumor volume change over time in SCID Beige mice with JIMT1 CDX model dosed with 5 mg/kg LC1184(8), LC1184(4), LC301-2-1(2), LC302-2-1(4), LC302-2-4(4).

For in vivo anti-tumor efficacy study, $5 \times 10^6$ JIMT-1 human breast cancer cells (HER2 medium) were inoculated subcutaneously in the right flank in SCID Beige mice. After 7 days, when tumor volume reached 142 mm³ on average, the tumor bearing mice were assigned and administrated intravenously of LC1184(8) and other five different conjugates at 5 mg/kg. The tumor volume was measured twice weekly with calipers. LC1184(8) showed better efficacy than LC1184(4), suggesting that with same payload, higher DAR would result in better efficacy. LC302-2-1(4) and LC302-2-4(4) showed better efficacy than LC1184(8). LC301-2-1(4) showed comparable efficacy to LC1184(8), while LC301-2-1(2) demonstrated comparable efficacy to LC1184(4) (FIG. 6). The conjugate of the present invention achieves great efficacy in lower DAR.

Figure 7:
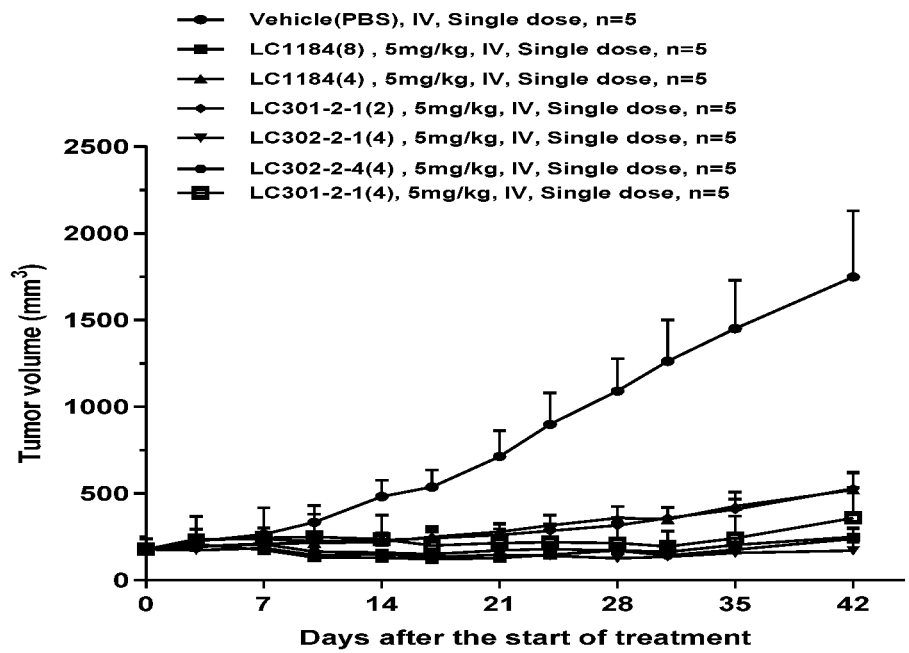
FIG. 7 shows the mean tumor volume change over time in BALB/c nude mice with Capan-1 CDX model dosed with 5 mg/kg LC1184(8), LC1184(4), LC301-2-1(2), LC302-2-1(4), LC302-2-4(4).

$5 \times 10^6$ Capan-1 human pancreatic cancer cells (HER2 low) were inoculated subcutaneously in the right flank in BALB/c nude mice to generate xenograft model. After 8 days, when tumor volume reached 178 mm³ on average, the tumor bearing mice were administrated intravenously of LC1184(8) and other five different conjugates at 5 mg/kg. The tumor volume was measured twice weekly with calipers. LC1184(8) showed better efficacy than LC1184(4). LC302-2-1(4), LC302-2-4(4) and LC301-2-1(4) showed comparable efficacy to LC1184(8), while LC301-2-1(2) demonstrated comparable efficacy to LC1184(4) (FIG. 7).

Effect Example 3: Ex-Vivo Serum Stability of the Conjugates

For ex-vivo serum stability study, the conjugates LC302-2-1(4), LC302-2-4(4) and LC1184(8) were inoculated in pooled human serum at 37° C., respectively. At 0, 24, 48 and 96 h, the conjugates were captured by antigen, then deglycosylated by glycosidase and dissociated by acid. Supernatant were collected and centrifuged, and then detected by high resolution LC-MS to determine DAR.

Figure 8:
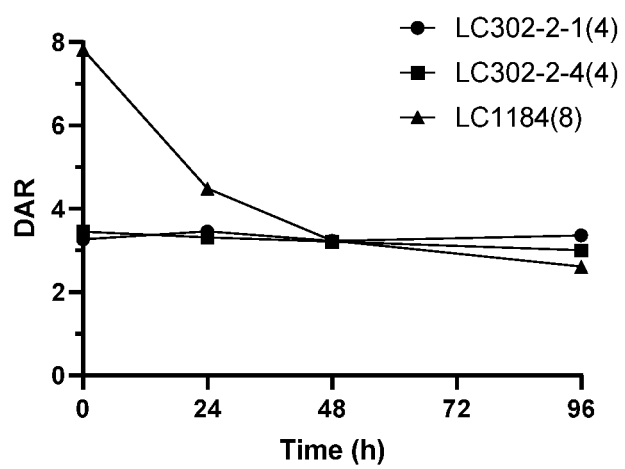
FIG. 8 shows the ex-vivo serum stability of the conjugates after 0, 24, 48 and 96 h of incubation in pooled human serum.

LC302-2-1(4) and LC302-2-4(4) are quite stable after incubated in serum for 96 hours. There is no observable decrease in the DARs of LC302-2-1(4) and LC302-2-4(4) after incubation for 96 h. However, the DAR of LC1184(8) dropped from 7.8 to 2.6 after incubation for 96 h (FIG. 8). Stability of the linker indicates the delivery of more payloads to target tumour and decrease of off-target free payload release, and thus increases therapeutic index.

---

Sequence Listing

SEQ ID No. 1: Ab0001-LCCT$_L$-HC Light chain:

DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPP

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGECGALPETGG

SEQ ID No. 2: Ab0001-LCCT$_L$-HC Heavy chain:

EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMH

EALHNHYTQKSLSLSPGK

SEQ ID No. 3: Ab0001-LCCT$_L$-HCCT$_L$ Light chain:

DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPP

TFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGECGALPETGG

SEQ ID No. 4: Ab0001-LCCT$_L$-HCCT$_L$ Heavy chain:

EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

| Sequence Listing |
|---|
| SRWGGDGFYAMDYWGQGTLVTVSSASTKGPSVFPLAPSSKSTSGGTAA |
| LGCLVKDYFPEPVTVSWNSGALTSGVHTFPAVLQSSGLYSLSSVVTVP |
| SSSLGTQTYICNVNHKPSNTKVDKKVEPKSCDKTHTCPPCPAPELLGG |
| PSVFLFPPKPKDTLMISRTPEVTCVVVDVSHEDPEVKFNWYVDGVEVH |

| Sequence Listing |
|---|
| NAKTKPREEQYNSTYRVVSVLTVLHQDWLNGKEYKCKVSNKALPAPIE |
| KTISKAKGQPREPQVYTLPPSREEMTKNQVSLTCLVKGFYPSDIAVEW |
| ESNGQPENNYKTTPPVLDSDGSFFLYSKLTVDKSRWQQGNVFSCSVMH |
| EALHNHYTQKSLSLSPGKGALPETGG |

The invention claimed is:
1. A conjugate, wherein the conjugate has the structure of the following:

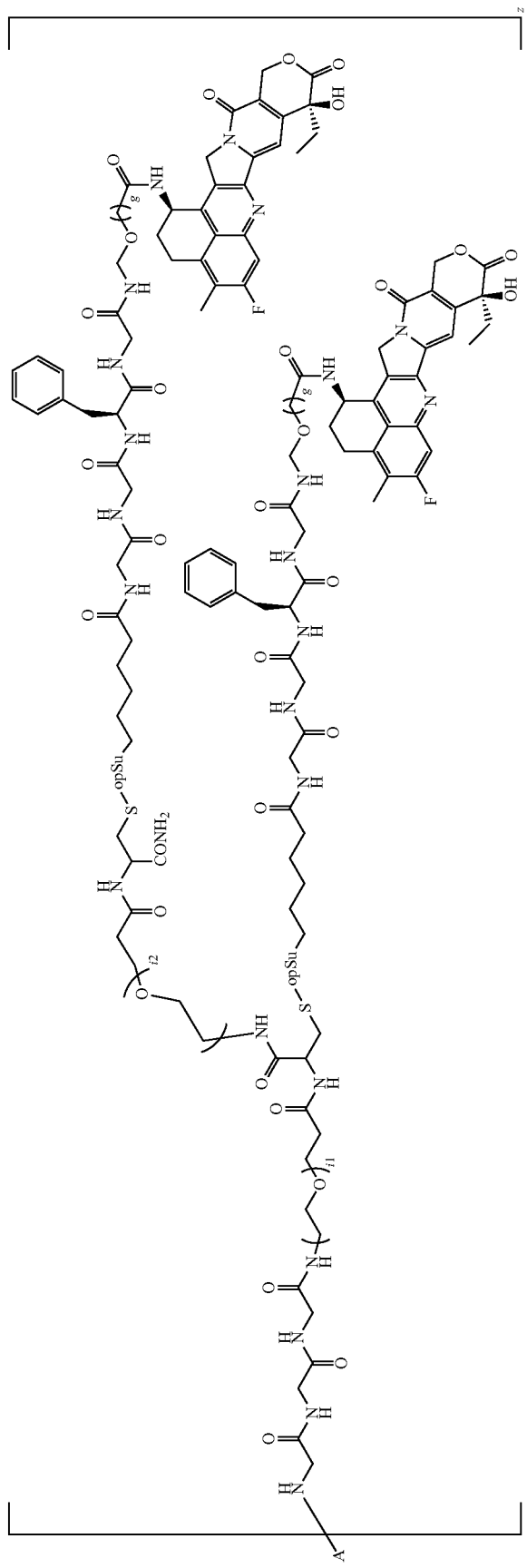

-continued
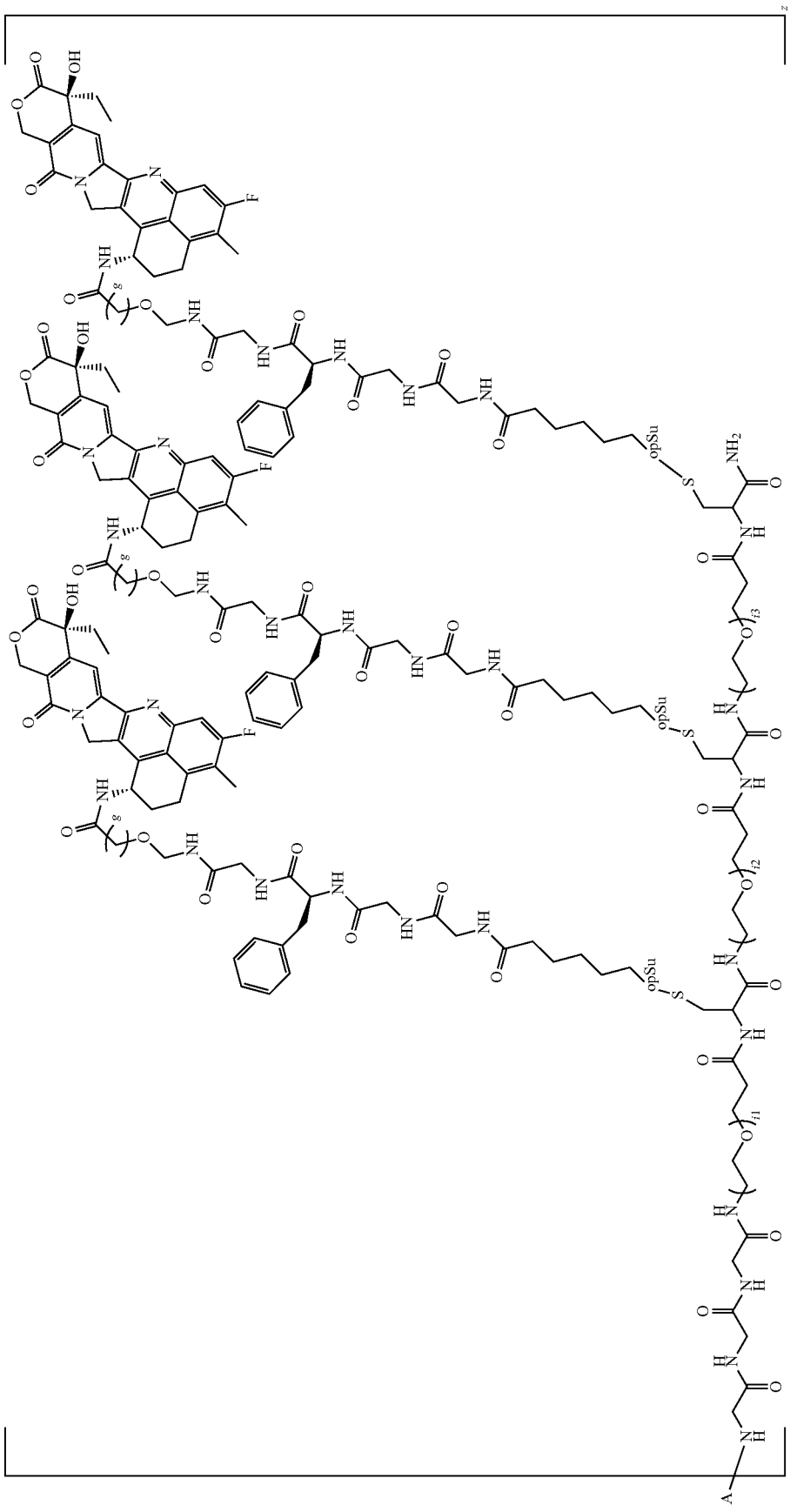

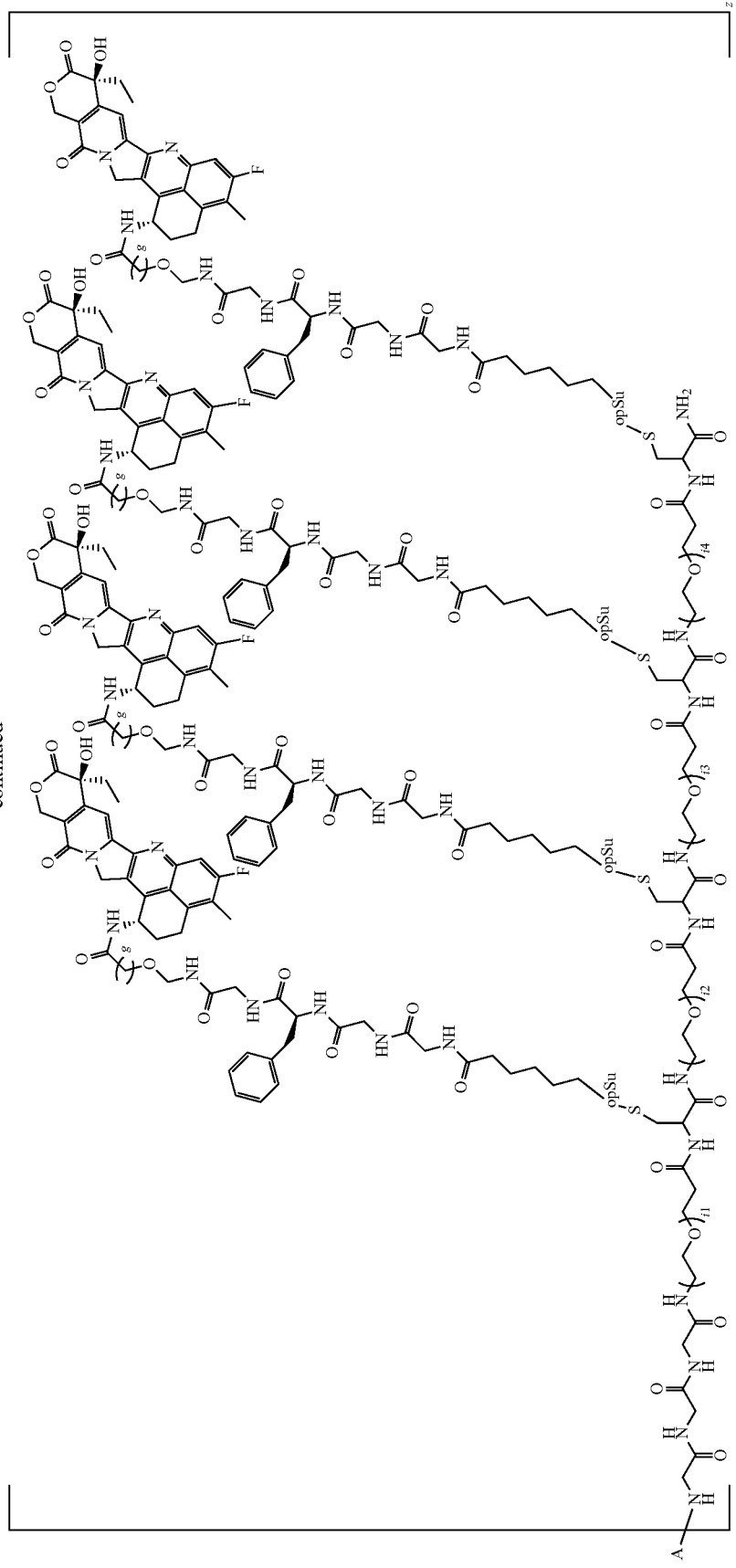

-continued
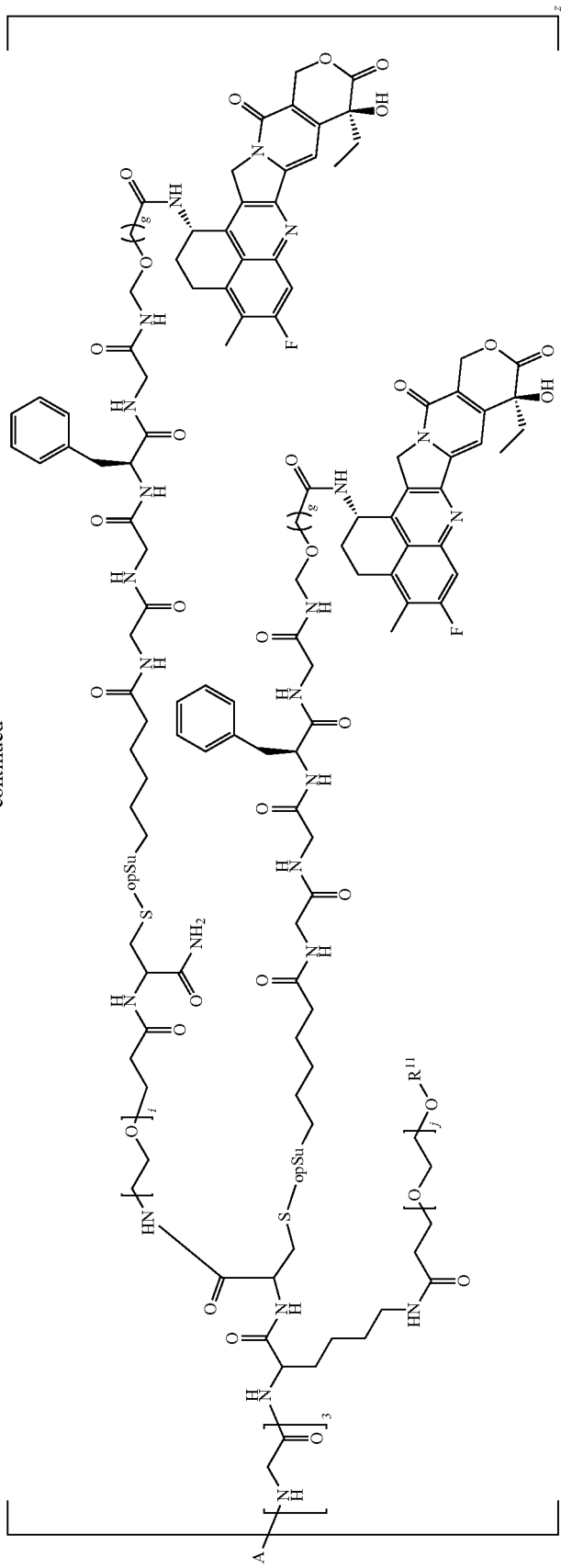

-continued
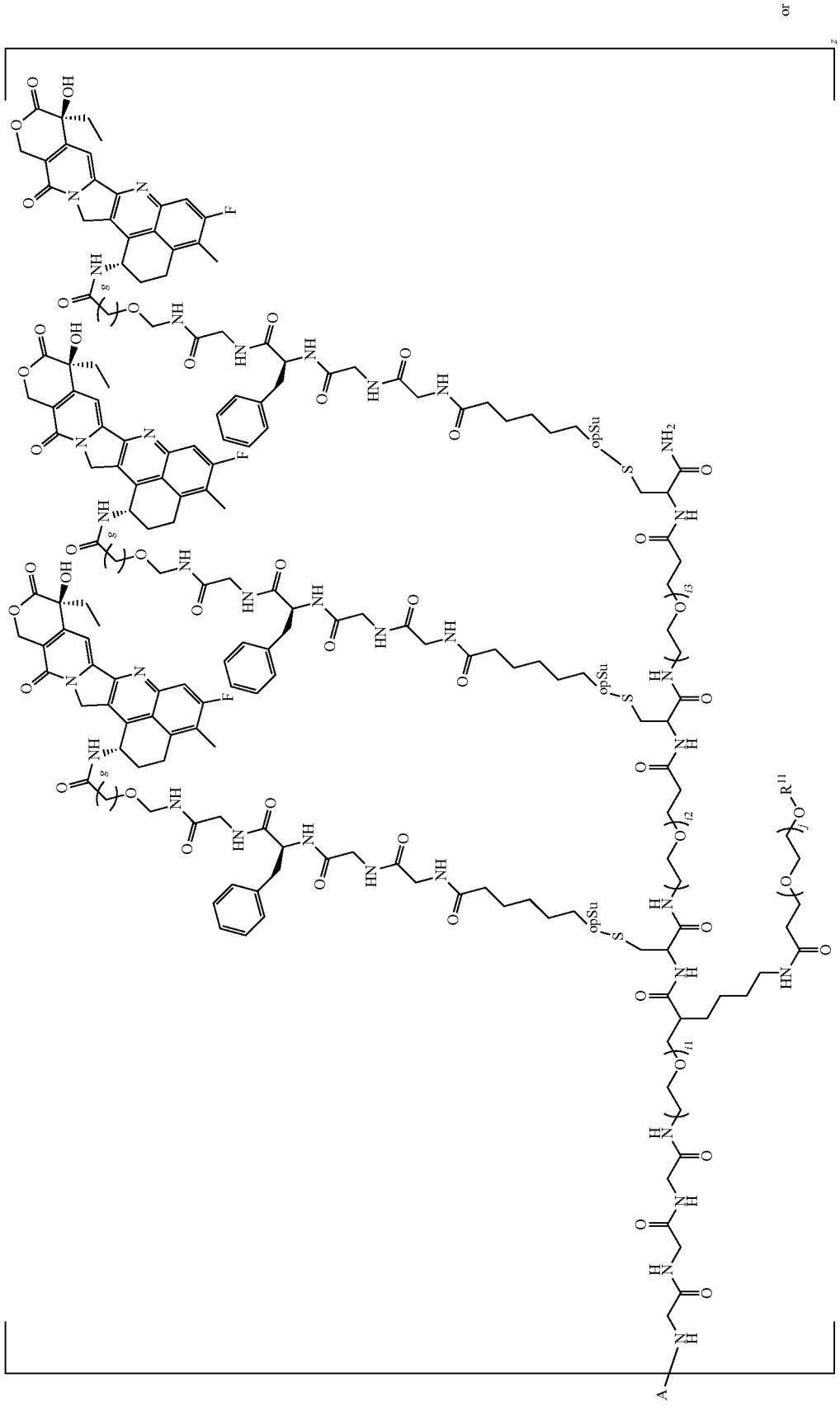

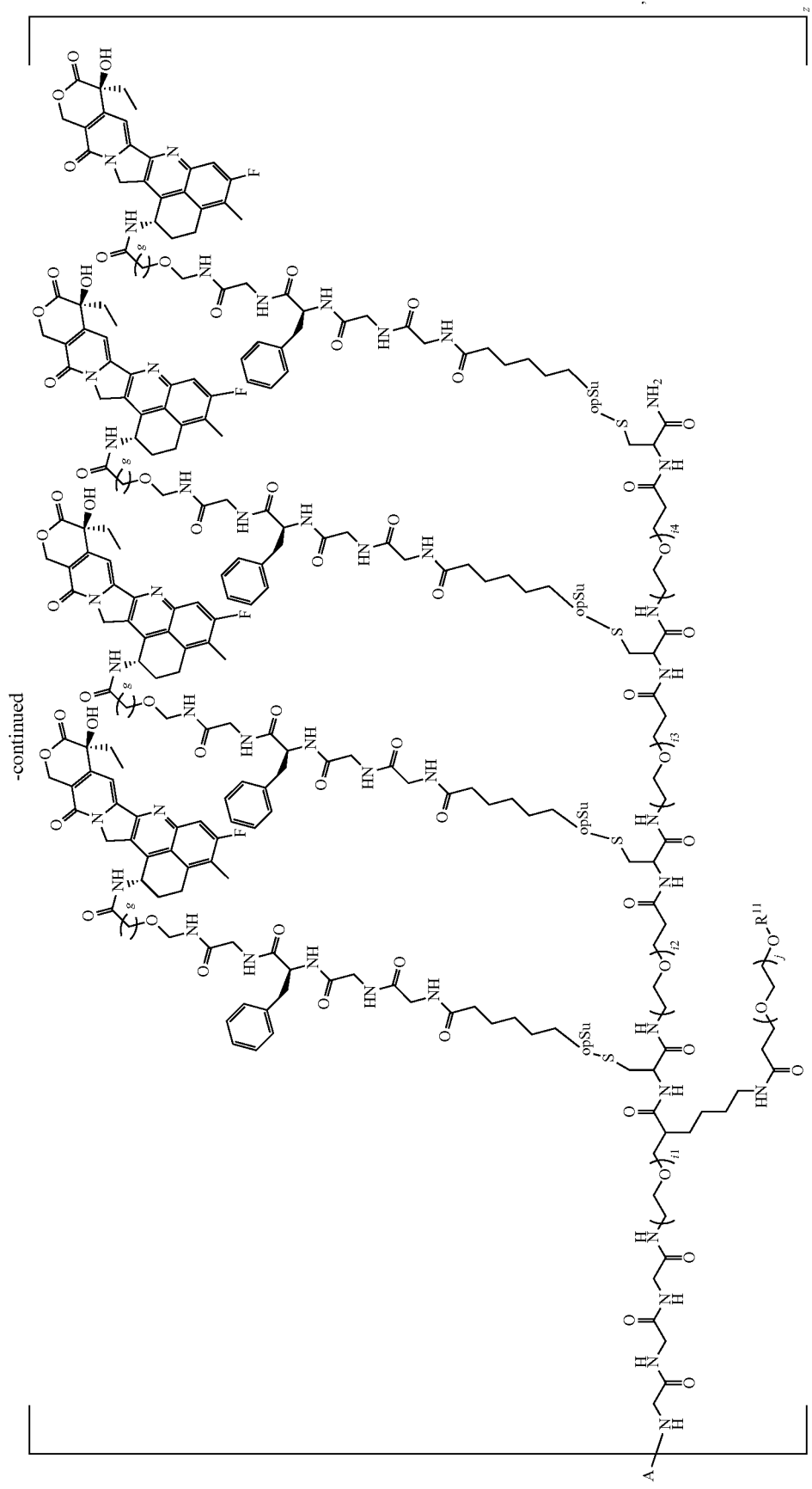

wherein each g is independently an integer of 1 to 6;
each i, i1, i2, i3, and i4 is independently an integer of 2 to 8;
each j is independently an integer of 8 to 12;
$R^{11}$ is $C_{1-10}$ alkyl;
z is 1 to 4;
opSu is

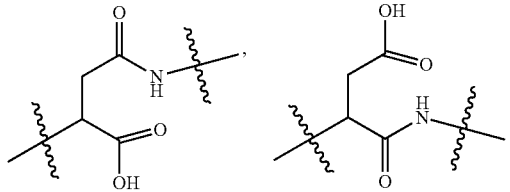 [SMILES: *NC(=O)CC(*)C(=O)O ; *NC(=O)C(*)CC(=O)O]

or a mixture thereof; and

A is an anti-human monoclonal HER2 antibody connected to the rest of the conjugate through a modified heavy chain and/or light chain C-terminal, wherein the modified heavy chain and/or light chain C-terminal is modified to comprise Leu-Pro-Xaa-Thr (SEQ ID NO:22), wherein Xaa is any natural or unnatural single amino acid.

2. The conjugate of claim 1,
wherein each g is 1.

3. A pharmaceutical composition comprising a therapeutically effective amount of the conjugate of claim 1, and at least one pharmaceutically acceptable carrier.

4. A method of treating a disease in a subject in need thereof, wherein the disease is a HER2-positive tumor, wherein the method comprises administering a pharmaceutical composition comprising a therapeutically effective amount of the conjugate of claim 1 to the subject.

5. The method of claim 4, wherein the HER2-positive tumor is selected from breast cancer, gastric cancer, lung cancer, ovarian cancer, and urothelial cancer.

6. The conjugate of claim 1, wherein each i, i1, i2, i3, and i4 is 4; and
each j is 8 or 12.

7. A conjugate, wherein the conjugate has the structure:

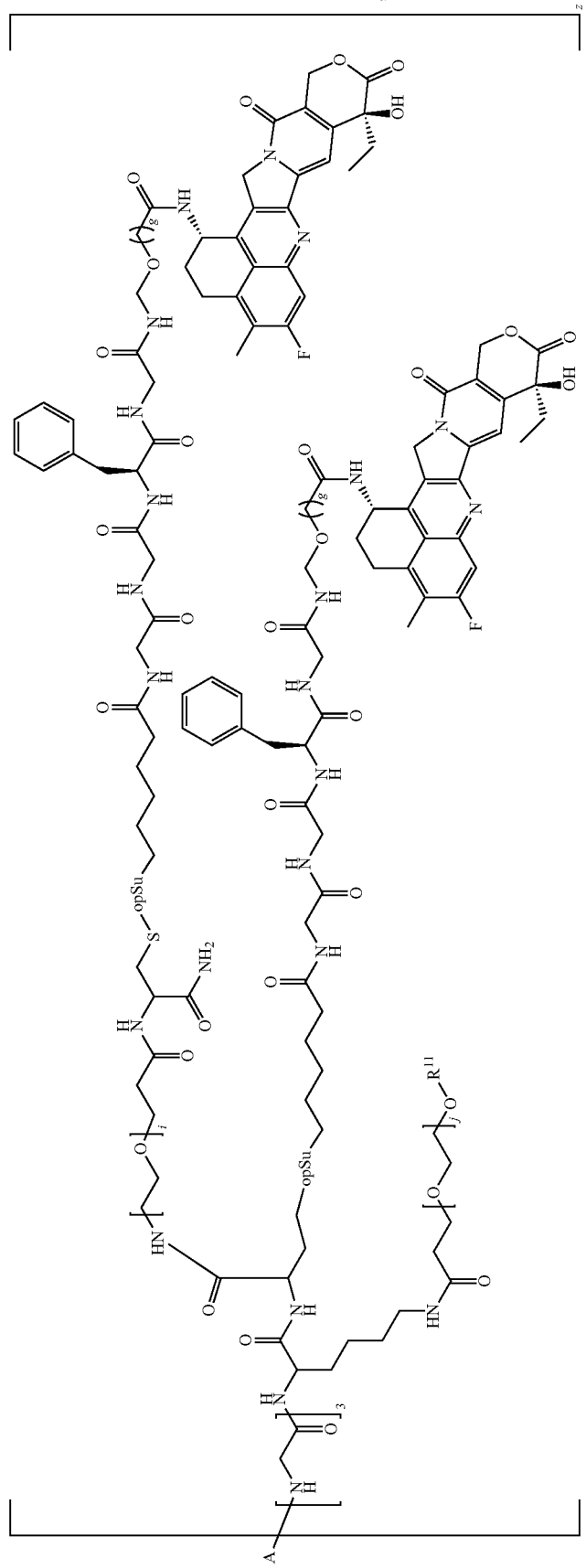

wherein i is 4, j is 8 or 12, $R^{11}$ is methyl, g is 1, opSu is

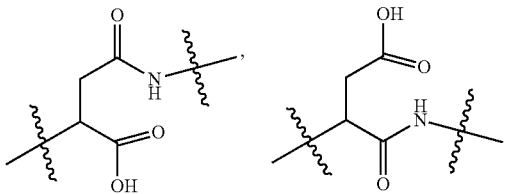 [SMILES: *NC(=O)CC(*)C(=O)O ; *NC(=O)C(*)CC(=O)O]

or a mixture thereof,

A is an anti-human monoclonal HER2 antibody connected to the rest of the conjugate through a modified heavy chain and/or light chain C-terminal, wherein the modified heavy chain and/or light chain C-terminal is modified to comprise Leu-Pro-Xaa-Thr (SEQ ID NO:22), wherein Xaa is any natural or unnatural single amino acid, and z is 2.

8. A pharmaceutical composition comprising a therapeutically effective amount of the conjugate of claim 7, and at least one pharmaceutically acceptable carrier.

9. The conjugate of claim 7, wherein the antibody comprises the light chain amino acid sequence of SEQ ID NO: 19 and the heavy chain amino acid sequence of SEQ ID NO:2 or the heavy chain sequence amino acid sequence of SEQ ID NO:21.

10. The conjugate of claim 7, wherein j is 8.

11. The conjugate of claim 7, wherein j is 12.

12. The conjugate of claim 7, wherein Xaa is Glu.

13. The conjugate of claim 1, wherein Xaa is Glu.

14. The conjugate of claim 1, wherein the modified heavy chain and/or light chain C-terminal is modified to comprise Gly-Ala-Leu-Pro-Xaa-Thr (SEQ ID NO:23).

15. The conjugate of claim 7, wherein the modified heavy chain and/or light chain C-terminal is modified to comprise Gly-Ala-Leu-Pro-Xaa-Thr (SEQ ID NO:23).

16. A pharmaceutical composition comprising a therapeutically effective amount of the conjugate of claim 9, and at least one pharmaceutically acceptable carrier.

17. A pharmaceutical composition comprising a therapeutically effective amount of the conjugate of claim 10, and at least one pharmaceutically acceptable carrier.

18. A pharmaceutical composition comprising a therapeutically effective amount of the conjugate of claim 11, and at least one pharmaceutically acceptable carrier.

19. A method of treating a disease in a subject in need thereof, wherein the disease is a HER2-positive tumor, wherein the method comprises administering a pharmaceutical composition comprising a therapeutically effective amount of the conjugate of claim 7 to the subject.

20. The method of claim 19, wherein the HER2-positive tumor is selected from breast cancer, gastric cancer, lung cancer, ovarian cancer, and urothelial cancer.

21. A method of treating a disease in a subject in need thereof, wherein the disease is a HER2-positive tumor, wherein the method comprises administering a pharmaceutical composition comprising a therapeutically effective amount of the conjugate of claim 9 to the subject.

22. The method of claim 21, wherein the HER2-positive tumor is selected from breast cancer, gastric cancer, lung cancer, ovarian cancer, and urothelial cancer.

23. A method of treating a disease in a subject in need thereof, wherein the disease is a HER2-positive tumor, wherein the method comprises administering a pharmaceutical composition comprising a therapeutically effective amount of the conjugate of claim 10 to the subject.

24. The method of claim 23, wherein the HER2-positive tumor is selected from breast cancer, gastric cancer, lung cancer, ovarian cancer, and urothelial cancer.

25. A method of treating a disease in a subject in need thereof, wherein the disease is a HER2-positive tumor, wherein the method comprises administering a pharmaceutical composition comprising a therapeutically effective amount of the conjugate of claim 11 to the subject.

26. The method of claim 25, wherein the HER2-positive tumor is selected from breast cancer, gastric cancer, lung cancer, ovarian cancer, and urothelial cancer.

\* \* \* \* \*